(12) United States Patent
Dales et al.

(10) Patent No.: US 10,633,350 B2
(45) Date of Patent: Apr. 28, 2020

(54) DIPHENYL DERIVATIVES AND USES THEREOF

(71) Applicant: NOVARTIS AG, Basel (CH)

(72) Inventors: Natalie Dales, Arlington, MA (US); Paul Gormisky, Brookline, MA (US); John Ryan Kerrigan, Wakefield, MA (US); Lei Shu, Lexington, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/129,199

(22) Filed: Sep. 12, 2018

(65) Prior Publication Data

US 2019/0077773 A1  Mar. 14, 2019

Related U.S. Application Data

(60) Provisional application No. 62/558,065, filed on Sep. 13, 2017.

(51) Int. Cl.

| | |
|---|---|
| C07D 231/14 | (2006.01) |
| C07D 249/10 | (2006.01) |
| C07D 401/10 | (2006.01) |
| C07D 401/14 | (2006.01) |
| C07D 487/04 | (2006.01) |
| C07D 405/10 | (2006.01) |
| C07D 403/10 | (2006.01) |
| A61P 27/16 | (2006.01) |
| A61P 21/00 | (2006.01) |
| A61P 25/28 | (2006.01) |
| A61P 17/02 | (2006.01) |
| C07D 413/10 | (2006.01) |
| C07D 405/14 | (2006.01) |
| C07D 417/10 | (2006.01) |
| C07D 491/04 | (2006.01) |
| C07D 333/20 | (2006.01) |
| C07D 498/04 | (2006.01) |

(52) U.S. Cl.
CPC ............ *C07D 249/10* (2013.01); *A61P 17/02* (2018.01); *A61P 21/00* (2018.01); *A61P 25/28* (2018.01); *A61P 27/16* (2018.01); *C07D 231/14* (2013.01); *C07D 333/20* (2013.01); *C07D 401/10* (2013.01); *C07D 401/14* (2013.01); *C07D 403/10* (2013.01); *C07D 405/10* (2013.01); *C07D 405/14* (2013.01); *C07D 413/10* (2013.01); *C07D 417/10* (2013.01); *C07D 487/04* (2013.01); *C07D 491/04* (2013.01); *C07D 498/04* (2013.01)

(58) Field of Classification Search
CPC .. C07D 231/14; C07D 249/10; C07D 401/10; C07D 401/14; C07D 487/04
See application file for complete search history.

(56) References Cited

U.S. PATENT DOCUMENTS

2007/0191371 A1   8/2007  Bennett et al.

FOREIGN PATENT DOCUMENTS

| WO | WO 2004/092140 A1 | 10/2004 |
| WO | WO 2013/159094 A2 | 10/2013 |
| WO | WO 2014/023367 A1 | 2/2014 |
| WO | WO 2014/026039 A2 | 2/2014 |
| WO | WO 2015/056180 A1 | 4/2015 |

OTHER PUBLICATIONS

Walters et al. Int. J. Mol. Sci. pp. 1-33. (Year: 2018).*
Liguori et al. Clin Interv Aging vol. 13, p. 913-927. (Year: 2018).*
Castilho et al. Oral Diseases. vol. 19, p. 551-558. (Year: 2013).*
Wang, Yizhong et al., "Synthesis and Evaluation of Photoreactive Tetrazole Amino Acids" Organic Letters, (Jun. 10, 2009) vol. 11. No. 16. pp. 3570-3573.
El Khadem, Hassan, et al. "Mass Spectra of 5-Styryl and 5-Acylpyrazoles", (Aug. 1974) Journal of Heterocyclic Chemistry, vol. 11 (4), pp. 575-585.
International Search Report and Written Opinion of the International Searching Authority, International Patent Application No. PCT/EP2018/074662 (dated Oct. 24, 2018).

* cited by examiner

*Primary Examiner* — Emily A Bernhardt

(74) *Attorney, Agent, or Firm* — Asimina T. Georges Evangelinos

(57) ABSTRACT

The present disclosure provides a compound of formula (I):

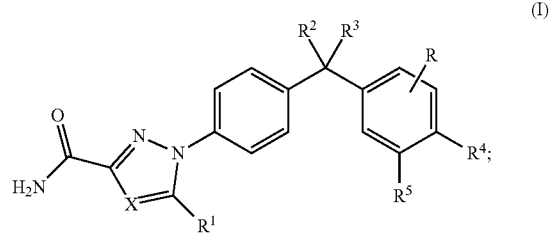

or a pharmaceutically acceptable salt thereof, and its therapeutic uses for activating a growth factor pathway, promoting wound healing, promoting tissue repair, and treating hearing loss, skeletal muscle loss, organ degeneration, tissue damage, neurodegeneration, and muscular atrophy. The disclosure further provides pharmaceutical compositions and combinations. The present disclosure also relates to the use of such compounds for research or other non-therapeutic purposes.

16 Claims, No Drawings

DIPHENYL DERIVATIVES AND USES THEREOF

CROSS-REFERENCE TO RELATED APPLICATIONS

This application claims the benefit of U.S. Provisional Application No. 62/558,065, filed Sep. 13, 2017, which is incorporated by reference in its entirety.

FIELD

The disclosure provides diphenyl compounds and the use thereof as growth factor pathway activators.

BACKGROUND

Growth factors are signaling molecules which bind their cognate cell surface receptors initiating signaling cascades that stimulate a variety of cellular processes including growth, metabolism, survival, migration and differentiation. One of the key growth factor signaling pathways is the PI3K (Phosphoinositide 3 Kinase)/Akt/mTOR (Mechanistic Target of Rapamycin) pathway. Akt (also called Protein Kinase B, PKB) is a serine/threonine kinase that mediates growth factor signaling by phosphorylating multiple cellular targets. (Manning B D, Cantley L C. AKT/PKB signaling: navigating downstream. Cell. 2007 Jun. 29; 129(7):1261-74.)

Impaired growth factor signaling can lead to various disease conditions including skeletal muscle loss, hearing loss, degeneration of a number of organ systems and delayed wound healing. (Rüegg M A, Glass D J. Molecular mechanisms and treatment options for muscle wasting diseases. Annu Rev Pharmacol Toxicol. 2011; 51:373-95; Yamamoto N, Nakagawa T, Ito J. Application of insulin-like growth factor-1 in the treatment of inner ear disorders. Front Pharmacol. 2014 Sep. 10; 5:208; Böhm F, Kohler U A, Speicher T, Werner S. Regulation of liver regeneration by growth factors and cytokines. EMBO Mol Med. 2010 August; 2(8):294-305; Sádaba M C, Martin-Estal I, Puche J E, Castilla-Cortázar I. Insulin-like growth factor 1 (IGF-1) therapy: Mitochondrial dysfunction and diseases. Biochim Biophys Acta. 2016 July; 1862(7):1267-78; Bach L A, Hale L J. Insulin-like growth factors and kidney disease. Am J Kidney Dis. 2015 February; 65(2):327-36; Mitchell A C, Briquez P S, Hubbell J A, Cochran J R. Engineering growth factors for regenerative medicine applications. Acta Biomater. 2016 January; 30:1-12.) With the dramatic rise in the prevalence of diabetes, age and diabetes-associated non-healing chronic wounds are a critical health problem in the world today. (Demidova-Rice T N, Hamblin M R, Herman I M. Acute and impaired wound healing: pathophysiology and current methods for drug delivery, part 1: normal and chronic wounds: biology, causes, and approaches to care. Adv Skin Wound Care. 2012 July; 25(7):304-14.) Injury typically induces expression of growth factor receptors, and growth factors are involved in all stages of the wound healing process: coagulation, inflammation, formation of granulation tissue and remodeling or scar formation. (Demidova-Rice T N, Hamblin M R, Herman I M. Acute and impaired wound healing: pathophysiology and current methods for drug delivery, part 2: role of growth factors in normal and pathological wound healing: therapeutic potential and methods of delivery. Adv Skin Wound Care. 2012 August; 25(8):349-70; Goldman R. Growth factors and chronic wound healing: past, present, and future. Adv Skin Wound Care. 2004 January-February; 17(1):24-35.) Chronic wounds (vascular ulcers, diabetic ulcers and pressure ulcers) are characterized by decreased density of growth factor receptors and reduced mitogenic response to growth factors. (Demidova-Rice T N et al., supra, Adv Skin Wound Care. 2012 August; 25(8):349-70; Goldman R., supra, Adv Skin Wound Care. 2004 January-February; 17(1):24-35.)

The current paradigm for treating chronic wounds involves debridement (surgical or with debridement agents), control of infection and inflammation (with antibiotics and anti-inflammatory agents), correction of moisture imbalance (with wound dressings) and promotion of re-epithelialization/granulation tissue formation (with growth factors). (Demidova-Rice T N et al., supra, Adv Skin Wound Care. 2012 July; 25(7):304-14.) IGF-1/Insulin are well validated in wound healing both in preclinical and clinical settings, and mouse models of activated PI3K/Akt/mTOR signaling axis show accelerated wound closure. (Mori R, Tanaka K, de Kerckhove M, Okamoto M, Kashiyama K, Tanaka K, Kim S, Kawata T, Komatsu T, Park S, Ikematsu K, Hirano A, Martin P, Shimokawa I. Reduced FOXO1 expression accelerates skin wound healing and attenuates scarring. Am J Pathol. 2014 September; 184(9):2465-79; Lima M H, Caricilli A M, de Abreu L L, Araijo E P, Pelegrinelli F F, Thirone A C, Tsukumo D M, Pessoa A F, dos Santos M F, de Moraes M A, Carvalheira J B, Velloso L A, Saad M J. Topical insulin accelerates wound healing in diabetes by enhancing the AKT and ERK pathways: a double-blind placebo-controlled clinical trial. PLoS One. 2012; 7(5):e3697; Harding K, Aldons P, Edwards H, Stacey M, Finlayson K, Gibb M, Jenkins L, Shooter G, Lonkhuyzen D V, Lynam E, Heinrichs E L, Upton Z. Effectiveness of an acellular synthetic matrix in the treatment of hard-to-heal leg ulcers. Int Wound J. 2014 April; 11(2):129-37; Balaji S, LeSaint M, Bhattacharya S S, Moles C, Dhamija Y, Kidd M, Le L D, King A, Shaaban A, Crombleholme T M, Bollyky P, Keswani S G. Adenoviral-mediated gene transfer of insulin-like growth factor 1 enhances wound healing and induces angiogenesis. J Surg Res. 2014 July; 190(1):367-77; Squarize C H, Castilho R M, Bugge T H, Gutkind J S. Accelerated wound healing by mTOR activation in genetically defined mouse models. PLoS One. 2010 May 13; 5(5):e10643.)

The only FDA approved treatment for chronic wounds is Becaplermin (Regranex) which contains recombinant PDGF and has had limited efficacy. (Eaglstein W H, Kirsner R S, Robson M C. Food and Drug Administration (FDA) drug approval end points for chronic cutaneous ulcer studies. Wound Repair Regen. 2012 November-December; 20(6): 793-6.) Recombinant PDGF has several drawbacks as a treatment for chronic wounds, including its short half-life in the protease-rich hostile wound microenvironment and insufficient delivery mechanisms. A need remains for growth factor pathway activators that bypass growth factor receptors (which are downregulated in chronic wounds), have increased stability, and pose no risk for immunogenicity.

SUMMARY

The disclosure provides compounds, pharmaceutically acceptable salts thereof, pharmaceutical compositions thereof and combinations thereof. The compounds can or may activate growth factor pathways, including the PI3K/Akt/mTOR pathway.

In one aspect, the disclosure provides a compound of formula (I):

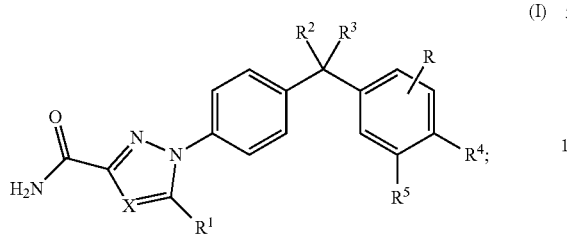

or a pharmaceutically acceptable salt thereof.

In another aspect, the disclosure provides a pharmaceutical composition comprising a compound of formula (I), or a pharmaceutically acceptable salt thereof, e.g., in a therapeutically effective amount, and one or more pharmaceutically acceptable carriers.

In another aspect, the disclosure provides a pharmaceutical combination comprising a compound of formula (I) or a pharmaceutically acceptable salt thereof, e.g., in a therapeutically effective amount, and one or more other therapeutic agents.

In another aspect, the disclosure provides a method of activating a growth factor pathway in a subject in need thereof, comprising administering to the subject a therapeutically effective amount of a compound of formula (I) or a pharmaceutically acceptable salt thereof, or a pharmaceutical composition of the compound or a pharmaceutically acceptable salt thereof.

In another aspect, the disclosure provides a method of promoting wound healing, promoting tissue repair, or treating hearing loss, skeletal muscle loss, organ degeneration, tissue damage, neurodegeneration, or muscular atrophy in a subject in need thereof, comprising administering to the subject a therapeutically effective amount of a compound of formula (I) or a pharmaceutically acceptable salt thereof, or a pharmaceutical composition of the compound or a pharmaceutically acceptable salt thereof.

Further, the compounds or methods described herein may be used for research (e.g., studying growth factor signaling pathways) and other non-therapeutic purposes.

Unless otherwise defined, all technical and scientific terms used herein have the same meaning as commonly understood by one of ordinary skill in the art to which this disclosure belongs. In the specification and claims, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference for all purposes. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of compounds, compositions and methods disclosed herein will be apparent from the following detailed description and claims.

DETAILED DESCRIPTION

In one aspect, the disclosure provides a compound of formula (I) or a pharmaceutically acceptable salt thereof:

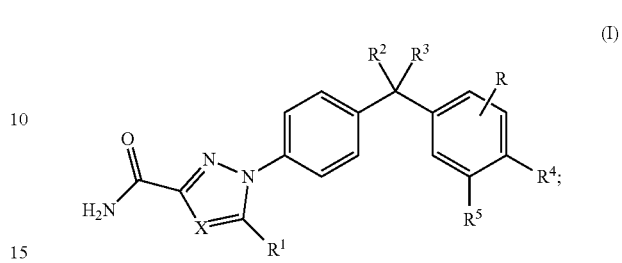

wherein:

X is CH or N;

R is H, halo, —OH, $C_{1-4}$alkyl, $C_{1-4}$alkoxy, $C_{1-4}$haloalkyl or $C_{1-4}$ haloalkoxy;

$R^1$ is H, $C_{1-4}$alkyl, $C_{1-4}$haloalkyl, or 3-6 membered cycloalkyl;

$R^2$ and $R^3$ are each, independently, H or $C_{1-4}$alkyl;

$R^4$ is halo, —C≡C—$R^6$, —$C_6H_4$—$R^6$, -(4-10 membered heterocyclyl)-$R^6$, a 5-10 membered heteroaryl optionally substituted with 1-3 $R^6$ groups, -(4-10 membered carbocyclyl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups;

$R^5$ is H, or $R^4$ and $R^5$ together with the carbon atoms to which they are attached form a 5-12 membered carbocyclic, heterocyclic, aryl, heteroaryl, fused heterocyclyl-aryl, fused heterocyclyl-heteroaryl, fused carbocyclyl-aryl, or fused carbocyclyl-heteroaryl ring, wherein said carbocyclic, heterocyclic, aryl, heteroaryl, fused heterocyclyl-aryl, fused heterocyclyl-heteroaryl, fused carbocyclyl-aryl, or fused carbocyclyl-heteroaryl ring is optionally substituted with 1-3 $C_{1-4}$alkyl groups;

each $R^6$ is independently —$(CH_2)_m$—$(CO)_n$—$(CH_2)_p$—$R^{6a}$, —O—$R^{6a}$, —$(CH_2)_m$—$(CO)_n$—$(CH_2)_p$—$R^{6b}$, —O—$R^{6b}$, —$(CH_2)_m$—$(CO)_n$—$(CH_2)_p$—$R^{6c}$, —O—$R^{6c}$, —$(CH_2)_m$—$(CO)_n$—$(CH_2)_p$—$R^{6d}$, or —O—$R^{6d}$;

$R^{6a}$ is H, —OH, —$NR^7R^8$, —CN, oxo, $C_{1-4}$alkyl, $C_{1-4}$haloalkyl, $C_{1-4}$hydroxyalkyl, —CH($NR^7R^8$)—$C_{1-4}$haloalkyl, —CH($NR^7R^8$)—$C_{1-3}$alkyl, —C($CH_3$)($NR^7R^8$)—$C_{1-3}$alkyl, —$SO_2C_{1-4}$alkyl, —$SO_2C_{1-4}$hydroxyalkyl, or —$SO_2NR^7R^8$;

$R^{6b}$ is a 4-10 membered heterocyclyl optionally substituted with 1-3 substituents independently selected from a group consisting of halo, —OH, —$NR^7R^8$, $C_{1-4}$alkyl, —$C_{1-4}$ haloalkyl, —$C_{1-4}$hydroxyalkyl, —$C_{1-4}$alkyl-$NR^7R^8$, —$SO_2C_{1-4}$alkyl, and 4-6 membered heterocyclyl;

$R^{6c}$ is a 5-10 membered heteroaryl optionally substituted with 1-3 substituents independently selected from a group consisting of —$NR^7R^8$, $C_{1-4}$alkyl, —$C_{1-4}$hydroxyalkyl, and —$C_{1-4}$ alkyl-$NR^7R^8$;

$R^{6d}$ is a 4-10 membered carbocyclyl optionally substituted with 1-3 substituents independently selected from a group consisting of halo, —OH, —$NR^7R^8$, $C_{1-4}$alkyl, —$C_{1-4}$ haloalkyl, —$C_{1-4}$hydroxyalkyl, —$C_{1-4}$alkyl-$NR^7R^8$, —$SO_2C_{1-4}$alkyl, and 4-6 membered heterocyclyl;

$R^7$ and $R^8$ are each, independently, selected from a group consisting of H, $C_{1-4}$alkyl, $C_{1-4}$ hydroxyalkyl, a 4-6 membered heterocyclyl, and a 4-6 membered cycloalkyl;

m is 0 or 1;

n is 0 or 1; and p is 0 or 1.

In an embodiment, the disclosure provides a compound of formula (I) or a pharmaceutically acceptable salt thereof:

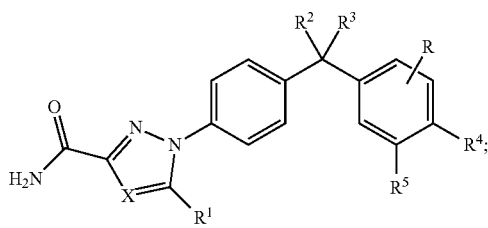

wherein:
X is CH or N;
R is H, halo, —OH, $C_{1-4}$alkyl, $C_{1-4}$alkoxy, $C_{1-4}$haloalkyl or $C_{1-4}$ haloalkoxy;
$R^1$ is H, $C_{1-4}$alkyl, $C_{1-4}$haloalkyl, or 3-6 membered cycloalkyl;
$R^2$ and $R^3$ are each, independently, H or $C_{1-4}$alkyl;
$R^4$ is halo, —$C_6H_4$—$R^6$, -(4-10 membered heterocyclyl)-$R^6$, -(5-10 membered heteroaryl)-$R^6$, -(4-6 membered carbocyclyl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups;
$R^5$ is H, or $R^4$ and $R^5$ together with the carbon atoms to which they are attached form a 5-12 membered carbocyclic, heterocyclic, aryl, heteroaryl, fused heterocyclyl-aryl, fused heterocyclyl-heteroaryl, fused carbocyclyl-aryl, or fused carbocyclyl-heteroaryl ring, wherein said carbocyclic, heterocyclic, aryl, heteroaryl, fused heterocyclyl-aryl, fused heterocyclyl-heteroaryl, fused carbocyclyl-aryl, or fused carbocyclyl-heteroaryl ring is optionally substituted with 1-3 $C_{1-4}$alkyl groups;
$R^6$ is —$(CH_2)_m$—$(CO)_n$—$(CH_2)_p$—$R^{6a}$, —$(CH_2)_m$—$(CO)_n$—$(CH_2)_p$—$R^{6b}$, or —$(CH_2)_m$—$(CO)_n$—$(CH_2)_p$—$R^{6c}$;
$R^{6a}$ is H, —OH, —$NR^7R^8$, —CN, oxo, $C_{1-4}$alkyl, $C_{1-4}$haloalkyl, —$CH(NR^7R^8)$—$C_{1-3}$haloalkyl, —$CH(NR^7R^8)$—$C_{1-3}$alkyl, —$SO_2C_{1-4}$alkyl, or —$SO_2NR^7R^8$;
$R^{6b}$ is a 4-10 membered heterocyclyl optionally substituted with 1-3 substituents independently selected from a group consisting of —$NR^7R^8$, $C_{1-4}$alkyl, —$C_{1-4}$hydroxyalkyl, and —$C_{1-4}$alkyl-$NR^7R^8$;
$R^{6c}$ is a 5-10 membered heteroaryl optionally substituted with 1-3 substituents independently selected from a group consisting of —$NR^7R^8$, $C_{1-4}$alkyl, —$C_{1-4}$hydroxyalkyl, and —$C_{1-4}$alkyl-$NR^7R^8$;
$R^7$ and $R^8$ are each, independently, selected from a group consisting of H, $C_{1-4}$alkyl, $C_{1-4}$hydroxyalkyl, a 4-6 membered heterocyclyl, and a 4-6 membered cycloalkyl;
m is 0 or 1;
n is 0 or 1; and
p is 0 or 1.

In the formulas, a line traversing a ring and bonded to a substituent group (e.g., an R group) means that the substituent may be bound in place of hydrogen to any ring atom where the valency of the atom allows. For example, the R group in formula (I) may be bound to any carbon atom of the phenyl ring traversed by the line, except for the carbon atom bound to the rest of the molecule through the methylene group and the carbon atom bound to the $R^4$ substituent. Where the line traverses a ring in a bicyclic ring system (fused, bridged, or spiro), the substituent group may be bound to any ring atom in any ring of the system.

As used herein, the term "compound(s) disclosed herein" refers to compound(s) of formula (I), and subformulae thereof. The terms "compound" and "pharmaceutically acceptable salt" include the specified compounds and pharmaceutically acceptable salts in any form, including any solid form thereof (including any polymorphic form thereof), any solvate or hydrate form thereof, and any solution thereof.

As used herein, the term "$C_{1-4}$alkyl" refers to a straight or branched hydrocarbon chain radical group consisting solely of carbon and hydrogen atoms, containing no unsaturation, having from one to four carbon atoms, and which is attached to the rest of the molecule by a single bond. Examples of $C_{1-4}$alkyl groups include, but are not limited to, methyl, ethyl, n-propyl, n-butyl, 1-methylethyl (iso-propyl), 1-methylpropyl (sec-butyl), 2-methylpropyl (iso-butyl), 1,1-dimethylethyl (t-butyl), and the like. Analogous terms referring to alkyl groups having different numbers of carbon atoms (e.g., "$C_{1-6}$alkyl") refer to analogous alkyl groups having the specified numbers of carbon atoms.

As used herein, the term "—$C_{1-4}$alkyl-" refers to a straight or branched divalent hydrocarbon chain consisting solely of carbon and hydrogen atoms, containing no unsaturation, having from one to four carbon atoms, and which is attached to the rest of the molecule by single bonds. Examples of —$C_{1-4}$alkyl-groups include, but are not limited to, methylene, ethylene, n-propylene, n-butylene, 1-methylethylene, and the like. Analogous terms referring to groups having different numbers of carbon atoms (e.g., "—$C_{1-6}$alkyl-") refer to analogous groups having the specified numbers of carbon atoms.

As used herein, the term "$C_{1-4}$haloalkyl" refers to a $C_{1-4}$alkyl group, wherein one or more of the hydrogen atoms of the $C_{1-4}$alkyl group are replaced by a halo group. Examples of $C_{1-4}$haloalkyl include, but are not limited to, trifluoromethyl, 2,2,2-trifluoroethyl, 1,1-difluoroethyl, and the like. Analogous terms referring to haloalkyl groups having different numbers of carbon atoms (e.g., "$C_{1-6}$haloalkyl") refer to analogous haloalkyl groups having the specified numbers of carbon atoms.

As used herein, the term "—$C_{1-4}$alkyl-$NR_7R_8$" refers to a $C_{1-4}$alkyl group, wherein one or more of the hydrogen atoms (e.g., one hydrogen atom) of the $C_{1-4}$alkyl group is replaced by an $NR_7R_8$ group. Analogous terms referring to alkyl-$NR_7R_8$ groups having different numbers of carbon atoms (e.g., "—$C_{1-6}$alkyl-$NR_7R_8$") refer to analogous alkyl-$NR_7R_8$ groups having the specified numbers of carbon atoms.

As used herein, the term "halo" refers to bromo, chloro, fluoro or iodo.

As used herein, the term "$C_{1-4}$alkoxy" refers to a radical of the formula —$OR_a$ where $R_a$ is a $C_{1-4}$alkyl group. Examples of $C_{1-4}$alkoxy include, but are not limited to, methoxy, ethoxy, propoxy, isopropoxy, butoxy, isobutoxy, and the like. Analogous terms referring to alkoxy groups having different numbers of carbon atoms (e.g., "$C_{1-6}$alkoxy") refer to analogous alkoxy groups having the specified numbers of carbon atoms.

As used herein, the term "$C_{1-4}$haloalkoxy" refers to a $C_{1-4}$alkoxy group, wherein one or more of the hydrogen atoms of the $C_{1-4}$alkyl group are each independently replaced by a halo group. Examples of $C_{1-4}$haloalkoxy include, but are not limited to, trifluoromethoxy, 2,2,2-trifluoroethoxy, 1,1-difluoroethoxy, and the like. Analogous terms referring to haloalkoxy groups having different numbers of carbon atoms (e.g., "$C_{1-6}$haloalkoxy") refer to analogous haloalkoxy groups having the specified numbers of carbon atoms.

As used herein, the term "$C_{1-4}$hydroxyalkyl" refers to a $C_{1-4}$alkyl group, wherein one or more of the hydrogen atoms (e.g., one hydrogen atom) of the $C_{1-4}$alkyl group are each replaced by OH. Examples of $C_{1-4}$hydroxyalkyl include, but are not limited to, hydroxy-methyl, 2-hydroxy-ethyl, 2-hydroxy-propyl, 3-hydroxy-propyl, and the like. Analogous terms referring to hydroxyalkyl groups having different numbers of carbon atoms (e.g., "$C_{1-6}$hydroxyalkyl") refer to analogous hydroxyalkyl groups having the specified numbers of carbon atoms.

As used herein, the term "cycloalkyl" refers to a stable, non-aromatic, mono- or bicyclic (fused, bridged, or spiro) saturated hydrocarbon radical consisting solely of carbon and hydrogen atoms, having the specified number of carbon ring atoms, and which is attached to the rest of the molecule by a single bond. Examples of cycloalkyl groups include, but are not limited to, cyclopropyl, cyclobutyl, cyclopentyl, cyclohexyl, and the like.

As used herein, the term "carbocyclyl" refers to a stable, saturated or unsaturated, non-aromatic, mono- or bicyclic (fused, bridged, or spiro) ring radical having the specified number of ring carbon atoms. Examples of carbocyclyl groups include, but are not limited to, the cycloalkyl groups identified above, cyclobutenyl, cyclopentenyl, cyclohexenyl, and the like. Where additional substituent(s) on the carbocyclyl group are indicated (e.g., -(4-6 membered carbocyclyl)-$R^6$), one or more hydrogen atoms bound to the ring atom(s) are replaced by the substituent(s). The related term "carbocyclic ring" likewise refers to a stable, saturated or unsaturated, non-aromatic, mono- or bicyclic (fused, bridged, or spiro) ring having the specified number of ring carbon atoms.

As used herein, the term "heterocyclyl" refers to a stable, saturated or unsaturated, non-aromatic, mono- or bicyclic (fused, bridged, or spiro) ring radical having the specified number of ring atoms and comprising one or more heteroatoms individually selected from nitrogen, oxygen and sulfur. The heterocyclyl radical may be bonded via a carbon atom or heteroatom. Examples of heterocyclyl groups include, but are not limited to, azetidinyl, oxetanyl, pyrrolinyl, pyrrolidinyl, tetrahydrofuryl, tetrahydrothienyl, piperidyl, piperazinyl, tetrahydropyranyl, morpholinyl, perhydroazepinyl, tetrahydropyridinyl, tetrahydroazepinyl, octahydropyrrolopyrrolyl, and the like. Where additional substituent(s) on the heterocyclyl group are indicated (e.g., -(4-10 membered heterocyclyl)-$R^6$), one or more hydrogen atoms bound to the ring atom(s) are replaced by the substituent(s). The related term "heterocyclic ring" likewise refers to a stable, saturated or unsaturated, non-aromatic, mono- or bicyclic (fused, bridged, or spiro) ring having the specified number of ring atoms and comprising one or more heteroatoms individually selected from nitrogen, oxygen and sulfur.

As used herein, the term "aryl" refers to a stable, aromatic, mono- or bicyclic ring radical having the specified number of ring carbon atoms. Examples of aryl groups include, but are not limited to, phenyl, 1-naphthyl, 2-naphthyl, and the like. The related term "aryl ring" likewise refers to a stable, aromatic, mono- or bicyclic ring having the specified number of ring carbon atoms.

As used herein, the term "heteroaryl" refers to a stable, aromatic, mono- or bicyclic ring radical having the specified number of ring atoms and comprising one or more heteroatoms individually selected from nitrogen, oxygen and sulfur. The heteroaryl radical may be bonded via a carbon atom or heteroatom. Examples of heteroaryl groups include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl, pyridyl, quinolinyl, isoquinolinyl, indolyl, indazolyl, oxadiazolyl, benzothiazolyl, quinoxalinyl, and the like. Where additional substituent(s) on the heteroaryl group are indicated (e.g., -(5-10 membered heteroaryl)-$R^6$), one or more hydrogen atoms bound to the ring atom(s) are replaced by the substituent(s). The related term "heteroaryl ring" likewise refers to a stable, aromatic, mono- or bicyclic ring having the specified number of ring atoms and comprising one or more heteroatoms individually selected from nitrogen, oxygen and sulfur.

As used herein, the term "fused heterocyclyl-aryl" refers to a stable bicyclic ring radical having the specified number of ring atoms and comprising a heterocyclyl ring (as defined above) fused to an aryl ring (as defined above). The specified number of ring atoms refers to the total number of ring atoms in the heterocyclyl and aryl rings. The radical may be bonded via a carbon atom or heteroatom on either the heterocyclyl ring or the aryl ring. Examples of fused heterocyclyl-aryl groups include, but are not limited to, the following:

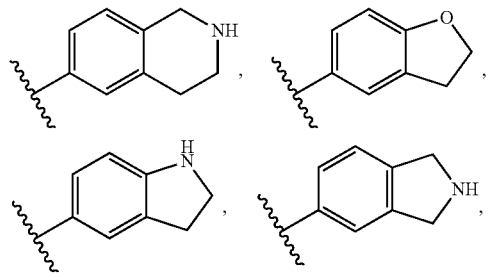

and the like. The related term "fused heterocyclyl-aryl ring" refers to a stable bicyclic ring having the specified number of ring atoms and comprising a heterocyclyl ring (as defined above) fused to an aryl ring (as defined above).

As used herein, the term "fused heterocyclyl-heteroaryl" refers to a stable bicyclic ring radical having the specified number of ring atoms and comprising a heterocyclyl ring (as defined above) fused to a heteroaryl ring (as defined above). The specified number of ring atoms refers to the total number of ring atoms in the heterocyclyl and heteroaryl rings. The radical may be bonded via a carbon atom or heteroatom on either the heterocyclyl ring or the heteroaryl ring. Examples of fused heterocyclyl-heteroaryl groups include, but are not limited to, the following:

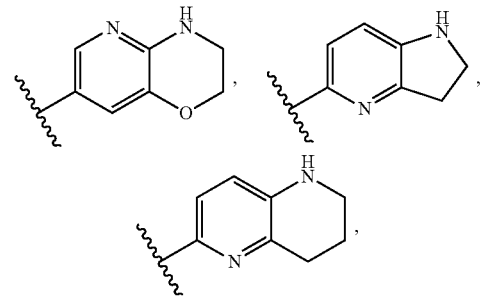

and the like. The related term "fused heterocyclyl-heteroaryl ring" refers to a stable bicyclic ring having the specified number of ring atoms and comprising a heterocyclyl ring (as defined above) fused to a heteroaryl ring (as defined above).

As used herein, the term "fused carbocyclyl-aryl" refers to a stable bicyclic ring radical having the specified number of ring atoms and comprising a carbocyclyl ring (as defined above) fused to an aryl ring (as defined above). The specified number of ring atoms refers to the total number of ring atoms in the carbocyclyl and aryl rings. The radical may be bonded via a carbon atom on either the carbocyclyl ring or the aryl ring. Examples of fused carbocyclyl-aryl groups include, but are not limited to, the following:

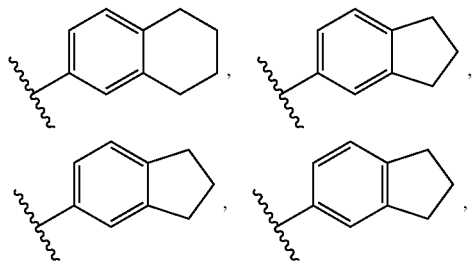

and the like. The related term "fused carbocyclyl-aryl ring" refers to a stable bicyclic ring having the specified number of ring atoms and comprising a carbocyclyl ring (as defined above) fused to an aryl ring (as defined above).

As used herein, the term "fused carbocyclyl-heteroaryl" refers to a stable bicyclic ring radical having the specified number of ring atoms and comprising a carbocyclyl ring (as defined above) fused to a heteroaryl ring (as defined above). The specified number of ring atoms refers to the total number of ring atoms in the carbocyclyl and heteroaryl rings. The radical may be bonded via a carbon atom on the carbocyclyl ring or a carbon atom or heteroatom on the heteroaryl ring. Examples of fused carbocyclyl-heteroaryl groups include, but are not limited to, the following:

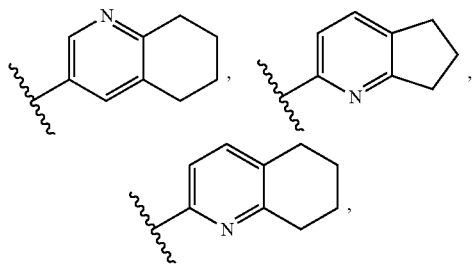

and the like. The related term "fused carbocyclyl-heteroaryl ring" refers to a stable bicyclic ring having the specified number of ring atoms and comprising a carbocyclyl ring (as defined above) fused to a heteroaryl ring (as defined above).

As used herein, the term "optionally substituted" means that the group in question may be substituted, for example, with the specified number of identified groups, but that such substitution is not required. For example, a group that is "optionally substituted with 1-3 $C_{1-4}$alkyl groups" may be unsubstituted or may be substituted with 1, 2, or 3 $C_{1-4}$ alkyl groups.

Various embodiments of the disclosure are described herein. It will be recognized that features specified in each embodiment may be combined with other specified features, including as indicated in the enumerated embodiments below, to provide further embodiments of the present disclosure.

It is understood that in the following embodiments, combinations of substituents and/or variables of the depicted formulae are permissible only if such combinations result in stable compounds.

Embodiment 1

A compound of formula (I) or a pharmaceutically acceptable salt thereof:

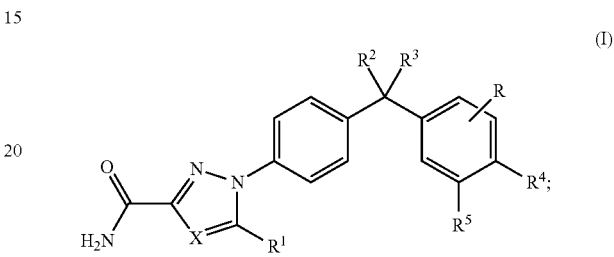

wherein:
X is CH or N;
R is H, halo, —OH, $C_{1-4}$alkyl, $C_{1-4}$alkoxy, $C_{1-4}$haloalkyl or $C_{1-4}$ haloalkoxy;
$R^1$ is H, $C_{1-4}$alkyl, $C_{1-4}$haloalkyl, or 3-6 membered cycloalkyl;
$R^2$ and $R^3$ are each, independently, H or $C_{1-4}$alkyl;
$R^4$ is halo, —C≡C—$R^6$, —$C_6H_4$—$R^6$, -(4-10 membered heterocyclyl)-$R^6$, a 5-10 membered heteroaryl optionally substituted with 1-3 $R^6$ groups, -(4-10 membered carbocyclyl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups;
$R^5$ is H, or $R^4$ and $R^5$ together with the carbon atoms to which they are attached form a 5-12 membered carbocyclic, heterocyclic, aryl, heteroaryl, fused heterocyclyl-aryl, fused heterocyclyl-heteroaryl, fused carbocyclyl-aryl, or fused carbocyclyl-heteroaryl ring, wherein said carbocyclic, heterocyclic, aryl, heteroaryl, fused heterocyclyl-aryl, fused heterocyclyl-heteroaryl, fused carbocyclyl-aryl, or fused carbocyclyl-heteroaryl ring is optionally substituted with 1-3 $C_{1-4}$alkyl groups;
$R^6$ is —$(CH_2)_m$—$(CO)_n$—$(CH_2)_p$—$R^{6a}$, —O—$R^{6a}$, —$(CH_2)_m$—$(CO)_n$—$(CH_2)_p$—$R^{6b}$, —O—$R^{6b}$, —$(CH_2)_m$—$(CO)_n$—$(CH_2)_p$—$R^{6c}$, —O—$R^{6c}$, —$(CH_2)_m$—$(CO)_n$—$(CH_2)_p$—$R^{6d}$, or —O—$R^{6d}$;
$R^{6a}$ is H, —OH, —$NR^7R^8$, —CN, oxo, $C_{1-4}$alkyl, $C_{1-4}$haloalkyl, $C_{1-4}$hydroxyalkyl, —CH($NR^7R^8$)—$C_{1-3}$haloalkyl, —CH($NR^7R^8$)—$C_{1-3}$alkyl, —C($CH_3$)($NR^7R^8$)—$C_{1-3}$alkyl, —$SO_2C_{1-4}$alkyl, —$SO_2C_{1-4}$hydroxyalkyl, or —$SO_2NR^7R^8$;
$R^{6b}$ is a 4-10 membered heterocyclyl optionally substituted with 1-3 substituents independently selected from a group consisting of halo, —OH, —$NR^7R^8$, $C_{1-4}$alkyl, —$C_{1-4}$ haloalkyl, —$C_{1-4}$hydroxyalkyl, —$C_{1-4}$alkyl-$NR^7R^8$, —$SO_2C_{1-4}$alkyl, and 4-6 membered heterocyclyl;
$R^6$ is a 5-10 membered heteroaryl optionally substituted with 1-3 substituents independently selected from a group consisting of —$NR^7R^8$, $C_{1-4}$alkyl, —$C_{1-4}$hydroxyalkyl, and —$C_{1-4}$alkyl-$NR^7R^8$;
$R^{6d}$ is a 4-10 membered carbocyclyl optionally substituted with 1-3 substituents independently selected from a group consisting of halo, —OH, —NR⁷R⁸, $C_{1-4}$alkyl, —$C_{1-4}$ haloalkyl, —$C_{1-4}$hydroxyalkyl, —$C_{1-4}$alkyl-NR⁷R⁸, —SO₂$C_{1-4}$alkyl, and 4-6 membered heterocyclyl;

R⁷ and R⁸ are each, independently, selected from a group consisting of H, $C_{1-4}$alkyl, $C_{1-4}$hydroxyalkyl, a 4-6 membered heterocyclyl, and a 4-6 membered cycloalkyl;

m is 0 or 1;
n is 0 or 1; and
p is 0 or 1.

Embodiment 2

A compound of formula (I) or a pharmaceutically acceptable salt thereof:

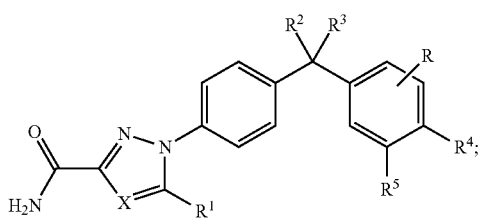

(I)

wherein:
X is CH or N;
R is H, halo, —OH, $C_{1-4}$alkyl, $C_{1-4}$alkoxy, $C_{1-4}$haloalkyl or $C_{1-4}$ haloalkoxy;
R¹ is H, $C_{1-4}$alkyl, $C_{1-4}$haloalkyl, or 3-6 membered cycloalkyl;
R² and R³ are each, independently, H or $C_{1-4}$alkyl;
R⁴ is halo, —C₆H₄—R⁶, -(4-10 membered heterocyclyl)-R⁶, -(5-10 membered heteroaryl)-R⁶, -(4-6 membered carbocyclyl)-R⁶, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups;
R⁵ is H, or R⁴ and R⁵ together with the carbon atoms to which they are attached form a 5-12 membered carbocyclic, heterocyclic, aryl, heteroaryl, fused heterocyclyl-aryl, fused heterocyclyl-heteroaryl, fused carbocyclyl-aryl, or fused carbocyclyl-heteroaryl ring, wherein said carbocyclic, heterocyclic, aryl, heteroaryl, fused heterocyclyl-aryl, fused heterocyclyl-heteroaryl, fused carbocyclyl-aryl, or fused carbocyclyl-heteroaryl ring is optionally substituted with 1-3 $C_{1-4}$alkyl groups;
R⁶ is —(CH₂)$_m$—(CO)$_n$—(CH₂)$_p$—R⁶ᵃ, —(CH₂)$_m$—(CO)$_n$—(CH₂)$_p$—R⁶ᵇ, or —(CH₂)$_m$—(CO)$_n$—(CH₂)$_p$—R⁶ᶜ;
R⁶ᵃ is H, —OH, —NR⁷R⁸, —CN, oxo, $C_{1-4}$alkyl, $C_{1-4}$haloalkyl, —CH(NR⁷R⁸)—$C_{1-3}$haloalkyl, —CH(NR⁷R⁸)—$C_{1-3}$alkyl, —SO₂$C_{1-4}$alkyl, or —SO₂NR⁷R⁸;
R⁶ᵇ is a 4-10 membered heterocyclyl optionally substituted with 1-3 substituents independently selected from a group consisting of —NR⁷R⁸, $C_{1-4}$alkyl, —$C_{1-4}$hydroxyalkyl, and —$C_{1-4}$alkyl-NR⁷R⁸;
R⁶ is a 5-10 membered heteroaryl optionally substituted with 1-3 substituents independently selected from a group consisting of —NR⁷R⁸, $C_{1-4}$alkyl, —$C_{1-4}$hydroxyalkyl, and —$C_{1-4}$alkyl-NR⁷R⁸;
R⁷ and R⁸ are each, independently, selected from a group consisting of H, $C_{1-4}$alkyl, $C_{1-4}$hydroxyalkyl, a 4-6 membered heterocyclyl, and a 4-6 membered cycloalkyl;
m is 0 or 1;
n is 0 or 1; and
p is 0 or 1.

Embodiment 3

A compound according to embodiment 1 or 2, wherein the compound is of formula (I-A):

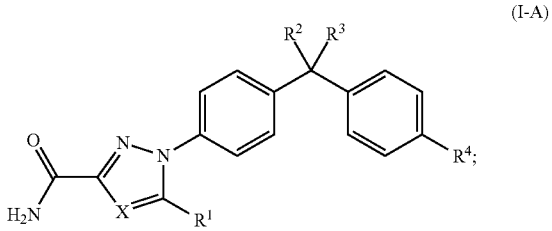

(I-A)

or a pharmaceutically acceptable salt thereof.

Embodiment 4

A compound according to embodiment 1 or 2, wherein the compound is of formula (I-B):

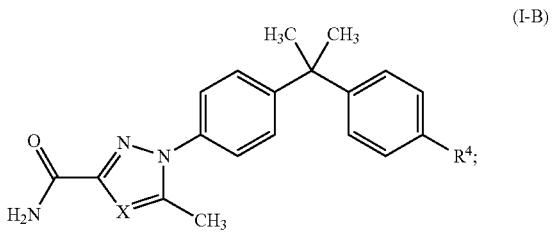

(I-B)

or a pharmaceutically acceptable salt thereof.

Embodiment 5

A compound according to embodiment 1 or 2, wherein the compound is of formula (I-C):

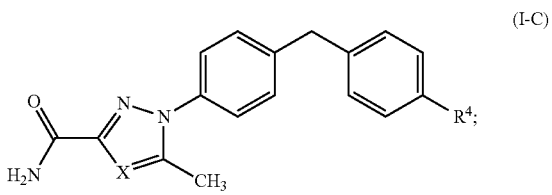

(I-C)

or a pharmaceutically acceptable salt thereof.

Embodiment 6

A compound according to any one of the preceding embodiments, or a pharmaceutically acceptable salt thereof, wherein X is CH.

Embodiment 7

A compound according to any one of the preceding embodiments, or a pharmaceutically acceptable salt thereof, wherein X is N.

Embodiment 8

A compound according to any one of the preceding embodiments, or a pharmaceutically acceptable salt thereof, wherein R is H, halo, $C_{1-4}$alkyl, or $C_{1-4}$haloalkyl.

Embodiment 9

A compound according to any one of the preceding embodiments, or a pharmaceutically acceptable salt thereof, wherein R is H or $C_{1-4}$alkyl.

Embodiment 10

A compound according to any one of the preceding embodiments, or a pharmaceutically acceptable salt thereof, wherein R is H.

Embodiment 11

A compound according to any one of the preceding embodiments, or a pharmaceutically acceptable salt thereof, wherein $R^1$ is H, $C_{1-4}$alkyl, or $C_{1-4}$haloalkyl.

Embodiment 12

A compound according to any one of the preceding embodiments, or a pharmaceutically acceptable salt thereof, wherein $R^1$ is H or $C_{1-4}$alkyl.

Embodiment 13

A compound according to any one of the preceding embodiments, or a pharmaceutically acceptable salt thereof, wherein $R^1$ is $C_{1-4}$alkyl or $C_{1-4}$haloalkyl.

Embodiment 14

A compound according to any one of the preceding embodiments, or a pharmaceutically acceptable salt thereof, wherein $R^1$ is $C_{1-4}$alkyl.

Embodiment 15

A compound according to any one of the preceding embodiments, or a pharmaceutically acceptable salt thereof, wherein $R^1$ is $CH_3$.

Embodiment 16

A compound according to any one of the preceding embodiments, or a pharmaceutically acceptable salt thereof, wherein $R^1$ is H.

Embodiment 17

A compound according to any one of the preceding embodiments, or a pharmaceutically acceptable salt thereof, wherein $R^2$ is H.

Embodiment 18

A compound according to any one of the preceding embodiments, or a pharmaceutically acceptable salt thereof, wherein $R^2$ is $C_{1-4}$alkyl.

Embodiment 19

A compound according to any one of the preceding embodiments, or a pharmaceutically acceptable salt thereof, wherein $R^2$ is H or $CH_3$.

Embodiment 20

A compound according to any one of the preceding embodiments, or a pharmaceutically acceptable salt thereof, wherein $R^2$ is $CH_3$.

Embodiment 21

A compound according to any one of the preceding embodiments, or a pharmaceutically acceptable salt thereof, wherein $R^3$ is H.

Embodiment 22

A compound according to any one of the preceding embodiments, or a pharmaceutically acceptable salt thereof, wherein $R^3$ is $C_{1-4}$alkyl.

Embodiment 23

A compound according to any one of the preceding embodiments, or a pharmaceutically acceptable salt thereof, wherein $R^3$ is H or $CH_3$.

Embodiment 24

A compound according to any one of the preceding embodiments, or a pharmaceutically acceptable salt thereof, wherein $R^3$ is $CH_3$.

Embodiment 25

A compound according to any one of the preceding embodiments, or a pharmaceutically acceptable salt thereof, wherein $R^4$ is —$C_6H_4$—$R^6$, -(4-10 membered heterocyclyl)-$R^6$, -(5-10 membered heteroaryl)-$R^6$, -(4-6 membered carbocyclyl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups.

Embodiment 26

A compound according to any one of the preceding embodiments, or a pharmaceutically acceptable salt thereof, wherein $R^4$ is halo, -(4-10 membered heterocyclyl)-$R^6$, -(5-10 membered heteroaryl)-$R^6$, -(4-6 membered carbocyclyl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups.

Embodiment 27

A compound according to any one of the preceding embodiments, or a pharmaceutically acceptable salt thereof, wherein $R^4$ is halo, —$C_6H_4$—$R^6$, -(5-10 membered heteroaryl)-$R^6$, -(4-6 membered carbocyclyl)-$R^6$, a 6-10 membered fused heterocyclyl-aryl optionally substituted with 1-3

$C_{1-4}$alkyl groups, or a 6-10 membered fused heterocyclyl-heteroaryl optionally substituted with 1-3 $C_{1-4}$alkyl groups.

Embodiment 28

A compound according to any one of the preceding embodiments, or a pharmaceutically acceptable salt thereof, wherein $R^4$ is halo, —$C_6H_4$—$R^6$, -(4-10 membered heterocyclyl)-$R^6$, -(4-6 membered carbocyclyl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups.

Embodiment 29

A compound according to any one of the preceding embodiments, or a pharmaceutically acceptable salt thereof, wherein $R^4$ is halo, —$C_6H_4$—$R^6$, -(4-10 membered heterocyclyl)-$R^6$, -(5-10 membered heteroaryl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups.

Embodiment 30

A compound according to any one of the preceding embodiments, or a pharmaceutically acceptable salt thereof, wherein $R^4$ is halo, —$C_6H_4$—$R^6$, -(4-10 membered heterocyclyl)-$R^6$, -(5-10 membered heteroaryl)-$R^6$, -(4-6 membered carbocyclyl)-$R^6$, or a 6-10 membered fused heterocyclyl-heteroaryl optionally substituted with 1-3 $C_{1-4}$alkyl groups.

Embodiment 31

A compound according to any one of the preceding embodiments, or a pharmaceutically acceptable salt thereof, wherein $R^4$ is halo, —$C_6H_4$—$R^6$, -(4-10 membered heterocyclyl)-$R^6$, -(5-10 membered heteroaryl)-$R^6$, -(4-6 membered carbocyclyl)-$R^6$, or a 6-10 membered fused heterocyclyl-aryl optionally substituted with 1-3 $C_{1-4}$alkyl groups.

Embodiment 32

A compound according to any one of the preceding embodiments, or a pharmaceutically acceptable salt thereof, wherein $R^4$ is —C≡C—$R^6$, —$C_6H_4$—$R^6$, -(4-10 membered heterocyclyl)-$R^6$, a 5-10 membered heteroaryl optionally substituted with 1-3 $R^6$ groups, -(4-10 membered carbocyclyl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups.

Embodiment 33

A compound according to any one of the preceding embodiments, or a pharmaceutically acceptable salt thereof, wherein $R^4$ is halo, —$C_6H_4$—$R^6$, -(4-10 membered heterocyclyl)-$R^6$, a 5-10 membered heteroaryl optionally substituted with 1-3 $R^6$ groups, -(4-10 membered carbocyclyl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups.

Embodiment 34

A compound according to any one of the preceding embodiments, or a pharmaceutically acceptable salt thereof, wherein $R^4$ is halo, —C≡C—$R^6$, -(4-10 membered heterocyclyl)-$R^6$, a 5-10 membered heteroaryl optionally substituted with 1-3 $R^6$ groups, -(4-10 membered carbocyclyl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups.

Embodiment 35

A compound according to any one of the preceding embodiments, or a pharmaceutically acceptable salt thereof, wherein $R^4$ is halo, —C≡C—$R^6$, —$C_6H_4$—$R^6$, a 5-10 membered heteroaryl optionally substituted with 1-3 $R^6$ groups, -(4-10 membered carbocyclyl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups.

Embodiment 36

A compound according to any one of the preceding embodiments, or a pharmaceutically acceptable salt thereof, wherein $R^4$ is halo, —C≡C—$R^6$, —$C_6H_4$—$R^6$, -(4-10 membered heterocyclyl)-$R^6$, -(4-10 membered carbocyclyl)-$R^6$, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups.

Embodiment 37

A compound according to any one of the preceding embodiments, or a pharmaceutically acceptable salt thereof, wherein $R^4$ is halo, —C≡C—$R^6$, —$C_6H_4$—$R^6$, -(4-10 membered heterocyclyl)-$R^6$, a 5-10 membered heteroaryl optionally substituted with 1-3 $R^6$ groups, a 6-10 membered fused heterocyclyl-aryl optionally substituted with 1-3 $C_{1-4}$alkyl groups, or a 6-10 membered fused heterocyclyl-heteroaryl optionally substituted with 1-3 $C_{1-4}$alkyl groups.

Embodiment 38

A compound according to any one of the preceding embodiments, or a pharmaceutically acceptable salt thereof, wherein $R^4$ is halo, —C≡C—$R^6$, —$C_6H_4$—$R^6$, -(4-10 membered heterocyclyl)-$R^6$, a 5-10 membered heteroaryl optionally substituted with 1-3 $R^6$ groups, -(4-10 membered carbocyclyl)-$R^6$, or a 6-10 membered fused heterocyclyl-heteroaryl optionally substituted with 1-3 $C_{1-4}$alkyl groups.

Embodiment 39

A compound according to any one of the preceding embodiments, or a pharmaceutically acceptable salt thereof, wherein $R^4$ is halo, —C≡C—$R^6$, —$C_6H_4$—$R^6$, -(4-10 membered heterocyclyl)-$R^6$, a 5-10 membered heteroaryl optionally substituted with 1-3 $R^6$ groups, -(4-10 membered carbocyclyl)-$R^6$, or a 6-10 membered fused heterocyclyl-aryl optionally substituted with 1-3 $C_{1-4}$alkyl groups.

Embodiment 40

A compound according to any one of the preceding embodiments, or a pharmaceutically acceptable salt thereof, wherein $R^4$ is halo.

Embodiment 41

A compound according to any one of the preceding embodiments, or a pharmaceutically acceptable salt thereof, wherein $R^4$ is —$C_6H_4$—$R^6$.

Embodiment 42

A compound according to any one of the preceding embodiments, or a pharmaceutically acceptable salt thereof, wherein $R^4$ is -(4-10 membered heterocyclyl)-$R^6$.

Embodiment 43

A compound according to any one of the preceding embodiments, or a pharmaceutically acceptable salt thereof, wherein $R^4$ is -(5-10 membered heteroaryl)-$R^6$.

Embodiment 44

A compound according to any one of the preceding embodiments, or a pharmaceutically acceptable salt thereof, wherein $R^4$ is -(4-6 membered carbocyclyl)-$R^6$.

Embodiment 45

A compound according to any one of the preceding embodiments, or a pharmaceutically acceptable salt thereof, wherein $R^4$ is a 6-10 membered fused heterocyclyl-aryl optionally substituted with 1-3 $C_{1-4}$alkyl groups.

Embodiment 46

A compound according to any one of the preceding embodiments, or a pharmaceutically acceptable salt thereof, wherein $R^4$ is a 6-10 membered fused heterocyclyl-heteroaryl optionally substituted with 1-3 $C_{1-4}$alkyl groups.

Embodiment 47

A compound according to any one of the preceding embodiments, or a pharmaceutically acceptable salt thereof, wherein $R^4$ is —C≡C—$R^6$.

Embodiment 48

A compound according to any one of the preceding embodiments, or a pharmaceutically acceptable salt thereof, wherein $R^4$ is a 5-10 membered heteroaryl optionally substituted with 1-3 $R^6$ groups.

Embodiment 49

A compound according to any one of the preceding embodiments, or a pharmaceutically acceptable salt thereof, wherein $R^4$ is -(4-10 membered carbocyclyl)-$R^6$.

Embodiment 50

A compound according to any one of the preceding embodiments, or a pharmaceutically acceptable salt thereof, wherein $R^4$ is selected from a group consisting of:

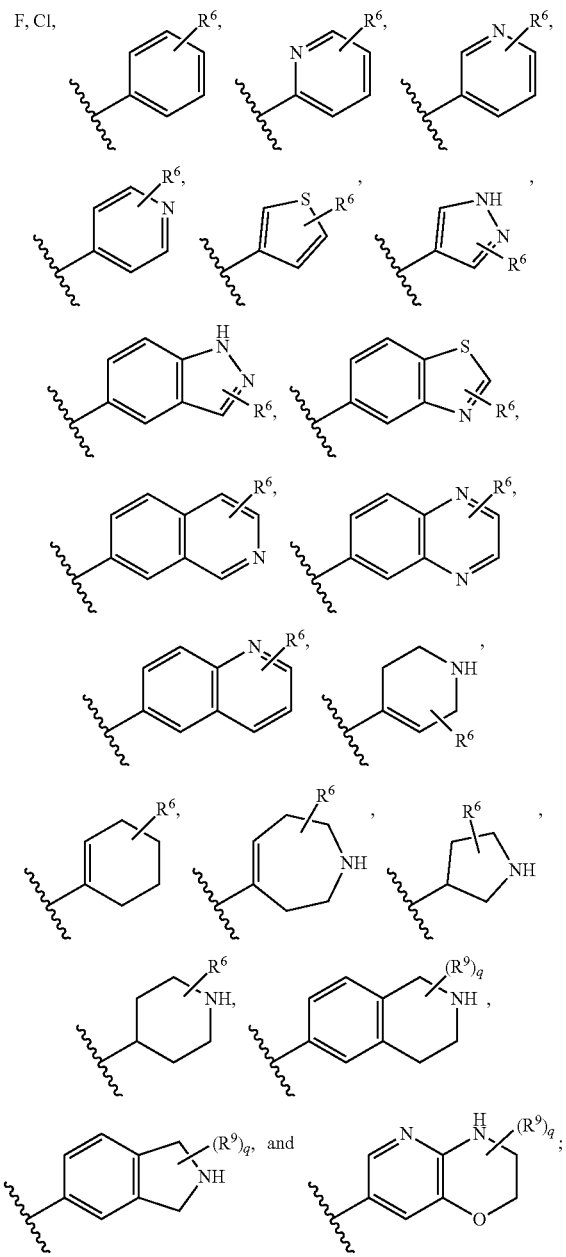

$R^9$ is $C_{1-4}$alkyl; and q is 0, 1, 2, or 3.

Embodiment 51

A compound according to any one of the preceding embodiments, or a pharmaceutically acceptable salt thereof, wherein $R^4$ is selected from a group consisting of:

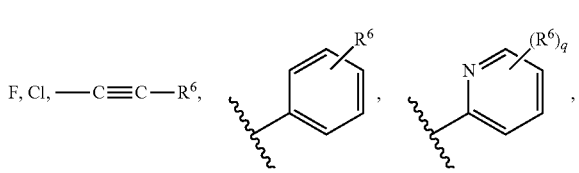

-continued

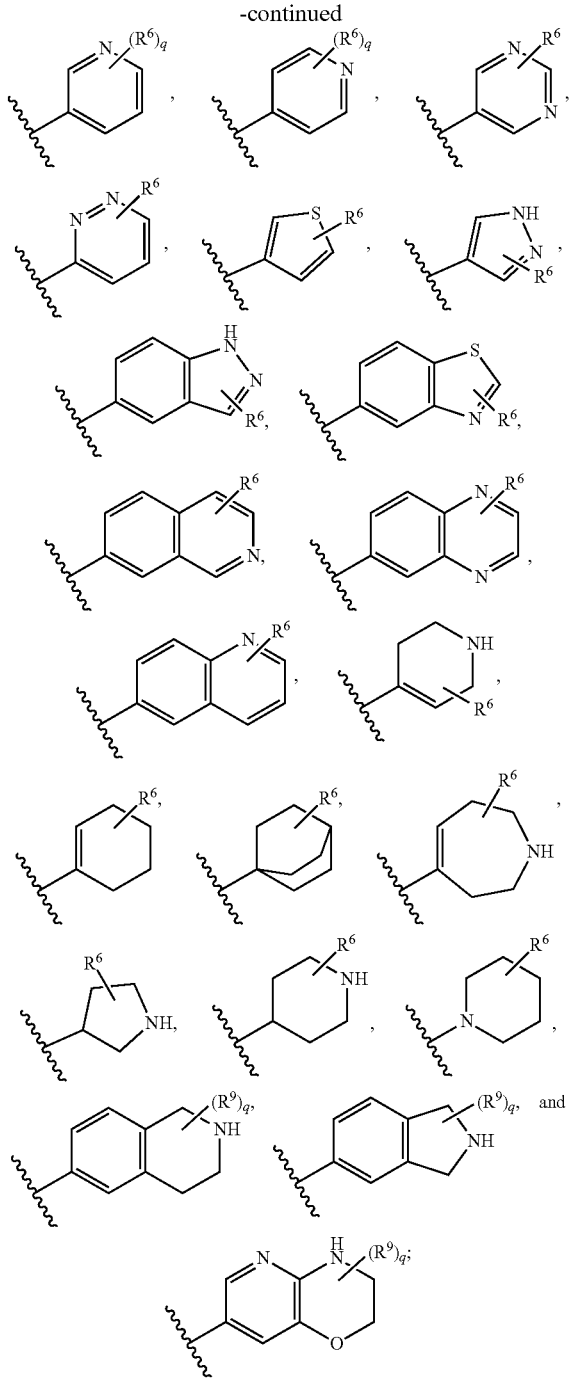

and $R^9$ is $C_{1-4}$alkyl; and
q is 0, 1, 2, or 3.

Embodiment 52

A compound according to any one of the preceding embodiments, or a pharmaceutically acceptable salt thereof, wherein $R^4$ is F or Cl.

Embodiment 53

A compound according to any one of the preceding embodiments, or a pharmaceutically acceptable salt thereof, wherein $R^4$ is F.

Embodiment 54

A compound according to any one of the preceding embodiments, or a pharmaceutically acceptable salt thereof, wherein $R^4$ is Cl.

Embodiment 55

A compound according to any one of the preceding embodiments, or a pharmaceutically acceptable salt thereof, wherein $R^4$ is selected from a group consisting of:

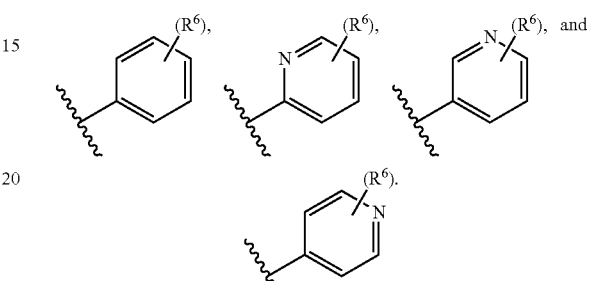

Embodiment 56

A compound according to any one of the preceding embodiments, or a pharmaceutically acceptable salt thereof, wherein $R^4$ is selected from a group consisting of:

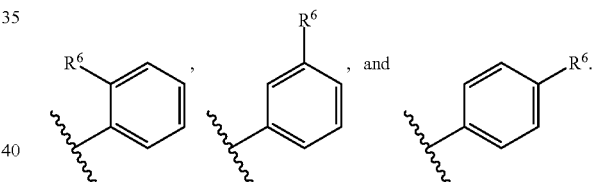

Embodiment 56 may also be described as a compound according to any one of the preceding embodiments, or a pharmaceutically acceptable salt thereof, wherein $R^4$ is $-C_6H_4-R^6$.

Embodiment 57

A compound according to any one of the preceding embodiments, or a pharmaceutically acceptable salt thereof, wherein $R^4$ is

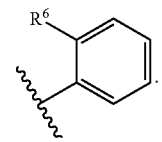

Embodiment 58

A compound according to any one of the preceding embodiments, or a pharmaceutically acceptable salt thereof, wherein $R^4$ is

21

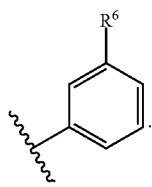

Embodiment 59

A compound according to any one of the preceding embodiments, or a pharmaceutically acceptable salt thereof, wherein $R^4$ is

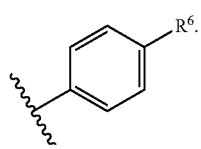

Embodiment 60

A compound according to any one of the preceding embodiments, or a pharmaceutically acceptable salt thereof, wherein $R^4$ is selected from a group consisting of:

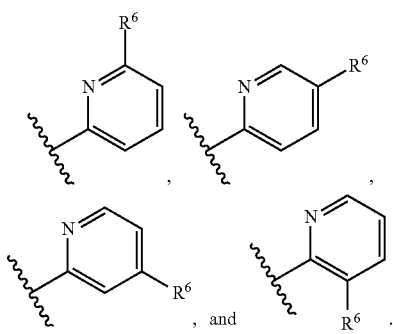

Embodiment 61

A compound according to any one of the preceding embodiments, or a pharmaceutically acceptable salt thereof, wherein $R^4$ is

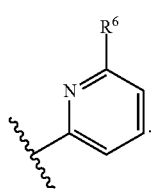

Embodiment 62

A compound according to any one of the preceding embodiments, or a pharmaceutically acceptable salt thereof, wherein $R^4$ is

22

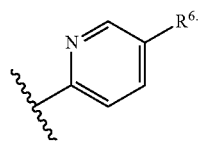

Embodiment 63

A compound according to any one of the preceding embodiments, or a pharmaceutically acceptable salt thereof, wherein $R^4$ is

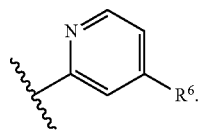

Embodiment 64

A compound according to any one of the preceding embodiments, or a pharmaceutically acceptable salt thereof, wherein $R^4$ is

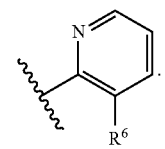

Embodiment 65

A compound according to any one of the preceding embodiments, or a pharmaceutically acceptable salt thereof, wherein $R^4$ is selected from a group consisting of:

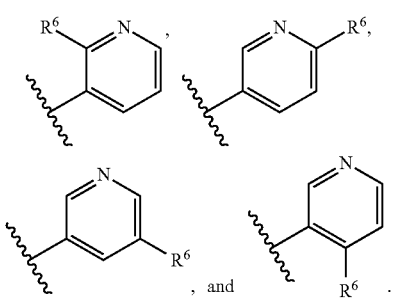

Embodiment 66

A compound according to any one of the preceding embodiments, or a pharmaceutically acceptable salt thereof, wherein $R^4$ is

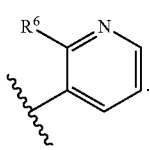

Embodiment 67

A compound according to any one of the preceding embodiments, or a pharmaceutically acceptable salt thereof, wherein $R^4$ is

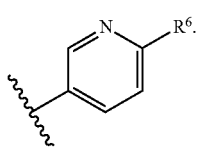

Embodiment 68

A compound according to any one of the preceding embodiments, or a pharmaceutically acceptable salt thereof, wherein $R^4$ is

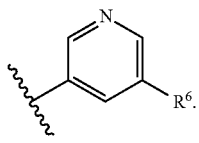

Embodiment 69

A compound according to any one of the preceding embodiments, or a pharmaceutically acceptable salt thereof, wherein $R^4$ is

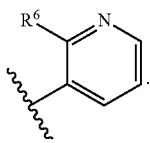

Embodiment 70

A compound according to any one of the preceding embodiments, or a pharmaceutically acceptable salt thereof, wherein $R^4$ is selected from a group consisting of:

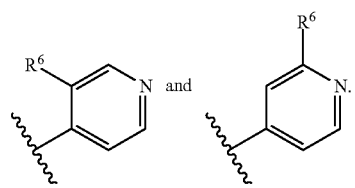

Embodiment 71

A compound according to any one of the preceding embodiments, or a pharmaceutically acceptable salt thereof, wherein $R^4$ is

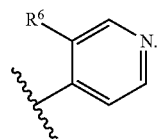

Embodiment 72

A compound according to any one of the preceding embodiments, or a pharmaceutically acceptable salt thereof, wherein $R^4$ is

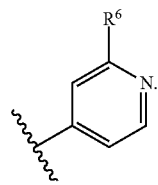

Embodiment 73

A compound according to any one of the preceding embodiments, or a pharmaceutically acceptable salt thereof, wherein $R^4$ is selected from a group consisting of:

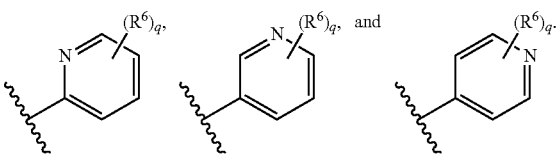

Embodiment 74

A compound according to any one of the preceding embodiments, or a pharmaceutically acceptable salt thereof, wherein $R^4$ is selected from a group consisting of:

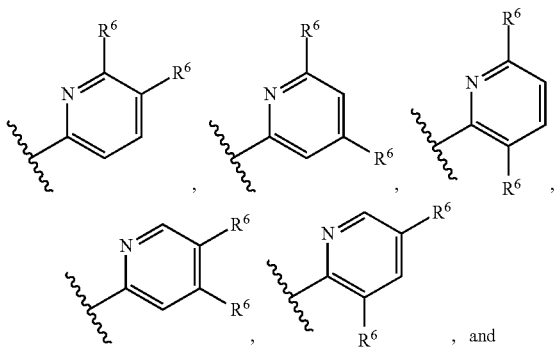

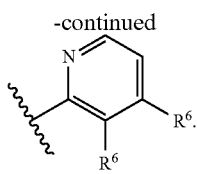

Embodiment 75

A compound according to any one of the preceding embodiments, or a pharmaceutically acceptable salt thereof, wherein $R^4$ is

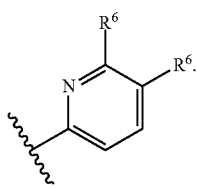

Embodiment 76

A compound according to any one of the preceding embodiments, or a pharmaceutically acceptable salt thereof, wherein $R^4$ is

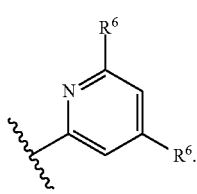

Embodiment 77

A compound according to any one of the preceding embodiments, or a pharmaceutically acceptable salt thereof, wherein $R^4$ is

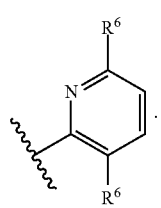

Embodiment 78

A compound according to any one of the preceding embodiments, or a pharmaceutically acceptable salt thereof, wherein $R^4$ is

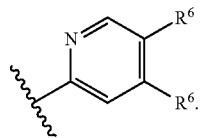

Embodiment 79

A compound according to any one of the preceding embodiments, or a pharmaceutically acceptable salt thereof, wherein $R^4$ is

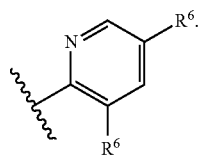

Embodiment 80

A compound according to any one of the preceding embodiments, or a pharmaceutically acceptable salt thereof, wherein $R^4$ is

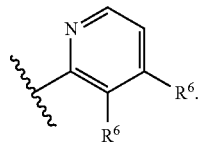

Embodiment 81

A compound according to any one of the preceding embodiments, or a pharmaceutically acceptable salt thereof, wherein $R^4$ is selected from a group consisting of:

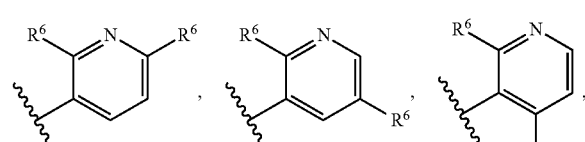

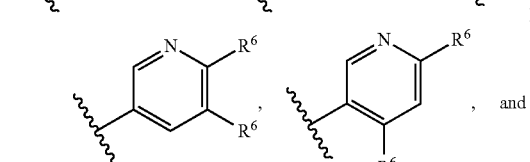

, and

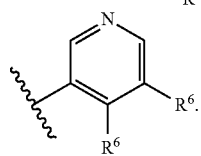

Embodiment 82

A compound according to any one of the preceding embodiments, or a pharmaceutically acceptable salt thereof, wherein $R^4$ is

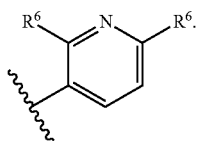

Embodiment 83

A compound according to any one of the preceding embodiments, or a pharmaceutically acceptable salt thereof, wherein $R^4$ is

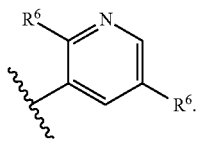

Embodiment 84

A compound according to any one of the preceding embodiments, or a pharmaceutically acceptable salt thereof, wherein $R^4$ is

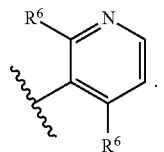

Embodiment 85

A compound according to any one of the preceding embodiments, or a pharmaceutically acceptable salt thereof, wherein $R^4$ is

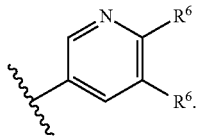

Embodiment 86

A compound according to any one of the preceding embodiments, or a pharmaceutically acceptable salt thereof, wherein $R^4$ is

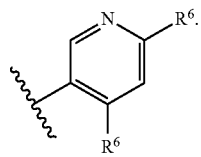

Embodiment 87

A compound according to any one of the preceding embodiments, or a pharmaceutically acceptable salt thereof, wherein $R^4$ is

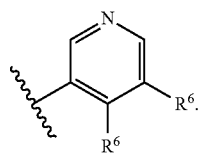

Embodiment 88

A compound according to any one of the preceding embodiments, or a pharmaceutically acceptable salt thereof, wherein $R^4$ is selected from a group consisting of:

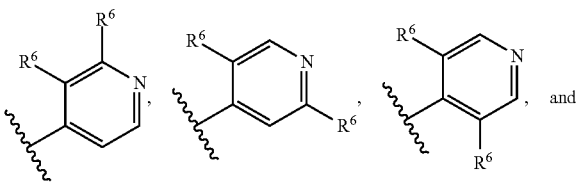

Embodiment 89

A compound according to any one of the preceding embodiments, or a pharmaceutically acceptable salt thereof, wherein $R^4$ is

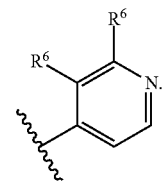

Embodiment 90

A compound according to any one of the preceding embodiments, or a pharmaceutically acceptable salt thereof, wherein $R^4$ is

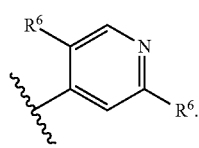

Embodiment 91

A compound according to any one of the preceding embodiments, or a pharmaceutically acceptable salt thereof, wherein $R^4$ is

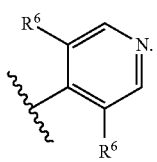

Embodiment 92

A compound according to any one of the preceding embodiments, or a pharmaceutically acceptable salt thereof, wherein $R^4$ is

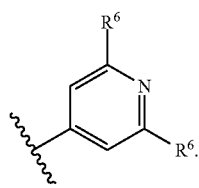

Embodiment 93

A compound according to any one of the preceding embodiments, or a pharmaceutically acceptable salt thereof, wherein $R^4$ is selected from a group consisting of:

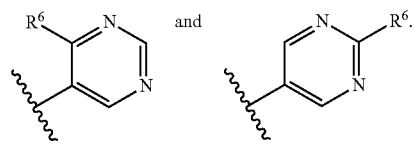

Embodiment 94

A compound according to any one of the preceding embodiments, or a pharmaceutically acceptable salt thereof, wherein $R^4$ is

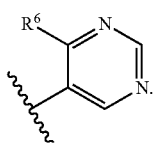

Embodiment 95

A compound according to any one of the preceding embodiments, or a pharmaceutically acceptable salt thereof, wherein $R^4$ is

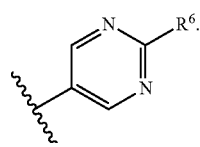

Embodiment 96

A compound according to any one of the preceding embodiments, or a pharmaceutically acceptable salt thereof, wherein $R^4$ is selected from a group consisting of:

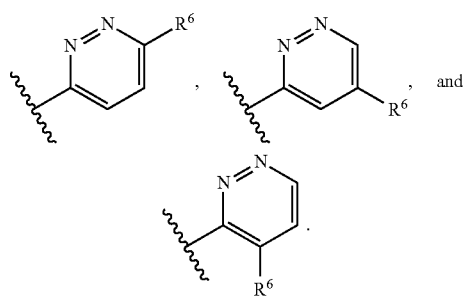

Embodiment 97

A compound according to any one of the preceding embodiments, or a pharmaceutically acceptable salt thereof, wherein $R^4$ is

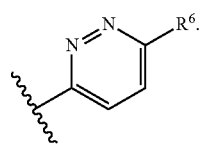

Embodiment 98

A compound according to any one of the preceding embodiments, or a pharmaceutically acceptable salt thereof, wherein $R^4$ is

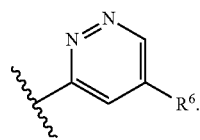

Embodiment 99

A compound according to any one of the preceding embodiments, or a pharmaceutically acceptable salt thereof, wherein $R^4$ is

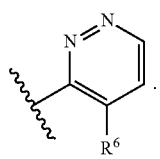

Embodiment 100

A compound according to any one of the preceding embodiments, or a pharmaceutically acceptable salt thereof, wherein $R^4$ is selected from a group consisting of:

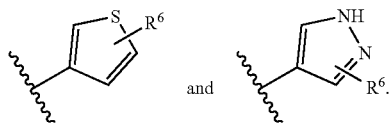

Embodiment 101

A compound according to any one of the preceding embodiments, or a pharmaceutically acceptable salt thereof, wherein $R^4$ is selected from a group consisting of:

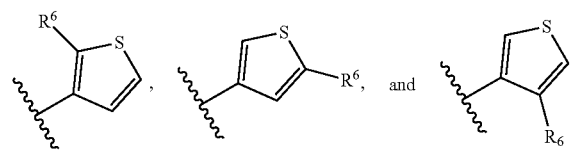

Embodiment 102

A compound according to any one of the preceding embodiments, or a pharmaceutically acceptable salt thereof, wherein $R^4$ is

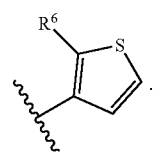

Embodiment 103

A compound according to any one of the preceding embodiments, or a pharmaceutically acceptable salt thereof, wherein $R^4$ is

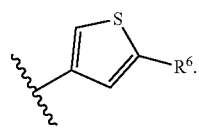

Embodiment 104

A compound according to any one of the preceding embodiments, or a pharmaceutically acceptable salt thereof, wherein $R^4$ is

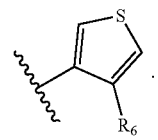

Embodiment 105

A compound according to any one of the preceding embodiments, or a pharmaceutically acceptable salt thereof, wherein $R^4$ is selected from a group consisting of:

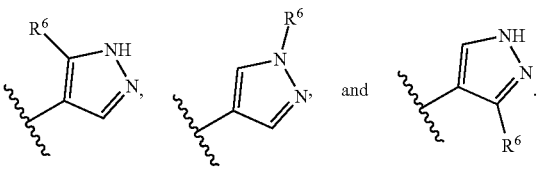

Embodiment 106

A compound according to any one of the preceding embodiments, or a pharmaceutically acceptable salt thereof, wherein $R^4$ is

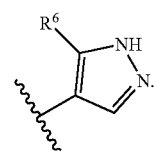

Embodiment 107

A compound according to any one of the preceding embodiments, or a pharmaceutically acceptable salt thereof, wherein $R^4$ is

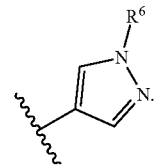

Embodiment 108

A compound according to any one of the preceding embodiments, or a pharmaceutically acceptable salt thereof, wherein $R^4$ is

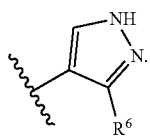

Embodiment 109

A compound according to any one of the preceding embodiments, or a pharmaceutically acceptable salt thereof, wherein $R^4$ is selected from a group consisting of:

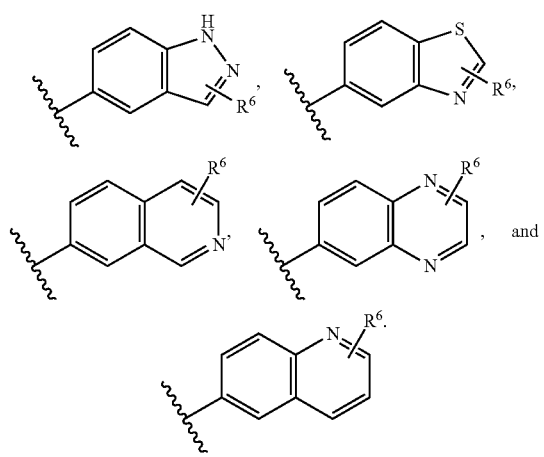

Embodiment 110

A compound according to any one of the preceding embodiments, or a pharmaceutically acceptable salt thereof, wherein $R^4$ is selected from a group consisting of:

Embodiment 111

A compound according to any one of the preceding embodiments, or a pharmaceutically acceptable salt thereof, wherein $R^4$ is

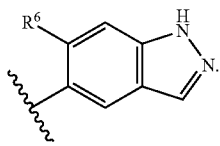

Embodiment 112

A compound according to any one of the preceding embodiments, or a pharmaceutically acceptable salt thereof, wherein $R^4$ is

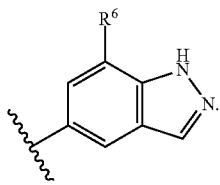

Embodiment 113

A compound according to any one of the preceding embodiments, or a pharmaceutically acceptable salt thereof, wherein $R^4$ is

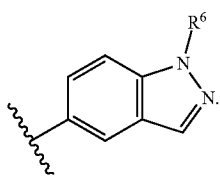

Embodiment 114

A compound according to any one of the preceding embodiments, or a pharmaceutically acceptable salt thereof, wherein $R^4$ is

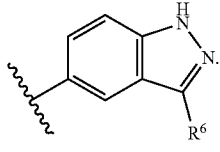

Embodiment 115

A compound according to any one of the preceding embodiments, or a pharmaceutically acceptable salt thereof, wherein $R^4$ is

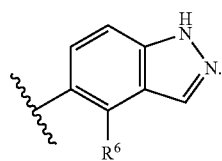

Embodiment 116

A compound according to any one of the preceding embodiments, or a pharmaceutically acceptable salt thereof, wherein $R^4$ is selected from a group consisting of:

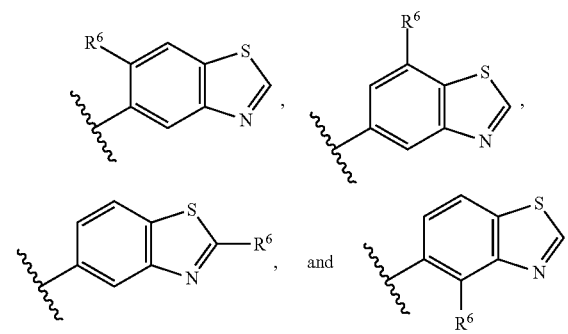

Embodiment 117

A compound according to any one of the preceding embodiments, or a pharmaceutically acceptable salt thereof, wherein $R^4$ is

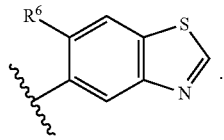

Embodiment 118

A compound according to any one of the preceding embodiments, or a pharmaceutically acceptable salt thereof, wherein $R^4$ is

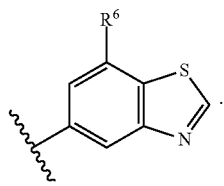

Embodiment 119

A compound according to any one of the preceding embodiments, or a pharmaceutically acceptable salt thereof, wherein $R^4$ is

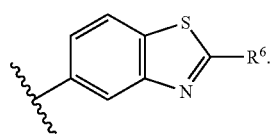

Embodiment 120

A compound according to any one of the preceding embodiments, or a pharmaceutically acceptable salt thereof, wherein $R^4$ is

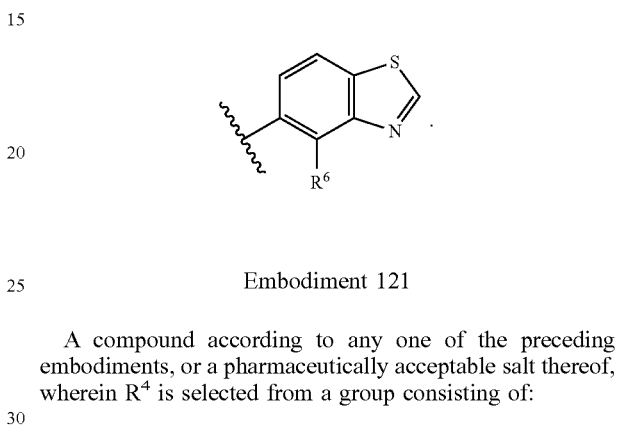

Embodiment 121

A compound according to any one of the preceding embodiments, or a pharmaceutically acceptable salt thereof, wherein $R^4$ is selected from a group consisting of:

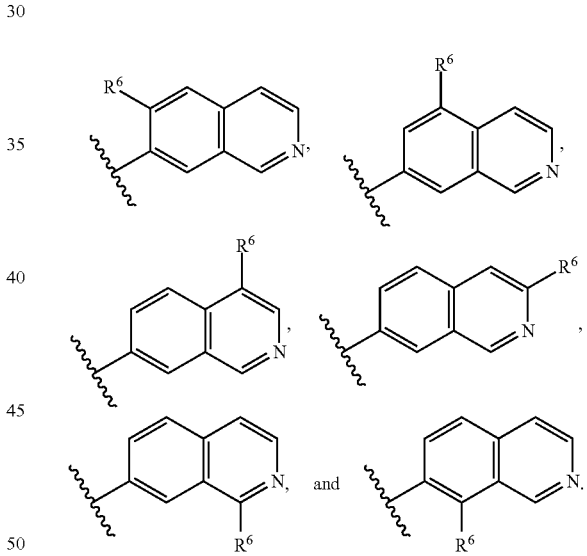

Embodiment 122

A compound according to any one of the preceding embodiments, or a pharmaceutically acceptable salt thereof, wherein $R^4$ is

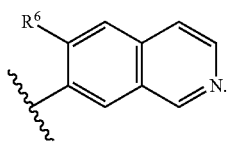

Embodiment 123

A compound according to any one of the preceding embodiments, or a pharmaceutically acceptable salt thereof, wherein $R^4$ is

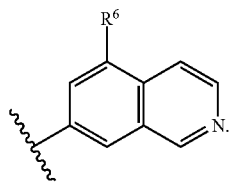

Embodiment 124

A compound according to any one of the preceding embodiments, or a pharmaceutically acceptable salt thereof, wherein $R^4$ is

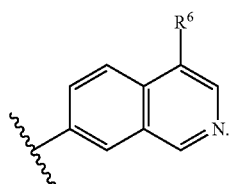

Embodiment 125

A compound according to any one of the preceding embodiments, or a pharmaceutically acceptable salt thereof, wherein $R^4$ is

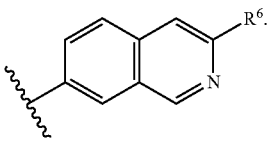

Embodiment 126

A compound according to any one of the preceding embodiments, or a pharmaceutically acceptable salt thereof, wherein $R^4$ is

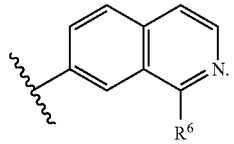

Embodiment 127

A compound according to any one of the preceding embodiments, or a pharmaceutically acceptable salt thereof, wherein $R^4$ is

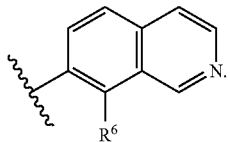

Embodiment 128

A compound according to any one of the preceding embodiments, or a pharmaceutically acceptable salt thereof, wherein $R^4$ is selected from a group consisting of:

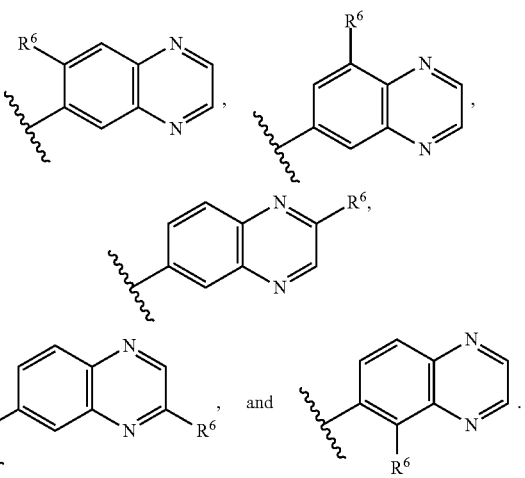

Embodiment 129

A compound according to any one of the preceding embodiments, or a pharmaceutically acceptable salt thereof, wherein $R^4$ is

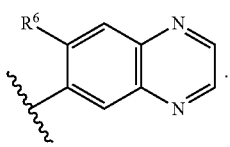

Embodiment 130

A compound according to any one of the preceding embodiments, or a pharmaceutically acceptable salt thereof, wherein $R^4$ is

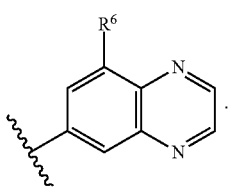

Embodiment 131

A compound according to any one of the preceding embodiments, or a pharmaceutically acceptable salt thereof, wherein $R^4$ is

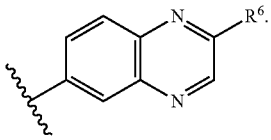

Embodiment 132

A compound according to any one of the preceding embodiments, or a pharmaceutically acceptable salt thereof, wherein $R^4$ is

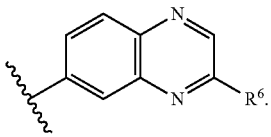

Embodiment 133

A compound according to any one of the preceding embodiments, or a pharmaceutically acceptable salt thereof, wherein $R^4$ is

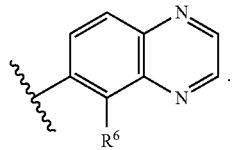

Embodiment 134

A compound according to any one of the preceding embodiments, or a pharmaceutically acceptable salt thereof, wherein $R^4$ is selected from a group consisting of:

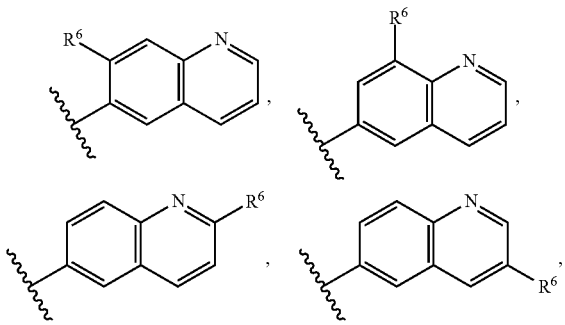

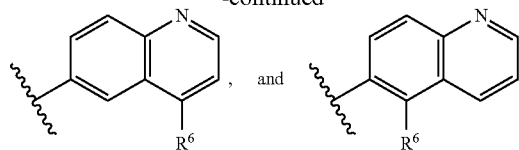

Embodiment 135

A compound according to any one of the preceding embodiments, or a pharmaceutically acceptable salt thereof, wherein $R^4$ is

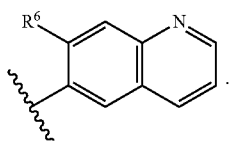

Embodiment 136

A compound according to any one of the preceding embodiments, or a pharmaceutically acceptable salt thereof, wherein $R^4$ is

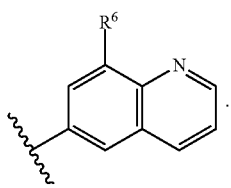

Embodiment 137

A compound according to any one of the preceding embodiments, or a pharmaceutically acceptable salt thereof, wherein $R^4$ is

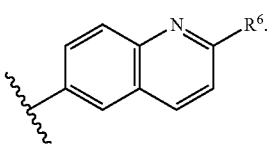

Embodiment 138

A compound according to any one of the preceding embodiments, or a pharmaceutically acceptable salt thereof, wherein $R^4$ is

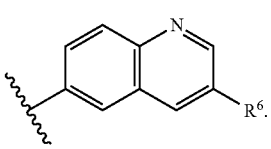

Embodiment 139

A compound according to any one of the preceding embodiments, or a pharmaceutically acceptable salt thereof, wherein R⁴ is

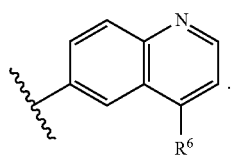

Embodiment 140

A compound according to any one of the preceding embodiments, or a pharmaceutically acceptable salt thereof, wherein R⁴ is

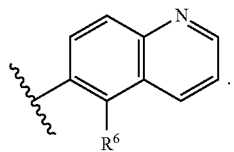

Embodiment 141

A compound according to any one of the preceding embodiments, or a pharmaceutically acceptable salt thereof, wherein R⁴ is selected from a group consisting of:

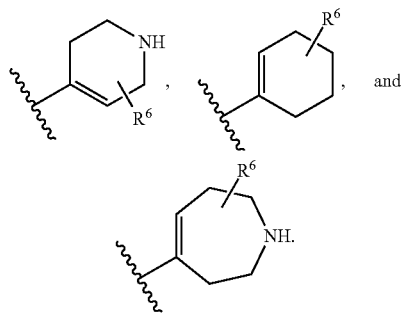

Embodiment 142

A compound according to any one of the preceding embodiments, or a pharmaceutically acceptable salt thereof, wherein R⁴ is selected from a group consisting of:

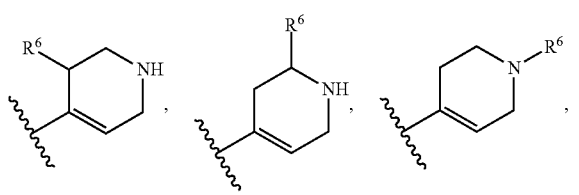

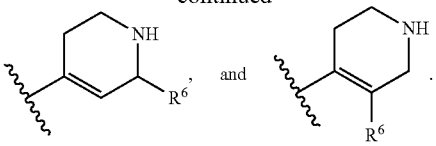

Embodiment 143

A compound according to any one of the preceding embodiments, or a pharmaceutically acceptable salt thereof, wherein R⁴ is

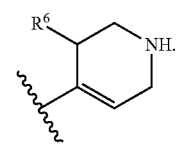

Embodiment 144

A compound according to any one of the preceding embodiments, or a pharmaceutically acceptable salt thereof, wherein R⁴ is

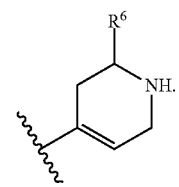

Embodiment 145

A compound according to any one of the preceding embodiments, or a pharmaceutically acceptable salt thereof, wherein R⁴ is

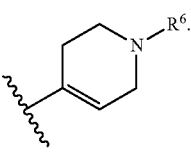

Embodiment 146

A compound according to any one of the preceding embodiments, or a pharmaceutically acceptable salt thereof, wherein R⁴ is

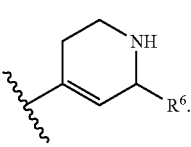

Embodiment 147

A compound according to any one of the preceding embodiments, or a pharmaceutically acceptable salt thereof, wherein $R^4$ is

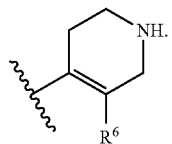

Embodiment 148

A compound according to any one of the preceding embodiments, or a pharmaceutically acceptable salt thereof, wherein $R^4$ is selected from a group consisting of:

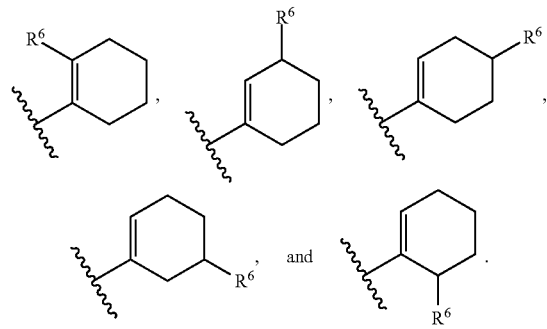

Embodiment 149

A compound according to any one of the preceding embodiments, or a pharmaceutically acceptable salt thereof, wherein $R^4$ is

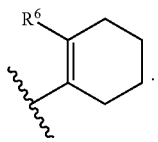

Embodiment 150

A compound according to any one of the preceding embodiments, or a pharmaceutically acceptable salt thereof, wherein $R^4$ is

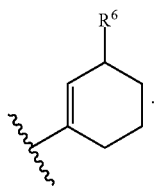

Embodiment 151

A compound according to any one of the preceding embodiments, or a pharmaceutically acceptable salt thereof, wherein $R^4$ is

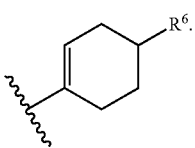

Embodiment 152

A compound according to any one of the preceding embodiments, or a pharmaceutically acceptable salt thereof, wherein $R^4$ is

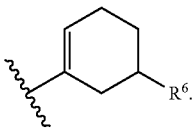

Embodiment 153

A compound according to any one of the preceding embodiments, or a pharmaceutically acceptable salt thereof, wherein $R^4$ is

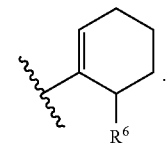

Embodiment 154

A compound according to any one of the preceding embodiments, or a pharmaceutically acceptable salt thereof, wherein $R^4$ is selected from a group consisting of:

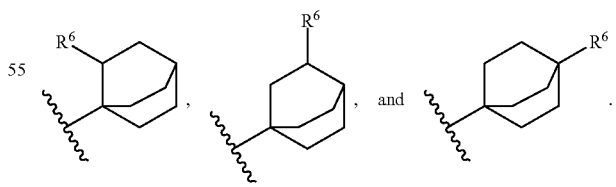

Embodiment 155

A compound according to any one of the preceding embodiments, or a pharmaceutically acceptable salt thereof, wherein $R^4$ is

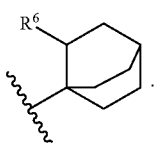

Embodiment 156

A compound according to any one of the preceding embodiments, or a pharmaceutically acceptable salt thereof, wherein $R^4$ is

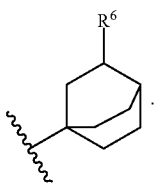

Embodiment 157

A compound according to any one of the preceding embodiments, or a pharmaceutically acceptable salt thereof, wherein $R^4$ is

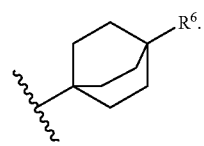

Embodiment 158

A compound according to any one of the preceding embodiments, or a pharmaceutically acceptable salt thereof, wherein $R^4$ is selected from a group consisting of:

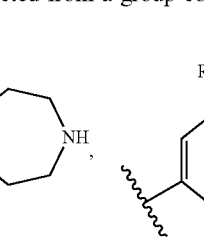

and

Embodiment 159

A compound according to any one of the preceding embodiments, or a pharmaceutically acceptable salt thereof, wherein $R^4$ is

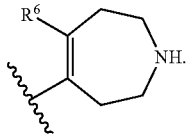

Embodiment 160

A compound according to any one of the preceding embodiments, or a pharmaceutically acceptable salt thereof, wherein $R^4$ is

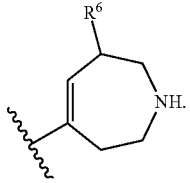

Embodiment 161

A compound according to any one of the preceding embodiments, or a pharmaceutically acceptable salt thereof, wherein $R^4$ is

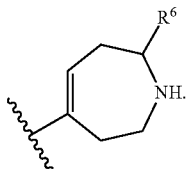

Embodiment 162

A compound according to any one of the preceding embodiments, or a pharmaceutically acceptable salt thereof, wherein $R^4$ is

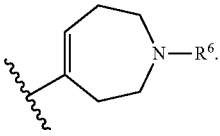

Embodiment 163

A compound according to any one of the preceding embodiments, or a pharmaceutically acceptable salt thereof, wherein $R^4$ is

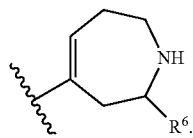

Embodiment 164

A compound according to any one of the preceding embodiments, or a pharmaceutically acceptable salt thereof, wherein $R^4$ is

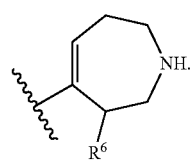

Embodiment 165

A compound according to any one of the preceding embodiments, or a pharmaceutically acceptable salt thereof, wherein $R^4$ is selected from a group consisting of:

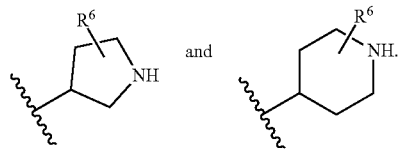

Embodiment 166

A compound according to any one of the preceding embodiments, or a pharmaceutically acceptable salt thereof, wherein $R^4$ is selected from a group consisting of:

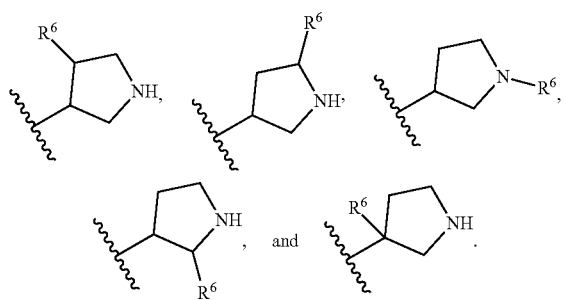

Embodiment 167

A compound according to any one of the preceding embodiments, or a pharmaceutically acceptable salt thereof, wherein $R^4$ is

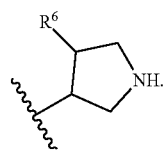

Embodiment 168

A compound according to any one of the preceding embodiments, or a pharmaceutically acceptable salt thereof, wherein $R^4$ is

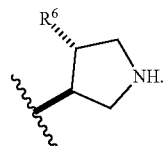

Embodiment 169

A compound according to any one of the preceding embodiments, or a pharmaceutically acceptable salt thereof, wherein $R^4$ is Embodiment 170

A compound according to any one of the preceding embodiments, or a pharmaceutically acceptable salt thereof, wherein $R^4$ is Embodiment 171

A compound according to any one of the preceding embodiments, or a pharmaceutically acceptable salt thereof, wherein $R^4$ is

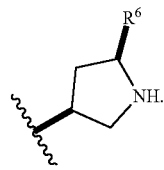

Embodiment 172

A compound according to any one of the preceding embodiments, or a pharmaceutically acceptable salt thereof, wherein $R^4$ is

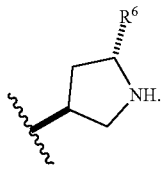

Embodiment 173

A compound according to any one of the preceding embodiments, or a pharmaceutically acceptable salt thereof, wherein $R^4$ is

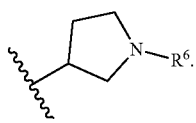

Embodiment 174

A compound according to any one of the preceding embodiments, or a pharmaceutically acceptable salt thereof, wherein $R^4$ is

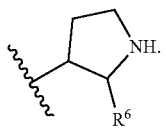

Embodiment 175

A compound according to any one of the preceding embodiments, or a pharmaceutically acceptable salt thereof, wherein $R^4$ is

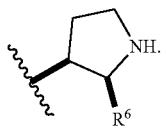

Embodiment 176

A compound according to any one of the preceding embodiments, or a pharmaceutically acceptable salt thereof, wherein $R^4$ is

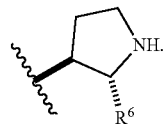

Embodiment 177

A compound according to any one of the preceding embodiments, or a pharmaceutically acceptable salt thereof, wherein $R^4$ is

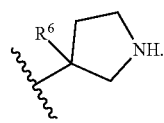

Embodiment 178

A compound according to any one of the preceding embodiments, or a pharmaceutically acceptable salt thereof, wherein $R^4$ is selected from a group consisting of:

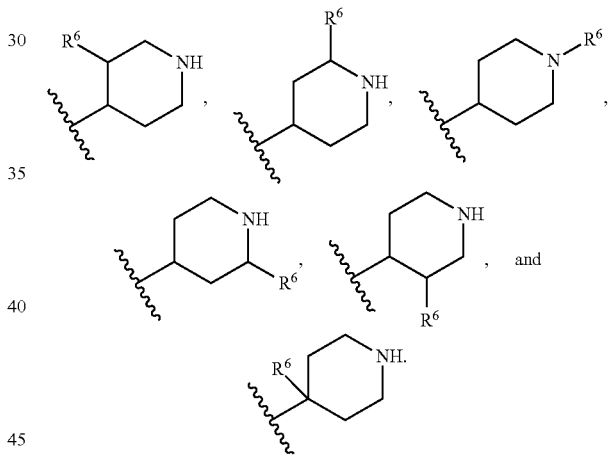

Embodiment 179

A compound according to any one of the preceding embodiments, or a pharmaceutically acceptable salt thereof, wherein $R^4$ is

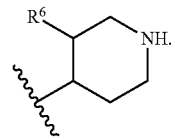

Embodiment 180

A compound according to any one of the preceding embodiments, or a pharmaceutically acceptable salt thereof, wherein $R^4$ is

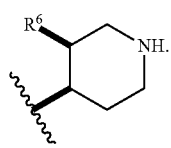

Embodiment 181

A compound according to any one of the preceding embodiments, or a pharmaceutically acceptable salt thereof, wherein $R^4$ is

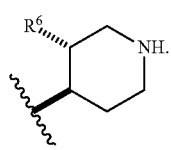

Embodiment 182

A compound according to any one of the preceding embodiments, or a pharmaceutically acceptable salt thereof, wherein $R^4$ is

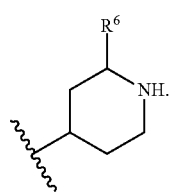

Embodiment 183

A compound according to any one of the preceding embodiments, or a pharmaceutically acceptable salt thereof, wherein $R^4$ is

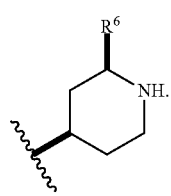

Embodiment 184

A compound according to any one of the preceding embodiments, or a pharmaceutically acceptable salt thereof, wherein $R^4$ is

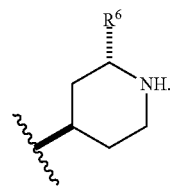

Embodiment 185

A compound according to any one of the preceding embodiments, or a pharmaceutically acceptable salt thereof, wherein $R^4$ is

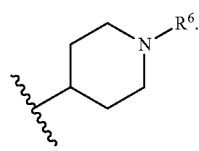

Embodiment 186

A compound according to any one of the preceding embodiments, or a pharmaceutically acceptable salt thereof, wherein $R^4$ is

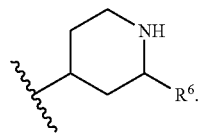

Embodiment 187

A compound according to any one of the preceding embodiments, or a pharmaceutically acceptable salt thereof, wherein $R^4$ is

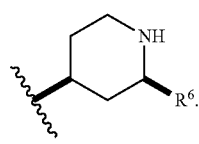

Embodiment 188

A compound according to any one of the preceding embodiments, or a pharmaceutically acceptable salt thereof, wherein $R^4$ is

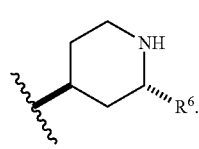

Embodiment 89

A compound according to any one of the preceding embodiments, or a pharmaceutically acceptable salt thereof, wherein R⁴ is

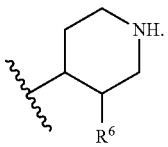

Embodiment 190

A compound according to any one of the preceding embodiments, or a pharmaceutically acceptable salt thereof, wherein R⁴ is

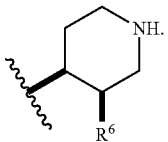

Embodiment 191

A compound according to any one of the preceding embodiments, or a pharmaceutically acceptable salt thereof, wherein R⁴ is

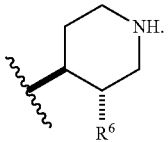

Embodiment 192

A compound according to any one of the preceding embodiments, or a pharmaceutically acceptable salt thereof, wherein R⁴ is

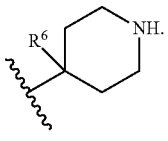

Embodiment 193

A compound according to any one of the preceding embodiments, or a pharmaceutically acceptable salt thereof, wherein R⁴ is selected from a group consisting of:

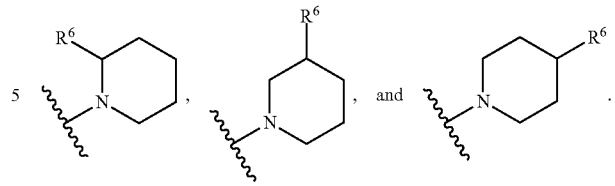

Embodiment 194

A compound according to any one of the preceding embodiments, or a pharmaceutically acceptable salt thereof, wherein R⁴ is

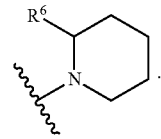

Embodiment 195

A compound according to any one of the preceding embodiments, or a pharmaceutically acceptable salt thereof, wherein R⁴ is

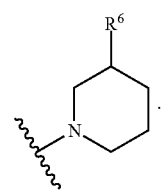

Embodiment 196

A compound according to any one of the preceding embodiments, or a pharmaceutically acceptable salt thereof, wherein R⁴ is

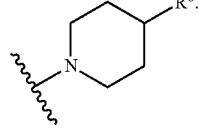

Embodiment 197

A compound according to any one of the preceding embodiments, or a pharmaceutically acceptable salt thereof, wherein R⁴ is selected from a group consisting of:

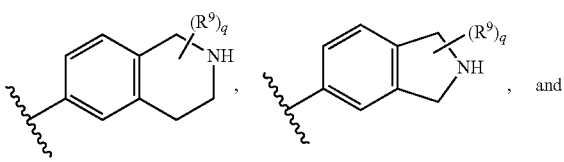

-continued

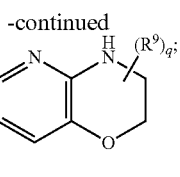

$R^9$ is $C_{1-4}$alkyl; and q is 0, 1, 2, or 3.

Embodiment 198

A compound according to any one of the preceding embodiments, or a pharmaceutically acceptable salt thereof, wherein $R^4$ is selected from a group consisting of:

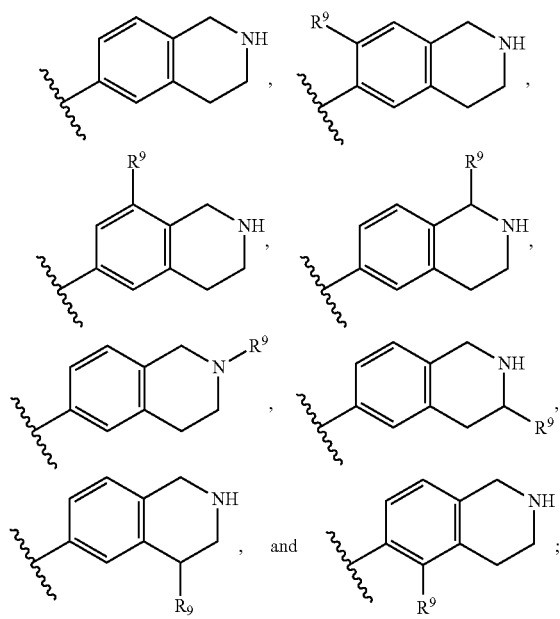

and $R^9$ is $C_{1-4}$alkyl.

Embodiment 199

A compound according to any one of the preceding embodiments, or a pharmaceutically acceptable salt thereof, wherein $R^4$ is

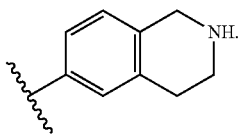 [SMILES: *c1ccc2c(c1)CCNC2]

Embodiment 200

A compound according to any one of the preceding embodiments, or a pharmaceutically acceptable salt thereof, wherein $R^4$ is

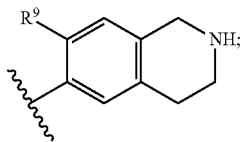

and $R^9$ is $C_{1-4}$alkyl.

Embodiment 201

A compound according to any one of the preceding embodiments, or a pharmaceutically acceptable salt thereof, wherein $R^4$ is

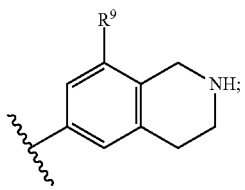

and $R^9$ is $C_{1-4}$alkyl.

Embodiment 202

A compound according to any one of the preceding embodiments, or a pharmaceutically acceptable salt thereof, wherein $R^4$ is

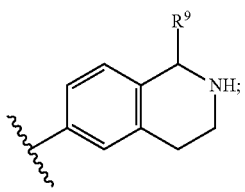

and $R^9$ is $C_{1-4}$alkyl.

Embodiment 203

A compound according to any one of the preceding embodiments, or a pharmaceutically acceptable salt thereof, wherein $R^4$ is

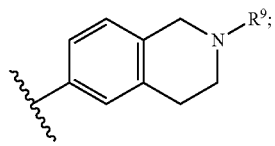

and $R^9$ is $C_{1-4}$alkyl.

Embodiment 204

A compound according to any one of the preceding embodiments, or a pharmaceutically acceptable salt thereof, wherein $R^4$ is

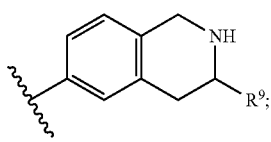

and $R^9$ is $C_{1-4}$alkyl.

Embodiment 205

A compound according to any one of the preceding embodiments, or a pharmaceutically acceptable salt thereof, wherein $R^4$ is

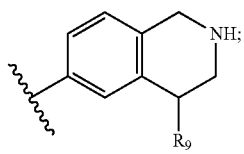

and $R^9$ is $C_{1-4}$alkyl.

Embodiment 206

A compound according to any one of the preceding embodiments, or a pharmaceutically acceptable salt thereof, wherein $R^4$ is

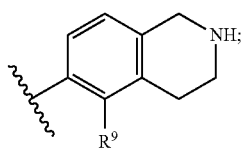

and $R^9$ is $C_{1-4}$alkyl.

Embodiment 207

A compound according to any one of the preceding embodiments, or a pharmaceutically acceptable salt thereof, wherein $R^4$ is selected from a group consisting of:

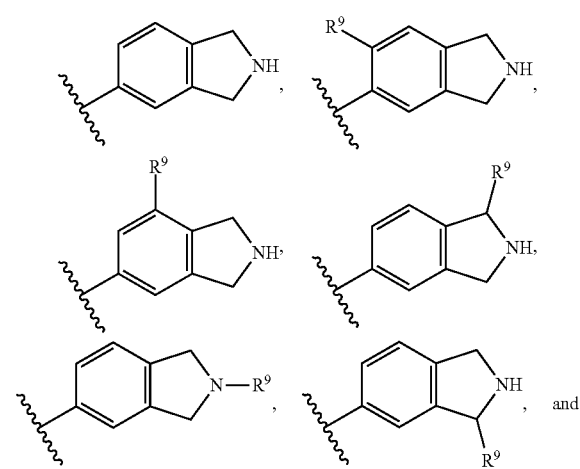

-continued

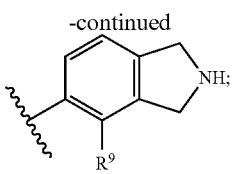

$R^9$ is $C_{1-4}$alkyl.

Embodiment 208

A compound according to any one of the preceding embodiments, or a pharmaceutically acceptable salt thereof, wherein $R^4$ is

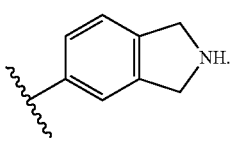 [SMILES: *c1ccc2c(c1)CNC2]

Embodiment 209

A compound according to any one of the preceding embodiments, or a pharmaceutically acceptable salt thereof, wherein $R^4$ is

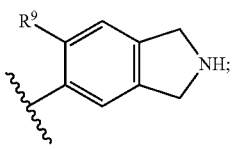

and $R^9$ is $C_{1-4}$alkyl.

Embodiment 210

A compound according to any one of the preceding embodiments, or a pharmaceutically acceptable salt thereof, wherein $R^4$ is

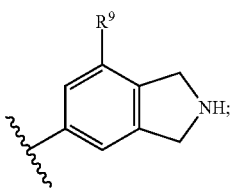

and $R^9$ is $C_{1-4}$alkyl.

Embodiment 211

A compound according to any one of the preceding embodiments, or a pharmaceutically acceptable salt thereof, wherein $R^4$ is

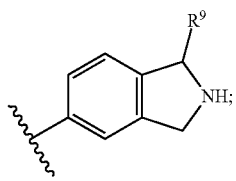

and R⁹ is $C_{1-4}$alkyl.

Embodiment 212

A compound according to any one of the preceding embodiments, or a pharmaceutically acceptable salt thereof, wherein R⁴ is

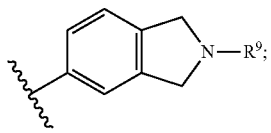

and R⁹ is $C_{1-4}$alkyl.

Embodiment 213

A compound according to any one of the preceding embodiments, or a pharmaceutically acceptable salt thereof, wherein R⁴ is

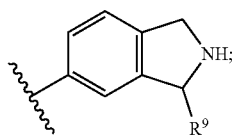

and R⁹ is $C_{1-4}$alkyl.

Embodiment 214

A compound according to any one of the preceding embodiments, or a pharmaceutically acceptable salt thereof, wherein R⁴ is

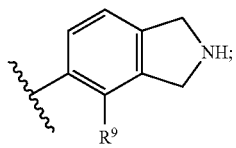

and R⁹ is $C_{1-4}$alkyl.

Embodiment 215

A compound according to any one of the preceding embodiments, or a pharmaceutically acceptable salt thereof, wherein R⁴ is selected from a group consisting of:

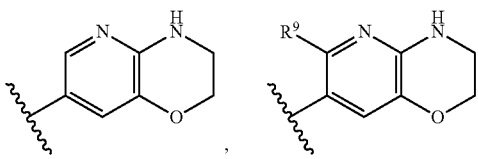

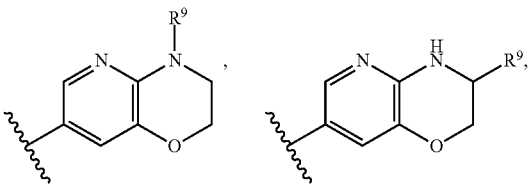

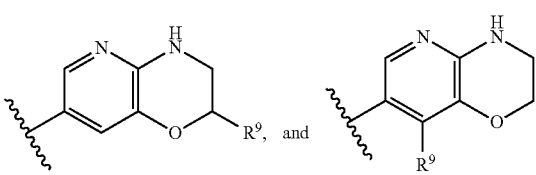

and R⁹ is $C_{1-4}$alkyl.

Embodiment 216

A compound according to any one of the preceding embodiments, or a pharmaceutically acceptable salt thereof, wherein R⁴ is

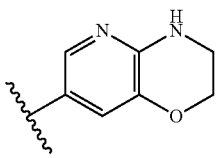

Embodiment 217

A compound according to any one of the preceding embodiments, or a pharmaceutically acceptable salt thereof, wherein R⁴ is

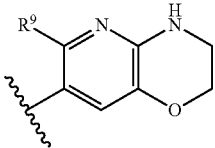

and R⁹ is $C_{1-4}$alkyl.

Embodiment 218

A compound according to any one of the preceding embodiments, or a pharmaceutically acceptable salt thereof, wherein R⁴ is

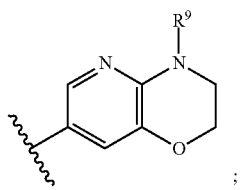

$R^9$ is $C_{1-4}$alkyl.

Embodiment 219

A compound according to any one of the preceding embodiments, or a pharmaceutically acceptable salt thereof, wherein $R^4$ is

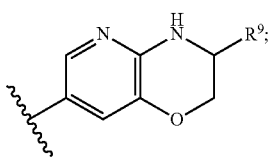

$R^9$ is $C_{1-4}$alkyl.

Embodiment 220

A compound according to any one of the preceding embodiments, or a pharmaceutically acceptable salt thereof, wherein $R^4$ is

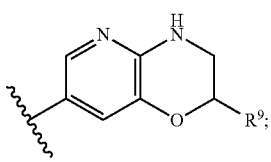

and $R^9$ is $C_{1-4}$alkyl.

Embodiment 221

A compound according to any one of the preceding embodiments, or a pharmaceutically acceptable salt thereof, wherein $R^4$ is

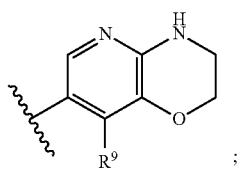

and $R^9$ is $C_{1-4}$alkyl.

Embodiment 222

A compound according to any one of the preceding embodiments, or a pharmaceutically acceptable salt thereof, wherein $R^6$ is —$(CH_2)_m$—$(CO)_n$—$(CH_2)_p$—$R^{6a}$.

Embodiment 223

A compound according to any one of the preceding embodiments, or a pharmaceutically acceptable salt thereof, wherein $R^6$ is —O—$R^{6a}$.

Embodiment 224

A compound according to any one of the preceding embodiments, or a pharmaceutically acceptable salt thereof, wherein $R^{6a}$ is H, —OH, —$NR^7R^8$, —CN, oxo, $C_{1-4}$alkyl, $C_{1-4}$hydroxyalkyl, —CH($NR^7R^8$)—$C_{1-3}$haloalkyl, —C($CH_3$)($NR^7R^8$)—$C_{1-3}$alkyl, —$SO_2C_{1-4}$alkyl, —$SO_2C_{1-4}$hydroxyalkyl, or —$SO_2NR^7R^8$.

Embodiment 225

A compound according to any one of the preceding embodiments, or a pharmaceutically acceptable salt thereof, wherein $R^{6a}$ is H, —OH, —$NR^7R^8$, —CN, oxo, $C_{1-4}$ alkyl, —CH($NR^7R^8$)—$C_{1-3}$haloalkyl, —$SO_2C_{1-4}$alkyl, or —$SO_2NR^7R^8$.

Embodiment 226

A compound according to any one of the preceding embodiments, or a pharmaceutically acceptable salt thereof, wherein $R^{6a}$ is H.

Embodiment 227

A compound according to any one of the preceding embodiments, or a pharmaceutically acceptable salt thereof, wherein $R^{6a}$ is —OH, —$NR^7R^8$, —CN, or oxo.

Embodiment 228

A compound according to any one of the preceding embodiments, or a pharmaceutically acceptable salt thereof, wherein $R^{6a}$ is —OH.

Embodiment 229

A compound according to any one of the preceding embodiments, or a pharmaceutically acceptable salt thereof, wherein $R^{6a}$ is —$NR^7R^8$.

Embodiment 230

A compound according to any one of the preceding embodiments, or a pharmaceutically acceptable salt thereof, wherein $R^{6a}$ is —CN.

Embodiment 231

A compound according to any one of the preceding embodiments, or a pharmaceutically acceptable salt thereof, wherein $R^{6a}$ is oxo.

Embodiment 232

A compound according to any one of the preceding embodiments, or a pharmaceutically acceptable salt thereof, wherein $R^{6a}$ is $C_{1-4}$alkyl or —CH($NR^7R^8$)—$C_{1-3}$haloalkyl.

Embodiment 233

A compound according to any one of the preceding embodiments, or a pharmaceutically acceptable salt thereof, wherein $R^{6a}$ is $C_{1-4}$alkyl.

Embodiment 234

A compound according to any one of the preceding embodiments, or a pharmaceutically acceptable salt thereof, wherein $R^{6a}$ is —CH(NR$^7$R$^8$)—C$_{1-3}$haloalkyl.

Embodiment 235

A compound according to any one of the preceding embodiments, or a pharmaceutically acceptable salt thereof, wherein $R^{6a}$ is $C_{1-4}$hydroxyalkyl.

Embodiment 236

A compound according to any one of the preceding embodiments, or a pharmaceutically acceptable salt thereof, wherein $R^{6a}$ is —C(CH$_3$)(NR$^7$R$^8$)—C$_{1-3}$alkyl.

Embodiment 237

A compound according to any one of the preceding embodiments, or a pharmaceutically acceptable salt thereof, wherein $R^{6a}$ is —SO$_2$C$_{1-4}$alkyl or —SO$_2$NR$^7$R$^8$.

Embodiment 238

A compound according to any one of the preceding embodiments, or a pharmaceutically acceptable salt thereof, wherein $R^{6a}$ is —SO$_2$C$_{1-4}$alkyl.

Embodiment 239

A compound according to any one of the preceding embodiments, or a pharmaceutically acceptable salt thereof, wherein $R^{6a}$ is —SO$_2$C$_{1-4}$hydroxyalkyl.

Embodiment 240

A compound according to any one of the preceding embodiments, or a pharmaceutically acceptable salt thereof, wherein $R^{6a}$ is —SO$_2$NR$^7$R$^8$.

Embodiment 241

A compound according to any one of the preceding embodiments, or a pharmaceutically acceptable salt thereof, wherein $R^{6a}$ is H, —OH, —NH$_2$, —N(CH$_3$)$_2$, —N(CH$_2$CH$_3$)$_2$, —NHCH$_2$CH$_2$OH,

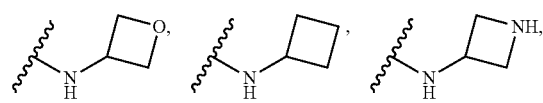 [SMILES: *NC1COC1 ; *NC1CCC1 ; *NC1CNC1]

—CN, oxo, CH$_3$, —CH(NH$_2$)CF$_3$, —SO$_2$CH$_3$, —SO$_2$N(CH$_3$)$_2$, —C(CH$_3$)$_2$OH, —C(CH$_3$)$_2$CH$_2$OH, —C(CH$_3$)$_2$NHCH$_2$C(CH$_3$)$_2$OH, —NHCH$_2$C(CH$_3$)$_2$OH, —SO$_2$CH$_2$CH$_2$OH, —CH$_2$OH, or —SO$_2$NHCH$_2$C(CH$_3$)$_2$OH.

Embodiment 242

A compound according to any one of the preceding embodiments, or a pharmaceutically acceptable salt thereof, wherein $R^{6a}$ is H, —OH, —NH$_2$, —N(CH$_3$)$_2$, —N(CH$_2$CH$_3$)$_2$, —NHCH$_2$CH$_2$OH,

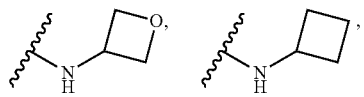 [SMILES: *NC1COC1 ; *NC1CCC1]

—CN, oxo, CH$_3$, —CH(NH$_2$)CF$_3$, —SO$_2$CH$_3$, or —SO$_2$N(CH$_3$)$_2$.

Embodiment 243

A compound according to any one of the preceding embodiments, or a pharmaceutically acceptable salt thereof, wherein $R^6$ is —(CH$_2$)$_m$—(CO)$_n$—(CH$_2$)$_p$—R$^{6b}$.

Embodiment 244

A compound according to any one of the preceding embodiments, or a pharmaceutically acceptable salt thereof, wherein $R^6$ is —O—R$^{6b}$.

Embodiment 245

A compound according to any one of the preceding embodiments, or a pharmaceutically acceptable salt thereof, wherein $R^{6b}$ is a 4-10 membered heterocyclyl optionally substituted with 1-2 substituents selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl.

Embodiment 246

A compound according to any one of the preceding embodiments, or a pharmaceutically acceptable salt thereof, wherein $R^{6b}$ is a 4-10 membered heterocyclyl optionally substituted with 1 substituent selected from a group consisting of —NR$^7$R$^8$, C$_{1-4}$alkyl, —C$_{1-4}$hydroxyalkyl, and —C$_{1-4}$alkyl-NR$^7$R$^8$. Alternatively, a compound according to any one of the preceding embodiments, or a pharmaceutically acceptable salt thereof, wherein $R^{6b}$ is a 4-10 membered heterocyclyl optionally substituted with 1-3 substituents independently selected from a group consisting of —NR$^7$R$^8$, C$_{1-4}$alkyl, —C$_{1-4}$hydroxyalkyl, and —C$_{1-4}$alkyl-NR$^7$R$^8$. For example, a compound according to any one of the preceding embodiments, or a pharmaceutically acceptable salt thereof, wherein $R^4$ is —C$_6$H$_4$—R$^6$; $R^6$ is —(CH$_2$)$_m$—(CO)$_n$—(CH$_2$)$_p$—R$^{6b}$; and $R^{6b}$ is a 4-10 membered heterocyclyl optionally substituted with 1-3 substituents independently selected from a group consisting of —NR$^7$R$^8$, C$_{1-4}$alkyl, —C$_{1-4}$hydroxyalkyl, and —C$_{1-4}$alkyl-NR$^7$R$^8$.

Embodiment 247

A compound according to any one of the preceding embodiments, or a pharmaceutically acceptable salt thereof, wherein $R^{6b}$ is selected from a group consisting of:

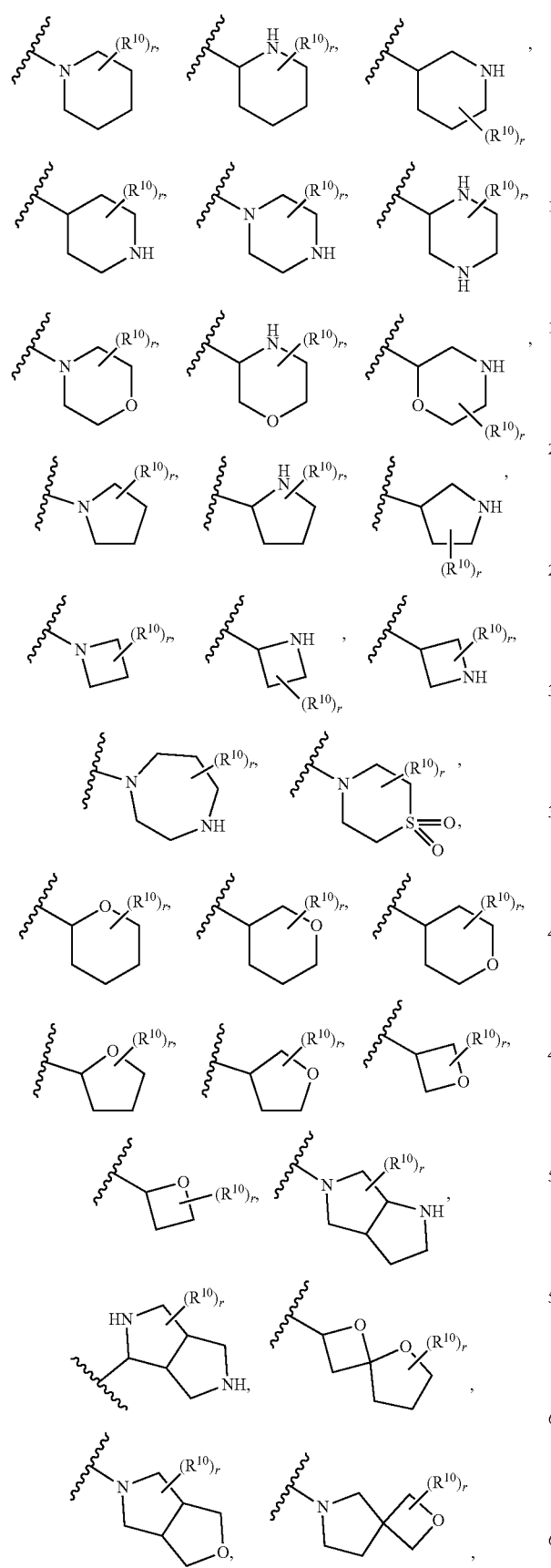
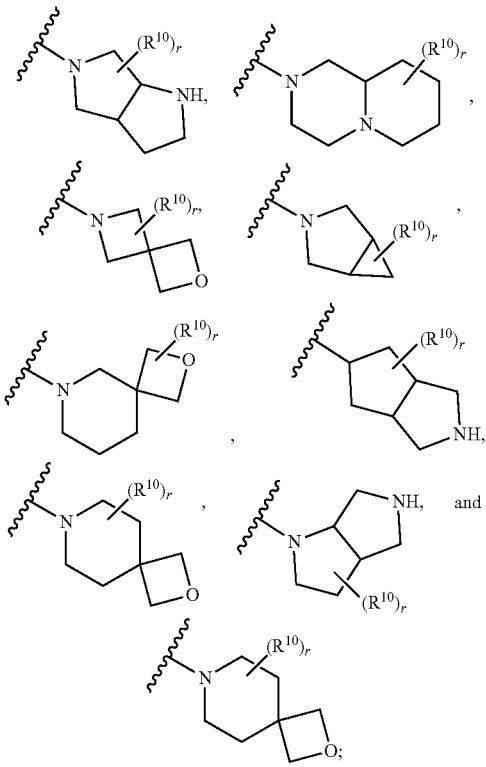
and $R^{10}$ is selected from a group consisting of halo, —OH, —$NR^7R^8$, $C_{1-4}$alkyl, —$C_{1-4}$haloalkyl, —$C_{1-4}$hydroxyalkyl, —$C_{1-4}$alkyl-$NR^7R^8$, —$SO_2C_{1-4}$alkyl, and 4-6 membered heterocyclyl; and r is 0 or 1 or 2.
Embodiment 248
A compound according to any one of the preceding embodiments, or a pharmaceutically acceptable salt thereof, wherein $R^{6b}$ is selected from a group consisting of:
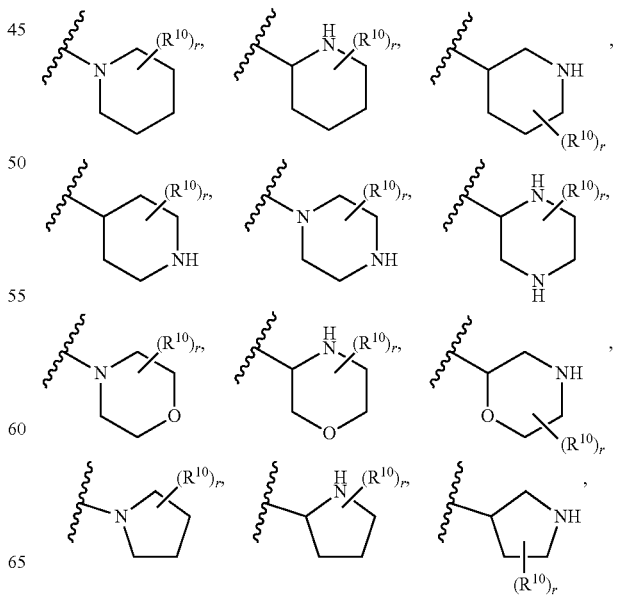

-continued

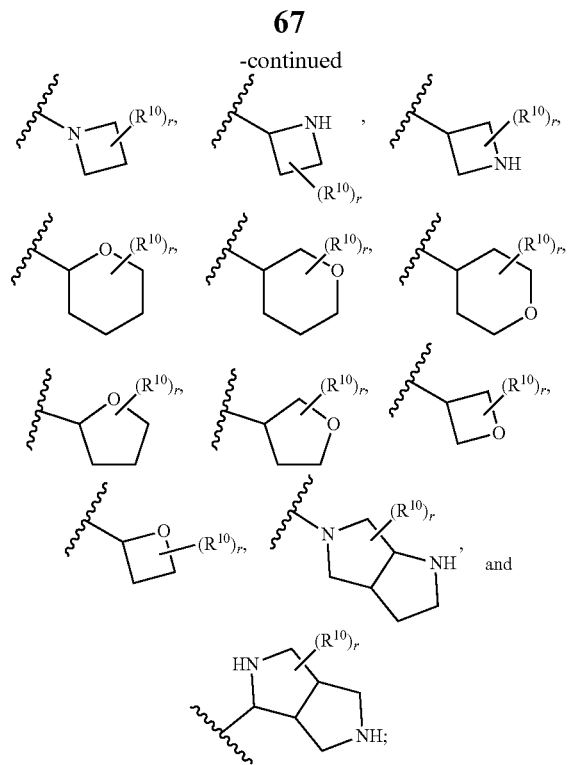

$R^{10}$ is selected from a group consisting of —$NR^7R^8$, —$C_{1-4}$alkyl, —$C_{1-4}$hydroxyalkyl, and —$C_{1-4}$alkyl-$NR^7R^8$; and r is 0 or 1.

Embodiment 249

A compound according to any one of the preceding embodiments, or a pharmaceutically acceptable salt thereof, wherein $R^{6b}$ is selected from a group consisting of:

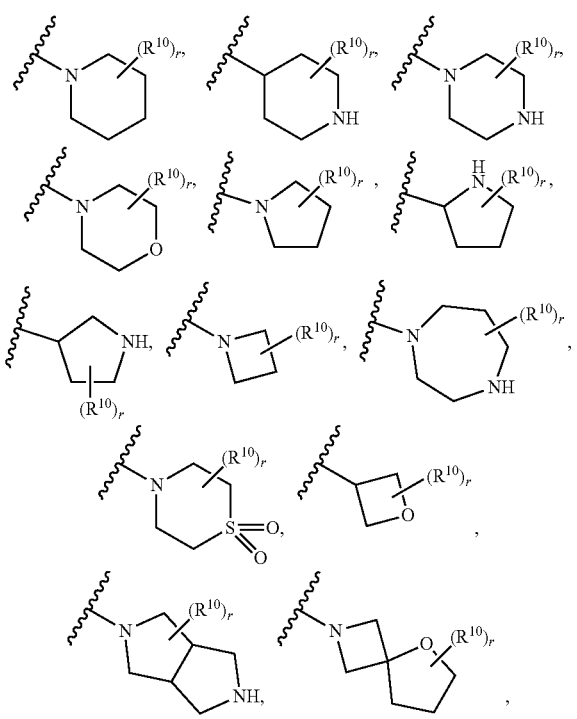

-continued

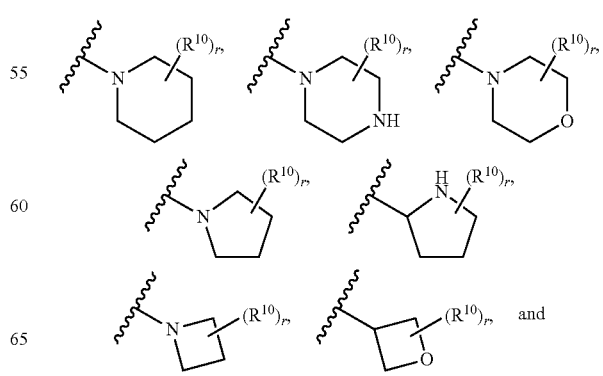

and $R^{10}$ is selected from a group consisting of halo, —OH, —$NR^7R^8$, $C_{1-4}$alkyl, —$C_{1-4}$haloalkyl, —$C_{1-4}$hydroxyalkyl, —$C_{1-4}$alkyl-$NR^7R^8$, —$SO_2C_{1-4}$alkyl, and 4-6 membered heterocyclyl; and r is 0 or 1 or 2.

Embodiment 250

A compound according to any one of the preceding embodiments, or a pharmaceutically acceptable salt thereof, wherein $R^{6b}$ is selected from a group consisting of:

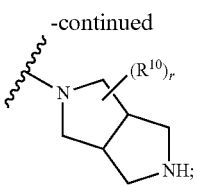

R$^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$; and r is 0 or 1.

Embodiment 251

A compound according to any one of the preceding embodiments, or a pharmaceutically acceptable salt thereof, wherein R$^{6b}$ is

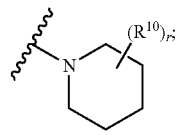

R$^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 252

A compound according to any one of the preceding embodiments, or a pharmaceutically acceptable salt thereof, wherein R$^{6b}$ is

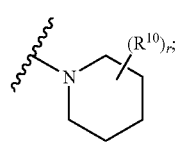

R$^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$; and r is 0 or 1.

Embodiment 253

A compound according to any one of the preceding embodiments, or a pharmaceutically acceptable salt thereof, wherein R$^{6b}$ is

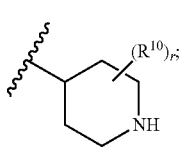

R$^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 254

A compound according to any one of the preceding embodiments, or a pharmaceutically acceptable salt thereof, wherein R$^{6b}$ is

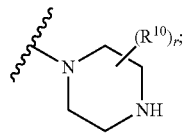

R$^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 255

A compound according to any one of the preceding embodiments, or a pharmaceutically acceptable salt thereof, wherein R$^{6b}$ is

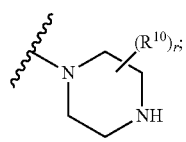

R$^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$; and r is 0 or 1.

Embodiment 256

A compound according to any one of the preceding embodiments, or a pharmaceutically acceptable salt thereof, wherein R$^{6b}$ is

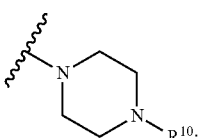

R$^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$; and r is 0 or 1.

Embodiment 257

A compound according to any one of the preceding embodiments, or a pharmaceutically acceptable salt thereof, wherein R$^{6b}$ is

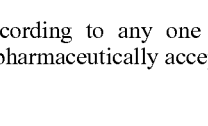

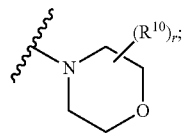

$R^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$; and r is 0 or 1.

Embodiment 258

A compound according to any one of the preceding embodiments, or a pharmaceutically acceptable salt thereof, wherein R$^{6b}$ is

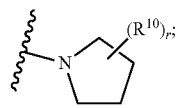

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 259

A compound according to any one of the preceding embodiments, or a pharmaceutically acceptable salt thereof, wherein R$^{6b}$ is

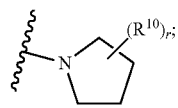

$R^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$; and r is 0 or 1.

Embodiment 260

A compound according to any one of the preceding embodiments, or a pharmaceutically acceptable salt thereof, wherein R$^{6b}$ is

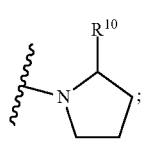

and $R^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$.

Embodiment 261

A compound according to any one of the preceding embodiments, or a pharmaceutically acceptable salt thereof, wherein R$^{6b}$ is

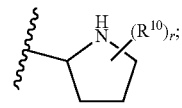

$R^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$; and r is 0 or 1.

Embodiment 262

A compound according to any one of the preceding embodiments, or a pharmaceutically acceptable salt thereof, wherein R$^{6b}$ is

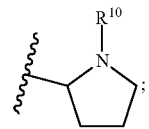

and $R^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$.

Embodiment 263

A compound according to any one of the preceding embodiments, or a pharmaceutically acceptable salt thereof, wherein R$^{6b}$ is

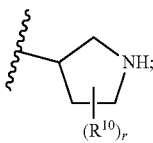
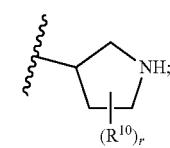

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 264

A compound according to any one of the preceding embodiments, or a pharmaceutically acceptable salt thereof, wherein R$^{6b}$ is

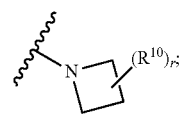

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 265

A compound according to any one of the preceding embodiments, or a pharmaceutically acceptable salt thereof, wherein R$^{6b}$ is

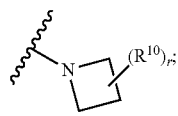

$R^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$; and r is 0 or 1.

Embodiment 266

A compound according to any one of the preceding embodiments, or a pharmaceutically acceptable salt thereof, wherein R$^{6b}$ is

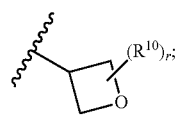

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 267

A compound according to any one of the preceding embodiments, or a pharmaceutically acceptable salt thereof, wherein R$^{6b}$ is

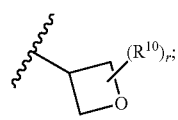

$R^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$; and r is 0 or 1.

Embodiment 268

A compound according to any one of the preceding embodiments, or a pharmaceutically acceptable salt thereof, wherein R$^{6b}$ is

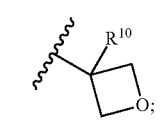

and $R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl.

Embodiment 269

A compound according to any one of the preceding embodiments, or a pharmaceutically acceptable salt thereof, wherein R$^{6b}$ is

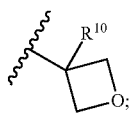

and $R^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$.

Embodiment 270

A compound according to any one of the preceding embodiments, or a pharmaceutically acceptable salt thereof, wherein R$^{6b}$ is

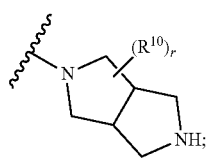

$R^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$; and r is 0 or 1.

Embodiment 271

A compound according to any one of the preceding embodiments, or a pharmaceutically acceptable salt thereof, wherein R$^{6b}$ is

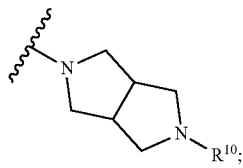

and $R^{10}$ is selected from a group consisting of —NR$^7$R$^8$, C$_{1-4}$alkyl, —C$_{1-4}$hydroxyalkyl, and —C$_{1-4}$alkyl-NR$^7$R$^8$.

Embodiment 272

A compound according to any one of the preceding embodiments, or a pharmaceutically acceptable salt thereof, wherein R$^{6b}$ is

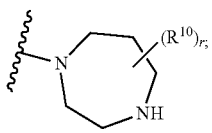

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 273

A compound according to any one of the preceding embodiments, or a pharmaceutically acceptable salt thereof, wherein R$^{6b}$ is

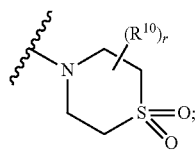

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 274

A compound according to any one of the preceding embodiments, or a pharmaceutically acceptable salt thereof, wherein R$^{6b}$ is

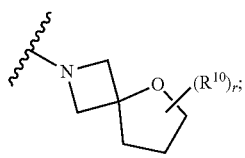

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 275

A compound according to any one of the preceding embodiments, or a pharmaceutically acceptable salt thereof, wherein R$^{6b}$ is

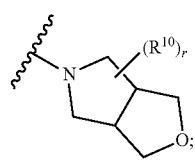

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 276

A compound according to any one of the preceding embodiments, or a pharmaceutically acceptable salt thereof, wherein R$^{6b}$ is

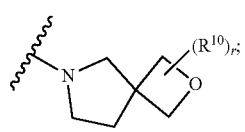

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 277

A compound according to any one of the preceding embodiments, or a pharmaceutically acceptable salt thereof, wherein R$^{6b}$ is

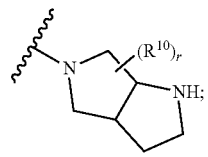

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 278

A compound according to any one of the preceding embodiments, or a pharmaceutically acceptable salt thereof, wherein R$^{6b}$ is

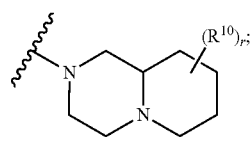

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 279

A compound according to any one of the preceding embodiments, or a pharmaceutically acceptable salt thereof, wherein R$^{6b}$ is

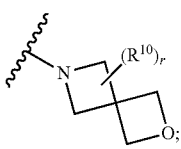

$R^{10}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and r is 0 or 1 or 2.

Embodiment 280

A compound according to any one of the preceding embodiments, or a pharmaceutically acceptable salt thereof, wherein R$^{6b}$ is

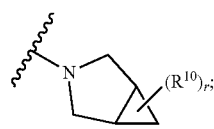

R[10] is selected from a group consisting of halo, —OH, —NR[7]R[8], $C_{1-4}$alkyl, —$C_{1-4}$haloalkyl, —$C_{1-4}$hydroxyalkyl, —$C_{1-4}$alkyl-NR[7]R[8], —SO$_2$$C_{1-4}$alkyl, and 4-6 membered heterocyclyl; and r is 0 or 1 or 2.

Embodiment 281

A compound according to any one of the preceding embodiments, or a pharmaceutically acceptable salt thereof, wherein R[6b] is

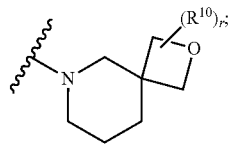

R[10] is selected from a group consisting of halo, —OH, —NR[7]R[8], $C_{1-4}$alkyl, —$C_{1-4}$haloalkyl, —$C_{1-4}$hydroxyalkyl, —$C_{1-4}$alkyl-NR[7]R[8], —SO$_2$$C_{1-4}$alkyl, and 4-6 membered heterocyclyl; and r is 0 or 1 or 2.

Embodiment 282

A compound according to any one of the preceding embodiments, or a pharmaceutically acceptable salt thereof, wherein R[6b] is

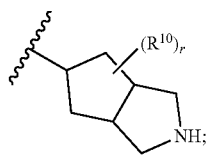

R[10] is selected from a group consisting of halo, —OH, —NR[7]R[8], $C_{1-4}$alkyl, —$C_{1-4}$haloalkyl, —$C_{1-4}$hydroxyalkyl, —$C_{1-4}$alkyl-NR[7]R[8], —SO$_2$$C_{1-4}$alkyl, and 4-6 membered heterocyclyl; and r is 0 or 1 or 2.

Embodiment 283

A compound according to any one of the preceding embodiments, or a pharmaceutically acceptable salt thereof, wherein R[6b] is

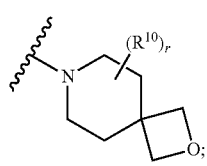

R[10] is selected from a group consisting of halo, —OH, —NR[7]R[8], $C_{1-4}$alkyl, —$C_{1-4}$haloalkyl, —$C_{1-4}$hydroxyalkyl, —$C_{1-4}$alkyl-NR[7]R[8], —SO$_2$$C_{1-4}$alkyl, and 4-6 membered heterocyclyl; and r is 0 or 1 or 2.

Embodiment 284

A compound according to any one of the preceding embodiments, or a pharmaceutically acceptable salt thereof, wherein R[6b] is

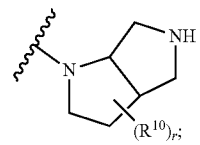

R[10] is selected from a group consisting of halo, —OH, —NR[7]R[8], $C_{1-4}$alkyl, —$C_{1-4}$haloalkyl, —$C_{1-4}$hydroxyalkyl, —$C_{1-4}$alkyl-NR[7]R[8], —SO$_2$$C_{1-4}$alkyl, and 4-6 membered heterocyclyl; and r is 0 or 1 or 2.

Embodiment 285

A compound according to any one of the preceding embodiments, or a pharmaceutically acceptable salt thereof, wherein R[6b] is

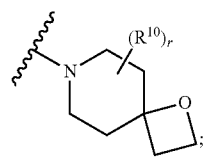

R[10] is selected from a group consisting of halo, —OH, —NR[7]R[8], $C_{1-4}$alkyl, —$C_{1-4}$haloalkyl, —$C_{1-4}$hydroxyalkyl, —$C_{1-4}$alkyl-NR[7]R[8], —SO$_2$$C_{1-4}$alkyl, and 4-6 membered heterocyclyl; and r is 0 or 1 or 2.

Embodiment 286

A compound according to any one of the preceding embodiments, or a pharmaceutically acceptable salt thereof, wherein R[6b] is selected from a group consisting of:

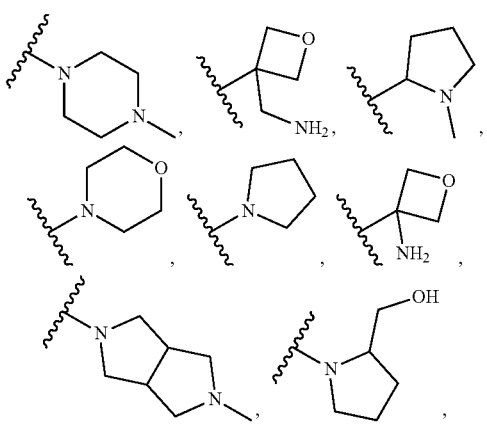

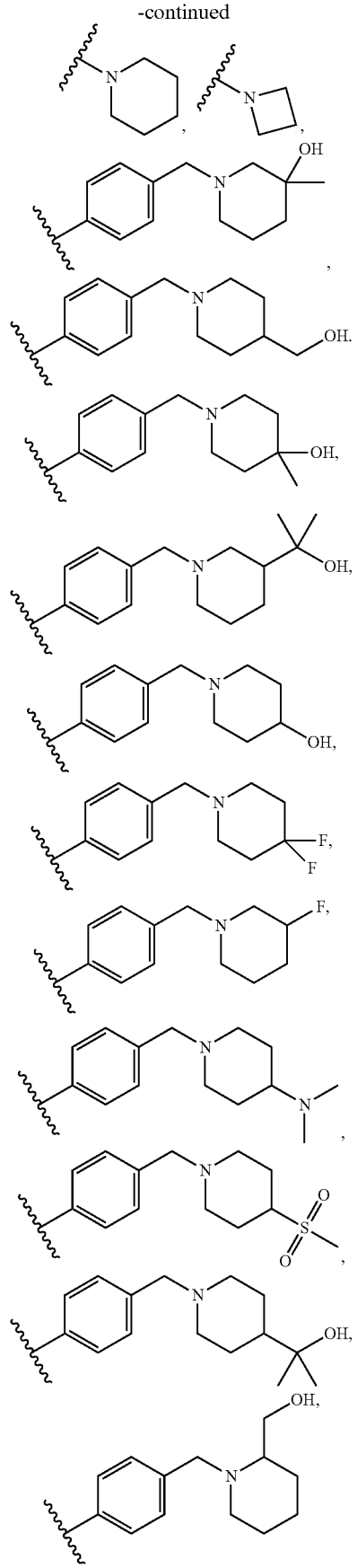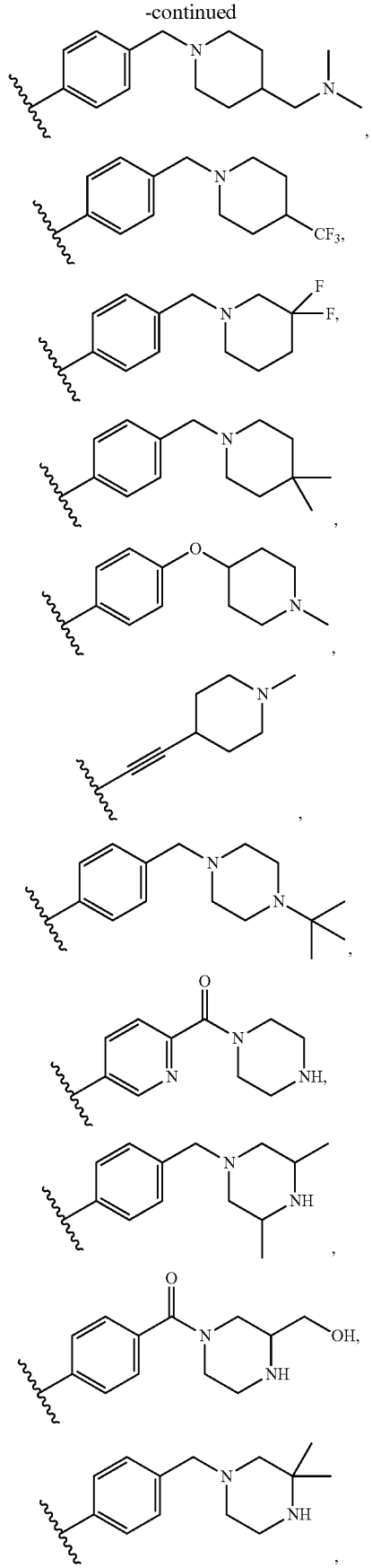

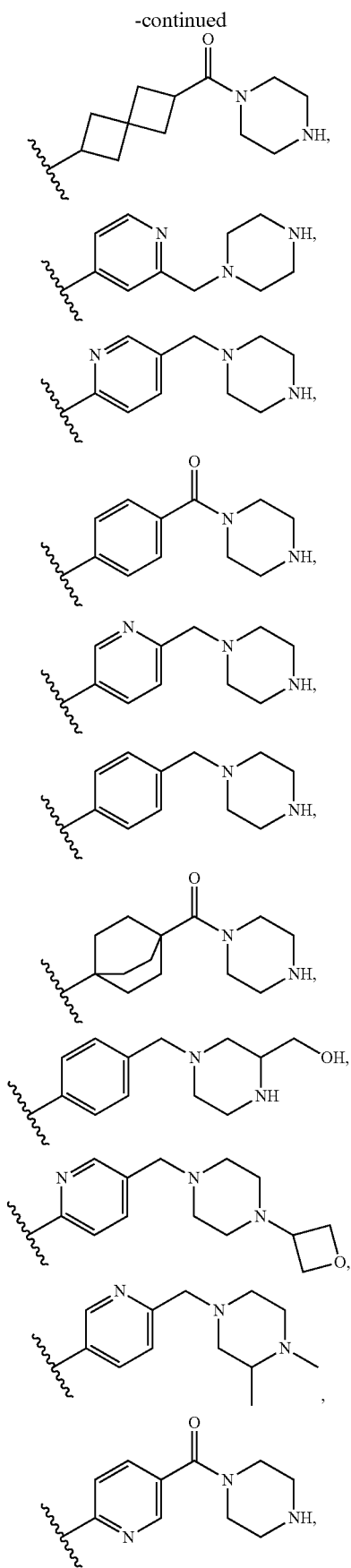
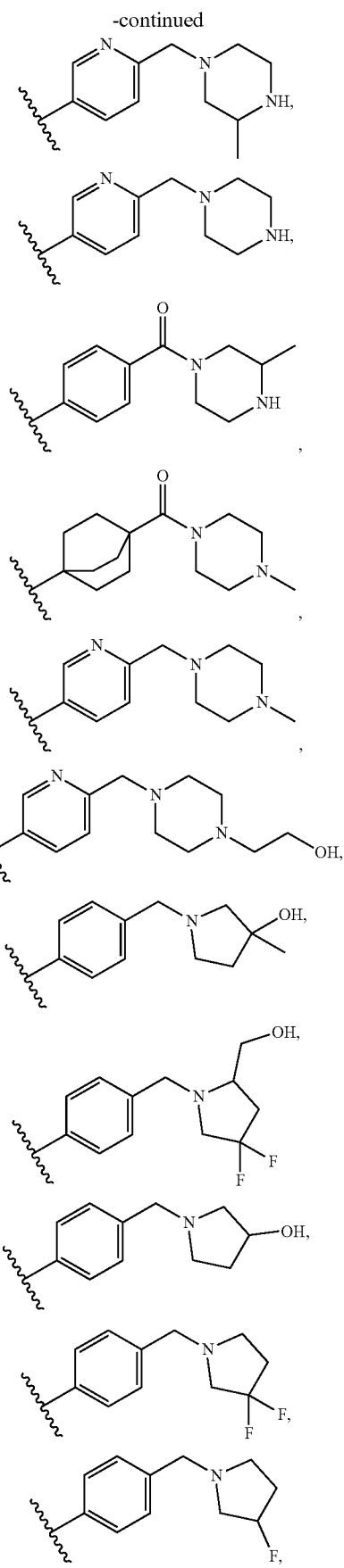

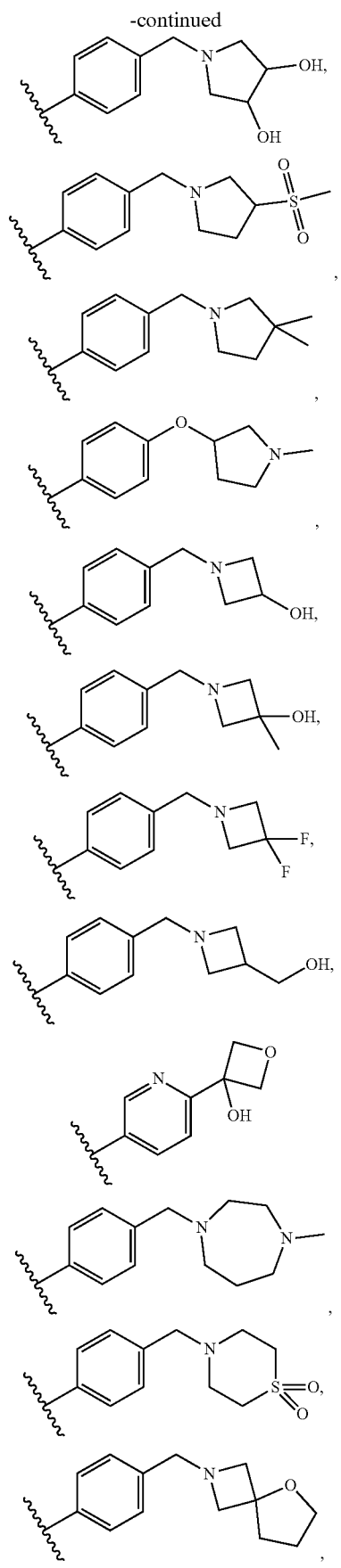
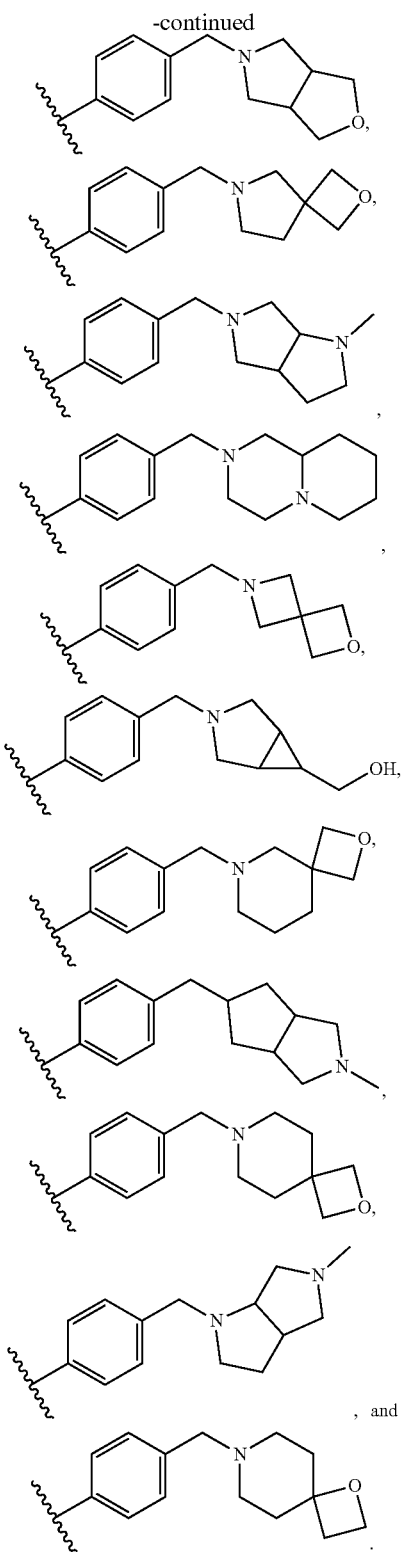
Embodiment 287
A compound according to any one of the preceding embodiments, or a pharmaceutically acceptable salt thereof, wherein $R^{6b}$ is selected from a group consisting of:

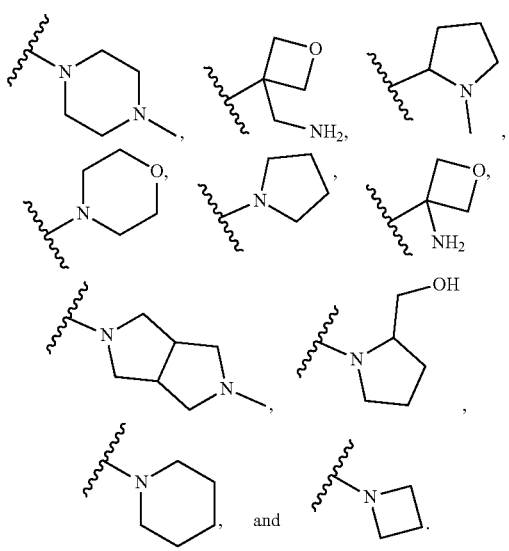

Embodiment 288

A compound according to any one of the preceding embodiments, or a pharmaceutically acceptable salt thereof, wherein $R^{6b}$ is selected from a group consisting of:

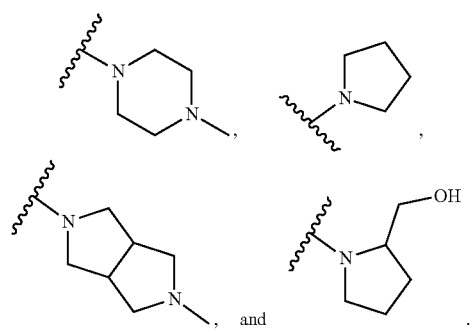

Embodiment 289

A compound according to any one of the preceding embodiments, or a pharmaceutically acceptable salt thereof, wherein $R^{6b}$ is

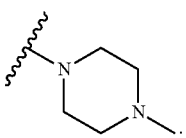 [SMILES: *N1CCN(C)CC1]

Embodiment 290

A compound according to any one of the preceding embodiments, or a pharmaceutically acceptable salt thereof, wherein $R^{6b}$ is

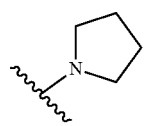

Embodiment 291

A compound according to any one of the preceding embodiments, or a pharmaceutically acceptable salt thereof, wherein $R^{6b}$ is

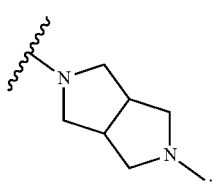 [SMILES: *N1CC2CN(C)CC2C1]

Embodiment 292

A compound according to any one of the preceding embodiments, or a pharmaceutically acceptable salt thereof, wherein $R^{6b}$ is

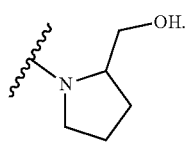 [SMILES: *N1CCCC1CO]

Embodiment 293

A compound according to any one of the preceding embodiments, or a pharmaceutically acceptable salt thereof, wherein $R^6$ is $-(CH_2)_m-(CO)_n-(CH_2)_p-R^{6c}$.

Embodiment 294

A compound according to any one of the preceding embodiments, or a pharmaceutically acceptable salt thereof, wherein $R^6$ is $-O-R^{6c}$.

Embodiment 295

A compound according to any one of the preceding embodiments, or a pharmaceutically acceptable salt thereof, wherein $R^{6c}$ is a 5 membered heteroaryl optionally substituted with 1 substituent selected from a group consisting of $-NR^7R^8$, $C_{1-4}$alkyl, $-C_{1-4}$hydroxyalkyl, and $-C_{1-4}$alkyl-$NR^7R^8$.

Embodiment 296

A compound according to any one of the preceding embodiments, or a pharmaceutically acceptable salt thereof, wherein $R^{6c}$ is selected from a group consisting of:

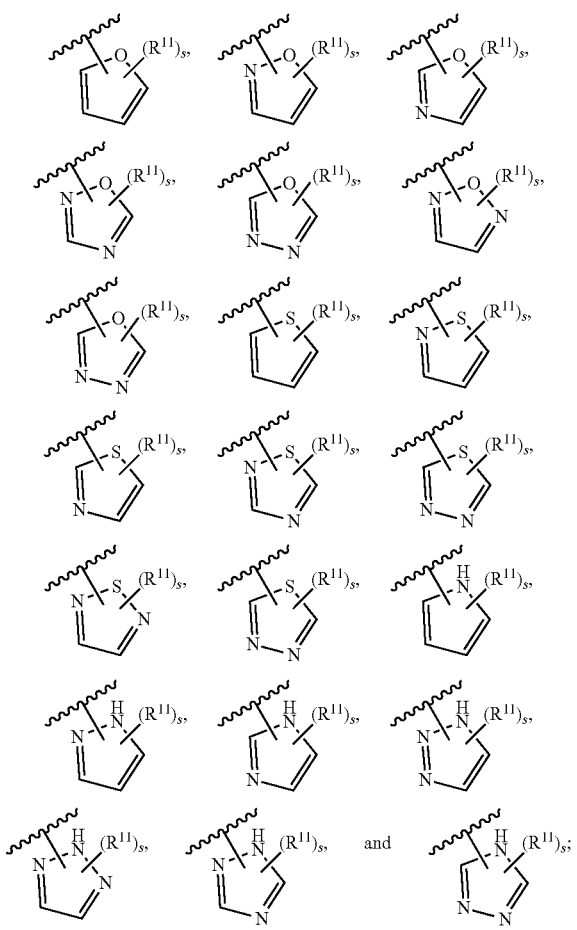

$R^{11}$ is selected from a group consisting of —NR$^7$R$^8$, C$_{1-4}$alkyl, —C$_{1-4}$hydroxyalkyl, and —C$_{1-4}$alkyl-NR$^7$R$^8$; and s is 0 or 1.

Embodiment 297

A compound according to any one of the preceding embodiments, or a pharmaceutically acceptable salt thereof, wherein R$^{6c}$ is

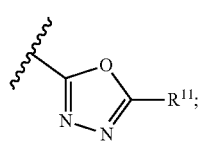

$R^{11}$ is selected from a group consisting of —NR$^7$R$^8$, C$_{1-4}$alkyl, —C$_{1-4}$hydroxyalkyl, and —C$_{1-4}$alkyl-NR$^7$R$^8$.

Embodiment 298

A compound according to any one of the preceding embodiments, or a pharmaceutically acceptable salt thereof, wherein R$^{6c}$ is

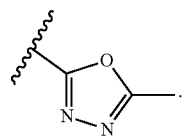 [SMILES: *c1nnc(C)o1]

Embodiment 299

A compound according to any one of the preceding embodiments, or a pharmaceutically acceptable salt thereof, wherein R$^6$ is —(CH$_2$)$_m$—(CO)$_n$—(CH$_2$)$_p$—R$^{6d}$.

Embodiment 300

A compound according to any one of the preceding embodiments, or a pharmaceutically acceptable salt thereof, wherein R$^6$ is —O—R$^{6d}$.

A compound according to any one of the preceding embodiments, or a pharmaceutically acceptable salt thereof, wherein R$^{6d}$ is

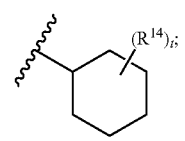

$R^{14}$ is selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl; and t is 0 or 1 or 2.

Embodiment 301

A compound according to any one of the preceding embodiments, or a pharmaceutically acceptable salt thereof, wherein R$^4$ is selected from a group consisting of:

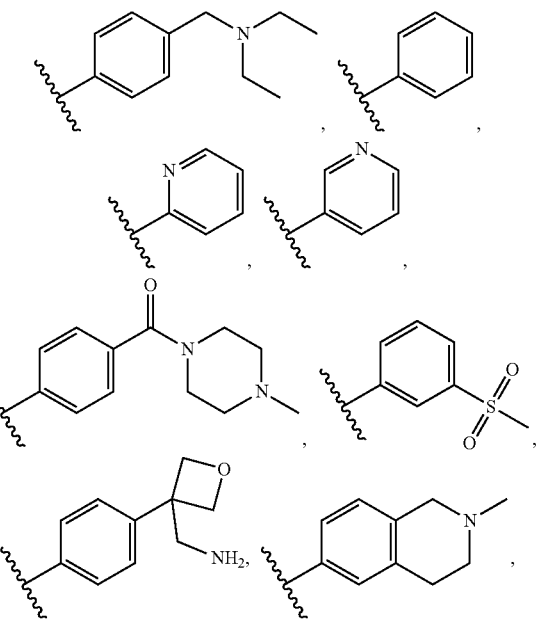

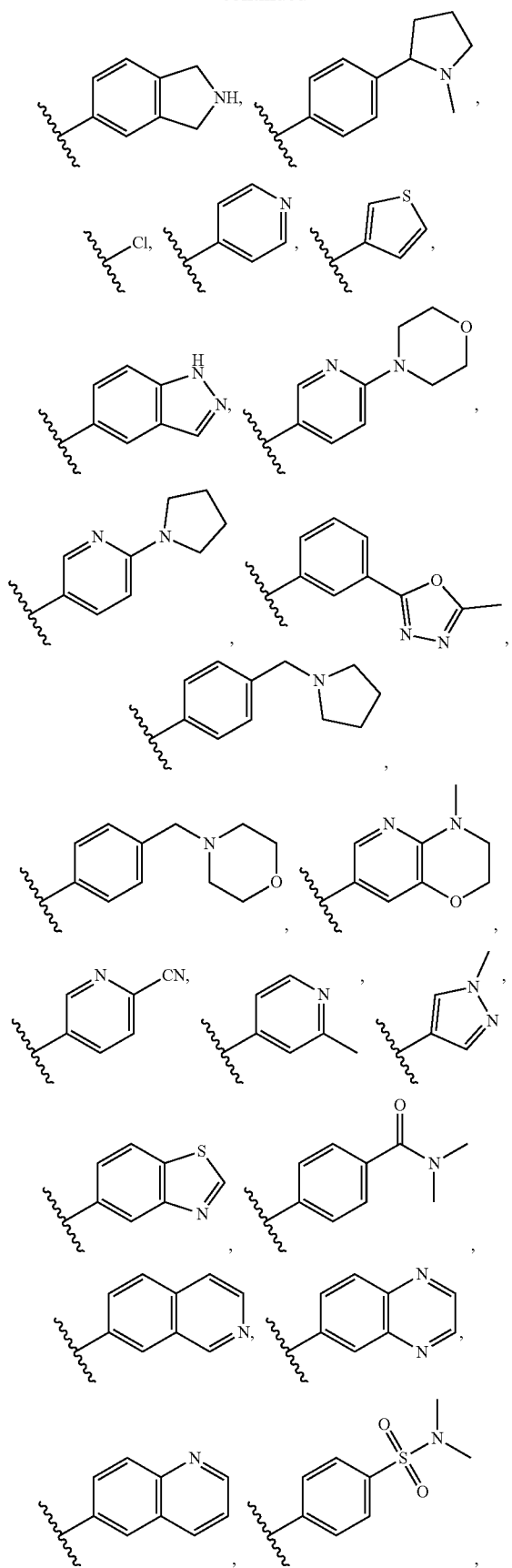
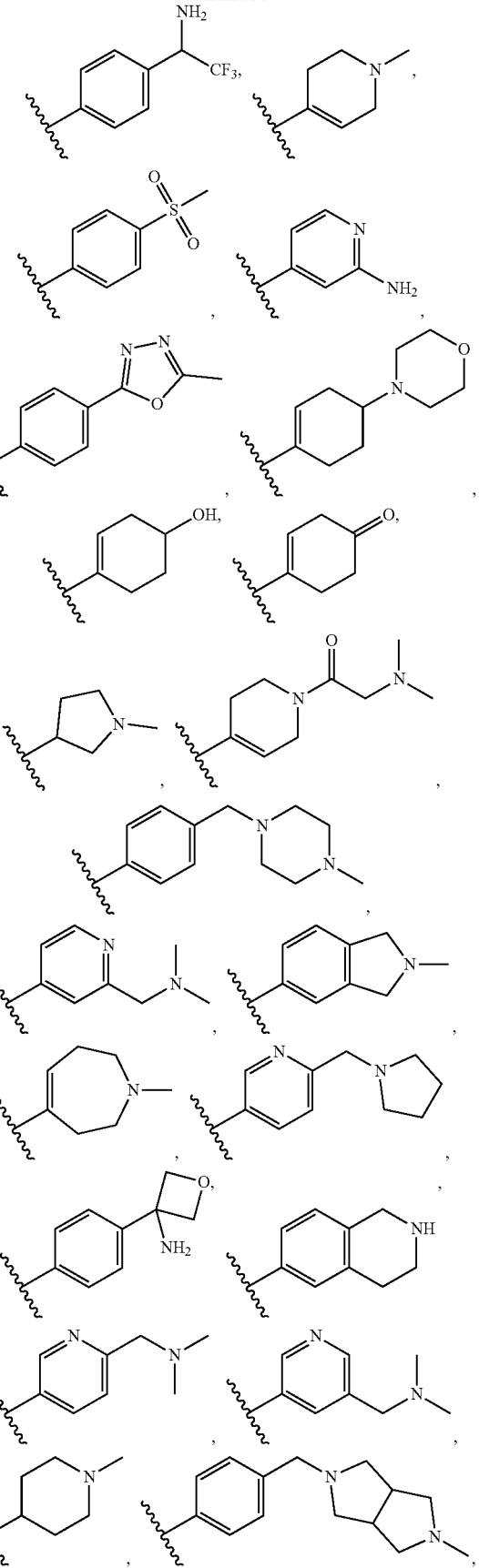

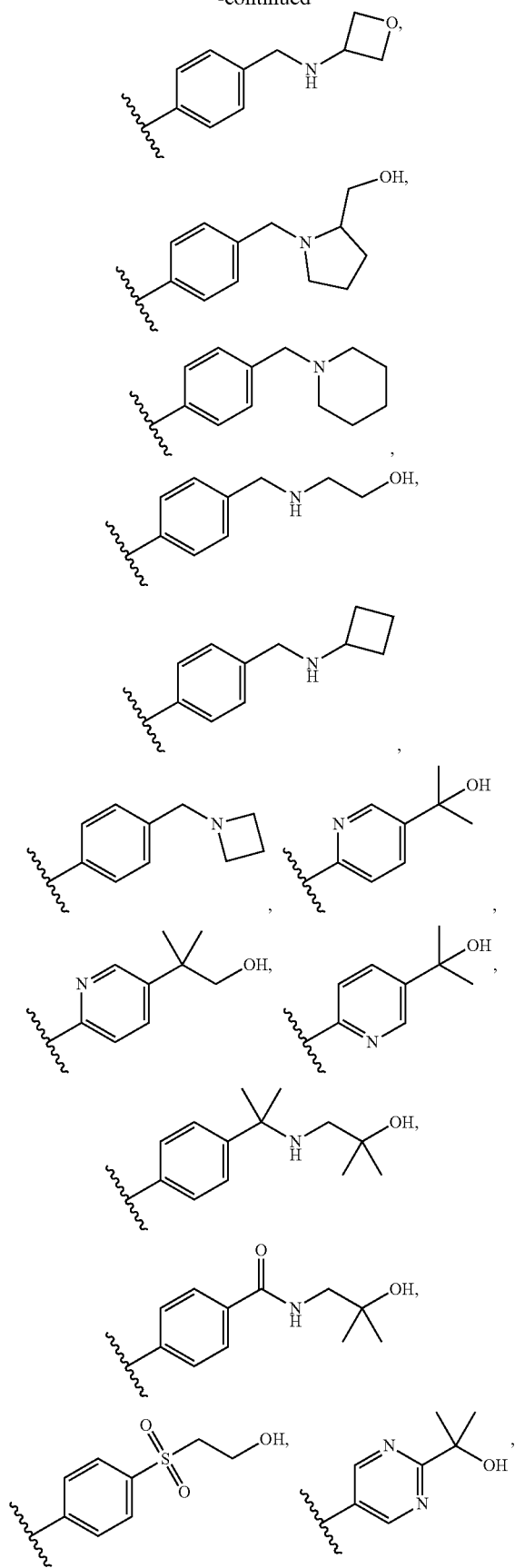
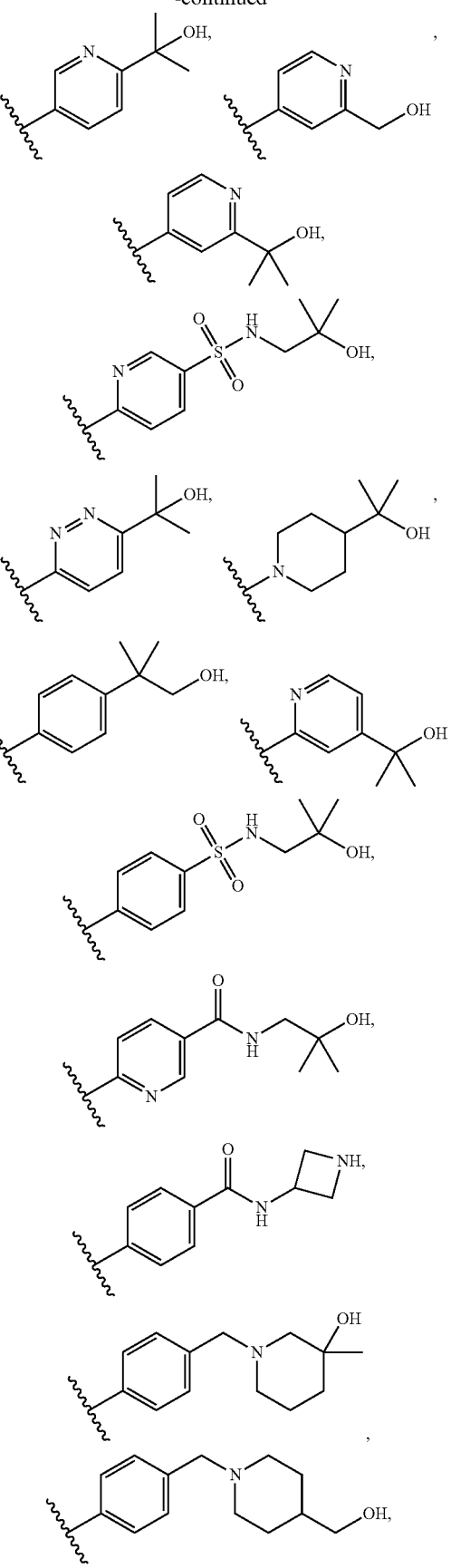

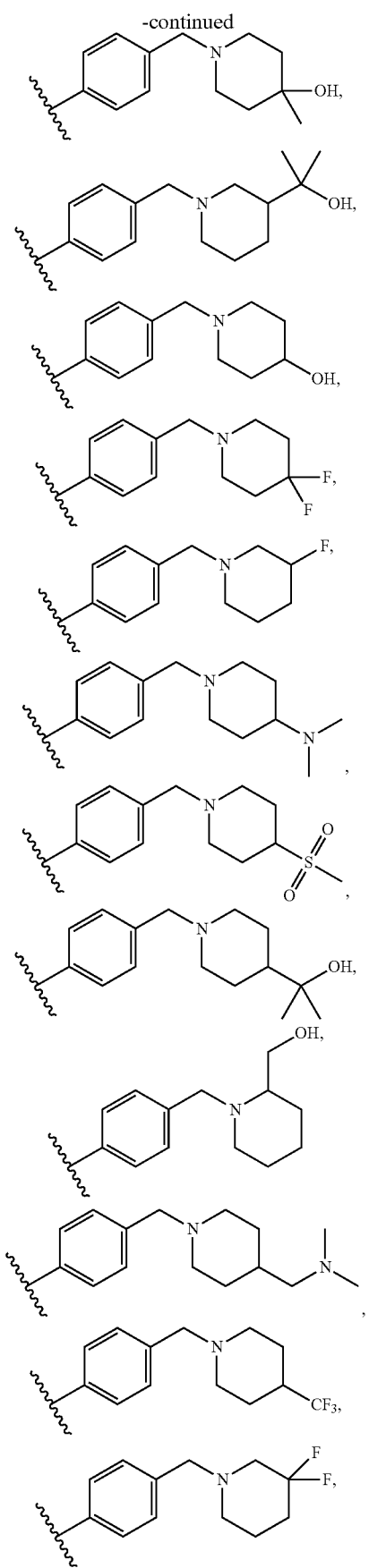
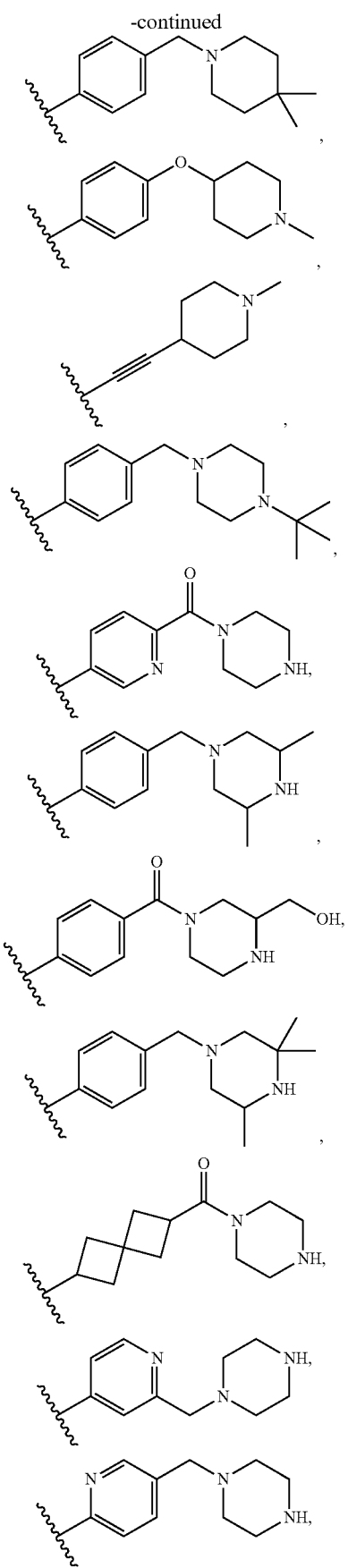

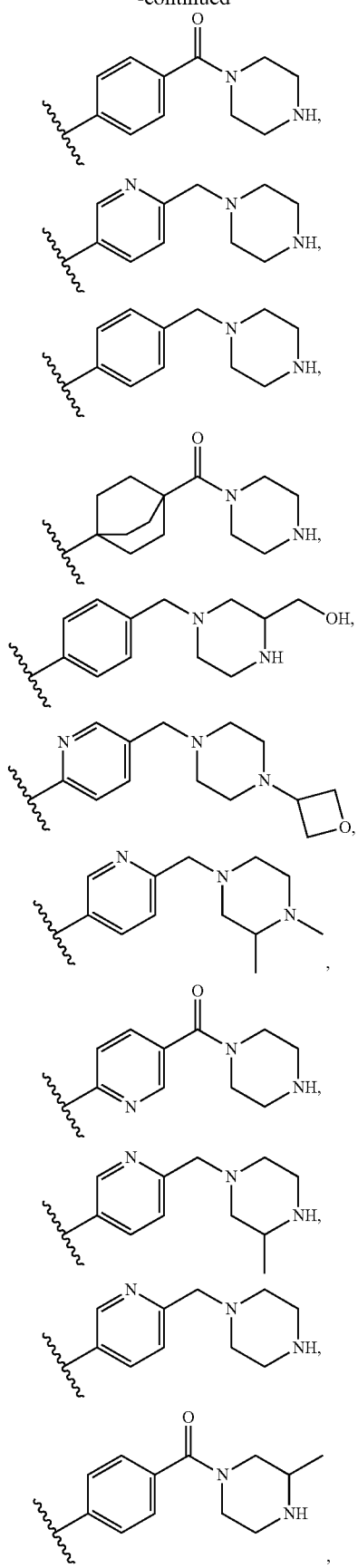
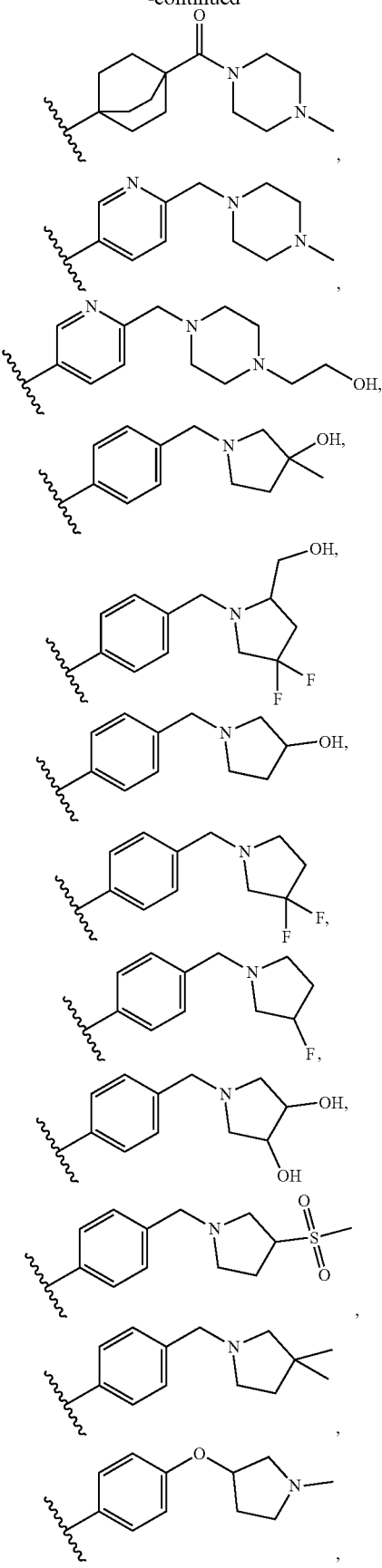

97
-continued
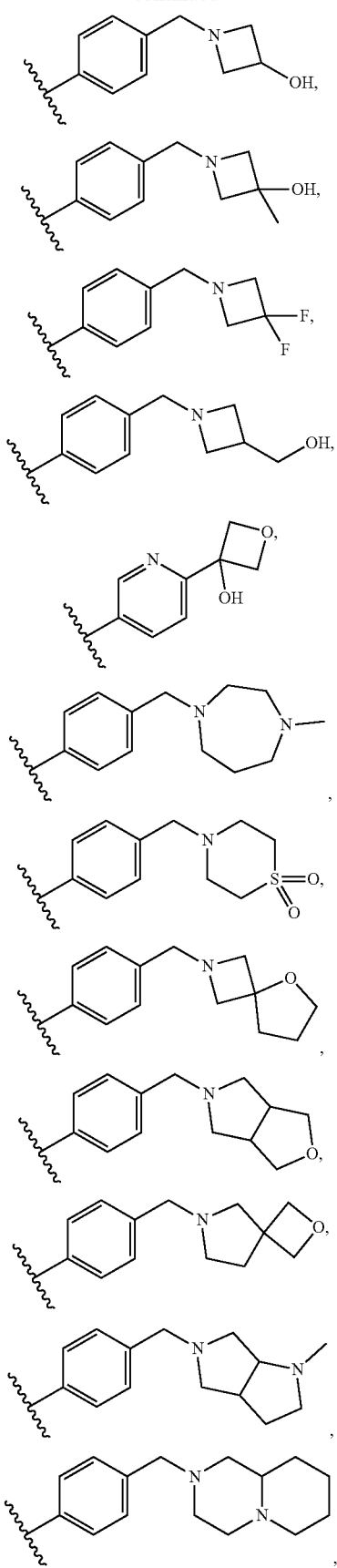
98
-continued
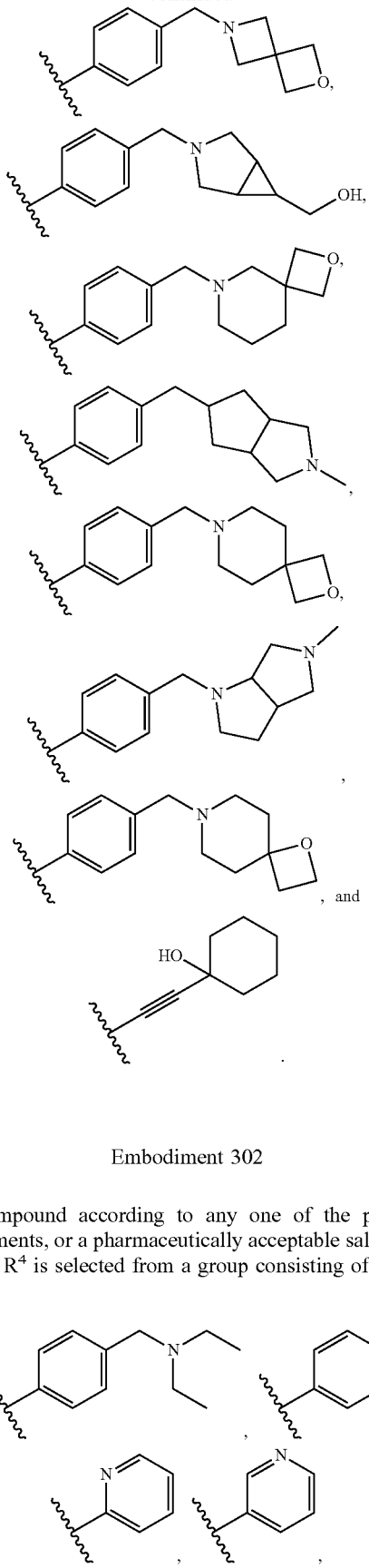
, and
Embodiment 302
A compound according to any one of the preceding embodiments, or a pharmaceutically acceptable salt thereof, wherein $R^4$ is selected from a group consisting of:
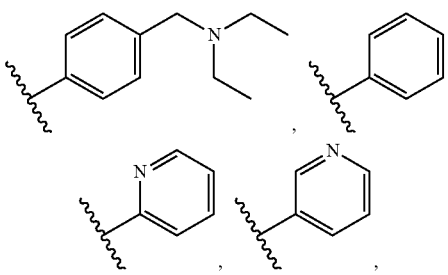

-continued
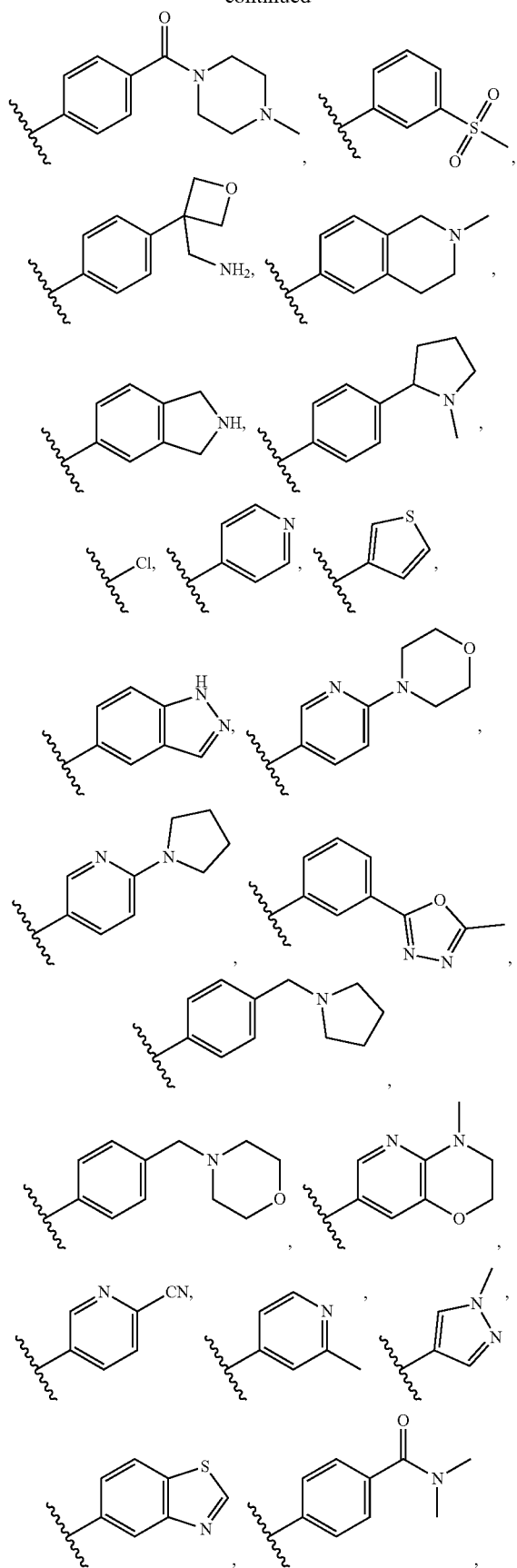
-continued
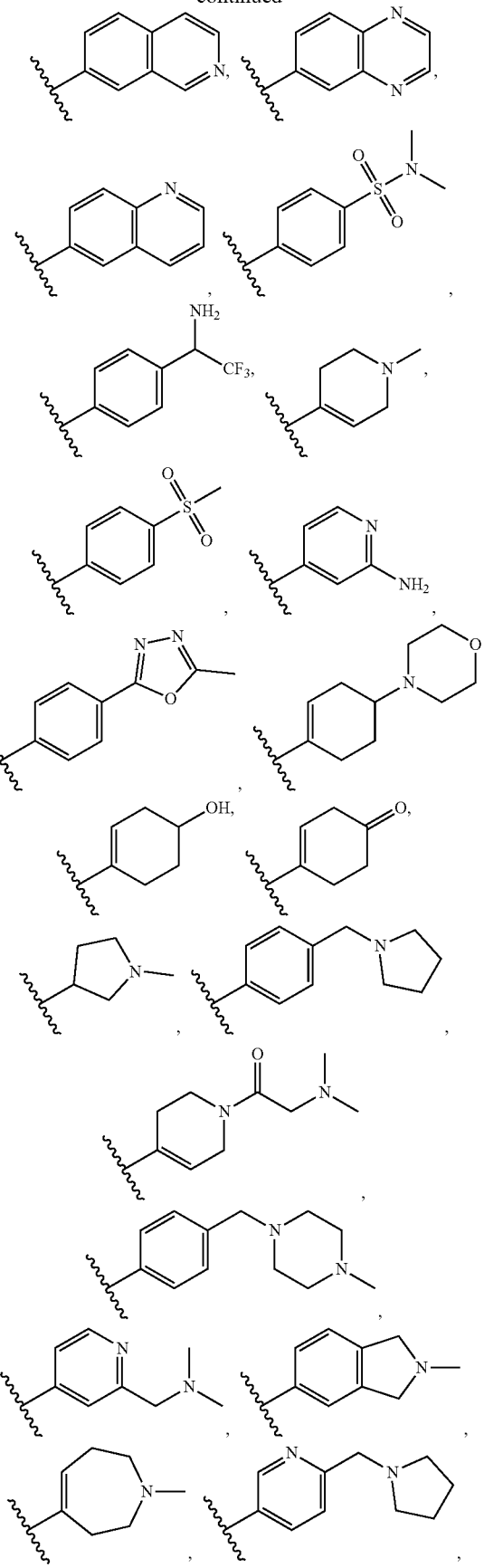

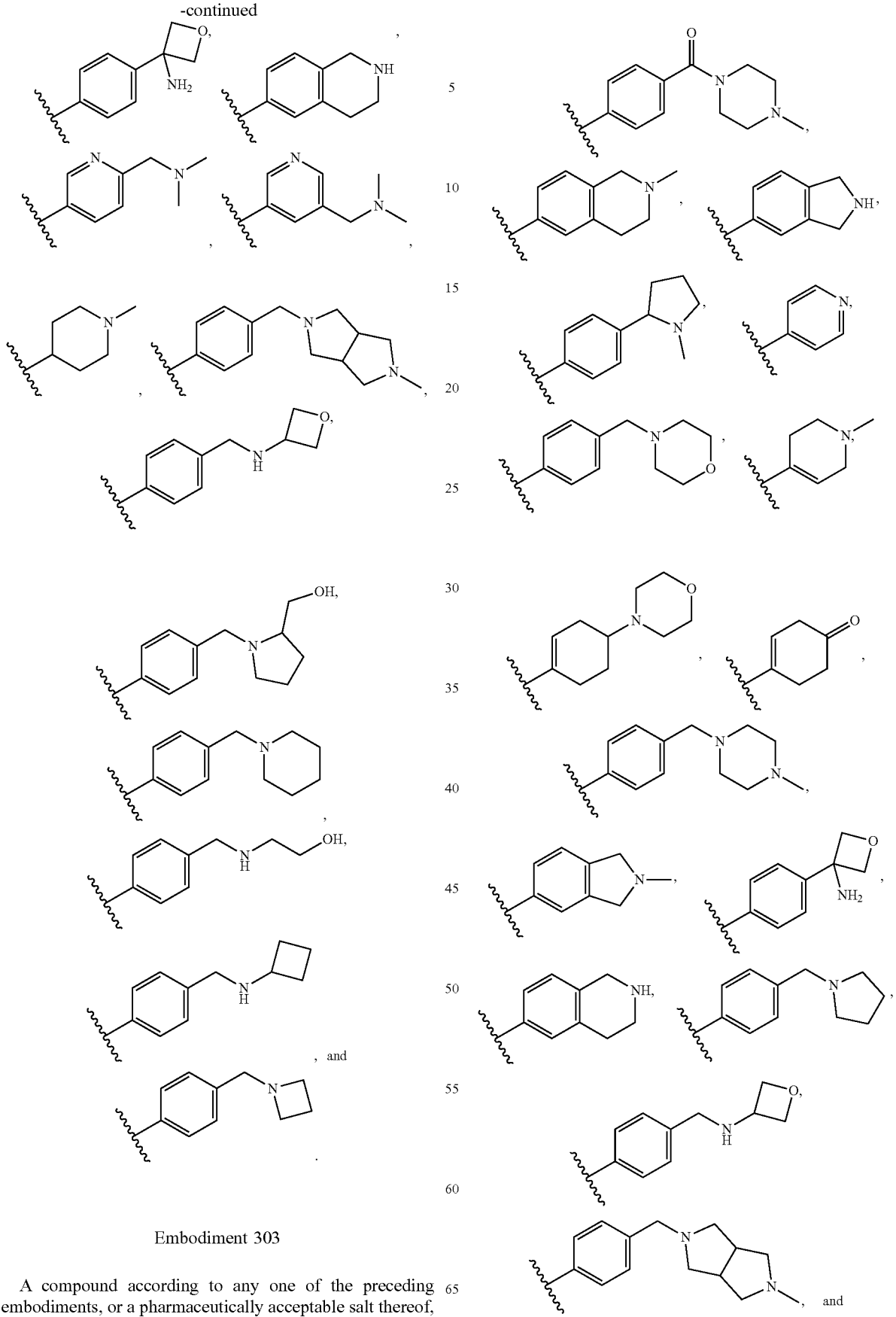
Embodiment 303
A compound according to any one of the preceding embodiments, or a pharmaceutically acceptable salt thereof, wherein $R^4$ is selected from a group consisting of:

-continued

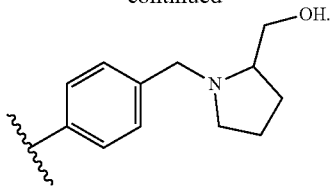

Embodiment 304

A compound according to any one of the preceding embodiments, or a pharmaceutically acceptable salt thereof, wherein $R^4$ is selected from a group consisting of:

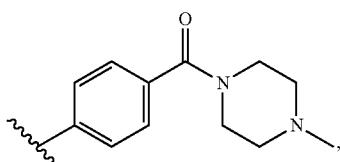

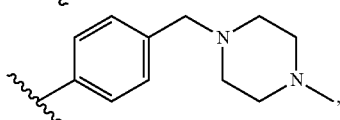

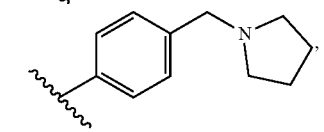

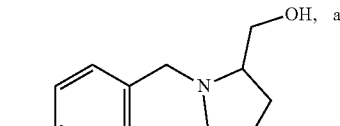

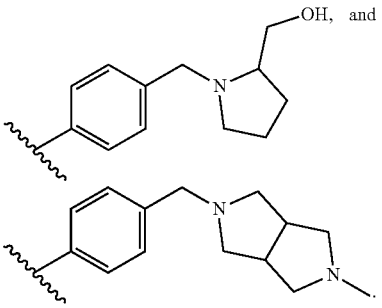

Alternatively, a compound according to any one of the preceding embodiments, or a pharmaceutically acceptable salt thereof, wherein $R^4$ is selected from a group consisting of:

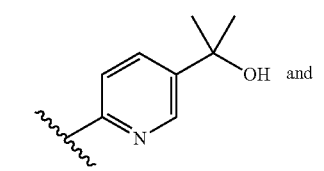

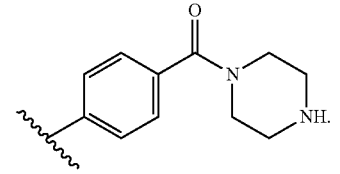

Embodiment 305

A compound according to any one of the preceding embodiments, or a pharmaceutically acceptable salt thereof, wherein $R^4$ is

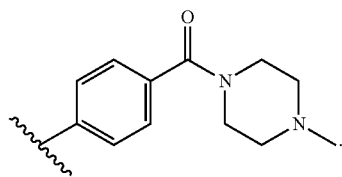 [SMILES: *c1ccc(C(=O)N2CCN(C)CC2)cc1]

Embodiment 306

A compound according to any one of the preceding embodiments, or a pharmaceutically acceptable salt thereof, wherein $R^4$ is

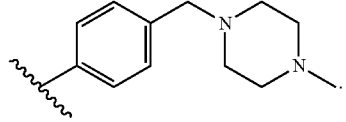 [SMILES: *c1ccc(CN2CCN(C)CC2)cc1]

Embodiment 307

A compound according to any one of the preceding embodiments, or a pharmaceutically acceptable salt thereof, wherein $R^4$ is

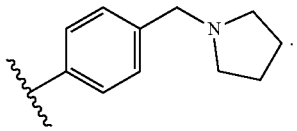 [SMILES: *c1ccc(CN2CCCC2)cc1]

Embodiment 308

A compound according to any one of the preceding embodiments, or a pharmaceutically acceptable salt thereof, wherein $R^4$ is

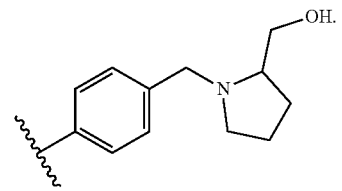 [SMILES: *c1ccc(CN2CCCC2CO)cc1]

Embodiment 309

A compound according to any one of the preceding embodiments, or a pharmaceutically acceptable salt thereof, wherein $R^4$ is

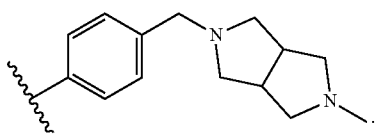 [SMILES: *c1ccc(CN2CC3CN(C)CC3C2)cc1]

Embodiment 310

A compound according to any one of the preceding embodiments, or a pharmaceutically acceptable salt thereof, wherein $R^5$ is H.

Embodiment 311

A compound according to any one of the preceding embodiments, or a pharmaceutically acceptable salt thereof, wherein $R^4$ and $R^5$ together with the carbon atoms to which they are attached form a 5-12 membered carbocyclic, heterocyclic, aryl, heteroaryl, fused heterocyclyl-aryl, fused heterocyclyl-heteroaryl, fused carbocyclyl-aryl, or fused carbocyclyl-heteroaryl ring, wherein said carbocyclic, heterocyclic, aryl, heteroaryl, fused heterocyclyl-aryl, fused heterocyclyl-heteroaryl, fused carbocyclyl-aryl, or fused carbocyclyl-heteroaryl ring is optionally substituted with 1-3 $C_{1-4}$alkyl groups.

Embodiment 312

A compound according to any one of the preceding embodiments, or a pharmaceutically acceptable salt thereof, wherein $R^4$ and $R^5$ together with the carbon atoms to which they are attached form a 5-12 membered carbocyclic ring, wherein said carbocyclic ring is optionally substituted with 1-3 $C_{1-4}$alkyl groups.

Embodiment 313

A compound according to any one of the preceding embodiments, or a pharmaceutically acceptable salt thereof, wherein $R^4$ and $R^5$ together with the carbon atoms to which they are attached form a 5-12 membered heterocyclic ring, wherein said heterocyclic ring is optionally substituted with 1-3 $C_{1-4}$alkyl groups.

Embodiment 314

A compound according to any one of the preceding embodiments, or a pharmaceutically acceptable salt thereof, wherein $R^4$ and $R^5$ together with the carbon atoms to which they are attached form a 5-12 membered aryl ring, wherein said aryl ring is optionally substituted with 1-3 $C_{1-4}$alkyl groups.

Embodiment 315

A compound according to any one of the preceding embodiments, or a pharmaceutically acceptable salt thereof, wherein $R^4$ and $R^5$ together with the carbon atoms to which they are attached form a 5-12 membered heteroaryl ring, wherein said heteroaryl ring is optionally substituted with 1-3 $C_{1-4}$alkyl groups.

Embodiment 316

A compound according to any one of the preceding embodiments, or a pharmaceutically acceptable salt thereof, wherein $R^4$ and $R^5$ together with the carbon atoms to which they are attached form a 5-12 membered fused heterocyclyl-aryl ring, wherein said fused heterocyclyl-aryl ring is optionally substituted with 1-3 $C_{1-4}$alkyl groups.

Embodiment 317

A compound according to any one of the preceding embodiments, or a pharmaceutically acceptable salt thereof, wherein $R^4$ and $R^5$ together with the carbon atoms to which they are attached form a 5-12 membered fused heterocyclyl-heteroaryl ring, wherein said fused heterocyclyl-heteroaryl ring is optionally substituted with 1-3 $C_{1-4}$alkyl groups.

Embodiment 318

A compound according to any one of the preceding embodiments, or a pharmaceutically acceptable salt thereof, wherein $R^4$ and $R^5$ together with the carbon atoms to which they are attached form a 5-12 membered fused carbocyclyl-aryl ring, wherein said fused carbocyclyl-aryl ring is optionally substituted with 1-3 $C_{1-4}$alkyl groups.

Embodiment 319

A compound according to any one of the preceding embodiments, or a pharmaceutically acceptable salt thereof, wherein $R^4$ and $R^5$ together with the carbon atoms to which they are attached form a 5-12 membered fused carbocyclyl-heteroaryl ring, wherein said fused carbocyclyl-heteroaryl ring is optionally substituted with 1-3 $C_{1-4}$alkyl groups.

Embodiment 320

A compound according to any one of the preceding embodiments, or a pharmaceutically acceptable salt thereof, wherein $R^4$ and $R^5$ together with the carbon atoms to which they are attached form

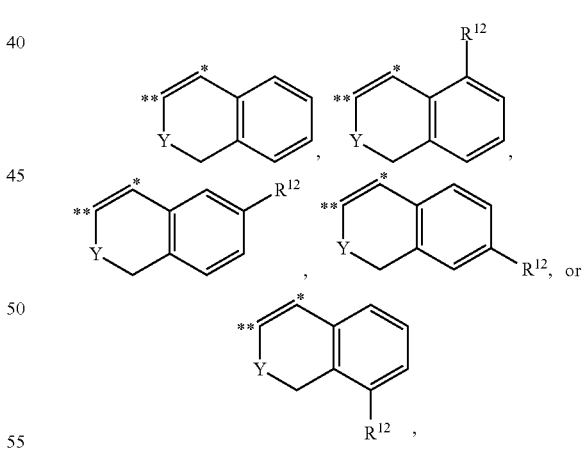

wherein the carbon atom designated * is the carbon atom bearing $R^4$, and the carbon atom designated ** is the carbon atom bearing $R^5$; wherein Y is $CH_2$, O, $NR^{13}$, or S; $R^{12}$ is $C_{1-4}$alkyl; and $R^{13}$ is H or $C_{1-4}$alkyl.

Embodiment 321

A compound according to any one of the preceding embodiments, or a pharmaceutically acceptable salt thereof, wherein $R^4$ and $R^5$ together with the carbon atoms to which they are attached form

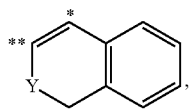

wherein the carbon atom designated * is the carbon atom bearing $R^4$, and the carbon atom designated ** is the carbon atom bearing $R^5$; wherein Y is $CH_2$, O, $NR^{13}$, or S; $R^{12}$ is $C_{1-4}$alkyl; and $R^{13}$ is H or $C_{1-4}$alkyl.

Embodiment 322

A compound according to any one of the preceding embodiments, or a pharmaceutically acceptable salt thereof, wherein $R^4$ and $R^5$ together with the carbon atoms to which they are attached form

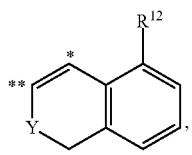

wherein the carbon atom designated * is the carbon atom bearing $R^4$, and the carbon atom designated ** is the carbon atom bearing $R^5$; wherein Y is $CH_2$, O, $NR^{13}$, or S; $R^{12}$ is $C_{1-4}$alkyl; and $R^{13}$ is H or $C_{1-4}$alkyl.

Embodiment 323

A compound according to any one of the preceding embodiments, or a pharmaceutically acceptable salt thereof, wherein $R^4$ and $R^5$ together with the carbon atoms to which they are attached form

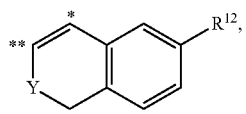

wherein the carbon atom designated * is the carbon atom bearing $R^4$, and the carbon atom designated ** is the carbon atom bearing $R^5$; wherein Y is $CH_2$, O, $NR^{13}$, or S; $R^{12}$ is $C_{1-4}$alkyl; and $R^{13}$ is H or $C_{1-4}$alkyl.

Embodiment 324

A compound according to any one of the preceding embodiments, or a pharmaceutically acceptable salt thereof, wherein $R^4$ and $R^5$ together with the carbon atoms to which they are attached form

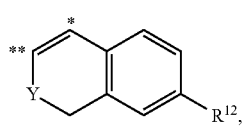

wherein the carbon atom designated * is the carbon atom bearing $R^4$, and the carbon atom designated ** is the carbon atom bearing $R^5$; wherein Y is $CH_2$, O, $NR^{13}$, or S; $R^{12}$ is $C_{1-4}$alkyl; and $R^{13}$ is H or $C_{1-4}$alkyl.

Embodiment 325

A compound according to any one of the preceding embodiments, or a pharmaceutically acceptable salt thereof, wherein $R^4$ and $R^5$ together with the carbon atoms to which they are attached form

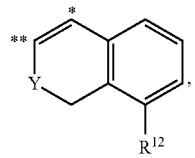

wherein the carbon atom designated * is the carbon atom bearing $R^4$, and the carbon atom designated ** is the carbon atom bearing $R^5$; wherein Y is $CH_2$, O, $NR^{13}$, or S; $R^{12}$ is $C_{1-4}$alkyl; and $R^{13}$ is H or $C_{1-4}$alkyl.

Embodiment 326

A compound according to any one of the preceding embodiments, or a pharmaceutically acceptable salt thereof, wherein $R^4$ and $R^5$ together with the carbon atoms to which they are attached form

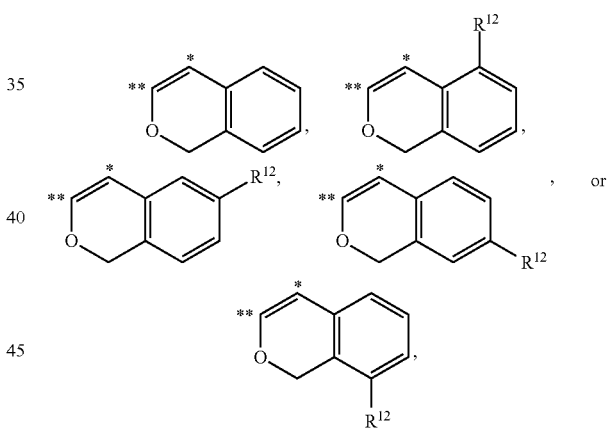

wherein the carbon atom designated * is the carbon atom bearing $R^4$, and the carbon atom designated ** is the carbon atom bearing $R^5$; wherein $R^{12}$ is $C_{1-4}$alkyl.

Embodiment 327

A compound according to any one of the preceding embodiments, or a pharmaceutically acceptable salt thereof, wherein $R^4$ and $R^5$ together with the carbon atoms to which they are attached form

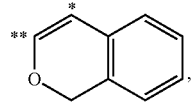

wherein the carbon atom designated * is the carbon atom bearing $R^4$, and the carbon atom designated ** is the carbon atom bearing $R^5$.

Embodiment 328

A compound according to any one of the preceding embodiments, or a pharmaceutically acceptable salt thereof, wherein $R^4$ and $R^5$ together with the carbon atoms to which they are attached form

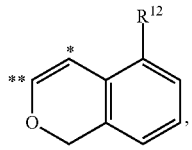

wherein the carbon atom designated * is the carbon atom bearing $R^4$, and the carbon atom designated ** is the carbon atom bearing $R^5$; wherein $R^{12}$ is $C_{1-4}$alkyl.

Embodiment 329

A compound according to any one of the preceding embodiments, or a pharmaceutically acceptable salt thereof, wherein $R^4$ and $R^5$ together with the carbon atoms to which they are attached form

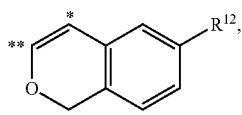

wherein the carbon atom designated * is the carbon atom bearing $R^4$, and the carbon atom designated ** is the carbon atom bearing $R^5$; wherein $R^{12}$ is $C_{1-4}$alkyl.

Embodiment 330

A compound according to any one of the preceding embodiments, or a pharmaceutically acceptable salt thereof, wherein $R^4$ and $R^5$ together with the carbon atoms to which they are attached form

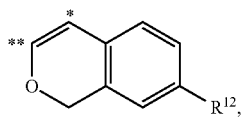

wherein the carbon atom designated * is the carbon atom bearing $R^4$, and the carbon atom designated ** is the carbon atom bearing $R^5$; wherein $R^{12}$ is $C_{1-4}$alkyl.

Embodiment 331

A compound according to any one of the preceding embodiments, or a pharmaceutically acceptable salt thereof, wherein $R^4$ and $R^5$ together with the carbon atoms to which they are attached form

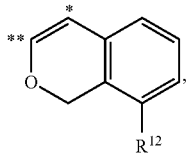

wherein the carbon atom designated * is the carbon atom bearing $R^4$, and the carbon atom designated ** is the carbon atom bearing $R^5$; wherein $R^{12}$ is $C_{1-4}$alkyl.

Embodiment 332

A compound according to any one of the preceding embodiments, or a pharmaceutically acceptable salt thereof, wherein $R^7$ is selected from a group consisting of H, $C_{1-4}$alkyl, $C_{1-4}$hydroxyalkyl, a 4-6 membered heterocyclyl, and a 4-6 membered cycloalkyl.

Embodiment 333

A compound according to any one of the preceding embodiments, or a pharmaceutically acceptable salt thereof, wherein $R^7$ is selected from a group consisting of H, $C_{1-4}$alkyl, $C_{1-4}$hydroxyalkyl, 2-oxetanyl, 3-oxetanyl, 2-tetrahydrofuranyl, 3-tetrahydrofuranyl, 2-tetrahydropyranyl, 3-tetrahydropyranyl, 4-tetrahydropyranyl, 2-azetidinyl, 3-azetidinyl, 2-pyrrolidinyl, 3-pyrrolidinyl, 2-piperidinyl, 3-piperidinyl, 4-piperidinyl, 2-morpholinyl, 3-morpholinyl, 2-piperazinyl, cyclobutyl, cyclopentyl, and cyclohexyl.

Embodiment 334

A compound according to any one of the preceding embodiments, or a pharmaceutically acceptable salt thereof, wherein $R^7$ is selected from a group consisting of H, $C_{1-4}$alkyl, $C_{1-4}$hydroxyalkyl, 3-oxetanyl, and cyclobutyl.

Embodiment 335

A compound according to any one of the preceding embodiments, or a pharmaceutically acceptable salt thereof, wherein $R^7$ is H.

Embodiment 336

A compound according to any one of the preceding embodiments, or a pharmaceutically acceptable salt thereof, wherein $R^7$ is $C_{1-4}$alkyl.

Embodiment 337

A compound according to any one of the preceding embodiments, or a pharmaceutically acceptable salt thereof, wherein $R^7$ is $CH_3$.

Embodiment 338

A compound according to any one of the preceding embodiments, or a pharmaceutically acceptable salt thereof, wherein $R^7$ is $CH_2CH_3$.

Embodiment 339

A compound according to any one of the preceding embodiments, or a pharmaceutically acceptable salt thereof, wherein $R^7$ is $C_{1-4}$hydroxyalkyl.

Embodiment 340

A compound according to any one of the preceding embodiments, or a pharmaceutically acceptable salt thereof, wherein $R^7$ is $CH_2CH_2OH$.

Embodiment 341

A compound according to any one of the preceding embodiments, or a pharmaceutically acceptable salt thereof, wherein $R^7$ is $CH_2C(CH_3)_2OH$.

Embodiment 342

A compound according to any one of the preceding embodiments, or a pharmaceutically acceptable salt thereof, wherein $R^7$ is a 4-6 membered heterocyclyl.

Embodiment 343

A compound according to any one of the preceding embodiments, or a pharmaceutically acceptable salt thereof, wherein $R^7$ is 2-oxetanyl, 3-oxetanyl, 2-tetrahydrofuranyl, 3-tetrahydrofuranyl, 2-tetrahydropyranyl, 3-tetrahydropyranyl, 4-tetrahydropyranyl, 2-azetidinyl, 3-azetidinyl, 2-pyrrolidinyl, 3-pyrrolidinyl, 2-piperidinyl, 3-piperidinyl, 4-piperidinyl, 2-morpholinyl, 3-morpholinyl, or 2-piperazinyl.

Embodiment 344

A compound according to any one of the preceding embodiments, or a pharmaceutically acceptable salt thereof, wherein $R^7$ is 3-oxetanyl.

Embodiment 345

A compound according to any one of the preceding embodiments, or a pharmaceutically acceptable salt thereof, wherein $R^7$ is 3-azetidinyl.

Embodiment 346

A compound according to any one of the preceding embodiments, or a pharmaceutically acceptable salt thereof, wherein $R^7$ is a 4-6 membered cycloalkyl.

Embodiment 347

A compound according to any one of the preceding embodiments, or a pharmaceutically acceptable salt thereof, wherein $R^7$ is cyclobutyl, cyclopentyl, or cyclohexyl.

Embodiment 348

A compound according to any one of the preceding embodiments, or a pharmaceutically acceptable salt thereof, wherein $R^7$ is cyclobutyl.

Embodiment 349

A compound according to any one of the preceding embodiments, or a pharmaceutically acceptable salt thereof, wherein $R^8$ is selected from a group consisting of H, $C_{1-4}$alkyl, $C_{1-4}$hydroxyalkyl, a 4-6 membered heterocyclyl, and a 4-6 membered cycloalkyl.

Embodiment 350

A compound according to any one of the preceding embodiments, or a pharmaceutically acceptable salt thereof, wherein $R^8$ is selected from a group consisting of H, $C_{1-4}$alkyl, $C_{1-4}$hydroxyalkyl, 2-oxetanyl, 3-oxetanyl, 2-tetrahydrofuranyl, 3-tetrahydrofuranyl, 2-tetrahydropyranyl, 3-tetrahydropyranyl, 4-tetrahydropyranyl, 2-azetidinyl, 3-azetidinyl, 2-pyrrolidinyl, 3-pyrrolidinyl, 2-piperidinyl, 3-piperidinyl, 4-piperidinyl, 2-morpholinyl, 3-morpholinyl, 2-piperazinyl, cyclobutyl, cyclopentyl, and cyclohexyl.

Embodiment 351

A compound according to any one of the preceding embodiments, or a pharmaceutically acceptable salt thereof, wherein $R^8$ is selected from a group consisting of H, $C_{1-4}$alkyl, $C_{1-4}$hydroxyalkyl, 3-oxetanyl, and cyclobutyl.

Embodiment 352

A compound according to any one of the preceding embodiments, or a pharmaceutically acceptable salt thereof, wherein $R^8$ is H.

Embodiment 353

A compound according to any one of the preceding embodiments, or a pharmaceutically acceptable salt thereof, wherein $R^8$ is $C_{1-4}$alkyl.

Embodiment 354

A compound according to any one of the preceding embodiments, or a pharmaceutically acceptable salt thereof, wherein $R^8$ is $CH_3$.

Embodiment 355

A compound according to any one of the preceding embodiments, or a pharmaceutically acceptable salt thereof, wherein $R^8$ is $CH_2CH_3$.

Embodiment 356

A compound according to any one of the preceding embodiments, or a pharmaceutically acceptable salt thereof, wherein $R^8$ is $C_{1-4}$hydroxyalkyl.

Embodiment 357

A compound according to any one of the preceding embodiments, or a pharmaceutically acceptable salt thereof, wherein $R^8$ is $CH_2CH_2OH$.

Embodiment 358

A compound according to any one of the preceding embodiments, or a pharmaceutically acceptable salt thereof, wherein $R^8$ is $CH_2C(CH_3)_2OH$.

Embodiment 359

A compound according to any one of the preceding embodiments, or a pharmaceutically acceptable salt thereof, wherein $R^8$ is a 4-6 membered heterocyclyl.

Embodiment 360

A compound according to any one of the preceding embodiments, or a pharmaceutically acceptable salt thereof, wherein $R^8$ is 2-oxetanyl, 3-oxetanyl, 2-tetrahydrofuranyl, 3-tetrahydrofuranyl, 2-tetrahydropyranyl, 3-tetrahydropyranyl, 4-tetrahydropyranyl, 2-azetidinyl, 3-azetidinyl, 2-pyrrolidinyl, 3-pyrrolidinyl, 2-piperidinyl, 3-piperidinyl, 4-piperidinyl, 2-morpholinyl, 3-morpholinyl, or 2-piperazinyl.

Embodiment 361

A compound according to any one of the preceding embodiments, or a pharmaceutically acceptable salt thereof, wherein $R^8$ is 3-oxetanyl.

Embodiment _

A compound according to any one of the preceding embodiments, or a pharmaceutically acceptable salt thereof, wherein $R^8$ is 3-azetidinyl.

Embodiment 362

A compound according to any one of the preceding embodiments, or a pharmaceutically acceptable salt thereof, wherein $R^8$ is a 4-6 membered cycloalkyl.

Embodiment 363

A compound according to any one of the preceding embodiments, or a pharmaceutically acceptable salt thereof, wherein $R^8$ is cyclobutyl, cyclopentyl, or cyclohexyl.

Embodiment 364

A compound according to any one of the preceding embodiments, or a pharmaceutically acceptable salt thereof, wherein $R^8$ is cyclobutyl.

Embodiment 365

A compound according to any one of the preceding embodiments, or a pharmaceutically acceptable salt thereof, wherein $R^9$ is $CH_3$.

Embodiment 366

A compound according to any one of the preceding embodiments, or a pharmaceutically acceptable salt thereof, wherein $R^{10}$ is selected from a group consisting of F, —OH, —$NR^7R^8$, $CH_3$, $C(CH_3)_3$, $CF_3$, —$CH_2OH$, —$CH_2CH_2OH$, —$C(CH_3)_2OH$, —$CH_2NR^7R^8$, —$SO_2CH_3$, and 3-oxetanyl.

Embodiment 367

A compound according to any one of the preceding embodiments, or a pharmaceutically acceptable salt thereof, wherein $R^{10}$ is selected from a group consisting of —$NR^7R^8$, $CH_3$, —$CH_2OH$, and —$CH_2NR^7R^8$.

Embodiment 368

A compound according to any one of the preceding embodiments, or a pharmaceutically acceptable salt thereof, wherein $R^{10}$ is halo.

Embodiment 369

A compound according to any one of the preceding embodiments, or a pharmaceutically acceptable salt thereof, wherein $R^{10}$ is F.

Embodiment 370

A compound according to any one of the preceding embodiments, or a pharmaceutically acceptable salt thereof, wherein $R^{10}$ is —OH.

Embodiment 371

A compound according to any one of the preceding embodiments, or a pharmaceutically acceptable salt thereof, wherein $R^{10}$ is —$NR^7R^8$.

Embodiment 372

A compound according to any one of the preceding embodiments, or a pharmaceutically acceptable salt thereof, wherein $R^{10}$ is $C_{1-4}$alkyl.

Embodiment 373

A compound according to any one of the preceding embodiments, or a pharmaceutically acceptable salt thereof, wherein $R^{10}$ is $CH_3$.

Embodiment 374

A compound according to any one of the preceding embodiments, or a pharmaceutically acceptable salt thereof, wherein $R^{10}$ is $C(CH_3)_3$.

Embodiment 375

A compound according to any one of the preceding embodiments, or a pharmaceutically acceptable salt thereof, wherein $R^{10}$ is $C_{1-4}$haloalkyl.

Embodiment 376

A compound according to any one of the preceding embodiments, or a pharmaceutically acceptable salt thereof, wherein $R^{10}$ is $CF_3$.

Embodiment 377

A compound according to any one of the preceding embodiments, or a pharmaceutically acceptable salt thereof, wherein $R^{10}$ is $C_{1-4}$hydroxyalkyl.

Embodiment 378

A compound according to any one of the preceding embodiments, or a pharmaceutically acceptable salt thereof, wherein $R^{10}$ is $CH_2OH$.

Embodiment 379

A compound according to any one of the preceding embodiments, or a pharmaceutically acceptable salt thereof, wherein $R^{10}$ is —$CH_2CH_2OH$.

Embodiment 380

A compound according to any one of the preceding embodiments, or a pharmaceutically acceptable salt thereof, wherein $R^{10}$ is —$C(CH_3)_2OH$.

Embodiment 381

A compound according to any one of the preceding embodiments, or a pharmaceutically acceptable salt thereof, wherein $R^{10}$ is —$C_{1-4}$alkyl-$NR^7R^8$.

Embodiment 382

A compound according to any one of the preceding embodiments, or a pharmaceutically acceptable salt thereof, wherein $R^{10}$ is —$CH_2NR^7R^8$.

Embodiment 383

A compound according to any one of the preceding embodiments, or a pharmaceutically acceptable salt thereof, wherein $R^{11}$ is $C_{1-4}$alkyl.

Embodiment 384

A compound according to any one of the preceding embodiments, or a pharmaceutically acceptable salt thereof, wherein $R^{10}$ is —$SO_2C_{1-4}$alkyl.

Embodiment 385

A compound according to any one of the preceding embodiments, or a pharmaceutically acceptable salt thereof, wherein $R^{10}$ is —$SO_2CH_3$.

Embodiment 386

A compound according to any one of the preceding embodiments, or a pharmaceutically acceptable salt thereof, wherein $R^{10}$ is 4-6 membered heterocyclyl.

Embodiment 387

A compound according to any one of the preceding embodiments, or a pharmaceutically acceptable salt thereof, wherein $R^{10}$ is 3-oxetanyl.

Embodiment 388

A compound according to any one of the preceding embodiments, or a pharmaceutically acceptable salt thereof, wherein $R^{11}$ is $CH_3$.

Embodiment 389

A compound according to any one of the preceding embodiments, or a pharmaceutically acceptable salt thereof, wherein $R^{14}$ is OH.

Embodiment 390

A compound according to any one of the preceding embodiments, or a pharmaceutically acceptable salt thereof, wherein m is 0.

Embodiment 391

A compound according to any one of the preceding embodiments, or a pharmaceutically acceptable salt thereof, wherein m is 1.

Embodiment 392

A compound according to any one of the preceding embodiments, or a pharmaceutically acceptable salt thereof, wherein n is 0.

Embodiment 393

A compound according to any one of the preceding embodiments, or a pharmaceutically acceptable salt thereof, wherein n is 1.

Embodiment 394

A compound according to any one of the preceding embodiments, or a pharmaceutically acceptable salt thereof, wherein p is 0.

Embodiment 395

A compound according to any one of the preceding embodiments, or a pharmaceutically acceptable salt thereof, wherein p is 1.

Embodiment 396

A compound according to any one of the preceding embodiments, or a pharmaceutically acceptable salt thereof, wherein q is 0.

Embodiment 397

A compound according to any one of the preceding embodiments, or a pharmaceutically acceptable salt thereof, wherein q is 1.

Embodiment 398

A compound according to any one of the preceding embodiments, or a pharmaceutically acceptable salt thereof, wherein q is 2.

Embodiment 399

A compound according to any one of the preceding embodiments, or a pharmaceutically acceptable salt thereof, wherein q is 3.

Embodiment 400

A compound according to any one of the preceding embodiments, or a pharmaceutically acceptable salt thereof, wherein r is 0.

Embodiment 401

A compound according to any one of the preceding embodiments, or a pharmaceutically acceptable salt thereof, wherein r is 1.

Embodiment 402

A compound according to any one of the preceding embodiments, or a pharmaceutically acceptable salt thereof, wherein r is 2.

Embodiment 403

A compound according to any one of the preceding embodiments, or a pharmaceutically acceptable salt thereof, wherein s is 0.

Embodiment 404

A compound according to any one of the preceding embodiments, or a pharmaceutically acceptable salt thereof, wherein s is 1.

Embodiment 405

A compound according to any one of the preceding embodiments, or a pharmaceutically acceptable salt thereof, wherein t is 0.

Embodiment 406

A compound according to any one of the preceding embodiments, or a pharmaceutically acceptable salt thereof, wherein t is 1.

Embodiment 407

A compound according to any one of the preceding embodiments, or a pharmaceutically acceptable salt thereof, wherein t is 2.

Embodiment 408

A compound according to embodiment 1, or a pharmaceutically acceptable salt thereof, wherein the compound is selected from a group consisting of:
1-(4-(2-(4-chlorophenyl)propan-2-yl)phenyl)-5-methyl-1H-1,2,4-triazole-3-carboxamide;
1-(4-((6H-benzo[c]chromen-3-yl)methyl)phenyl)-5-methyl-1H-pyrazole-3-carboxamide;
5-methyl-1-(4-((4'-(pyrrolidin-1-ylmethyl)-[1,1'-biphenyl]-4-yl)methyl)phenyl)-1H-pyrazole-3-carboxamide;
1-(4-((4'-((diethylamino)methyl)-[1,1'-biphenyl]-4-yl)methyl)phenyl)-5-methyl-1H-pyrazole-3-carboxamide;
5-methyl-1-(4-(4-(2-methyl-1,2,3,4-tetrahydroisoquinolin-6-yl)benzyl)phenyl)-1H-pyrazole-3-carboxamide;
1-(4-(4-(isoindolin-5-yl)benzyl)phenyl)-5-methyl-1H-pyrazole-3-carboxamide;
5-methyl-1-(4-(4-(pyridin-4-yl)benzyl)phenyl)-1H-pyrazole-3-carboxamide;
5-methyl-1-(4-((4'-(methylsulfonyl)-[1,1'-biphenyl]-4-yl)methyl)phenyl)-1H-pyrazole-3-carboxamide;
5-methyl-1-(4-((3'-(5-methyl-1,3,4-oxadiazol-2-yl)-[1,1'-biphenyl]-4-yl)methyl)phenyl)-1H-pyrazole-3-carboxamide;
1-(4-([1,1'-biphenyl]-4-ylmethyl)phenyl)-5-methyl-1H-pyrazole-3-carboxamide;
5-methyl-1-(4-((4'-(5-methyl-1,3,4-oxadiazol-2-yl)-[1,1'-biphenyl]-4-yl)methyl)phenyl)-1H-pyrazole-3-carboxamide;
5-methyl-1-(4-(4-(pyridin-3-yl)benzyl)phenyl)-1H-pyrazole-3-carboxamide;
1-(4-(4-(1-(dimethylglycyl)-1,2,3,6-tetrahydropyridin-4-yl)benzyl)phenyl)-5-methyl-1H-pyrazole-3-carboxamide;
5-methyl-1-(4-((4'-((4-methylpiperazin-1-yl)methyl)-[1,1'-biphenyl]-4-yl)methyl)phenyl)-1H-pyrazole-3-carboxamide;
5-methyl-1-(4-(4-(2-methylisoindolin-5-yl)benzyl)phenyl)-1H-pyrazole-3-carboxamide;
5-methyl-1-(4-(4-(1,2,3,4-tetrahydroisoquinolin-6-yl)benzyl)phenyl)-1H-pyrazole-3-carboxamide;
5-methyl-1-(4-(4-(1-methyl-1,2,3,6-tetrahydropyridin-4-yl)benzyl)phenyl)-1H-pyrazole-3-carboxamide;
5-methyl-1-(4-(4-(1-methylpiperidin-4-yl)benzyl)phenyl)-1H-pyrazole-3-carboxamide;
5-methyl-1-(4-(4-(1-methylpyrrolidin-3-yl)benzyl)phenyl)-1H-pyrazole-3-carboxamide;
(R)-5-methyl-1-(4-(4-(1-methylpyrrolidin-3-yl)benzyl)phenyl)-1H-pyrazole-3-carboxamide;
(S)-5-methyl-1-(4-(4-(1-methylpyrrolidin-3-yl)benzyl)phenyl)-1H-pyrazole-3-carboxamide;
1-(4-(4-(6-((dimethylamino)methyl)pyridin-3-yl)benzyl)phenyl)-5-methyl-1H-pyrazole-3-carboxamide;
1-(4-(4-(2-((dimethylamino)methyl)pyridin-4-yl)benzyl)phenyl)-5-methyl-1H-pyrazole-3-carboxamide;
5-methyl-1-(4-(4-(6-(pyrrolidin-1-ylmethyl)pyridin-3-yl)benzyl)phenyl)-1H-pyrazole-3-carboxamide;
1-(4-(4-(5-((dimethylamino)methyl)pyridin-3-yl)benzyl)phenyl)-5-methyl-1H-pyrazole-3-carboxamide;
5-methyl-1-(4-(4-(1-methyl-2,3,6,7-tetrahydro-1H-azepin-4-yl)benzyl)phenyl)-1H-pyrazole-3-carboxamide;
5-methyl-1-(4-((4'-(1-methylpyrrolidin-2-yl)-[1,1'-biphenyl]-4-yl)methyl)phenyl)-1H-pyrazole-3-carboxamide;
(S)-5-methyl-1-(4-((4'-(1-methyl pyrrolidin-2-yl)-[1,1'-biphenyl]-4-yl)methyl)phenyl)-1H-pyrazole-3-carboxamide;
5-methyl-1-(4-(2-(4'-(pyrrolidin-1-ylmethyl)-[1,1'-biphenyl]-4-yl)propan-2-yl)phenyl)-1H-pyrazole-3-carboxamide;
5-methyl-1-(4-(2-(3'-(methylsulfonyl)-[1,1'-biphenyl]-4-yl)propan-2-yl)phenyl)-1H-pyrazole-3-carboxamide;
5-methyl-1-(4-(2-(4-(pyridin-4-yl)phenyl)propan-2-yl)phenyl)-1H-pyrazole-3-carboxamide;
1-(4-(2-(4-(1H-indazol-5-yl)phenyl)propan-2-yl)phenyl)-5-methyl-1H-pyrazole-3-carboxamide;
1-(4-(2-(4-(2-aminopyridin-4-yl)phenyl)propan-2-yl)phenyl)-5-methyl-1H-pyrazole-3-carboxamide;
5-methyl-1-(4-(2-(4'-(5-methyl-1,3,4-oxadiazol-2-yl)-[1,1'-biphenyl]-4-yl)propan-2-yl)phenyl)-1H-pyrazole-3-carboxamide;
5-methyl-1-(4-(2-(4'-(pyrrolidin-1-ylmethyl)-[1,1'-biphenyl]-4-yl)propan-2-yl)phenyl)-1H-pyrazole-3-carboxamide;
5-methyl-1-(4-(2-(4'-morpholino-2',3',4',5'-tetrahydro-[1,1'-biphenyl]-4-yl)propan-2-yl)phenyl)-1H-pyrazole-3-carboxamide;
1-(4-(2-(4'-hydroxy-2',3',4',5'-tetrahydro-[1,1'-biphenyl]-4-yl)propan-2-yl)phenyl)-5-methyl-1H-pyrazole-3-carboxamide;
5-methyl-1-(4-(2-(4-(pyridin-2-yl)phenyl)propan-2-yl)phenyl)-1H-pyrazole-3-carboxamide;

1-(4-(2-(4'-(3-(aminomethyl)oxetan-3-yl)-[1,1'-biphenyl]-4-yl)propan-2-yl)phenyl)-5-methyl-1H-pyrazole-3-carboxamide;

1-(4-(2-(4'-(3-aminooxetan-3-yl)-[1,1'-biphenyl]-4-yl)propan-2-yl)phenyl)-5-methyl-1H-pyrazole-3-carboxamide;

5-methyl-1-(4-(2-(4'-(pyrrolidin-1-ylmethyl)-[1,1'-biphenyl]-4-yl)propan-2-yl)phenyl)-1H-1,2,4-triazole-3-carboxamide;

1-(4-(2-(4'-(N, N-dimethylsulfamoyl)-[1,1'-biphenyl]-4-yl)propan-2-yl)phenyl)-5-methyl-1H-1,2,4-triazole-3-carboxamide;

5-methyl-1-(4-(2-(4-(quinolin-6-yl)phenyl)propan-2-yl)phenyl)-1H-1,2,4-triazole-3-carboxamide;

5-methyl-1-(4-(2-(4-(quinoxalin-6-yl)phenyl)propan-2-yl)phenyl)-1H-1,2,4-triazole-3-carboxamide;

1-(4-(2-(4-(isoquinolin-7-yl)phenyl)propan-2-yl)phenyl)-5-methyl-1H-1,2,4-triazole-3-carboxamide;

1-(4-(2-(4'-(dimethylcarbamoyl)-[1,1'-biphenyl]-4-yl)propan-2-yl)phenyl)-5-methyl-1H-1,2,4-triazole-3-carboxamide;

1-(4-(2-(4-(benzo[d]thiazol-5-yl)phenyl)propan-2-yl)phenyl)-5-methyl-1H-1,2,4-triazole-3-carboxamide;

5-methyl-1-(4-(2-(4-(1-methyl-1H-pyrazol-4-yl)phenyl)propan-2-yl)phenyl)-1H-1,2,4-triazole-3-carboxamide;

5-methyl-1-(4-(2-(4-(2-methylpyridin-4-yl)phenyl)propan-2-yl)phenyl)-1H-1,2,4-triazole-3-carboxamide;

1-(4-(2-(4-(6-cyanopyridin-3-yl)phenyl)propan-2-yl)phenyl)-5-methyl-1H-1,2,4-triazole-3-carboxamide;

5-methyl-1-(4-(2-(4-(4-methyl-3,4-dihydro-2H-pyrido[3,2-b][1,4]oxazin-7-yl)phenyl) propan-2-yl)phenyl)-1H-1,2,4-triazole-3-carboxamide;

5-methyl-1-(4-(2-(4'-(morpholinomethyl)-[1,1'-biphenyl]-4-yl)propan-2-yl)phenyl)-1H-1,2,4-triazole-3-carboxamide;

5-methyl-1-(4-(2-(3'-(5-methyl-1,3,4-oxadiazol-2-yl)-[1,1'-biphenyl]-4-yl)propan-2-yl)phenyl)-1H-1,2,4-triazole-3-carboxamide;

5-methyl-1-(4-(2-(4-(6-(pyrrolidin-1-yl)pyridin-3-yl)phenyl)propan-2-yl)phenyl)-1H-1,2,4-triazole-3-carboxamide;

5-methyl-1-(4-(2-(4-(6-morpholinopyridin-3-yl)phenyl)propan-2-yl)phenyl)-1H-1,2,4-triazole-3-carboxamide;

5-methyl-1-(4-(2-(4-(thiophen-3-yl)phenyl)propan-2-yl)phenyl)-1H-1,2,4-triazole-3-carboxamide;

1-(4-(2-(4'-(1-amino-2,2,2-trifluoroethyl)-[1,1'-biphenyl]-4-yl)propan-2-yl)phenyl)-5-methyl-1H-1,2,4-triazole-3-carboxamide;

5-methyl-1-(4-((4'-((4-methylpiperazin-1-yl)methyl)-[1,1'-biphenyl]-4-yl)methyl)phenyl)-1H-1,2,4-triazole-3-carboxamide;

5-methyl-1-(4-(4-(pyridin-3-yl)benzyl)phenyl)-1H-1,2,4-triazole-3-carboxamide;

5-methyl-1-(4-((4'-(4-methylpiperazine-1-carbonyl)-[1,1'-biphenyl]-4-yl)methyl)phenyl)-1H-1,2,4-triazole-3-carboxamide;

5-methyl-1-(4-((4'-(pyrrolidin-1-ylmethyl)-[1,1'-biphenyl]-4-yl)methyl)phenyl)-1H-1,2,4-triazole-3-carboxamide;

1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide;

(S)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide;

1-(4-((4'-(((2-hydroxyethyl)amino)methyl)-[1,1'-biphenyl]-4-yl)methyl)phenyl)-5-methyl-1H-pyrazole-3-carboxamide;

1-(4-((4'-((cyclobutylamino)methyl)-[1,1'-biphenyl]-4-yl)methyl)phenyl)-5-methyl-1H-pyrazole-3-carboxamide;

5-methyl-1-(4-((4'-((oxetan-3-ylamino)methyl)-[1,1'-biphenyl]-4-yl)methyl)phenyl)-1H-pyrazole-3-carboxamide;

5-methyl-1-(4-((4'-((5-methylhexahydropyrrolo[3,4-c]pyrrol-2(1H)-yl)methyl)-[1,1'-biphenyl]-4-yl)methyl)phenyl)-1H-pyrazole-3-carboxamide;

5-methyl-1-(4-((4'-(piperidin-1-ylmethyl)-[1,1'-biphenyl]-4-yl)methyl)phenyl)-1H-pyrazole-3-carboxamide;

1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide;

(R)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide;

1-(4-((4'-(azetidin-1-ylmethyl)-[1,1'-biphenyl]-4-yl)methyl)phenyl)-5-methyl-1H-pyrazole-3-carboxamide;

1-(4-((4'-((2-hydroxyethyl)sulfonyl)-[1,1'-biphenyl]-4-yl)methyl)phenyl)-5-methyl-1H-pyrazole-3-carboxamide;

1-(4-((4'-((4,4-difluoro-2-(hydroxymethyl)pyrrolidin-1-yl)methyl)-[1,1'-biphenyl]-4-yl)methyl)phenyl)-5-methyl-1H-pyrazole-3-carboxamide (R)-1-(4-((4'-((4,4-difluoro-2-(hydroxymethyl)pyrrolidin-1-yl)methyl)-[1,1'-biphenyl]-4-yl)methyl)phenyl)-5-methyl-1H-pyrazole-3-carboxamide;

1-(4-(4-(5-(2-hydroxypropan-2-yl)pyridin-2-yl)benzyl)phenyl)-5-methyl-1H-pyrazole-3-carboxamide;

1-(4-(4-(5-(2-hydroxypropan-2-yl)-6-methylpyridin-2-yl)benzyl)phenyl)-5-methyl-1H-pyrazole-3-carboxamide;

1-(4-(4-(5-(2-hydroxypropan-2-yl)pyridin-2-yl)benzyl)phenyl)-5-methyl-1H-1,2,4-triazole-3-carboxamide;

1-(4-(4-(6-(3-hydroxyoxetan-3-yl)pyridin-3-yl)benzyl)phenyl)-5-methyl-1H-pyrazole-3-carboxamide;

1-(4-(4-(2-(2-hydroxypropan-2-yl)pyridin-4-yl)benzyl)phenyl)-5-methyl-1H-pyrazole-3-carboxamide;

5-methyl-1-(4-((4'-(piperazine-1-carbonyl)-[1,1'-biphenyl]-4-yl)methyl)phenyl)-1H-pyrazole-3-carboxamide;

5-methyl-1-(4-((4'-(piperazine-1-carbonyl)-[1,1'-biphenyl]-4-yl)methyl)phenyl)-1H-1,2,4-triazole-3-carboxamide;

5-methyl-1-(4-(4-(6-(piperazine-1-carbonyl)pyridin-3-yl)benzyl)phenyl)-1H-pyrazole-3-carboxamide;

5-methyl-1-(4-(4-(5-(piperazine-1-carbonyl)pyridin-2-yl)benzyl)phenyl)-1H-pyrazole-3-carboxamide;

1-(4-((4'-(3-(hydroxymethyl)piperazine-1-carbonyl)-[1,1'-biphenyl]-4-yl)methyl)phenyl)-5-methyl-1H-pyrazole-3-carboxamide;

(R)-1-(4-((4'-(3-(hydroxymethyl)piperazine-1-carbonyl)-[1,1'-biphenyl]-4-yl)methyl)phenyl)-5-methyl-1H-pyrazole-3-carboxamide;

5-methyl-1-(4-((4'-(3-methylpiperazine-1-carbonyl)-[1,1'-biphenyl]-4-yl)methyl)phenyl)-1H-1,2,4-triazole-3-carboxamide;

(S)-5-methyl-1-(4-((4'-(3-methylpiperazine-1-carbonyl)-[1,1'-biphenyl]-4-yl)methyl)phenyl)-1H-1,2,4-triazole-3-carboxamide;

1-(4-((4'-(azetidin-3-ylcarbamoyl)-[1,1'-biphenyl]-4-yl)methyl)phenyl)-5-methyl-1H-pyrazole-3-carboxamide;

5-methyl-1-(4-(4-(6-(piperazin-1-ylmethyl)pyridin-3-yl)benzyl)phenyl)-1H-pyrazole-3-carboxamide;

5-methyl-1-(4-(4-(2-(piperazin-1-ylmethyl)pyridin-4-yl)benzyl)phenyl)-1H-pyrazole-3-carboxamide;

5-methyl-1-(4-(4-(5-(piperazin-1-ylmethyl)pyridin-2-yl)benzyl)phenyl)-1H-pyrazole-3-carboxamide;

1-(4-(4-(6-((4-(2-hydroxyethyl)piperazin-1-yl)methyl)pyridin-3-yl)benzyl)phenyl)-5-methyl-1H-pyrazole-3-carboxamide;

5-methyl-1-(4-(4-(5-((4-(oxetan-3-yl)piperazin-1-yl)methyl)pyridin-2-yl)benzyl)phenyl)-1H-pyrazole-3-carboxamide;

5-methyl-1-(4-(4-(6-((4-methylpiperazin-1-yl)methyl)pyridin-3-yl)benzyl)phenyl)-1H-1,2,4-triazole-3-carboxamide;

5-methyl-1-(4-(4-(5-(piperazin-1-ylmethyl)pyridin-2-yl)benzyl)phenyl)-1H-1,2,4-triazole-3-carboxamide;

5-methyl-1-(4-(4-(6-((3-methylpiperazin-1-yl)methyl)pyridin-3-yl)benzyl)phenyl)-1H-1,2,4-triazole-3-carboxamide;

(S)-5-methyl-1-(4-(4-(6-((3-methylpiperazin-1-yl)methyl)pyridin-3-yl)benzyl)phenyl)-1H-1,2,4-triazole-3-carboxamide;

1-(4-(4-(6-((3,4-dimethylpiperazin-1-yl)methyl)pyridin-3-yl)benzyl)phenyl)-5-methyl-1H-1,2,4-triazole-3-carboxamide;

(S)-1-(4-(4-(6-((3,4-dimethylpiperazin-1-yl)methyl)pyridin-3-yl)benzyl)phenyl)-5-methyl-1H-1,2,4-triazole-3-carboxamide;

1-(4-((4'-((2-oxa-6-azaspiro[3.4]octan-6-yl)methyl)-[1,1'-biphenyl]-4-yl)methyl)phenyl)-5-methyl-1H-1,2,4-triazole-3-carboxamide;

1-(4-((4'-((3,3-difluoropyrrolidin-1-yl)methyl)-[1,1'-biphenyl]-4-yl)methyl)phenyl)-5-methyl-1H-1,2,4-triazole-3-carboxamide;

5-methyl-1-(4-((4'-(((3aR,6aS)-5-methylhexahydropyrrolo[3,4-c]pyrrol-2(1H)-yl)methyl)-[1,1'-biphenyl]-4-yl)methyl)phenyl)-1H-1,2,4-triazole-3-carboxamide;

1-(4-((4'-((2-oxa-6-azaspiro[3.3]heptan-6-yl)methyl)-[1,1'-biphenyl]-4-yl)methyl)phenyl)-5-methyl-1H-1,2,4-triazole-3-carboxamide;

1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide;

(R)-1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide;

1-(4-((4'-((2-oxa-6-azaspiro[3.5]nonan-6-yl)methyl)-[1,1'-biphenyl]-4-yl)methyl)phenyl)-5-methyl-1H-1,2,4-triazole-3-carboxamide;

1-(4-((4'-((3,3-dimethylpyrrolidin-1-yl)methyl)-[1,1'-biphenyl]-4-yl)methyl)phenyl)-5-methyl-1H-1,2,4-triazole-3-carboxamide;

1-(4-((4'-((2-oxa-7-azaspiro[3.5]nonan-7-yl)methyl)-[1,1'-biphenyl]-4-yl)methyl)phenyl)-5-methyl-1H-1,2,4-triazole-3-carboxamide;

1-(4-((4'-((3,3-difluoropiperidin-1-yl)methyl)-[1,1'-biphenyl]-4-yl)methyl)phenyl)-5-methyl-1H-1,2,4-triazole-3-carboxamide;

1-(4-((4'-((4,4-dimethylpiperidin-1-yl)methyl)-[1,1'-biphenyl]-4-yl)methyl)phenyl)-5-methyl-1H-1,2,4-triazole-3-carboxamide;

1-(4-((4'-((4-((dimethylamino)methyl)piperidin-1-yl)methyl)-[1,1'-biphenyl]-4-yl)methyl)phenyl)-5-methyl-1H-1,2,4-triazole-3-carboxamide;

1-(4-((4'-((4-(dimethylamino)piperidin-1-yl)methyl)-[1,1'-biphenyl]-4-yl)methyl)phenyl)-5-methyl-1H-1,2,4-triazole-3-carboxamide;

1-(4-((4'-((4-(2-hydroxypropan-2-yl)piperidin-1-yl)methyl)-[1,1'-biphenyl]-4-yl)methyl)phenyl)-5-methyl-1H-1,2,4-triazole-3-carboxamide;

1-(4-((4'-((3-hydroxypyrrolidin-1-yl)methyl)-[1,1'-biphenyl]-4-yl)methyl)phenyl)-5-methyl-1H-1,2,4-triazole-3-carboxamide;

(R)-1-(4-((4'-((3-hydroxypyrrolidin-1-yl)methyl)-[1,1'-biphenyl]-4-yl)methyl)phenyl)-5-methyl-1H-1,2,4-triazole-3-carboxamide;

(S)-1-(4-((4'-((3-hydroxypyrrolidin-1-yl)methyl)-[1,1'-biphenyl]-4-yl)methyl)phenyl)-5-methyl-1H-1,2,4-triazole-3-carboxamide;

1-(4-((4'-((4-hydroxy-4-methylpiperidin-1-yl)methyl)-[1,1'-biphenyl]-4-yl)methyl)phenyl)-5-methyl-1H-1,2,4-triazole-3-carboxamide;

1-(4-((4'-((3-(2-hydroxypropan-2-yl)piperidin-1-yl)methyl)-[1,1'-biphenyl]-4-yl)methyl)phenyl)-5-methyl-1H-1,2,4-triazole-3-carboxamide;

1-(4-((4'-((3-hydroxyazetidin-1-yl)methyl)-[1,1'-biphenyl]-4-yl)methyl)phenyl)-5-methyl-1H-1,2,4-triazole-3-carboxamide;

1-(4-((4'-((3,5-dimethylpiperazin-1-yl)methyl)-[1,1'-biphenyl]-4-yl)methyl)phenyl)-5-methyl-1H-1,2,4-triazole-3-carboxamide;

1-(4-((4'-(((3R,5R)-3,5-dimethylpiperazin-1-yl)methyl)-[1,1'-biphenyl]-4-yl)methyl)phenyl)-5-methyl-1H-1,2,4-triazole-3-carboxamide;

1-(4-((4'-((3-hydroxy-3-methylpyrrolidin-1-yl)methyl)-[1,1'-biphenyl]-4-yl)methyl)phenyl)-5-methyl-1H-1,2,4-triazole-3-carboxamide;

1-(4-((4'-((5-oxa-2-azaspiro[3.4]octan-2-yl)methyl)-[1,1'-biphenyl]-4-yl)methyl)phenyl)-5-methyl-1H-1,2,4-triazole-3-carboxamide;

1-(4-((4'-((3-(hydroxymethyl)piperazin-1-yl)methyl)-[1,1'-biphenyl]-4-yl)methyl)phenyl)-5-methyl-1H-1,2,4-triazole-3-carboxamide;

(R)-1-(4-((4'-((3-(hydroxymethyl)piperazin-1-yl)methyl)-[1,1'-biphenyl]-4-yl)methyl)phenyl)-5-methyl-1H-1,2,4-triazole-3-carboxamide;

1-(4-((4'-((3-fluoropyrrolidin-1-yl)methyl)-[1,1'-biphenyl]-4-yl)methyl)phenyl)-5-methyl-1H-1,2,4-triazole-3-carboxamide;

(R)-(4-((4'-((3-fluoropyrrolidin-1-yl)methyl)-[1,1'-biphenyl]-4-yl)methyl)phenyl)-5-methyl-1H-1,2,4-triazole-3-carboxamide;

5-methyl-1-(4-((4'-((3-(methylsulfonyl)pyrrolidin-1-yl)methyl)-[1,1'-biphenyl]-4-yl)methyl)phenyl)-1H-1,2,4-triazole-3-carboxamide;

5-methyl-1-(4-((4'-((5-methylhexahydropyrrolo[3,4-b]pyrrol-1(2H)-yl)methyl)-[1,1'-biphenyl]-4-yl)methyl)phenyl)-1H-1,2,4-triazole-3-carboxamide;

1-(4-((4'-((3-hydroxy-3-methylpiperidin-1-yl)methyl)-[1,1'-biphenyl]-4-yl)methyl)phenyl)-5-methyl-1H-1,2,4-triazole-3-carboxamide;

1-(4-((4'-((4-(tert-butyl)piperazin-1-yl)methyl)-[1,1'-biphenyl]-4-yl)methyl)phenyl)-5-methyl-1H-1,2,4-triazole-3-carboxamide;

1-(4-((4'-((3,3-dimethylpiperazin-1-yl)methyl)-[1,1'-biphenyl]-4-yl)methyl)phenyl)-5-methyl-1H-1,2,4-triazole-3-carboxamide;

1-(4-((4'-(((3S,5R)-3,5-dimethylpiperazin-1-yl)methyl)-[1,1'-biphenyl]-4-yl)methyl)phenyl)-5-methyl-1H-1,2,4-triazole-3-carboxamide;

1-(4-((4'-((4,4-difluoropiperidin-1-yl)methyl)-[1,1'-biphenyl]-4-yl)methyl)phenyl)-5-methyl-1H-1,2,4-triazole-3-carboxamide;

5-methyl-1-(4-((4'-((octahydro-2H-pyrido[1,2-a]pyrazin-2-yl)methyl)-[1,1'-biphenyl]-4-yl)methyl)phenyl)-1H-1,2,4-triazole-3-carboxamide;

1-(4-((4'-((2-(hydroxymethyl)piperidin-1-yl)methyl)-[1,1'-biphenyl]-4-yl)methyl)phenyl)-5-methyl-1H-1,2,4-triazole-3-carboxamide;

(S)-1-(4-((4'-((2-(hydroxymethyl)piperidin-1-yl)methyl)-[1,1'-biphenyl]-4-yl)methyl)phenyl)-5-methyl-1H-1,2,4-triazole-3-carboxamide;

1-(4-((4'-((4-(hydroxymethyl)piperidin-1-yl)methyl)-[1,1'-biphenyl]-4-yl)methyl)phenyl)-5-methyl-1H-1,2,4-triazole-3-carboxamide;

1-(4-((4'-((3-hydroxy-3-methylazetidin-1-yl)methyl)-[1,1'-biphenyl]-4-yl)methyl)phenyl)-5-methyl-1H-1,2,4-triazole-3-carboxamide;

1-(4-((4'-((4-hydroxypiperidin-1-yl)methyl)-[1,1'-biphenyl]-4-yl)methyl)phenyl)-5-methyl-1H-1,2,4-triazole-3-carboxamide;

5-methyl-1-(4-((4'-(((3aR,6aS)-tetrahydro-1H-furo[3,4-c]pyrrol-5(3H)-yl)methyl)-[1,1'-biphenyl]-4-yl)methyl)phenyl)-1H-1,2,4-triazole-3-carboxamide;

1-(4-((4'-((3-fluoropiperidin-1-yl)methyl)-[1,1'-biphenyl]-4-yl)methyl)phenyl)-5-methyl-1H-1,2,4-triazole-3-carboxamide;

5-methyl-1-(4-((4'-((4-methyl-1,4-diazepan-1-yl)methyl)-[1,1'-biphenyl]-4-yl)methyl)phenyl)-1H-1,2,4-triazole-3-carboxamide;

1-(4-((4'-((3,4-dihydroxypyrrolidin-1-yl)methyl)-[1,1'-biphenyl]-4-yl)methyl)phenyl)-5-methyl-1H-1,2,4-triazole-3-carboxamide;

1-(4-((4'-(((3S,4S)-3,4-dihydroxypyrrolidin-1-yl)methyl)-[1,1'-biphenyl]-4-yl)methyl)phenyl)-5-methyl-1H-1,2,4-triazole-3-carboxamide;

5-methyl-1-(4-((4'-((1-methylhexahydropyrrolo[3,4-b]pyrrol-5(1H)-yl)methyl)-[1,1'-biphenyl]-4-yl)methyl)phenyl)-1H-1,2,4-triazole-3-carboxamide;

5-methyl-1-(4-((4'-(((3aR,6aR)-1-methylhexahydropyrrolo[3,4-b]pyrrol-5(1H)-yl)methyl)-[1,1'-biphenyl]-4-yl)methyl)phenyl)-1H-1,2,4-triazole-3-carboxamide;

5-methyl-1-(4-((4'-((4-(methylsulfonyl)piperidin-1-yl)methyl)-[1,1'-biphenyl]-4-yl)methyl)phenyl)-1H-1,2,4-triazole-3-carboxamide;

1-(4-((4'-((1,1-dioxidothiomorpholino)methyl)-[1,1'-biphenyl]-4-yl)methyl)phenyl)-5-methyl-1H-1,2,4-triazole-3-carboxamide;

1-(4-((4'-((3,3-difluoroazetidin-1-yl)methyl)-[1,1'-biphenyl]-4-yl)methyl)phenyl)-5-methyl-1H-1,2,4-triazole-3-carboxamide;

1-(4-((4'-(((1R,5S)-6-(hydroxymethyl)-3-azabicyclo[3.1.0]hexan-3-yl)methyl)-[1,1'-biphenyl]-4-yl)methyl)phenyl)-5-methyl-1H-1,2,4-triazole-3-carboxamide;

1-(4-((4'-(((1R,5S,6r)-6-(hydroxymethyl)-3-azabicyclo[3.1.0]hexan-3-yl)methyl)-[1,1'-biphenyl]-4-yl)methyl)phenyl)-5-methyl-1H-1,2,4-triazole-3-carboxamide;

5-methyl-1-(4-((4'-((4-(trifluoromethyl)piperidin-1-yl)methyl)-[1,1'-biphenyl]-4-yl)methyl)phenyl)-1H-1,2,4-triazole-3-carboxamide;

1-(4-((4'-((3-(hydroxymethyl)azetidin-1-yl)methyl)-[1,1'-biphenyl]-4-yl)methyl)phenyl)-5-methyl-1H-1,2,4-triazole-3-carboxamide;

1-(4-((4'-((1-oxa-7-azaspiro[3.5]nonan-7-yl)methyl)-[1,1'-biphenyl]-4-yl)methyl)phenyl)-5-methyl-1H-1,2,4-triazole-3-carboxamide;

1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide;

(S)-1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide;

1-(4-((4'-((4-(dimethylamino)piperidin-1-yl)methyl)-[1,1'-biphenyl]-4-yl)methyl)phenyl)-5-methyl-1H-pyrazole-3-carboxamide;

5-methyl-1-(4-((4'-(((3aR,6aS)-2-methyloctahydrocyclopenta[c]pyrrol-5-yl)methyl)-[1,1'-biphenyl]-4-yl)methyl)phenyl)-1H-1,2,4-triazole-3-carboxamide;

5-methyl-1-(4-(4-(4-(piperazine-1-carbonyl)bicyclo[2.2.2]octan-1-yl)benzyl)phenyl)-1H-pyrazole-3-carboxamide;

5-methyl-1-(4-(4-(4-(4-methylpiperazine-1-carbonyl)bicyclo[2.2.2]octan-1-yl)benzyl)phenyl)-1H-pyrazole-3-carboxamide;

5-methyl-1-(4-(4-(6-(piperazine-1-carbonyl)spiro[3.3]heptan-2-yl)benzyl)phenyl)-1H-1,2,4-triazole-3-carboxamide;

5-methyl-1-(4-((4'-(piperazin-1-ylmethyl)-[1,1'-biphenyl]-4-yl)methyl)phenyl)-1H-1,2,4-triazole-3-carboxamide;

1-(4-(4-(6-(2-hydroxypropan-2-yl)pyridin-3-yl)benzyl)phenyl)-5-methyl-1H-1,2,4-triazole-3-carboxamide;

5-methyl-1-(4-((4'-((1-methylpiperidin-4-yl)oxy)-[1,1'-biphenyl]-4-yl)methyl)phenyl)-1H-1,2,4-triazole-3-carboxamide;

1-(4-((4'-(1-hydroxy-2-methylpropan-2-yl)-[1,1'-biphenyl]-4-yl)methyl)phenyl)-5-methyl-1H-1,2,4-triazole-3-carboxamide;

1-(4-(4-(4-(2-hydroxypropan-2-yl)piperidin-1-yl)benzyl)phenyl)-5-methyl-1H-1,2,4-triazole-3-carboxamide;

1-(4-((4'-(N-(2-hydroxy-2-methylpropyl)sulfamoyl)-[1,1'-biphenyl]-4-yl)methyl)phenyl)-5-methyl-1H-1,2,4-triazole-3-carboxamide;

1-(4-((4'-((2-hydroxy-2-methyl propyl)carbamoyl)-[1,1'-biphenyl]-4-yl)methyl)phenyl)-5-methyl-1H-1,2,4-triazole-3-carboxamide;

1-(4-(4-(5-(N-(2-hydroxy-2-methylpropyl)sulfamoyl)pyridin-2-yl)benzyl)phenyl)-5-methyl-1H-1,2,4-triazole-3-carboxamide;

1-(4-(4-(4-(2-hydroxypropan-2-yl)pyridin-2-yl)benzyl)phenyl)-5-methyl-1H-1,2,4-triazole-3-carboxamide;

5-methyl-1-(4-(4-((1-methylpiperidin-4-yl)ethynyl)benzyl)phenyl)-1H-1,2,4-triazole-3-carboxamide;

1-(4-(4-((1-hydroxycyclohexyl)ethynyl)benzyl)phenyl)-5-methyl-1H-1,2,4-triazole-3-carboxamide;

1-(4-(4-(5-(1-hydroxy-2-methylpropan-2-yl)pyridin-2-yl)benzyl)phenyl)-5-methyl-1H-1,2,4-triazole-3-carboxamide;

1-(4-(4-(5-(1-hydroxy-2-methylpropan-2-yl)pyridin-2-yl)benzyl)phenyl)-5-methyl-1H-pyrazole-3-carboxamide;

1-(4-(4-(6-(2-hydroxypropan-2-yl)pyridazin-3-yl)benzyl)phenyl)-5-methyl-1H-pyrazole-3-carboxamide;

6-(4-(4-(3-carbamoyl-5-methyl-1H-pyrazol-1-yl)benzyl)phenyl)-N-(2-hydroxy-2-methylpropyl)nicotinamide;

1-(4-(4-(2-(2-hydroxypropan-2-yl)pyrimidin-5-yl)benzyl)phenyl)-5-methyl-1H-pyrazole-3-carboxamide;

1-(4-(4-(2-(hydroxymethyl)pyridin-4-yl)benzyl)phenyl)-5-methyl-1H-pyrazole-3-carboxamide;

5-methyl-1-(4-((4'-((1-methylpyrrolidin-3-yl)oxy)-[1,1'-biphenyl]-4-yl)methyl)phenyl)-1H-1,2,4-triazole-3-carboxamide;

(S)-5-methyl-1-(4-((4'-((1-methylpyrrolidin-3-yl)oxy)-[1,1'-biphenyl]-4-yl)methyl)phenyl)-1H-1,2,4-triazole-3-carboxamide;

5-methyl-1-(4-((4'-((1-methylpyrrolidin-3-yl)oxy)-[1,1'-biphenyl]-4-yl)methyl)phenyl)-1H-1,2,4-triazole-3-carboxamide;

(R)-5-methyl-1-(4-((4'-((1-methylpyrrolidin-3-yl)oxy)-[1,1'-biphenyl]-4-yl)methyl)phenyl)-1H-1,2,4-triazole-3-carboxamide; and 1-(4-((4'-(2-((2-hydroxy-2-methylpropyl)amino)propan-2-yl)-[1,1'-biphenyl]-4-yl)methyl)phenyl)-5-methyl-1H-1,2,4-triazole-3-carboxamide.

Embodiment 409

A compound according to embodiment 1, or a pharmaceutically acceptable salt thereof, wherein the compound is selected from a group consisting of:

1-(4-(2-(4-chlorophenyl)propan-2-yl)phenyl)-5-methyl-1H-1,2,4-triazole-3-carboxamide;
1-(4-((6H-benzo[c]chromen-3-yl)methyl)phenyl)-5-methyl-1H-pyrazole-3-carboxamide;
5-methyl-1-(4-((4'-(pyrrolidin-1-ylmethyl)-[1,1'-biphenyl]-4-yl)methyl)phenyl)-1H-pyrazole-3-carboxamide;
1-(4-((4'-((diethylamino)methyl)-[1,1'-biphenyl]-4-yl)methyl)phenyl)-5-methyl-1H-pyrazole-3-carboxamide;
5-methyl-1-(4-(4-(2-methyl-1,2,3,4-tetrahydroisoquinolin-6-yl)benzyl)phenyl)-1H-pyrazole-3-carboxamide;
1-(4-(4-(isoindolin-5-yl)benzyl)phenyl)-5-methyl-1H-pyrazole-3-carboxamide;
5-methyl-1-(4-(4-(pyridin-4-yl)benzyl)phenyl)-1H-pyrazole-3-carboxamide;
5-methyl-1-(4-((4'-(methylsulfonyl)-[1,1'-biphenyl]-4-yl)methyl)phenyl)-1H-pyrazole-3-carboxamide;
5-methyl-1-(4-((3'-(5-methyl-1,3,4-oxadiazol-2-yl)-[1,1'-biphenyl]-4-yl)methyl)phenyl)-1H-pyrazole-3-carboxamide;
1-(4-([1,1'-biphenyl]-4-ylmethyl)phenyl)-5-methyl-1H-pyrazole-3-carboxamide;
5-methyl-1-(4-((4'-(5-methyl-1,3,4-oxadiazol-2-yl)-[1,1'-biphenyl]-4-yl)methyl)phenyl)-1H-pyrazole-3-carboxamide;
5-methyl-1-(4-(4-(pyridin-3-yl)benzyl)phenyl)-1H-pyrazole-3-carboxamide;
1-(4-(4-(1-(dimethylglycyl)-1,2,3,6-tetrahydropyridin-4-yl)benzyl)phenyl)-5-methyl-1H-pyrazole-3-carboxamide;
5-methyl-1-(4-((4'-((4-methylpiperazin-1-yl)methyl)-[1,1'-biphenyl]-4-yl)methyl)phenyl)-1H-pyrazole-3-carboxamide;
5-methyl-1-(4-(4-(2-methylisoindolin-5-yl)benzyl)phenyl)-1H-pyrazole-3-carboxamide;
5-methyl-1-(4-(4-(1,2,3,4-tetrahydroisoquinolin-6-yl)benzyl)phenyl)-1H-pyrazole-3-carboxamide;
5-methyl-1-(4-(4-(1-methyl-1,2,3,6-tetrahydropyridin-4-yl)benzyl)phenyl)-1H-pyrazole-3-carboxamide;
5-methyl-1-(4-(4-(1-methylpiperidin-4-yl)benzyl)phenyl)-1H-pyrazole-3-carboxamide;
5-methyl-1-(4-(4-(1-methylpyrrolidin-3-yl)benzyl)phenyl)-1H-pyrazole-3-carboxamide;
(R)-5-methyl-1-(4-(4-(1-methylpyrrolidin-3-yl)benzyl)phenyl)-1H-pyrazole-3-carboxamide;
(S)-5-methyl-1-(4-(4-(1-methylpyrrolidin-3-yl)benzyl)phenyl)-1H-pyrazole-3-carboxamide;
1-(4-(4-(6-((dimethylamino)methyl)pyridin-3-yl)benzyl)phenyl)-5-methyl-1H-pyrazole-3-carboxamide;
1-(4-(4-(2-((dimethylamino)methyl)pyridin-4-yl)benzyl)phenyl)-5-methyl-1H-pyrazole-3-carboxamide;
5-methyl-1-(4-(4-(6-(pyrrolidin-1-ylmethyl)pyridin-3-yl)benzyl)phenyl)-1H-pyrazole-3-carboxamide;
1-(4-(4-(5-((dimethylamino)methyl)pyridin-3-yl)benzyl)phenyl)-5-methyl-1H-pyrazole-3-carboxamide;
5-methyl-1-(4-(4-(1-methyl-2,3,6,7-tetrahydro-1H-azepin-4-yl)benzyl)phenyl)-1H-pyrazole-3-carboxamide;
5-methyl-1-(4-((4'-(1-methylpyrrolidin-2-yl)-[1,1'-biphenyl]-4-yl)methyl)phenyl)-1H-pyrazole-3-carboxamide;
(S)-5-methyl-1-(4-((4'-(1-methyl pyrrolidin-2-yl)-[1,1'-biphenyl]-4-yl)methyl)phenyl)-1H-pyrazole-3-carboxamide;
5-methyl-1-(4-(2-(4'-(pyrrolidin-1-ylmethyl)-[1,1'-biphenyl]-4-yl)propan-2-yl)phenyl)-1H-pyrazole-3-carboxamide;
5-methyl-1-(4-(2-(3'-(methylsulfonyl)-[1,1'-biphenyl]-4-yl)propan-2-yl)phenyl)-1H-pyrazole-3-carboxamide;
5-methyl-1-(4-(2-(4-(pyridin-4-yl)phenyl)propan-2-yl)phenyl)-1H-pyrazole-3-carboxamide;
1-(4-(2-(4-(1H-indazol-5-yl)phenyl)propan-2-yl)phenyl)-5-methyl-1H-pyrazole-3-carboxamide;
1-(4-(2-(4-(2-aminopyridin-4-yl)phenyl)propan-2-yl)phenyl)-5-methyl-1H-pyrazole-3-carboxamide;
5-methyl-1-(4-(2-(4'-(5-methyl-1,3,4-oxadiazol-2-yl)-[1,1'-biphenyl]-4-yl)propan-2-yl)phenyl)-1H-pyrazole-3-carboxamide;
5-methyl-1-(4-(2-(4'-(pyrrolidin-1-ylmethyl)-[1,1'-biphenyl]-4-yl)propan-2-yl)phenyl)-1H-pyrazole-3-carboxamide;
5-methyl-1-(4-(2-(4'-morpholino-2',3',4',5'-tetrahydro-[1,1'-biphenyl]-4-yl)propan-2-yl)phenyl)-1H-pyrazole-3-carboxamide;
1-(4-(2-(4'-hydroxy-2',3',4',5'-tetrahydro-[1,1'-biphenyl]-4-yl)propan-2-yl)phenyl)-5-methyl-1H-pyrazole-3-carboxamide;
5-methyl-1-(4-(2-(4-(pyridin-2-yl)phenyl)propan-2-yl)phenyl)-1H-pyrazole-3-carboxamide;
1-(4-(2-(4'-(3-(aminomethyl)oxetan-3-yl)-[1,1'-biphenyl]-4-yl)propan-2-yl)phenyl)-5-methyl-1H-pyrazole-3-carboxamide;
1-(4-(2-(4'-(3-aminooxetan-3-yl)-[1,1'-biphenyl]-4-yl)propan-2-yl)phenyl)-5-methyl-1H-pyrazole-3-carboxamide;
5-methyl-1-(4-(2-(4'-(pyrrolidin-1-ylmethyl)-[1,1'-biphenyl]-4-yl)propan-2-yl)phenyl)-1H-1,2,4-triazole-3-carboxamide;
1-(4-(2-(4'-(N, N-dimethylsulfamoyl)-[1,1'-biphenyl]-4-yl)propan-2-yl)phenyl)-5-methyl-1H-1,2,4-triazole-3-carboxamide;
5-methyl-1-(4-(2-(4-(quinolin-6-yl)phenyl)propan-2-yl)phenyl)-1H-1,2,4-triazole-3-carboxamide;
5-methyl-1-(4-(2-(4-(quinoxalin-6-yl)phenyl)propan-2-yl)phenyl)-1H-1,2,4-triazole-3-carboxamide;
1-(4-(2-(4-(isoquinolin-7-yl)phenyl)propan-2-yl)phenyl)-5-methyl-1H-1,2,4-triazole-3-carboxamide;
1-(4-(2-(4'-(dimethylcarbamoyl)-[1,1'-biphenyl]-4-yl)propan-2-yl)phenyl)-5-methyl-1H-1,2,4-triazole-3-carboxamide;
1-(4-(2-(4-(benzo[d]thiazol-5-yl)phenyl)propan-2-yl)phenyl)-5-methyl-1H-1,2,4-triazole-3-carboxamide;
5-methyl-1-(4-(2-(4-(1-methyl-1H-pyrazol-4-yl)phenyl)propan-2-yl)phenyl)-1H-1,2,4-triazole-3-carboxamide;
5-methyl-1-(4-(2-(4-(2-methylpyridin-4-yl)phenyl)propan-2-yl)phenyl)-1H-1,2,4-triazole-3-carboxamide;
1-(4-(2-(4-(6-cyanopyridin-3-yl)phenyl)propan-2-yl)phenyl)-5-methyl-1H-1,2,4-triazole-3-carboxamide;
5-methyl-1-(4-(2-(4-(4-methyl-3,4-dihydro-2H-pyrido[3,2-b][1,4]oxazin-7-yl)phenyl) propan-2-yl)phenyl)-1H-1,2,4-triazole-3-carboxamide;
5-methyl-1-(4-(2-(4'-(morpholinomethyl)-[1,1'-biphenyl]-4-yl)propan-2-yl)phenyl)-1H-1,2,4-triazole-3-carboxamide;
5-methyl-1-(4-(2-(3'-(5-methyl-1,3,4-oxadiazol-2-yl)-[1,1'-biphenyl]-4-yl)propan-2-yl)phenyl)-1H-1,2,4-triazole-3-carboxamide;
5-methyl-1-(4-(2-(4-(6-(pyrrolidin-1-yl)pyridin-3-yl)phenyl)propan-2-yl)phenyl)-1H-1,2,4-triazole-3-carboxamide;
5-methyl-1-(4-(2-(4-(6-morpholinopyridin-3-yl)phenyl)propan-2-yl)phenyl)-1H-1,2,4-triazole-3-carboxamide;

5-methyl-1-(4-(2-(4-(thiophen-3-yl)phenyl)propan-2-yl)
 phenyl)-1H-1,2,4-triazole-3-carboxamide;
1-(4-(2-(4'-(1-amino-2,2,2-trifluoroethyl)-[1,1'-biphenyl]-4-
 yl)propan-2-yl)phenyl)-5-methyl-1H-1,2,4-triazole-3-
 carboxamide;
5-methyl-1-(4-((4'-((4-methylpiperazin-1-yl)methyl)-[1,1'-
 biphenyl]-4-yl)methyl)phenyl)-1H-1,2,4-triazole-3-car-
 boxamide;
5-methyl-1-(4-(4-(pyridin-3-yl)benzyl)phenyl)-1H-1,2,4-
 triazole-3-carboxamide;
5-methyl-1-(4-((4'-(4-methylpiperazine-1-carbonyl)-[1,1'-
 biphenyl]-4-yl)methyl)phenyl)-1H-1,2,4-triazole-3-car-
 boxamide;
5-methyl-1-(4-((4'-(pyrrolidin-1-ylmethyl)-[1,1'-biphenyl]-
 4-yl)methyl)phenyl)-1H-1,2,4-triazole-3-carboxamide;
1-(4-((4'-((2-(hydroxymethyl)pyrrolidin-1-yl)methyl)-[1,1'-
 biphenyl]-4-yl)methyl)phenyl)-5-methyl-1H-pyrazole-3-
 carboxamide;
(S)-1-(4-((4'-((2-(hydroxymethyl)pyrrolidin-1-yl)methyl)-
 [1,1'-biphenyl]-4-yl)methyl)phenyl)-5-methyl-1H-pyra-
 zole-3-carboxamide;
1-(4-((4'-(((2-hydroxyethyl)amino)methyl)-[1,1'-biphenyl]-
 4-yl)methyl)phenyl)-5-methyl-1H-pyrazole-3-carboxam-
 ide;
1-(4-((4'-((cyclobutylamino)methyl)-[1,1'-biphenyl]-4-yl)
 methyl)phenyl)-5-methyl-1H-pyrazole-3-carboxamide;
5-methyl-1-(4-((4'-((oxetan-3-ylamino)methyl)-[1,1'-biphe-
 nyl]-4-yl)methyl)phenyl)-1H-pyrazole-3-carboxamide;
5-methyl-1-(4-((4'-((5-methylhexahydropyrrolo[3,4-c]pyr-
 rol-2(1H)-yl)methyl)-[1,1'-biphenyl]-4-yl)methyl)phe-
 nyl)-1H-pyrazole-3-carboxamide;
5-methyl-1-(4-((4'-(piperidin-1-ylmethyl)-[1,1'-biphenyl]-
 4-yl)methyl)phenyl)-1H-pyrazole-3-carboxamide;
1-(4-((4'-((2-(hydroxymethyl)pyrrolidin-1-yl)methyl)-[1,1'-
 biphenyl]-4-yl)methyl)phenyl)-5-methyl-1H-pyrazole-3-
 carboxamide;
(R)-1-(4-((4'-((2-(hydroxymethyl)pyrrolidin-1-yl)methyl)-
 [1,1'-biphenyl]-4-yl)methyl)phenyl)-5-methyl-1H-pyra-
 zole-3-carboxamide; and
1-(4-((4'-(azetidin-1-ylmethyl)-[1,1'-biphenyl]-4-yl)methyl)
 phenyl)-5-methyl-1H-pyrazole-3-carboxamide.

Embodiment 410

A compound according to embodiment 1, or a pharmaceutically acceptable salt thereof, wherein the compound is 1-(4-(2-(4-chlorophenyl)propan-2-yl)phenyl)-5-methyl-1H-1,2,4-triazole-3-carboxamide.

Embodiment 411

A compound according to embodiment 1, or a pharmaceutically acceptable salt thereof, wherein the compound is 1-(4-((6H-benzo[c]chromen-3-yl)methyl)phenyl)-5-methyl-1H-pyrazole-3-carboxamide.

Embodiment 412

A compound according to embodiment 1, or a pharmaceutically acceptable salt thereof, wherein the compound is 5-methyl-1-(4-((4'-(pyrrolidin-1-ylmethyl)-[1,1'-biphenyl]-4-yl)methyl)phenyl)-1H-pyrazole-3-carboxamide.

Embodiment 413

A compound according to embodiment 1, or a pharmaceutically acceptable salt thereof, wherein the compound is 1-(4-((4'-((diethylamino)methyl)-[1,1'-biphenyl]-4-yl)methyl)phenyl)-5-methyl-1H-pyrazole-3-carboxamide.

Embodiment 414

A compound according to embodiment 1, or a pharmaceutically acceptable salt thereof, wherein the compound is 5-methyl-1-(4-(4-(2-methyl-1,2,3,4-tetrahydroisoquinolin-6-yl)benzyl)phenyl)-1H-pyrazole-3-carboxamide.

Embodiment 415

A compound according to embodiment 1, or a pharmaceutically acceptable salt thereof, wherein the compound is 1-(4-(4-(isoindolin-5-yl)benzyl)phenyl)-5-methyl-1H-pyrazole-3-carboxamide.

Embodiment 416

A compound according to embodiment 1, or a pharmaceutically acceptable salt thereof, wherein the compound is 5-methyl-1-(4-(4-(pyridin-4-yl)benzyl)phenyl)-1H-pyrazole-3-carboxamide.

Embodiment 417

A compound according to embodiment 1, or a pharmaceutically acceptable salt thereof, wherein the compound is 5-methyl-1-(4-((4'-(methylsulfonyl)-[1,1'-biphenyl]-4-yl)methyl)phenyl)-1H-pyrazole-3-carboxamide.

Embodiment 418

A compound according to embodiment 1, or a pharmaceutically acceptable salt thereof, wherein the compound is 5-methyl-1-(4-((3'-(5-methyl-1,3,4-oxadiazol-2-yl)-[1,1'-biphenyl]-4-yl)methyl)phenyl)-1H-pyrazole-3-carboxamide.

Embodiment 419

A compound according to embodiment 1, or a pharmaceutically acceptable salt thereof, wherein the compound is 1-(4-([1,1'-biphenyl]-4-ylmethyl)phenyl)-5-methyl-1H-pyrazole-3-carboxamide.

Embodiment 420

A compound according to embodiment 1, or a pharmaceutically acceptable salt thereof, wherein the compound is 5-methyl-1-(4-((4'-(5-methyl-1,3,4-oxadiazol-2-yl)-[1,1'-biphenyl]-4-yl)methyl)phenyl)-1H-pyrazole-3-carboxamide.

Embodiment 421

A compound according to embodiment 1, or a pharmaceutically acceptable salt thereof, wherein the compound is 5-methyl-1-(4-(4-(pyridin-3-yl)benzyl)phenyl)-1H-pyrazole-3-carboxamide.

Embodiment 422

A compound according to embodiment 1, or a pharmaceutically acceptable salt thereof, wherein the compound is 1-(4-(4-(1-(dimethylglycyl)-1,2,3,6-tetrahydropyridin-4-yl)benzyl)phenyl)-5-methyl-1H-pyrazole-3-carboxamide.

Embodiment 423

A compound according to embodiment 1, or a pharmaceutically acceptable salt thereof, wherein the compound is 5-methyl-1-(4-((4'-((4-methylpiperazin-1-yl)methyl)-[1,1'-biphenyl]-4-yl)methyl)phenyl)-1H-pyrazole-3-carboxamide.

Embodiment 424

A compound according to embodiment 1, or a pharmaceutically acceptable salt thereof, wherein the compound is 5-methyl-1-(4-(4-(2-methylisoindolin-5-yl)benzyl)phenyl)-1H-pyrazole-3-carboxamide.

Embodiment 425

A compound according to embodiment 1, or a pharmaceutically acceptable salt thereof, wherein the compound is 5-methyl-1-(4-(4-(1,2,3,4-tetrahydroisoquinolin-6-yl)benzyl)phenyl)-1H-pyrazole-3-carboxamide.

Embodiment 426

A compound according to embodiment 1, or a pharmaceutically acceptable salt thereof, wherein the compound is 5-methyl-1-(4-(4-(1-methyl-1,2,3,6-tetrahydropyridin-4-yl)benzyl)phenyl)-1H-pyrazole-3-carboxamide.

Embodiment 427

A compound according to embodiment 1, or a pharmaceutically acceptable salt thereof, wherein the compound is 5-methyl-1-(4-(4-(1-methylpiperidin-4-yl)benzyl)phenyl)-1H-pyrazole-3-carboxamide.

Embodiment 428

A compound according to embodiment 1, or a pharmaceutically acceptable salt thereof, wherein the compound is 5-methyl-1-(4-(4-(1-methylpyrrolidin-3-yl)benzyl)phenyl)-1H-pyrazole-3-carboxamide.

Embodiment 429

A compound according to embodiment 1, or a pharmaceutically acceptable salt thereof, wherein the compound is (R)-5-methyl-1-(4-(4-(1-methylpyrrolidin-3-yl)benzyl)phenyl)-1H-pyrazole-3-carboxamide.

Embodiment 430

A compound according to embodiment 1, or a pharmaceutically acceptable salt thereof, wherein the compound is (S)-5-methyl-1-(4-(4-(1-methylpyrrolidin-3-yl)benzyl)phenyl)-1H-pyrazole-3-carboxamide.

Embodiment 431

A compound according to embodiment 1, or a pharmaceutically acceptable salt thereof, wherein the compound is 1-(4-(4-(6-((dimethylamino)methyl)pyridin-3-yl)benzyl)phenyl)-5-methyl-1H-pyrazole-3-carboxamide.

Embodiment 432

A compound according to embodiment 1, or a pharmaceutically acceptable salt thereof, wherein the compound is 1-(4-(4-(2-((dimethylamino)methyl)pyridin-4-yl)benzyl)phenyl)-5-methyl-1H-pyrazole-3-carboxamide.

Embodiment 433

A compound according to embodiment 1, or a pharmaceutically acceptable salt thereof, wherein the compound is 5-methyl-1-(4-(4-(6-(pyrrolidin-1-ylmethyl)pyridin-3-yl)benzyl)phenyl)-1H-pyrazole-3-carboxamide.

Embodiment 434

A compound according to embodiment 1, or a pharmaceutically acceptable salt thereof, wherein the compound is 1-(4-(4-(5-((dimethylamino)methyl)pyridin-3-yl)benzyl)phenyl)-5-methyl-1H-pyrazole-3-carboxamide.

Embodiment 435

A compound according to embodiment 1, or a pharmaceutically acceptable salt thereof, wherein the compound is 5-methyl-1-(4-(4-(1-methyl-2,3,6,7-tetrahydro-1H-azepin-4-yl)benzyl)phenyl)-1H-pyrazole-3-carboxamide.

Embodiment 436

A compound according to embodiment 1, or a pharmaceutically acceptable salt thereof, wherein the compound is 5-methyl-1-(4-((4'-(1-methylpyrrolidin-2-yl)-[1,1'-biphenyl]-4-yl)methyl)phenyl)-1H-pyrazole-3-carboxamide.

Embodiment 437

A compound according to embodiment 1, or a pharmaceutically acceptable salt thereof, wherein the compound is (R)-5-methyl-1-(4-((4'-(1-methylpyrrolidin-2-yl)-[1,1'-biphenyl]-4-yl)methyl)phenyl)-1H-pyrazole-3-carboxamide.

Embodiment 438

A compound according to embodiment 1, or a pharmaceutically acceptable salt thereof, wherein the compound is (S)-5-methyl-1-(4-((4'-(1-methylpyrrolidin-2-yl)-[1,1'-biphenyl]-4-yl)methyl)phenyl)-1H-pyrazole-3-carboxamide.

Embodiment 439

A compound according to embodiment 1, or a pharmaceutically acceptable salt thereof, wherein the compound is 5-methyl-1-(4-(2-(4'-(pyrrolidin-1-ylmethyl)-[1,1'-biphenyl]-4-yl)propan-2-yl)phenyl)-1H-pyrazole-3-carboxamide.

Embodiment 440

A compound according to embodiment 1, or a pharmaceutically acceptable salt thereof, wherein the compound is 5-methyl-1-(4-(2-(3'-(methylsulfonyl)-[1,1'-biphenyl]-4-yl)propan-2-yl)phenyl)-1H-pyrazole-3-carboxamide.

Embodiment 441

A compound according to embodiment 1, or a pharmaceutically acceptable salt thereof, wherein the compound is 5-methyl-1-(4-(2-(4-(pyridin-4-yl)phenyl)propan-2-yl)phenyl)-1H-pyrazole-3-carboxamide.

Embodiment 442

A compound according to embodiment 1, or a pharmaceutically acceptable salt thereof, wherein the compound is 1-(4-(2-(4-(1H-indazol-5-yl)phenyl)propan-2-yl)phenyl)-5-methyl-1H-pyrazole-3-carboxamide.

Embodiment 443

A compound according to embodiment 1, or a pharmaceutically acceptable salt thereof, wherein the compound is 1-(4-(2-(4-(2-aminopyridin-4-yl)phenyl)propan-2-yl)phenyl)-5-methyl-1H-pyrazole-3-carboxamide.

Embodiment 444

A compound according to embodiment 1, or a pharmaceutically acceptable salt thereof, wherein the compound is 5-methyl-1-(4-(2-(4'-(5-methyl-1,3,4-oxadiazol-2-yl)-[1,1'-biphenyl]-4-yl)propan-2-yl)phenyl)-1H-pyrazole-3-carboxamide.

Embodiment 445

A compound according to embodiment 1, or a pharmaceutically acceptable salt thereof, wherein the compound is 5-methyl-1-(4-(2-(4'-(pyrrolidin-1-ylmethyl)-[1,1'-biphenyl]-4-yl)propan-2-yl)phenyl)-1H-pyrazole-3-carboxamide.

Embodiment 446

A compound according to embodiment 1, or a pharmaceutically acceptable salt thereof, wherein the compound is 5-methyl-1-(4-(2-(4'-morpholino-2',3',4',5'-tetrahydro-[1,1'-biphenyl]-4-yl)propan-2-yl)phenyl)-1H-pyrazole-3-carboxamide.

Embodiment 447

A compound according to embodiment 1, or a pharmaceutically acceptable salt thereof, wherein the compound is (R)-5-methyl-1-(4-(2-(4'-morpholino-2',3',4',5'-tetrahydro-[1,1'-biphenyl]-4-yl)propan-2-yl)phenyl)-1H-pyrazole-3-carboxamide.

Embodiment 448

A compound according to embodiment 1, or a pharmaceutically acceptable salt thereof, wherein the compound is (S)-5-methyl-1-(4-(2-(4'-morpholino-2',3',4',5'-tetrahydro-[1,1'-biphenyl]-4-yl)propan-2-yl)phenyl)-1H-pyrazole-3-carboxamide.

Embodiment 449

A compound according to embodiment 1, or a pharmaceutically acceptable salt thereof, wherein the compound is 1-(4-(2-(4'-hydroxy-2',3',4',5'-tetrahydro-[1,1'-biphenyl]-4-yl)propan-2-yl)phenyl)-5-methyl-1H-pyrazole-3-carboxamide.

Embodiment 450

A compound according to embodiment 1, or a pharmaceutically acceptable salt thereof, wherein the compound is (R)-1-(4-(2-(4'-hydroxy-2',3',4',5'-tetrahydro-[1,1'-biphenyl]-4-yl)propan-2-yl)phenyl)-5-methyl-1H-pyrazole-3-carboxamide.

Embodiment 451

A compound according to embodiment 1, or a pharmaceutically acceptable salt thereof, wherein the compound is (S)-1-(4-(2-(4'-hydroxy-2',3',4',5'-tetrahydro-[1,1'-biphenyl]-4-yl)propan-2-yl)phenyl)-5-methyl-1H-pyrazole-3-carboxamide.

Embodiment 452

A compound according to embodiment 1, or a pharmaceutically acceptable salt thereof, wherein the compound is 5-methyl-1-(4-(2-(4-(pyridin-2-yl)phenyl)propan-2-yl)phenyl)-1H-pyrazole-3-carboxamide.

Embodiment 453

A compound according to embodiment 1, or a pharmaceutically acceptable salt thereof, wherein the compound is 1-(4-(2-(4'-(3-(aminomethyl)oxetan-3-yl)-[1,1'-biphenyl]-4-yl)propan-2-yl)phenyl)-5-methyl-1H-pyrazole-3-carboxamide.

Embodiment 454

A compound according to embodiment 1, or a pharmaceutically acceptable salt thereof, wherein the compound is 1-(4-(2-(4'-(3-aminooxetan-3-yl)-[1,1'-biphenyl]-4-yl)propan-2-yl)phenyl)-5-methyl-1H-pyrazole-3-carboxamide.

Embodiment 455

A compound according to embodiment 1, or a pharmaceutically acceptable salt thereof, wherein the compound is 5-methyl-1-(4-(2-(4'-(pyrrolidin-1-ylmethyl)-[1,1'-biphenyl]-4-yl)propan-2-yl)phenyl)-1H-1,2,4-triazole-3-carboxamide.

Embodiment 456

A compound according to embodiment 1, or a pharmaceutically acceptable salt thereof, wherein the compound is 1-(4-(2-(4'-(N,N-dimethylsulfamoyl)-[1,1'-biphenyl]-4-yl)propan-2-yl)phenyl)-5-methyl-1H-1,2,4-triazole-3-carboxamide.

Embodiment 457

A compound according to embodiment 1, or a pharmaceutically acceptable salt thereof, wherein the compound is 5-methyl-1-(4-(2-(4-(quinolin-6-yl)phenyl) propan-2-yl) phenyl)-1H-1,2,4-triazole-3-carboxamide.

Embodiment 458

A compound according to embodiment 1, or a pharmaceutically acceptable salt thereof, wherein the compound is 5-methyl-1-(4-(2-(4-(quinoxalin-6-yl)phenyl) propan-2-yl) phenyl)-1H-1,2,4-triazole-3-carboxamide.

Embodiment 459

A compound according to embodiment 1, or a pharmaceutically acceptable salt thereof, wherein the compound is 1-(4-(2-(4-(isoquinolin-7-yl)phenyl)propan-2-yl)phenyl)-5-methyl-1H-1,2,4-triazole-3-carboxamide.

Embodiment 460

A compound according to embodiment 1, or a pharmaceutically acceptable salt thereof, wherein the compound is 1-(4-(2-(4'-(dimethylcarbamoyl)-[1,1'-biphenyl]-4-yl) propan-2-yl)phenyl)-5-methyl-1H-1,2,4-triazole-3-carboxamide.

Embodiment 461

A compound according to embodiment 1, or a pharmaceutically acceptable salt thereof, wherein the compound is 1-(4-(2-(4-(benzo[d]thiazol-5-yl)phenyl) propan-2-yl)phenyl)-5-methyl-1H-1,2,4-triazole-3-carboxamide.

Embodiment 462

A compound according to embodiment 1, or a pharmaceutically acceptable salt thereof, wherein the compound is 5-methyl-1-(4-(2-(4-(1-methyl-1H-pyrazol-4-yl)phenyl)propan-2-yl)phenyl)-1H-1,2,4-triazole-3-carboxamide.

Embodiment 463

A compound according to embodiment 1, or a pharmaceutically acceptable salt thereof, wherein the compound is 5-methyl-1-(4-(2-(4-(2-methylpyridin-4-yl)phenyl) propan-2-yl)phenyl)-1H-1,2,4-triazole-3-carboxamide.

Embodiment 464

A compound according to embodiment 1, or a pharmaceutically acceptable salt thereof, wherein the compound is 1-(4-(2-(4-(6-cyanopyridin-3-yl)phenyl)propan-2-yl)phenyl)-5-methyl-1H-1,2,4-triazole-3-carboxamide.

Embodiment 465

A compound according to embodiment 1, or a pharmaceutically acceptable salt thereof, wherein the compound is 5-methyl-1-(4-(2-(4-(4-methyl-3,4-dihydro-2H-pyrido[3,2-b][1,4]oxazin-7-yl)phenyl)propan-2-yl)phenyl)-1H-1,2,4-triazole-3-carboxamide.

Embodiment 466

A compound according to embodiment 1, or a pharmaceutically acceptable salt thereof, wherein the compound is 5-methyl-1-(4-(2-(4'-(morpholinomethyl)-[1,1'-biphenyl]-4-yl) propan-2-yl)phenyl)-1H-1,2,4-triazole-3-carboxamide.

Embodiment 467

A compound according to embodiment 1, or a pharmaceutically acceptable salt thereof, wherein the compound is 5-methyl-1-(4-(2-(3'-(5-methyl-1,3,4-oxadiazol-2-yl)-[1,1'-biphenyl]-4-yl)propan-2-yl)phenyl)-1H-1,2,4-triazole-3-carboxamide.

Embodiment 468

A compound according to embodiment 1, or a pharmaceutically acceptable salt thereof, wherein the compound is 5-methyl-1-(4-(2-(4-(6-(pyrrolidin-1-yl)pyridin-3-yl)phenyl)propan-2-yl)phenyl)-1H-1,2,4-triazole-3-carboxamide.

Embodiment 469

A compound according to embodiment 1, or a pharmaceutically acceptable salt thereof, wherein the compound is 5-methyl-1-(4-(2-(4-(6-morpholinopyridin-3-yl)phenyl)propan-2-yl)phenyl)-1H-1,2,4-triazole-3-carboxamide.

Embodiment 470

A compound according to embodiment 1, or a pharmaceutically acceptable salt thereof, wherein the compound is 5-methyl-1-(4-(2-(4-(thiophen-3-yl)phenyl) propan-2-yl) phenyl)-1H-1,2,4-triazole-3-carboxamide.

Embodiment 471

A compound according to embodiment 1, or a pharmaceutically acceptable salt thereof, wherein the compound is 1-(4-(2-(4'-(1-amino-2,2,2-trifluoroethyl)-[1,1'-biphenyl]-4-yl) propan-2-yl)phenyl)-5-methyl-1H-1,2,4-triazole-3-carboxamide.

Embodiment 472

A compound according to embodiment 1, or a pharmaceutically acceptable salt thereof, wherein the compound is (R)-1-(4-(2-(4'-(1-amino-2,2,2-trifluoroethyl)-[1,1'-biphenyl]-4-yl)propan-2-yl)phenyl)-5-methyl-1H-1,2,4-triazole-3-carboxamide.

Embodiment 473

A compound according to embodiment 1, or a pharmaceutically acceptable salt thereof, wherein the compound is (S)-1-(4-(2-(4'-(1-amino-2,2,2-trifluoroethyl)-[1,1'-biphenyl]-4-yl)propan-2-yl)phenyl)-5-methyl-1H-1,2,4-triazole-3-carboxamide.

Embodiment 474

A compound according to embodiment 1, or a pharmaceutically acceptable salt thereof, wherein the compound is 5-methyl-1-(4-((4'-((4-methylpiperazin-1-yl)methyl)-[1,1'-biphenyl]-4-yl)methyl)phenyl)-1H-1,2,4-triazole-3-carboxamide.

Embodiment 475

A compound according to embodiment 1, or a pharmaceutically acceptable salt thereof, wherein the compound is 5-methyl-1-(4-(4-(pyridin-3-yl)benzyl)phenyl)-1H-1,2,4-triazole-3-carboxamide.

Embodiment 476

A compound according to embodiment 1, or a pharmaceutically acceptable salt thereof, wherein the compound is 5-methyl-1-(4-((4'-(4-methylpiperazine-1-carbonyl)-[1,1'-biphenyl]-4-yl)methyl)phenyl)-1H-1,2,4-triazole-3-carboxamide.

Embodiment 477

A compound according to embodiment 1, or a pharmaceutically acceptable salt thereof, wherein the compound is 5-methyl-1-(4-((4'-(pyrrolidin-1-ylmethyl)-[1,1'-biphenyl]-4-yl)methyl)phenyl)-1H-1,2,4-triazole-3-carboxamide.

Embodiment 478

A compound according to embodiment 1, or a pharmaceutically acceptable salt thereof, wherein the compound is 1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide.

Embodiment 479

A compound according to embodiment 1, or a pharmaceutically acceptable salt thereof, wherein the compound is (R)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide.

Embodiment 480

A compound according to embodiment 1, or a pharmaceutically acceptable salt thereof, wherein the compound is (S)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide.

Embodiment 481

A compound according to embodiment 1, or a pharmaceutically acceptable salt thereof, wherein the compound is 1-(4-((4'-(((2-hydroxyethyl)amino)methyl)-[1,1'-biphenyl]-4-yl)methyl)phenyl)-5-methyl-1H-pyrazole-3-carboxamide.

Embodiment 482

A compound according to embodiment 1, or a pharmaceutically acceptable salt thereof, wherein the compound is 1-(4-((4'-((cyclobutylamino)methyl)-[1,1'-biphenyl]-4-yl)methyl)phenyl)-5-methyl-1H-pyrazole-3-carboxamide.

Embodiment 483

A compound according to embodiment 1, or a pharmaceutically acceptable salt thereof, wherein the compound is 5-methyl-1-(4-((4'-((oxetan-3-ylamino)methyl)-[1,1'-biphenyl]-4-yl)methyl)phenyl)-1H-pyrazole-3-carboxamide.

Embodiment 484

A compound according to embodiment 1, or a pharmaceutically acceptable salt thereof, wherein the compound is 5-methyl-1-(4-((4'-((5-methylhexahydropyrrolo[3,4-c]pyrrol-2(1H)-yl)methyl)-[1,1'-biphenyl]-4-yl)methyl)phenyl)-1H-pyrazole-3-carboxamide.

Embodiment 485

A compound according to embodiment 1, or a pharmaceutically acceptable salt thereof, wherein the compound is 5-methyl-1-(4-((4'-(piperidin-1-ylmethyl)-[1,1'-biphenyl]-4-yl)methyl)phenyl)-1H-pyrazole-3-carboxamide.

Embodiment 486

A compound according to embodiment 1, or a pharmaceutically acceptable salt thereof, wherein the compound is 1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide.

Embodiment 487

A compound according to embodiment 1, or a pharmaceutically acceptable salt thereof, wherein the compound is (R)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide.

Embodiment 488

A compound according to embodiment 1, or a pharmaceutically acceptable salt thereof, wherein the compound is (S)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide.

Embodiment 489

A compound according to embodiment 1, or a pharmaceutically acceptable salt thereof, wherein the compound is 1-(4-((4'-(azetidin-1-ylmethyl)-[1,1'-biphenyl]-4-yl)methyl)phenyl)-5-methyl-1H-pyrazole-3-carboxamide.

Embodiment 490

A compound according to embodiment 1, or a pharmaceutically acceptable salt thereof, wherein the compound is 1-(4-((4'-((2-hydroxyethyl)sulfonyl)-[1,1'-biphenyl]-4-yl)methyl)phenyl)-5-methyl-1H-pyrazole-3-carboxamide.

Embodiment 491

A compound according to embodiment 1, or a pharmaceutically acceptable salt thereof, wherein the compound is 1-(4-((4'-((4,4-difluoro-2-(hydroxymethyl)pyrrolidin-1-yl)methyl)-[1,1'-biphenyl]-4-yl)methyl)phenyl)-5-methyl-1H-pyrazole-3-carboxamide.

Embodiment 492

A compound according to embodiment 1, or a pharmaceutically acceptable salt thereof, wherein the compound is (R)-1-(4-((4'-((4,4-difluoro-2-(hydroxymethyl)pyrrolidin-1-yl)methyl)-[1,1'-biphenyl]-4-yl)methyl)phenyl)-5-methyl-1H-pyrazole-3-carboxamide.

Embodiment 493

A compound according to embodiment 1, or a pharmaceutically acceptable salt thereof, wherein the compound is (S)-1-(4-((4'-((4,4-difluoro-2-(hydroxymethyl)pyrrolidin-1-yl)methyl)-[1,1'-biphenyl]-4-yl)methyl)phenyl)-5-methyl-1H-pyrazole-3-carboxamide.

Embodiment 494

A compound according to embodiment 1, or a pharmaceutically acceptable salt thereof, wherein the compound is 1-(4-(4-(5-(2-hydroxypropan-2-yl)pyridin-2-yl)benzyl)phenyl)-5-methyl-1H-pyrazole-3-carboxamide.

Embodiment 495

A compound according to embodiment 1, or a pharmaceutically acceptable salt thereof, wherein the compound is 1-(4-(4-(5-(2-hydroxypropan-2-yl)-6-methylpyridin-2-yl)benzyl)phenyl)-5-methyl-1H-pyrazole-3-carboxamide.

Embodiment 496

A compound according to embodiment 1, or a pharmaceutically acceptable salt thereof, wherein the compound is 1-(4-(4-(5-(2-hydroxypropan-2-yl)pyridin-2-yl)benzyl)phenyl)-5-methyl-1H-1,2,4-triazole-3-carboxamide.

Embodiment 497

A compound according to embodiment 1, or a pharmaceutically acceptable salt thereof, wherein the compound is 1-(4-(4-(6-(3-hydroxyoxetan-3-yl)pyridin-3-yl)benzyl)phenyl)-5-methyl-1H-pyrazole-3-carboxamide.

Embodiment 498

A compound according to embodiment 1, or a pharmaceutically acceptable salt thereof, wherein the compound is 1-(4-(4-(2-(2-hydroxypropan-2-yl)pyridin-4-yl)benzyl)phenyl)-5-methyl-1H-pyrazole-3-carboxamide.

Embodiment 499

A compound according to embodiment 1, or a pharmaceutically acceptable salt thereof, wherein the compound is 5-methyl-1-(4-((4'-(piperazine-1-carbonyl)-[1,1'-biphenyl]-4-yl)methyl)phenyl)-1H-pyrazole-3-carboxamide.

Embodiment 500

A compound according to embodiment 1, or a pharmaceutically acceptable salt thereof, wherein the compound is 5-methyl-1-(4-((4'-(piperazine-1-carbonyl)-[1,1'-biphenyl]-4-yl)methyl)phenyl)-1H-1,2,4-triazole-3-carboxamide.

Embodiment 501

A compound according to embodiment 1, or a pharmaceutically acceptable salt thereof, wherein the compound is 5-methyl-1-(4-(4-(6-(piperazine-1-carbonyl)pyridin-3-yl)benzyl)phenyl)-1H-pyrazole-3-carboxamide.

Embodiment 502

A compound according to embodiment 1, or a pharmaceutically acceptable salt thereof, wherein the compound is 5-methyl-1-(4-(4-(5-(piperazine-1-carbonyl)pyridin-2-yl)benzyl)phenyl)-1H-pyrazole-3-carboxamide.

Embodiment 503

A compound according to embodiment 1, or a pharmaceutically acceptable salt thereof, wherein the compound is 1-(4-((4'-(3-(hydroxymethyl)piperazine-1-carbonyl)-[1,1'-biphenyl]-4-yl)methyl)phenyl)-5-methyl-1H-pyrazole-3-carboxamide.

Embodiment 504

A compound according to embodiment 1, or a pharmaceutically acceptable salt thereof, wherein the compound is (R)-1-(4-((4'-(3-(hydroxymethyl)piperazine-1-carbonyl)-[1,1'-biphenyl]-4-yl)methyl)phenyl)-5-methyl-1H-pyrazole-3-carboxamide.

Embodiment 505

A compound according to embodiment 1, or a pharmaceutically acceptable salt thereof, wherein the compound is (S)-1-(4-((4'-(3-(hydroxymethyl)piperazine-1-carbonyl)-[1,1'-biphenyl]-4-yl)methyl)phenyl)-5-methyl-1H-pyrazole-3-carboxamide.

Embodiment 506

A compound according to embodiment 1, or a pharmaceutically acceptable salt thereof, wherein the compound is 5-methyl-1-(4-((4'-(3-methyl piperazine-1-carbonyl)-[1,1'-biphenyl]-4-yl)methyl)phenyl)-1H-1,2,4-triazole-3-carboxamide.

Embodiment 507

A compound according to embodiment 1, or a pharmaceutically acceptable salt thereof, wherein the compound is (S)-5-methyl-1-(4-((4'-(3-methylpiperazine-1-carbonyl)-[1,1'-biphenyl]-4-yl)methyl)phenyl)-1H-1,2,4-triazole-3-carboxamide.

Embodiment 508

A compound according to embodiment 1, or a pharmaceutically acceptable salt thereof, wherein the compound is (R)-5-methyl-1-(4-((4'-(3-methylpiperazine-1-carbonyl)-[1,1'-biphenyl]-4-yl)methyl)phenyl)-1H-1,2,4-triazole-3-carboxamide.

Embodiment 509

A compound according to embodiment 1, or a pharmaceutically acceptable salt thereof, wherein the compound is 1-(4-((4'-(azetidin-3-ylcarbamoyl)-[1,1'-biphenyl]-4-yl)methyl)phenyl)-5-methyl-1H-pyrazole-3-carboxamide.

Embodiment 510

A compound according to embodiment 1, or a pharmaceutically acceptable salt thereof, wherein the compound is 5-methyl-1-(4-(4-(6-(piperazin-1-ylmethyl)pyridin-3-yl)benzyl)phenyl)-1H-pyrazole-3-carboxamide.

Embodiment 511

A compound according to embodiment 1, or a pharmaceutically acceptable salt thereof, wherein the compound is 5-methyl-1-(4-(4-(2-(piperazin-1-ylmethyl)pyridin-4-yl)benzyl)phenyl)-1H-pyrazole-3-carboxamide.

Embodiment 512

A compound according to embodiment 1, or a pharmaceutically acceptable salt thereof, wherein the compound is 5-methyl-1-(4-(4-(5-(piperazin-1-ylmethyl)pyridin-2-yl)benzyl)phenyl)-1H-pyrazole-3-carboxamide.

Embodiment 513

A compound according to embodiment 1, or a pharmaceutically acceptable salt thereof, wherein the compound is 1-(4-(4-(6-((4-(2-hydroxyethyl)piperazin-1-yl)methyl)pyridin-3-yl)benzyl)phenyl)-5-methyl-1H-pyrazole-3-carboxamide.

Embodiment 514

A compound according to embodiment 1, or a pharmaceutically acceptable salt thereof, wherein the compound is 5-methyl-1-(4-(4-(5-((4-(oxetan-3-yl)piperazin-1-yl)methyl)pyridin-2-yl)benzyl)phenyl)-1H-pyrazole-3-carboxamide.

Embodiment 515

A compound according to embodiment 1, or a pharmaceutically acceptable salt thereof, wherein is 5-methyl-1-(4-(4-(6-((4-methylpiperazin-1-yl)methyl)pyridin-3-yl)benzyl)phenyl)-1H-1,2,4-triazole-3-carboxamide.

Embodiment 516

A compound according to embodiment 1, or a pharmaceutically acceptable salt thereof, wherein the compound is 5-methyl-1-(4-(4-(5-(piperazin-1-ylmethyl)pyridin-2-yl)benzyl)phenyl)-1H-1,2,4-triazole-3-carboxamide.

Embodiment 517

A compound according to embodiment 1, or a pharmaceutically acceptable salt thereof, wherein the compound is 5-methyl-1-(4-(4-(6-((3-methylpiperazin-1-yl)methyl)pyridin-3-yl)benzyl)phenyl)-1H-1,2,4-triazole-3-carboxamide.

Embodiment 518

A compound according to embodiment 1, or a pharmaceutically acceptable salt thereof, wherein the compound is (S)-5-methyl-1-(4-(4-(6-((3-methylpiperazin-1-yl)methyl)pyridin-3-yl)benzyl)phenyl)-1H-1,2,4-triazole-3-carboxamide.

Embodiment 519

A compound according to embodiment 1, or a pharmaceutically acceptable salt thereof, wherein the compound is (R)-5-methyl-1-(4-(4-(6-((3-methylpiperazin-1-yl)methyl)pyridin-3-yl)benzyl)phenyl)-1H-1,2,4-triazole-3-carboxamide.

Embodiment 520

A compound according to embodiment 1, or a pharmaceutically acceptable salt thereof, wherein the compound is 1-(4-(4-(6-((3,4-dimethylpiperazin-1-yl)methyl)pyridin-3-yl)benzyl)phenyl)-5-methyl-1H-1,2,4-triazole-3-carboxamide.

Embodiment 521

A compound according to embodiment 1, or a pharmaceutically acceptable salt thereof, wherein the compound is (S)-1-(4-(4-(6-((3,4-dimethylpiperazin-1-yl)methyl)pyridin-3-yl)benzyl)phenyl)-5-methyl-1H-1,2,4-triazole-3-carboxamide.

Embodiment 522

A compound according to embodiment 1, or a pharmaceutically acceptable salt thereof, wherein the compound is (R)-1-(4-(4-(6-((3,4-dimethylpiperazin-1-yl)methyl)pyridin-3-yl)benzyl)phenyl)-5-methyl-1H-1,2,4-triazole-3-carboxamide.

Embodiment 523

A compound according to embodiment 1, or a pharmaceutically acceptable salt thereof, wherein the compound is 1-(4-((4'-((2-oxa-6-azaspiro[3.4]octan-6-yl)methyl)-[1,1'-biphenyl]-4-yl)methyl)phenyl)-5-methyl-1H-1,2,4-triazole-3-carboxamide.

Embodiment 524

A compound according to embodiment 1, or a pharmaceutically acceptable salt thereof, wherein the compound is 1-(4-((4'-((3,3-difluoropyrrolidin-1-yl)methyl)-[1,1'-biphenyl]-4-yl)methyl)phenyl)-5-methyl-1H-1,2,4-triazole-3-carboxamide.

Embodiment 525

A compound according to embodiment 1, or a pharmaceutically acceptable salt thereof, wherein the compound is 5-methyl-1-(4-((4'-(((3aR,6aS)-5-methylhexahydropyrrolo[3,4-c]pyrrol-2(1H)-yl)methyl)-[1,1'-biphenyl]-4-yl)methyl)phenyl)-1H-1,2,4-triazole-3-carboxamide.

Embodiment 526

A compound according to embodiment 1, or a pharmaceutically acceptable salt thereof, wherein the compound is 1-(4-((4'-((2-oxa-6-azaspiro[3.3]heptan-6-yl)methyl)-[1,1'-biphenyl]-4-yl)methyl)phenyl)-5-methyl-1H-1,2,4-triazole-3-carboxamide.

Embodiment 527

A compound according to embodiment 1, or a pharmaceutically acceptable salt thereof, wherein the compound is 1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide.

Embodiment 528

A compound according to embodiment 1, or a pharmaceutically acceptable salt thereof, wherein the compound is (R)-1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide.

Embodiment 529

A compound according to embodiment 1, or a pharmaceutically acceptable salt thereof, wherein the compound is (S)-1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide.

Embodiment 530

A compound according to embodiment 1, or a pharmaceutically acceptable salt thereof, wherein the compound is 1-(4-((4'-((2-oxa-6-azaspiro[3.5]nonan-6-yl)methyl)-[1,1'-biphenyl]-4-yl)methyl)phenyl)-5-methyl-1H-1,2,4-triazole-3-carboxamide.

Embodiment 531

A compound according to embodiment 1, or a pharmaceutically acceptable salt thereof, wherein the compound is 1-(4-((4'-((3,3-dimethylpyrrolidin-1-yl)methyl)-[1,1'-biphenyl]-4-yl)methyl)phenyl)-5-methyl-1H-1,2,4-triazole-3-carboxamide.

Embodiment 532

A compound according to embodiment 1, or a pharmaceutically acceptable salt thereof, wherein the compound is 1-(4-((4'-((2-oxa-7-azaspiro[3.5]nonan-7-yl)methyl)-[1,1'-biphenyl]-4-yl)methyl)phenyl)-5-methyl-1H-1,2,4-triazole-3-carboxamide.

Embodiment 533

A compound according to embodiment 1, or a pharmaceutically acceptable salt thereof, wherein the compound is 1-(4-((4'-((3,3-difluoropiperidin-1-yl)methyl)-[1,1'-biphenyl]-4-yl)methyl)phenyl)-5-methyl-1H-1,2,4-triazole-3-carboxamide.

Embodiment 534

A compound according to embodiment 1, or a pharmaceutically acceptable salt thereof, wherein the compound is 1-(4-((4'-((4,4-dimethylpiperidin-1-yl)methyl)-[1,1'-biphenyl]-4-yl)methyl)phenyl)-5-methyl-1H-1,2,4-triazole-3-carboxamide.

Embodiment 535

A compound according to embodiment 1, or a pharmaceutically acceptable salt thereof, wherein the compound is 1-(4-((4'-((4-((dimethylamino)methyl)piperidin-1-yl)methyl)-[1,1'-biphenyl]-4-yl)methyl)phenyl)-5-methyl-1H-1,2,4-triazole-3-carboxamide.

Embodiment 536

A compound according to embodiment 1, or a pharmaceutically acceptable salt thereof, wherein the compound is 1-(4-((4'-((4-(dimethylamino)piperidin-1-yl)methyl)-[1,1'-biphenyl]-4-yl)methyl)phenyl)-5-methyl-1H-1,2,4-triazole-3-carboxamide.

Embodiment 537

A compound according to embodiment 1, or a pharmaceutically acceptable salt thereof, wherein the compound is 1-(4-((4'-((4-(2-hydroxypropan-2-yl)piperidin-1-yl)methyl)-[1,1'-biphenyl]-4-yl)methyl)phenyl)-5-methyl-1H-1,2,4-triazole-3-carboxamide.

Embodiment 538

A compound according to embodiment 1, or a pharmaceutically acceptable salt thereof, wherein the compound is 1-(4-((4'-((3-hydroxypyrrolidin-1-yl)methyl)-[1,1'-biphenyl]-4-yl)methyl)phenyl)-5-methyl-1H-1,2,4-triazole-3-carboxamide.

Embodiment 539

A compound according to embodiment 1, or a pharmaceutically acceptable salt thereof, wherein the compound is (R)-1-(4-((4'-((3-hydroxypyrrolidin-1-yl)methyl)-[1,1'-biphenyl]-4-yl)methyl)phenyl)-5-methyl-1H-1,2,4-triazole-3-carboxamide.

Embodiment 540

A compound according to embodiment 1, or a pharmaceutically acceptable salt thereof, wherein the compound is (S)-1-(4-((4'-((3-hydroxypyrrolidin-1-yl)methyl)-[1,1'-biphenyl]-4-yl)methyl)phenyl)-5-methyl-1H-1,2,4-triazole-3-carboxamide.

Embodiment 541

A compound according to embodiment 1, or a pharmaceutically acceptable salt thereof, wherein the compound is 1-(4-((4'-((4-hydroxy-4-methylpiperidin-1-yl)methyl)-[1,1'-biphenyl]-4-yl)methyl)phenyl)-5-methyl-1H-1,2,4-triazole-3-carboxamide.

Embodiment 542

A compound according to embodiment 1, or a pharmaceutically acceptable salt thereof, wherein the compound is 1-(4-((4'-((3-(2-hydroxypropan-2-yl)piperidin-1-yl)methyl)-[1,1'-biphenyl]-4-yl)methyl)phenyl)-5-methyl-1H-1,2,4-triazole-3-carboxamide.

Embodiment 543

A compound according to embodiment 1, or a pharmaceutically acceptable salt thereof, wherein the compound is 1-(4-((4'-((3-hydroxyazetidin-1-yl)methyl)-[1,1'-biphenyl]-4-yl)methyl)phenyl)-5-methyl-1H-1,2,4-triazole-3-carboxamide.

Embodiment 544

A compound according to embodiment 1, or a pharmaceutically acceptable salt thereof, wherein the compound is 1-(4-((4'-((3,5-dimethyl piperazin-1-yl)methyl)-[1,1'-biphenyl]-4-yl)methyl)phenyl)-5-methyl-1H-1,2,4-triazole-3-carboxamide.

Embodiment 545

A compound according to embodiment 1, or a pharmaceutically acceptable salt thereof, wherein the compound is 1-(4-((4'-(((3R,5R)-3,5-dimethylpiperazin-1-yl)methyl)-[1,1'-biphenyl]-4-yl)methyl)phenyl)-5-methyl-1H-1,2,4-triazole-3-carboxamide.

Embodiment 546

A compound according to embodiment 1, or a pharmaceutically acceptable salt thereof, wherein the compound is 1-(4-((4'-(((3S,5S)-3,5-dimethylpiperazin-1-yl)methyl)-[1,1'-biphenyl]-4-yl)methyl)phenyl)-5-methyl-1H-1,2,4-triazole-3-carboxamide.

Embodiment 547

A compound according to embodiment 1, or a pharmaceutically acceptable salt thereof, wherein the compound is 1-(4-((4'-((3-hydroxy-3-methylpyrrolidin-1-yl)methyl)-[1,1'-biphenyl]-4-yl)methyl)phenyl)-5-methyl-1H-1,2,4-triazole-3-carboxamide.

Embodiment 548

A compound according to embodiment 1, or a pharmaceutically acceptable salt thereof, wherein the compound is 1-(4-((4'-((5-oxa-2-azaspiro[3.4]octan-2-yl)methyl)-[1,1'-biphenyl]-4-yl)methyl)phenyl)-5-methyl-1H-1,2,4-triazole-3-carboxamide.

Embodiment 549

A compound according to embodiment 1, or a pharmaceutically acceptable salt thereof, wherein the compound is 1-(4-((4'-((3-(hydroxymethyl)piperazin-1-yl)methyl)-[1,1'-biphenyl]-4-yl)methyl)phenyl)-5-methyl-1H-1,2,4-triazole-3-carboxamide.

Embodiment 550

A compound according to embodiment 1, or a pharmaceutically acceptable salt thereof, wherein the compound is (R)-1-(4-((4'-((3-(hydroxymethyl)piperazin-1-yl)methyl)-[1,1'-biphenyl]-4-yl)methyl)phenyl)-5-methyl-1H-1,2,4-triazole-3-carboxamide.

Embodiment 551

A compound according to embodiment 1, or a pharmaceutically acceptable salt thereof, wherein the compound is (S)-1-(4-((4'-((3-(hydroxymethyl)piperazin-1-yl)methyl)-[1,1'-biphenyl]-4-yl)methyl)phenyl)-5-methyl-1H-1,2,4-triazole-3-carboxamide.

Embodiment 552

A compound according to embodiment 1, or a pharmaceutically acceptable salt thereof, wherein the compound is 1-(4-((4'-((3-fluoropyrrolidin-1-yl)methyl)-[1,1'-biphenyl]-4-yl)methyl)phenyl)-5-methyl-1H-1,2,4-triazole-3-carboxamide.

Embodiment 553

A compound according to embodiment 1, or a pharmaceutically acceptable salt thereof, wherein the compound is (R)-1-(4-((4'-((3-fluoropyrrolidin-1-yl)methyl)-[1,1'-biphenyl]-4-yl)methyl)phenyl)-5-methyl-1H-1,2,4-triazole-3-carboxamide.

Embodiment 554

A compound according to embodiment 1, or a pharmaceutically acceptable salt thereof, wherein the compound is (S)-1-(4-((4'-((3-fluoropyrrolidin-1-yl)methyl)-[1,1'-biphenyl]-4-yl)methyl)phenyl)-5-methyl-1H-1,2,4-triazole-3-carboxamide.

Embodiment 555

A compound according to embodiment 1, or a pharmaceutically acceptable salt thereof, wherein the compound is 5-methyl-1-(4-((4'-((3-(methylsulfonyl)pyrrolidin-1-yl)methyl)-[1,1'-biphenyl]-4-yl)methyl)phenyl)-1H-1,2,4-triazole-3-carboxamide.

Embodiment 556

A compound according to embodiment 1, or a pharmaceutically acceptable salt thereof, wherein the compound is 5-methyl-1-(4-((4'-((5-methylhexahydropyrrolo[3,4-b]pyrrol-1 (2H)-yl)methyl)-[1,1'-biphenyl]-4-yl)methyl)phenyl)-1H-1,2,4-triazole-3-carboxamide.

Embodiment 557

A compound according to embodiment 1, or a pharmaceutically acceptable salt thereof, wherein the compound is (R)-5-methyl-1-(4-((4'-((5-methylhexahydropyrrolo[3,4-b]pyrrol-1 (2H)-yl)methyl)-[1,1'-biphenyl]-4-yl)methyl)phenyl)-1H-1,2,4-triazole-3-carboxamide.

Embodiment 558

A compound according to embodiment 1, or a pharmaceutically acceptable salt thereof, wherein the compound is (S)-5-methyl-1-(4-((4'-((5-methylhexahydropyrrolo[3,4-b]pyrrol-1 (2H)-yl)methyl)-[1,1'-biphenyl]-4-yl)methyl)phenyl)-1H-1,2,4-triazole-3-carboxamide.

Embodiment 559

A compound according to embodiment 1, or a pharmaceutically acceptable salt thereof, wherein the compound is 1-(4-((4'-((3-hydroxy-3-methylpiperidin-1-yl)methyl)-[1,1'-biphenyl]-4-yl)methyl)phenyl)-5-methyl-1H-1,2,4-triazole-3-carboxamide.

Embodiment 560

A compound according to embodiment 1, or a pharmaceutically acceptable salt thereof, wherein the compound is (R)-1-(4-((4'-((3-hydroxy-3-methylpiperidin-1-yl)methyl)-[1,1'-biphenyl]-4-yl)methyl)phenyl)-5-methyl-1H-1,2,4-triazole-3-carboxamide.

Embodiment 561

A compound according to embodiment 1, or a pharmaceutically acceptable salt thereof, wherein the compound is (S)-1-(4-((4'-((3-hydroxy-3-methyl piperidin-1-yl)methyl)-[1,1'-biphenyl]-4-yl)methyl)phenyl)-5-methyl-1H-1,2,4-triazole-3-carboxamide.

Embodiment 562

A compound according to embodiment 1, or a pharmaceutically acceptable salt thereof, wherein the compound is 1-(4-((4'-((4-(tert-butyl)piperazin-1-yl)methyl)-[1,1'-biphenyl]-4-yl)methyl)phenyl)-5-methyl-1H-1,2,4-triazole-3-carboxamide.

Embodiment 563

A compound according to embodiment 1, or a pharmaceutically acceptable salt thereof, wherein the compound is 1-(4-((4'-((3,3-dimethylpiperazin-1-yl)methyl)-[1,1'-biphenyl]-4-yl)methyl)phenyl)-5-methyl-1H-1,2,4-triazole-3-carboxamide.

Embodiment 564

A compound according to embodiment 1, or a pharmaceutically acceptable salt thereof, wherein the compound is 1-(4-((4'-(((3S,5R)-3,5-dimethylpiperazin-1-yl)methyl)-[1,1'-biphenyl]-4-yl)methyl)phenyl)-5-methyl-1H-1,2,4-triazole-3-carboxamide.

Embodiment 565

A compound according to embodiment 1, or a pharmaceutically acceptable salt thereof, wherein the compound is 1-(4-((4'-((4,4-difluoropiperidin-1-yl)methyl)-[1,1'-biphenyl]-4-yl)methyl)phenyl)-5-methyl-1H-1,2,4-triazole-3-carboxamide.

Embodiment 566

A compound according to embodiment 1, or a pharmaceutically acceptable salt thereof, wherein the compound is 5-methyl-1-(4-((4'-((octahydro-2H-pyrido[1,2-a]pyrazin-2-yl)methyl)-[1,1'-biphenyl]-4-yl)methyl)phenyl)-1H-1,2,4-triazole-3-carboxamide.

Embodiment 567

A compound according to embodiment 1, or a pharmaceutically acceptable salt thereof, wherein the compound is (R)-5-methyl-1-(4-((4'-((octahydro-2H-pyrido[1,2-a]pyrazin-2-yl)methyl)-[1,1'-biphenyl]-4-yl)methyl)phenyl)-1H-1,2,4-triazole-3-carboxamide.

Embodiment 568

A compound according to embodiment 1, or a pharmaceutically acceptable salt thereof, wherein the compound is (S)-5-methyl-1-(4-((4'-((octahydro-2H-pyrido[1,2-a]pyrazin-2-yl)methyl)-[1,1'-biphenyl]-4-yl)methyl)phenyl)-1H-1,2,4-triazole-3-carboxamide.

Embodiment 569

A compound according to embodiment 1, or a pharmaceutically acceptable salt thereof, wherein the compound is 1-(4-((4'-((2-(hydroxymethyl)piperidin-1-yl)methyl)-[1,1'-biphenyl]-4-yl)methyl)phenyl)-5-methyl-1H-1,2,4-triazole-3-carboxamide.

Embodiment 570

A compound according to embodiment 1, or a pharmaceutically acceptable salt thereof, wherein the compound is (S)-1-(4-((4'-((2-(hydroxymethyl)piperidin-1-yl)methyl)-[1,1'-biphenyl]-4-yl)methyl)phenyl)-5-methyl-1H-1,2,4-triazole-3-carboxamide.

Embodiment 571

A compound according to embodiment 1, or a pharmaceutically acceptable salt thereof, wherein the compound is (R)-1-(4-((4'-((2-(hydroxymethyl)piperidin-1-yl)methyl)-[1,1'-biphenyl]-4-yl)methyl)phenyl)-5-methyl-1H-1,2,4-triazole-3-carboxamide.

Embodiment 572

A compound according to embodiment 1, or a pharmaceutically acceptable salt thereof, wherein the compound is 1-(4-((4'-((4-(hydroxymethyl)piperidin-1-yl)methyl)-[1,1'-biphenyl]-4-yl)methyl)phenyl)-5-methyl-1H-1,2,4-triazole-3-carboxamide.

Embodiment 573

A compound according to embodiment 1, or a pharmaceutically acceptable salt thereof, wherein the compound is 1-(4-((4'-((3-hydroxy-3-methylazetidin-1-yl)methyl)-[1,1'-biphenyl]-4-yl)methyl)phenyl)-5-methyl-1H-1,2,4-triazole-3-carboxamide.

Embodiment 574

A compound according to embodiment 1, or a pharmaceutically acceptable salt thereof, wherein the compound is 1-(4-((4'-((4-hydroxypiperidin-1-yl)methyl)-[1,1'-biphenyl]-4-yl)methyl)phenyl)-5-methyl-1H-1,2,4-triazole-3-carboxamide.

Embodiment 575

A compound according to embodiment 1, or a pharmaceutically acceptable salt thereof, wherein the compound is 5-methyl-1-(4-((4'-(((3aR,6aS)-tetrahydro-1H-furo[3,4-c]pyrrol-5(3H)-yl)methyl)-[1,1'-biphenyl]-4-yl)methyl)phenyl)-1H-1,2,4-triazole-3-carboxamide.

Embodiment 576

A compound according to embodiment 1, or a pharmaceutically acceptable salt thereof, wherein the compound is 1-(4-((4'-((3-fluoropiperidin-1-yl)methyl)-[1,1'-biphenyl]-4-yl)methyl)phenyl)-5-methyl-1H-1,2,4-triazole-3-carboxamide.

Embodiment 577

A compound according to embodiment 1, or a pharmaceutically acceptable salt thereof, wherein the compound is (R)-1-(4-((4'-((3-fluoropiperidin-1-yl)methyl)-[1,1'-biphenyl]-4-yl)methyl)phenyl)-5-methyl-1H-1,2,4-triazole-3-carboxamide.

Embodiment 578

A compound according to embodiment 1, or a pharmaceutically acceptable salt thereof, wherein the compound is (S)-1-(4-((4'-((3-fluoropiperidin-1-yl)methyl)-[1,1'-biphenyl]-4-yl)methyl)phenyl)-5-methyl-1H-1,2,4-triazole-3-carboxamide.

Embodiment 579

A compound according to embodiment 1, or a pharmaceutically acceptable salt thereof, wherein the compound is 5-methyl-1-(4-((4'-((4-methyl-1,4-diazepan-1-yl)methyl)-[1,1'-biphenyl]-4-yl)methyl)phenyl)-1H-1,2,4-triazole-3-carboxamide.

Embodiment 580

A compound according to embodiment 1, or a pharmaceutically acceptable salt thereof, wherein the compound is 1-(4-((4'-((3,4-dihydroxypyrrolidin-1-yl)methyl)-[1,1'-biphenyl]-4-yl)methyl)phenyl)-5-methyl-1H-1,2,4-triazole-3-carboxamide.

Embodiment 581

A compound according to embodiment 1, or a pharmaceutically acceptable salt thereof, wherein the compound is 1-(4-((4'-(((3S,4S)-3,4-dihydroxypyrrolidin-1-yl)methyl)-[1,1'-biphenyl]-4-yl)methyl)phenyl)-5-methyl-1H-1,2,4-triazole-3-carboxamide.

Embodiment 582

A compound according to embodiment 1, or a pharmaceutically acceptable salt thereof, wherein the compound is 1-(4-((4'-(((3R,4R)-3,4-dihydroxypyrrolidin-1-yl)methyl)-[1,1'-biphenyl]-4-yl)methyl)phenyl)-5-methyl-1H-1,2,4-triazole-3-carboxamide.

Embodiment 583

A compound according to embodiment 1, or a pharmaceutically acceptable salt thereof, wherein the compound is 5-methyl-1-(4-((4'-((1-methylhexahydropyrrolo[3,4-b]pyrrol-5(1H)-yl)methyl)-[1,1'-biphenyl]-4-yl)methyl)phenyl)-1H-1,2,4-triazole-3-carboxamide.

Embodiment 584

A compound according to embodiment 1, or a pharmaceutically acceptable salt thereof, wherein the compound is 5-methyl-1-(4-((4'-(((3aR,6aR)-1-methylhexahydropyrrolo[3,4-b]pyrrol-5(1H)-yl)methyl)-[1,1'-biphenyl]-4-yl)methyl)phenyl)-1H-1,2,4-triazole-3-carboxamide.

Embodiment 585

A compound according to embodiment 1, or a pharmaceutically acceptable salt thereof, wherein the compound is 5-methyl-1-(4-((4'-(((3aS,6aS)-1-methylhexahydropyrrolo[3,4-b]pyrrol-5(1H)-yl)methyl)-[1,1'-biphenyl]-4-yl)methyl)phenyl)-1H-1,2,4-triazole-3-carboxamide.

Embodiment 586

A compound according to embodiment 1, or a pharmaceutically acceptable salt thereof, wherein the compound is 5-methyl-1-(4-((4'-((4-(methylsulfonyl)piperidin-1-yl)methyl)-[1,1'-biphenyl]-4-yl)methyl)phenyl)-1H-1,2,4-triazole-3-carboxamide.

Embodiment 587

A compound according to embodiment 1, or a pharmaceutically acceptable salt thereof, wherein the compound is 1-(4-((4'-((1,1-dioxidothiomorpholino)methyl)-[1,1'-biphenyl]-4-yl)methyl)phenyl)-5-methyl-1H-1,2,4-triazole-3-carboxamide.

Embodiment 588

A compound according to embodiment 1, or a pharmaceutically acceptable salt thereof, wherein the compound is 1-(4-((4'-((3,3-difluoroazetidin-1-yl)methyl)-[1,1'-biphenyl]-4-yl)methyl)phenyl)-5-methyl-1H-1,2,4-triazole-3-carboxamide.

Embodiment 589

A compound according to embodiment 1, or a pharmaceutically acceptable salt thereof, wherein the compound is 1-(4-((4'-(((1R,5S)-6-(hydroxymethyl)-3-azabicyclo[3.1.0]hexan-3-yl)methyl)-[1,1'-biphenyl]-4-yl)methyl)phenyl)-5-methyl-1H-1,2,4-triazole-3-carboxamide.

Embodiment 590

A compound according to embodiment 1, or a pharmaceutically acceptable salt thereof, wherein the compound is 1-(4-((4'-(((1R,5S,6r)-6-(hydroxymethyl)-3-azabicyclo[3.1.0]hexan-3-yl)methyl)-[1,1'-biphenyl]-4-yl)methyl)phenyl)-5-methyl-1H-1,2,4-triazole-3-carboxamide.

Embodiment 591

A compound according to embodiment 1, or a pharmaceutically acceptable salt thereof, wherein the compound is 1-(4-((4'-(((1R,5S,6s)-6-(hydroxymethyl)-3-azabicyclo[3.1.0]hexan-3-yl)methyl)-[1,1'-biphenyl]-4-yl)methyl)phenyl)-5-methyl-1H-1,2,4-triazole-3-carboxamide.

Embodiment 592

A compound according to embodiment 1, or a pharmaceutically acceptable salt thereof, wherein the compound is 5-methyl-1-(4-((4'-((4-(trifluoromethyl)piperidin-1-yl)methyl)-[1,1'-biphenyl]-4-yl)methyl)phenyl)-1H-1,2,4-triazole-3-carboxamide.

Embodiment 593

A compound according to embodiment 1, or a pharmaceutically acceptable salt thereof, wherein the compound is 1-(4-((4'-((3-(hydroxymethyl)azetidin-1-yl)methyl)-[1,1'-biphenyl]-4-yl)methyl)phenyl)-5-methyl-1H-1,2,4-triazole-3-carboxamide.

Embodiment 594

A compound according to embodiment 1, or a pharmaceutically acceptable salt thereof, wherein the compound is 1-(4-((4'-((1-oxa-7-azaspiro[3.5]nonan-7-yl)methyl)-[1,1'-biphenyl]-4-yl)methyl)phenyl)-5-methyl-1H-1,2,4-triazole-3-carboxamide.

Embodiment 595

A compound according to embodiment 1, or a pharmaceutically acceptable salt thereof, wherein the compound is 1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide.

Embodiment 596

A compound according to embodiment 1, or a pharmaceutically acceptable salt thereof, wherein the compound is (S)-1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide.

Embodiment 597

A compound according to embodiment 1, or a pharmaceutically acceptable salt thereof, wherein the compound is (R)-1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide.

Embodiment 598

A compound according to embodiment 1, or a pharmaceutically acceptable salt thereof, wherein the compound is 1-(4-((4'-((4-(dimethylamino)piperidin-1-yl)methyl)-[1,1'-biphenyl]-4-yl)methyl)phenyl)-5-methyl-1H-pyrazole-3-carboxamide.

Embodiment 599

A compound according to embodiment 1, or a pharmaceutically acceptable salt thereof, wherein the compound is 5-methyl-1-(4-((4'-(((3aR,6aS)-2-methyloctahydrocyclopenta[c]pyrrol-5-yl)methyl)-[1,1'-biphenyl]-4-yl)methyl)phenyl)-1H-1,2,4-triazole-3-carboxamide.

Embodiment 600

A compound according to embodiment 1, or a pharmaceutically acceptable salt thereof, wherein the compound is 5-methyl-1-(4-(4-(4-(piperazine-1-carbonyl)bicyclo[2.2.2]octan-1-yl)benzyl)phenyl)-1H-pyrazole-3-carboxamide.

Embodiment 601

A compound according to embodiment 1, or a pharmaceutically acceptable salt thereof, wherein the compound is 5-methyl-1-(4-(4-(4-(4-methyl piperazine-1-carbonyl)bicyclo[2.2.2]octan-1-yl)benzyl)phenyl)-1H-pyrazole-3-carboxamide.

Embodiment 602

A compound according to embodiment 1, or a pharmaceutically acceptable salt thereof, wherein the compound is 5-methyl-1-(4-(4-(6-(piperazine-1-carbonyl)spiro[3.3]heptan-2-yl)benzyl)phenyl)-1H-1,2,4-triazole-3-carboxamide.

Embodiment 603

A compound according to embodiment 1, or a pharmaceutically acceptable salt thereof, wherein the compound is 5-methyl-1-(4-((4'-(piperazin-1-ylmethyl)-[1,1'-biphenyl]-4-yl)methyl)phenyl)-1H-1,2,4-triazole-3-carboxamide.

Embodiment 604

A compound according to embodiment 1, or a pharmaceutically acceptable salt thereof, wherein the compound is 1-(4-(4-(6-(2-hydroxypropan-2-yl)pyridin-3-yl)benzyl)phenyl)-5-methyl-1H-1,2,4-triazole-3-carboxamide.

Embodiment 605

A compound according to embodiment 1, or a pharmaceutically acceptable salt thereof, wherein the compound is 5-methyl-1-(4-((4'-((1-methylpiperidin-4-yl)oxy)-[1,1'-biphenyl]-4-yl)methyl)phenyl)-1H-1,2,4-triazole-3-carboxamide.

Embodiment 606

A compound according to embodiment 1, or a pharmaceutically acceptable salt thereof, wherein the compound is 1-(4-((4'-(1-hydroxy-2-methylpropan-2-yl)-[1,1'-biphenyl]-4-yl)methyl)phenyl)-5-methyl-1H-1,2,4-triazole-3-carboxamide.

Embodiment 607

A compound according to embodiment 1, or a pharmaceutically acceptable salt thereof, wherein the compound is 1-(4-(4-(4-(2-hydroxypropan-2-yl)piperidin-1-yl)benzyl)phenyl)-5-methyl-1H-1,2,4-triazole-3-carboxamide.

Embodiment 608

A compound according to embodiment 1, or a pharmaceutically acceptable salt thereof, wherein the compound is 1-(4-((4'-(N-(2-hydroxy-2-methylpropyl)sulfamoyl)-[1,1'-biphenyl]-4-yl)methyl)phenyl)-5-methyl-1H-1,2,4-triazole-3-carboxamide.

Embodiment 609

A compound according to embodiment 1, or a pharmaceutically acceptable salt thereof, wherein the compound is 1-(4-((4'-((2-hydroxy-2-methylpropyl)carbamoyl)-[1,1'-biphenyl]-4-yl)methyl)phenyl)-5-methyl-1H-1,2,4-triazole-3-carboxamide.

Embodiment 610

A compound according to embodiment 1, or a pharmaceutically acceptable salt thereof, wherein the compound is 1-(4-(4-(5-(N-(2-hydroxy-2-methylpropyl)sulfamoyl)pyridin-2-yl)benzyl)phenyl)-5-methyl-1H-1,2,4-triazole-3-carboxamide.

Embodiment 611

A compound according to embodiment 1, or a pharmaceutically acceptable salt thereof, wherein the compound is 1-(4-(4-(4-(2-hydroxypropan-2-yl)pyridin-2-yl)benzyl)phenyl)-5-methyl-1H-1,2,4-triazole-3-carboxamide.

Embodiment 612

A compound according to embodiment 1, or a pharmaceutically acceptable salt thereof, wherein the compound is 5-methyl-1-(4-(4-((1-methylpiperidin-4-yl)ethynyl)benzyl)phenyl)-1H-1,2,4-triazole-3-carboxamide.

Embodiment 613

A compound according to embodiment 1, or a pharmaceutically acceptable salt thereof, wherein the compound is 1-(4-(4-((1-hydroxycyclohexyl)ethynyl)benzyl)phenyl)-5-methyl-1H-1,2,4-triazole-3-carboxamide.

Embodiment 614

A compound according to embodiment 1, or a pharmaceutically acceptable salt thereof, wherein the compound is 1-(4-(4-(5-(1-hydroxy-2-methylpropan-2-yl)pyridin-2-yl)benzyl)phenyl)-5-methyl-1H-1,2,4-triazole-3-carboxamide.

Embodiment 615

A compound according to embodiment 1, or a pharmaceutically acceptable salt thereof, wherein the compound is 1-(4-(4-(5-(1-hydroxy-2-methylpropan-2-yl)pyridin-2-yl)benzyl)phenyl)-5-methyl-1H-pyrazole-3-carboxamide.

Embodiment 616

A compound according to embodiment 1, or a pharmaceutically acceptable salt thereof, wherein the compound is 1-(4-(4-(6-(2-hydroxypropan-2-yl)pyridazin-3-yl)benzyl)phenyl)-5-methyl-1H-pyrazole-3-carboxamide.

Embodiment 617

A compound according to embodiment 1, or a pharmaceutically acceptable salt thereof, wherein the compound is 6-(4-(4-(3-carbamoyl-5-methyl-1H-pyrazol-1-yl)benzyl)phenyl)-N-(2-hydroxy-2-methylpropyl) nicotinamide.

Embodiment 618

A compound according to embodiment 1, or a pharmaceutically acceptable salt thereof, wherein the compound is 1-(4-(4-(2-(2-hydroxypropan-2-yl)pyrimidin-5-yl)benzyl)phenyl)-5-methyl-1H-pyrazole-3-carboxamide.

151

Embodiment 619

A compound according to embodiment 1, or a pharmaceutically acceptable salt thereof, wherein the compound is 1-(4-(4-(2-(hydroxymethyl)pyridin-4-yl)benzyl)phenyl)-5-methyl-1H-pyrazole-3-carboxamide.

Embodiment 620

A compound according to embodiment 1, or a pharmaceutically acceptable salt thereof, wherein the compound is 5-methyl-1-(4-((4'-((1-methylpyrrolidin-3-yl)oxy)-[1,1'-biphenyl]-4-yl)methyl)phenyl)-1H-1,2,4-triazole-3-carboxamide.

Embodiment 621

A compound according to embodiment 1, or a pharmaceutically acceptable salt thereof, wherein the compound is (S)-5-methyl-1-(4-((4'-((1-methylpyrrolidin-3-yl)oxy)-[1,1'-biphenyl]-4-yl)methyl)phenyl)-1H-1,2,4-triazole-3-carboxamide.

Embodiment 622

A compound according to embodiment 1, or a pharmaceutically acceptable salt thereof, wherein the compound is (R)-5-methyl-1-(4-((4'-((1-methylpyrrolidin-3-yl)oxy)-[1,1'-biphenyl]-4-yl)methyl)phenyl)-1H-1,2,4-triazole-3-carboxamide.

Embodiment 623

A compound according to embodiment 1, or a pharmaceutically acceptable salt thereof, wherein the compound is 5-methyl-1-(4-((4'-((1-methylpyrrolidin-3-yl)oxy)-[1,1'-biphenyl]-4-yl)methyl)phenyl)-1H-1,2,4-triazole-3-carboxamide.

Embodiment 624

A compound according to embodiment 1, or a pharmaceutically acceptable salt thereof, wherein the compound is (R)-5-methyl-1-(4-((4'-((1-methylpyrrolidin-3-yl)oxy)-[1,1'-biphenyl]-4-yl)methyl)phenyl)-1H-1,2,4-triazole-3-carboxamide.

Embodiment 625

A compound according to embodiment 1, or a pharmaceutically acceptable salt thereof, wherein the compound is (S)-5-methyl-1-(4-((4'-((1-methylpyrrolidin-3-yl)oxy)-[1,1'-biphenyl]-4-yl)methyl)phenyl)-1H-1,2,4-triazole-3-carboxamide.

Embodiment 626

A compound according to embodiment 1, or a pharmaceutically acceptable salt thereof, wherein the compound is 1-(4-((4'-(2-((2-hydroxy-2-methylpropyl)amino)propan-2-yl)-[1,1'-biphenyl]-4-yl)methyl)phenyl)-5-methyl-1H-1,2,4-triazole-3-carboxamide.

152

Embodiment 627

A compound according to any one of the preceding embodiments. In this embodiment, the compound is present in its non-salt form.

Embodiment 628

A pharmaceutical composition comprising a therapeutically effective amount of a compound or pharmaceutically acceptable salt according to any one of embodiments 1-627 and one or more pharmaceutically acceptable carriers.

Embodiment 629

A pharmaceutical composition comprising a compound or pharmaceutically acceptable salt according to any one of embodiments 1-627 and one or more pharmaceutically acceptable carriers.

Embodiment 630

A method of activating a growth factor pathway in a subject in need thereof, comprising administering to the subject a therapeutically effective amount of a compound or pharmaceutically acceptable salt according to any one of embodiments 1-627 or a pharmaceutical composition according to embodiment 628 or 629.

Embodiment 631

A method of embodiment 630, wherein the growth factor pathway comprises the PI3K/Akt/mTOR pathway.

Embodiment 632

A method of promoting wound healing, promoting tissue repair, or treating hearing loss, skeletal muscle loss, organ degeneration, tissue damage, neurodegeneration, or muscular atrophy in a subject in need thereof, comprising administering to the subject a therapeutically effective amount of a compound or pharmaceutically acceptable salt according to any one of embodiments 1-627 or a pharmaceutical composition according to embodiment 628 or 629.

Embodiment 633

A method of embodiment 632, wherein the method comprises promoting wound healing.

Embodiment 634

A method of embodiment 633, wherein the method comprises promoting healing of a chronic wound.

Embodiment 635

A method of embodiment 634, wherein the chronic wound is a vascular ulcer.

Embodiment 636

A method of embodiment 634, wherein the chronic wound is a diabetic ulcer.

Embodiment 637

A method of embodiment 634, wherein the chronic wound is a pressure ulcer.

Embodiment 638

A method of embodiment 632, wherein the method comprises promoting tissue repair.

Embodiment 639

A method of embodiment 632, wherein the method comprises treating hearing loss.

Embodiment 640

A method of embodiment 632, wherein the method comprises treating skeletal muscle loss.

Embodiment 641

A method of embodiment 632, wherein the method comprises treating organ degeneration.

Embodiment 642

A method of embodiment 632, wherein the method comprises treating tissue damage.

Embodiment 643

A method of embodiment 632, wherein the method comprises treating neurodegeneration.

Embodiment 644

A method of embodiment 632, wherein the method comprises treating muscular atrophy.

Embodiment 645

A compound or pharmaceutically acceptable salt according to any one of embodiments 1-627, or a pharmaceutical composition according to embodiment 628 or 629, for use in activating a growth factor pathway in a subject in need thereof.

Embodiment 646

A compound, pharmaceutically acceptable salt thereof, or pharmaceutical composition of embodiment 645, wherein the growth factor pathway comprises the PI3K/Akt/mTOR pathway.

Embodiment 647

A compound or pharmaceutically acceptable salt according to any one of embodiments 1-627, or a pharmaceutical composition according to embodiment 628 or 629, for use in promoting wound healing, promoting tissue repair, or treating hearing loss, skeletal muscle loss, organ degeneration, tissue damage, neurodegeneration, or muscular atrophy in a subject in need thereof.

Embodiment 648

A compound, pharmaceutically acceptable salt thereof, or pharmaceutical composition of embodiment 647, for use in promoting wound healing.

Embodiment 649

A compound, pharmaceutically acceptable salt thereof, or pharmaceutical composition of embodiment 648, wherein promoting wound healing comprises promoting healing of a chronic wound.

Embodiment 650

A compound, pharmaceutically acceptable salt thereof, or pharmaceutical composition of embodiment 649, wherein the chronic wound is a vascular ulcer.

Embodiment 651

A compound, pharmaceutically acceptable salt thereof, or pharmaceutical composition of embodiment 649, wherein the chronic wound is a diabetic ulcer.

Embodiment 652

A compound, pharmaceutically acceptable salt thereof, or pharmaceutical composition of embodiment 649, wherein the chronic wound is a pressure ulcer.

Embodiment 653

A compound, pharmaceutically acceptable salt thereof, or pharmaceutical composition of embodiment 647, for use in promoting tissue repair.

Embodiment 654

A compound, pharmaceutically acceptable salt thereof, or pharmaceutical composition of embodiment 647, for use in treating hearing loss.

Embodiment 655

A compound, pharmaceutically acceptable salt thereof, or pharmaceutical composition of embodiment 647, for use in treating skeletal muscle loss.

Embodiment 656

A compound, pharmaceutically acceptable salt thereof, or pharmaceutical composition of embodiment 647, for use in treating organ degeneration.

Embodiment 657

A compound, pharmaceutically acceptable salt thereof, or pharmaceutical composition of embodiment 647, for use in treating tissue damage.

Embodiment 658

A compound, pharmaceutically acceptable salt thereof, or pharmaceutical composition of embodiment 647, for use in treating neurodegeneration.

Embodiment 659

A compound, pharmaceutically acceptable salt thereof, or pharmaceutical composition of embodiment 647, for use in treating muscular atrophy.

Embodiment 660

Use of a compound or pharmaceutically acceptable salt according to any one of embodiments 1-627, or a pharmaceutical composition according to embodiment 628 or 629, for the manufacture of a medicament for activating a growth factor pathway in a subject in need thereof.

Embodiment 661

Use of embodiment 650, wherein the growth factor pathway comprises the PI3K/Akt/mTOR pathway.

Embodiment 662

Use of a compound or pharmaceutically acceptable salt according to any one of embodiments 1-627, or a pharmaceutical composition according to embodiment 628 or 629, for the manufacture of a medicament for promoting wound healing, promoting tissue repair, or treating hearing loss, skeletal muscle loss, organ degeneration, tissue damage, neurodegeneration, or muscular atrophy in a subject in need thereof.

Embodiment 663

Use of embodiment 662, wherein the medicament is for promoting wound healing.

Embodiment 664

Use of embodiment 663, wherein promoting wound healing comprises promoting healing of a chronic wound.

Embodiment 665

Use of embodiment 664, wherein the chronic wound is a vascular ulcer.

Embodiment 666

Use of embodiment 664, wherein the chronic wound is a diabetic ulcer.

Embodiment 667

Use of embodiment 664, wherein the chronic wound is a pressure ulcer.

Embodiment 668

Use of embodiment 662, wherein the medicament is for promoting tissue repair.

Embodiment 669

Use of embodiment 662, wherein the medicament is for treating hearing loss.

Embodiment 670

Use of embodiment 662, wherein the medicament is for treating skeletal muscle loss.

Embodiment 671

Use of embodiment 662, wherein the medicament is for treating organ degeneration, tissue damage, neurodegeneration, or muscular atrophy.

Embodiment 672

Use of embodiment 662, wherein the medicament is for treating tissue damage.

Embodiment 673

Use of embodiment 662, wherein the medicament is for treating neurodegeneration.

Embodiment 674

Use of embodiment 662, wherein the medicament is for treating muscular atrophy.

Embodiment 675

A combination comprising a therapeutically effective amount of a compound or pharmaceutically acceptable salt according to any one of embodiments 1-627 and at least one other therapeutic agent.

Embodiment 676

A combination comprising a compound or pharmaceutically acceptable salt according to any one of embodiments 1-627 and at least one other therapeutic agent.

Embodiment 677

A combination according to embodiment 675 or 676, wherein the at least one other therapeutic agent comprises becaplermin (e.g., Regranex®).

Embodiment 678

A pharmaceutical composition according to embodiment 628 or 629, further comprising at least one other therapeutic agent.

Embodiment 679

A pharmaceutical composition according to embodiment 678, where the at least one other therapeutic agent comprises becaplermin (e.g., Regranex®).

Embodiment 680

A kit comprising a first pharmaceutical composition according to embodiment 628 or 629 and a second pharmaceutical composition comprising at least one other therapeutic agent.

Embodiment 681

A kit according to embodiment 680, wherein the at least one other therapeutic agent comprises becaplermin (e.g., Regranex®).

Embodiment 682

A method according to any one of embodiments 630-644, wherein the compound, pharmaceutically acceptable salt, or pharmaceutical composition is administered simultaneously with, or before or after, one or more other therapeutic agents.

Embodiment 683

A method according embodiment 682, wherein the one or more other therapeutic agents comprise becaplermin (e.g., Regranex®).

Embodiment 684

A compound, pharmaceutically acceptable salt thereof, or pharmaceutical composition of any one of embodiments 645-659, wherein the compound, pharmaceutically acceptable salt, or pharmaceutical composition is prepared for administration with at least one other therapeutic agent.

Embodiment 685

A compound, pharmaceutically acceptable salt thereof, or pharmaceutical composition of any one of embodiments 645-659, wherein the compound, pharmaceutically acceptable salt, or pharmaceutical composition is administered with at least one other therapeutic agent.

Embodiment 686

A compound, pharmaceutically acceptable salt thereof, or pharmaceutical composition of embodiment 684 or 685, wherein the at least one other therapeutic agent comprises becaplermin (e.g., Regranex®).

Embodiment 687

Use according to any one of embodiments 660-684, wherein the medicament is prepared for administration with at least one other therapeutic agent.

Embodiment 688

Use according to embodiment 687, wherein the at least one other therapeutic agent comprises becaplermin (e.g., Regranex®).

Isomeric Variants

Except where otherwise specified, the compounds disclosed herein include all stereoisomers (including diastereoisomers, enantiomers, and mixtures thereof), double-bond isomers, atropisomers, rotamers, tautomers, and isotopic variants of the specified compounds. The compounds can be present as a single stereoisomer (or double-bond isomer) or as a mixture thereof, for example as pure optical isomers, or as stereoisomer mixtures, such as racemates and diastereoisomer mixtures, depending on the number of stereocenters. Optically active (R)- and (S)-stereoisomers may be prepared using chiral synthons or chiral reagents, or resolved using conventional techniques.

Except where otherwise specified, each stereocenter (e.g., stereogenic carbon atom) of any compound disclosed herein may be present in a single configuration (e.g., (R)- or (S)-) or in a mixture of configurations ((R,S)-). Except where otherwise specified, each double bond of any compound disclosed herein may, if possible, be present in a single configuration (cis-(Z)- or trans-(E)-), or in a mixture of configurations.

Where a particular enantiomer is specified, a compound disclosed herein shall be understood to have at least 50% enantiomeric excess. In certain embodiments, a compound disclosed herein has at least 60% enantiomeric excess, at least 70% enantiomeric excess, at least 80% enantiomeric excess, at least 90% enantiomeric excess, at least 95% enantiomeric excess, or at least 99% enantiomeric excess.

Where a particular diastereomer is specified, a compound disclosed herein shall be understood to have at least 50% diastereomeric excess. In certain embodiments, a compound disclosed herein has at least 60% diastereomeric excess, at least 70% diastereomeric excess, at least 80% diastereomeric excess, at least 90% diastereomeric excess, at least 95% diastereomeric excess, or at least 99% diastereomeric excess.

Any mixtures of stereoisomers or double-bond isomers can be separated on the basis of the physicochemical differences of the constituents, into the pure or substantially pure isomers, for example, by chromatography and/or fractional crystallization. For example, mixtures of enantiomers can be resolved into their optical antipodes by known methods, e.g., by separation of the diastereomeric salts thereof, obtained with an optically active acid or base, and liberating the optically active acidic or basic compound. Suitable optically active acids include tartaric acid, dibenzoyl tartaric acid, diacetyl tartaric acid, di-O,O'-p-toluoyl tartaric acid, mandelic acid, malic acid and camphor-10-sulfonic acid. Racemic products can also be resolved by chiral chromatography, e.g., high pressure liquid chromatography (HPLC) using a chiral adsorbent.

Isotopic Variants

In the compounds disclosed herein, any atom not specifically designated as a particular isotope is meant to represent any isotope of that atom. Thus, unless otherwise specified, each compound disclosed herein includes both unlabeled forms as well as isotopically enriched forms of the compound.

Isotopes that can be incorporated into the compounds disclosed herein include, for example, isotopes of hydrogen, such as deuterium (D or $^2H$) and tritium ($^3H$). Other examples of isotopes that can be incorporated into compounds disclosed herein include isotopes of carbon, nitrogen, oxygen, fluorine, and chlorine, such as $^{11}C$, $^{13}C$, $^{14}C$, $^{15}N$, $^{18}F$, and $^{36}Cl$, respectively. Accordingly it should be understood that the disclosure includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present.

Isotopically-labeled compounds can generally be prepared by conventional techniques known to those skilled in the art or by processes analogous to those described in the accompanying Examples and Preparations using appropriate isotopically-labeled reagents.

Pharmaceutically Acceptable Salts

As used herein, the terms "salt" or "salts" refers to an acid addition or base addition salt of a compound disclosed herein. "Salts" include in particular "pharmaceutically acceptable salts". The term "pharmaceutically acceptable salts" refers to salts that retain the biological effectiveness and properties of the compounds disclosed herein and which typically are not biologically or otherwise undesirable. Many of the compounds disclosed herein are capable of forming acid addition salts by virtue of the presence of amino groups and other similar groups.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

For example, pharmaceutically acceptable acid addition salts of the compounds disclosed herein include acetate, ascorbate, adipate, aspartate, benzoate, besylate, bromide/hydrobromide, bicarbonate/carbonate, bisulfate/sulfate, camphorsulfonate, caprate, chloride/hydrochloride, chlorotheophyllonate, citrate, ethanedisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/di hydrogen phosphate, polygalacturonate, propionate, sebacate, stearate, succinate, sulfosalicylate, sulfate, tartrate, tosylate trifenatate, trifluoroacetate and xinafoate salts.

Pharmaceutical Compositions

In another aspect, the present disclosure provides a pharmaceutical composition comprising a compound disclosed herein, or a pharmaceutically acceptable salt thereof, and one or more pharmaceutically acceptable carriers. In further embodiments, the pharmaceutical composition comprises at least two pharmaceutically acceptable carriers, such as those described herein.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

The pharmaceutical composition may contain a compound disclosed herein, or a pharmaceutically acceptable salt thereof in a therapeutically effective amount. As used herein, the term "therapeutically effective amount," when referring to a compound disclosed herein, or a pharmaceutically acceptable salt thereof, refers to an amount of the compound or salt that will elicit a biological or medical response in a subject, such as reduce or inhibit an enzyme or a protein activity, ameliorate certain symptoms, alleviate conditions, slow or delay disease progression, or prevent a disease. In one non-limiting embodiment, the term "therapeutically effective amount" refers to the amount of a compound disclosed herein, or a pharmaceutically acceptable salt thereof, that, when administered to a subject, is effective to activate a growth factor pathway, such as the PI3K/Akt/mTOR pathway.

The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions can be made up in a solid form (including, without limitation, capsules, tablets, pills, granules, powders or suppositories), or in a liquid form (including, without limitation, solutions, gels, suspensions or emulsions). Tablets may be either film coated or enteric coated according to methods known in the art.

Where the pharmaceutical compositions are tablets or gelatin capsules, the tablets or capsules comprise a compound disclosed herein, or a pharmaceutically acceptable salt thereof, and one or more of:

a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

The pharmaceutical composition can be in unit dosage containing about 1-1000 mg, or about 1-500 mg or about 1-250 mg or about 1-150 mg or about 0.5-100 mg, or about 1-50 mg of the compound disclosed herein, or an equivalent amount on a molar basis of a pharmaceutically acceptable salt thereof, for a subject of about 50-70 kg.

The therapeutically effective dosage of the compounds disclosed herein is dependent on a variety of factors, including the species, body weight, age and individual condition of the subject, the particular compound being administered, the route of administration, and the disorder or disease being treated. A physician, clinician or veterinarian of ordinary skill can readily determine the effective amount of the compounds disclosed herein.

Uses of Compounds Disclosed Herein

The compounds disclosed herein, and pharmaceutically acceptable salts thereof, exhibit valuable pharmacological properties, including as growth factor pathway activators. As indicated in the assays described in the Examples, the compounds disclosed herein activate the PI3K/Akt/mTOR pathway downstream of growth factor signaling. Accordingly, the compounds disclosed herein may be used for promoting wound healing (including the healing of chronic wounds, such as vascular ulcers, diabetic ulcers and pressure ulcers), promoting tissue repair, and treating hearing loss, skeletal muscle loss, organ degeneration, tissue damage, neurodegeneration, and muscular atrophy.

Thus, in a further aspect, the disclosure provides a method of activating a growth factor pathway in a subject in need thereof, comprising administering to the subject a therapeutically effective amount of a compound disclosed herein, or a pharmaceutically acceptable salt or pharmaceutical composition thereof. In certain embodiments, the growth factor pathway comprises the PI3K/AKT/mTOR pathway.

In a further aspect, the disclosure provides a method of promoting wound healing, promoting tissue repair, or treating hearing loss, skeletal muscle loss, organ degeneration, tissue damage, neurodegeneration, or muscular atrophy in a subject in need thereof, comprising administering to the subject a therapeutically effective amount of a compound disclosed herein, or a pharmaceutically acceptable salt or pharmaceutical composition thereof.

In a further aspect, the disclosure provides a compound disclosed herein, or a pharmaceutically acceptable salt or pharmaceutical composition thereof, for use in activating a growth factor pathway in a subject in need thereof. In certain embodiments, the growth factor pathway comprises the PI3K/Akt/mTOR pathway.

In a further aspect, the disclosure provides a compound disclosed herein, or a pharmaceutically acceptable salt or pharmaceutical composition thereof, for use in promoting wound healing, promoting tissue repair, or treating hearing loss, skeletal muscle loss, organ degeneration, tissue damage, neurodegeneration, or muscular atrophy in a subject in need thereof.

In a further aspect, the disclosure provides the use of a compound disclosed herein, or a pharmaceutically acceptable salt or pharmaceutical composition thereof, for the manufacture of a medicament for activating a growth factor pathway in a subject in need thereof. In certain embodiments, the growth factor pathway comprises the PI3K/Akt/mTOR pathway.

In a further aspect, the disclosure provides the use of a compound disclosed herein, or a pharmaceutically acceptable salt or pharmaceutical composition thereof, for the manufacture of a medicament for promoting wound healing, promoting tissue repair, or treating hearing loss, skeletal muscle loss, organ degeneration, tissue damage, neurodegeneration, or muscular atrophy in a subject in need thereof.

As used herein, the term "subject" refers to a mammal, such as a primate (e.g., a human, male or female), dog, rabbit, guinea pig, pig, rat, or mouse, mice. In certain embodiments, the subject is a primate. In yet other embodiments, the subject is a human.

As used herein, the terms "treat", "treating" or "treatment," when referring to any disease or disorder, refer to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

Compounds described herein, once produced, can be characterized using a variety of assays known to those skilled in the art to determine whether the compounds have biological activity. For example, the molecules can be characterized by assays, including but not limited to those assays described below, to determine whether they have a predicted activity, e.g., activation or inhibition activity and/or specificity to a specific protein (e.g., Akt or forkhead box O family (FOXO) 3a (FoxO3a)).

In yet another aspect, the compounds described herein may be used for research (e.g., studying growth factor signaling pathways) and other non-therapeutic purposes.

Combination Therapy

The compounds disclosed herein, and pharmaceutically acceptable salts thereof, may be administered in combination with the standard of care for indications discussed herein. For example, when used for promoting the healing of diabetic ulcers, the compounds, and pharmaceutically acceptable salts thereof, may be administered as an adjunct to the standard of care treatment of diabetic ulcers, including without limitation debridement, infection control (e.g., antimicrobials), pressure relief, and application of an appropriate dressing. See, e.g., I. Kruse et al., *Evaluation and Treatment of Diabetic Foot Ulcers*, 24 Clinical Diabetes 91-93 (2006); Wounds International, *International Best Practice Guidelines: Wound Management in Diabetic Foot Ulcers* (2013) (available at www.woundsinternational.com).

The compounds disclosed herein, and pharmaceutically acceptable salts thereof, may be administered simultaneously with, or before or after, one or more other therapeutic agents. A compound disclosed herein, or a pharmaceutically acceptable salt thereof, may be administered separately, by the same or different route of administration, or together in the same pharmaceutical composition as the other therapeutic agent. The other therapeutic agent may be, for example, a chemical compound, peptide, antibody, antibody fragment or nucleic acid, which is therapeutically active or enhances the therapeutic activity when administered to a patient in combination with a compound disclosed herein, or a pharmaceutically acceptable salt thereof.

Other therapeutic agents useful for administration in combination with the compounds disclosed herein, and pharmaceutically acceptable salts thereof, include without limitation becaplermin (e.g., Regranex®).

In one embodiment, the disclosure provides a combination comprising a compound disclosed herein, or a pharmaceutically acceptable salt thereof, and at least one other therapeutic agent as a combined preparation for simultaneous, separate or sequential use in therapy. As used herein, the term "combination" means a fixed combination in one dosage unit form, or a combined administration where a compound disclosed herein and a combination partner may be administered independently at the same time or separately within time intervals that especially allow that the combination partners show a cooperative, e.g. synergistic effect. The single components may be packaged together in a kit or separately. One or both of the components (e.g., powders or liquids) may be reconstituted or diluted to a desired dose prior to administration.

In one embodiment, the disclosure provides a pharmaceutical composition comprising a compound disclosed herein, or a pharmaceutically acceptable salt thereof, and at least one other therapeutic agent. Optionally, the pharmaceutical composition may comprise a pharmaceutically acceptable carrier, as described above.

In one embodiment, the disclosure provides a kit comprising two or more separate pharmaceutical compositions, at least one of which contains a compound disclosed herein, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit may be used for administering different dosage forms, for example, oral and parenteral, for administering the separate compositions at different dosage intervals, or for titrating the separate compositions against one another. To assist compliance, the kit typically comprises directions for administration.

In the combination therapies, the compound disclosed herein and the other therapeutic agent may be manufactured and/or formulated by the same or different manufacturers. Moreover, the compound disclosed herein and the other therapeutic may be brought together into a combination therapy: (i) prior to release of the combination product to physicians (e.g. in the case of a kit comprising the compound disclosed herein and the other therapeutic agent); (ii) by the physician themselves (or under the guidance of the physician) shortly before administration; (iii) in the patient themselves, e.g. during sequential administration of the compound disclosed herein and the other therapeutic agent.

Accordingly, the disclosure provides a method of activating a growth factor pathway, promoting wound healing, promoting tissue repair, or treating hearing loss, skeletal muscle loss, organ degeneration, tissue damage, neurodegeneration, or muscular atrophy in a subject in need thereof, comprising administering to the subject a therapeutically effective amount of a compound disclosed herein, or a pharmaceutically acceptable salt thereof, wherein the compound disclosed herein, or a pharmaceutically acceptable salt thereof, is administered simultaneously with, or before or after, one or more other therapeutic agents.

The disclosure also provides the use of a compound disclosed herein, or a pharmaceutically acceptable salt thereof, for the manufacture of a medicament for modulating growth factor pathway signaling in a subject in need thereof, wherein the medicament is prepared for administration with another therapeutic agent.

The disclosure also provides a compound disclosed herein, or a pharmaceutically acceptable salt or pharmaceutical composition thereof, for use in activating a growth factor pathway, promoting wound healing, promoting tissue repair, or treating hearing loss, skeletal muscle loss, organ degeneration, tissue damage, neurodegeneration, or muscular atrophy in a subject in need thereof, wherein the compound disclosed herein, or pharmaceutically acceptable salt or pharmaceutical composition thereof, is prepared for administration with at least one other therapeutic agent. The disclosure also provides a compound disclosed herein, or a pharmaceutically acceptable salt or pharmaceutical composition thereof, for use in activating a growth factor pathway, promoting wound healing, promoting tissue repair, or treating hearing loss, skeletal muscle loss, organ degeneration, tissue damage, neurodegeneration, or muscular atrophy in a subject in need thereof, wherein the compound disclosed herein, or pharmaceutically acceptable salt or pharmaceutical composition thereof, is administered with at least one other therapeutic agent.

The disclosure also provides the use of a compound disclosed herein, or a pharmaceutically acceptable salt or pharmaceutical composition thereof, for the manufacture of a medicament for activating a growth factor pathway, promoting wound healing, promoting tissue repair, or treating hearing loss, skeletal muscle loss, organ degeneration, tissue damage, neurodegeneration, or muscular atrophy in a subject in need thereof, wherein the medicament is prepared for administration with at least one other therapeutic agent.

Preparation of Compounds

The following reaction schemes illustrate methods to make compounds disclosed herein. It is understood that one skilled in the art would be able to make these compounds by similar methods or by methods known to one skilled in the art. In general, starting components and reagents may be obtained from commercial vendors such as Sigma Aldrich, Lancaster Synthesis, Inc., Maybridge, Matrix Scientific, TCI, Fluorochem USA, Strem, or other commercial vendors, or may be synthesized according to procedures known to those skilled in the art.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes disclosed herein can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds disclosed herein can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 7th edition, John Wiley & Sons: New York, 2013; Greene, T. W., Wuts, P. G. M., Protective Groups in Organic Synthesis, 3rd edition, John Wiley & Sons: New York, 1999; R. Larock, Comprehensive Organic Transformations, VCH Publishers (1989); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds disclosed herein.

It will also be appreciated by those skilled in the art that the functional groups of intermediate compounds in the processes described below may need to be protected by suitable protecting groups. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in T. G. M. Wuts et al., *Greene's Protective Groups in Organic Synthesis* (4th ed. 2006). The protecting group may also be a polymer resin, such as a Wang resin or a 2-chlorotrityl-chloride resin.

In general, the compounds of formula (I) can be synthesized by following the general procedures outlined in Schemes 1-3 and the specific procedures discussed in the Examples. Intermediates useful in the synthesis of compounds of formula (I), where $R^2$ and $R^3$ are H, can be synthesized by following the general procedure described in General Scheme 1.

General Scheme 1. Synthesis of Intermediates (R² and R³ = H)

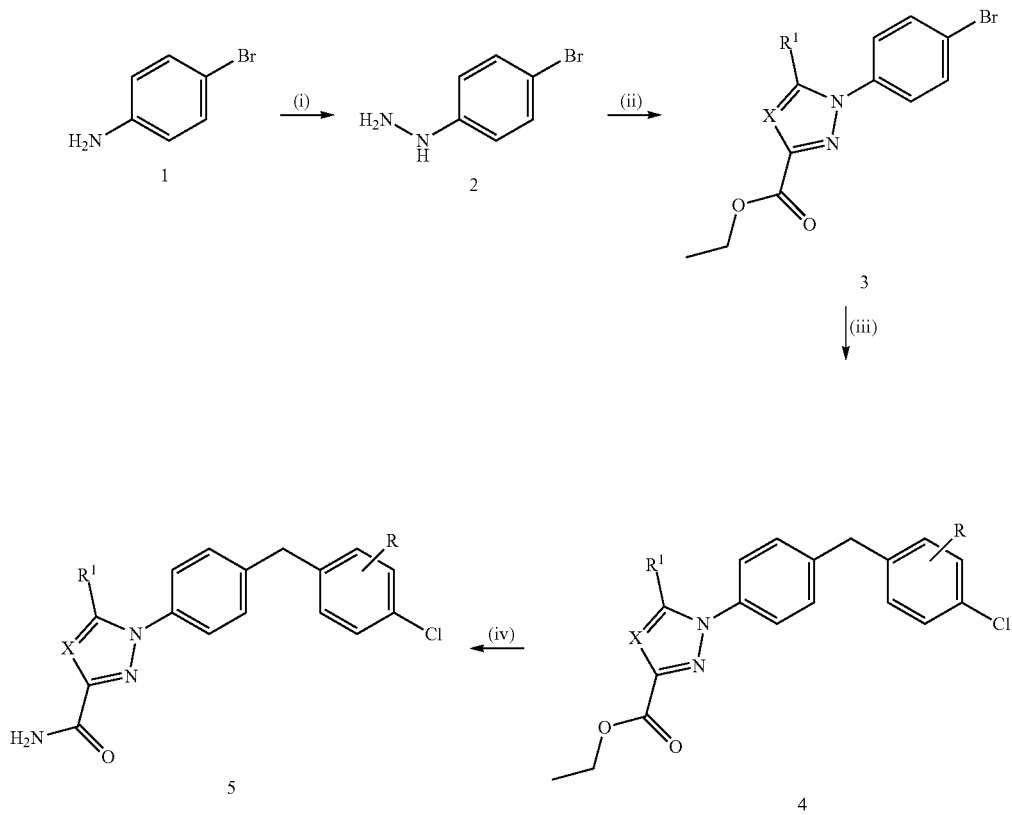

The starting materials for the synthesis described in General Scheme 1 are commercially available or can be prepared according to methods known to one skilled in the art or by methods disclosed herein. In general, the compounds are prepared as described in General Scheme 1 as follows:

In step (i) 4-bromoaniline (1) is treated with sodium nitrite and aqueous hydrogen chloride followed by tin(II) chloride to afford 4-bromophenyl hydrazine (2).

In step (ii), 4-bromophenyl hydrazine (2) is converted to pyrazole or triazole 3. Conversion to the pyrazole (X=CH) can be accomplished by treating hydrazine 2 with a suitable ethyl 2,4-dioxoalkanoate (EtOC(O)C(O)CH₂C(O)R¹). Conversion to the triazole (X=N) can be accomplished by treating the hydrazine 2 with ethyl 2-amino-2-thioxoacetate and a base, followed by acetic anhydride.

In step (iii), 4-bromophenyl pyrazole or triazole 3 is treated with a suitable 4-chlorobenzyl zinc bromide derivative (Br—Zn—CH₂—C₆H₃(R)Cl) in the presence of a palladium catalyst to afford compound 4.

In step (iv), ethyl ester 4 is converted to the corresponding amide 5 (which itself is a compound of formula (I)). The ester may be converted directly to the amide (e.g., by treatment with ammonia gas in dry methanol), or conversion may be accomplished by hydrolysis of the ester (e.g., by treatment with LiOH in methanol), followed by amide formation (e.g., by treatment with ammonia in the presence of HATU and a base). Steps (iii) and (iv) also may be performed in reverse order.

Intermediates useful in the synthesis of compounds of formula (I), where R² and R³ are C₁₋₄alkyl, can be synthesized by following the general procedure described in General Scheme 2.

General Scheme 2. Synthesis of Intermediates (R² and R³ = C₁₋₄alkyl)

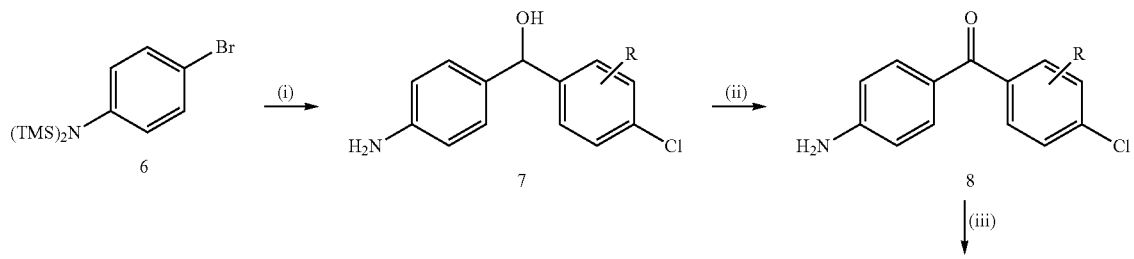

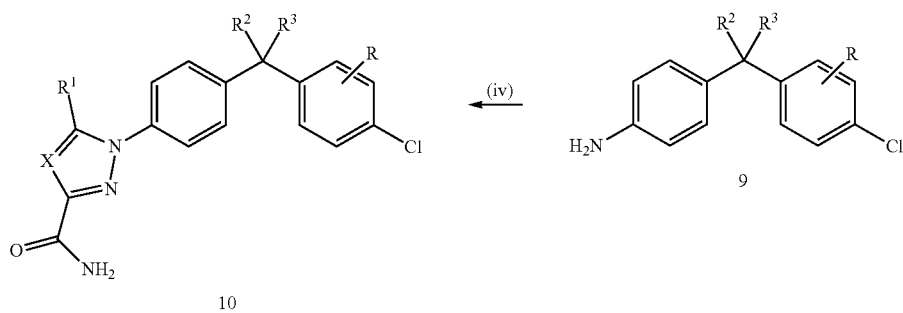

The starting materials for the synthesis described in General Scheme 2 are commercially available or can be prepared according to methods known to one skilled in the art or by methods disclosed herein. In general, the compounds are prepared as described in General Scheme 2 as follows:

In step (i), 4-bromo-N,N-bis(trimethylsily)aniline (6) is treated with an organolithium reagent (e.g., n-butyllithium), followed by a suitable 4-chlorobenzaldehyde derivative (HC(O)—$C_6H_3$(R)Cl), to afford diphenylcarbinol derivative 7.

In step (ii), oxidation of compound 7 (e.g., with $MnO_2$) affords benzophenone derivative 8.

In step (iii), benzophenone derivative 8 is treated with $TiCl_4$ and a suitable dialkylzinc reagent to afford geminal dialkyl compound 9.

In step (iv), compound 9 is converted to pyrazole or triazole 10 (both of which are themselves compounds of formula (I)). Conversion to the pyrazole (X=CH) can be accomplished by converting compound 9 to the corresponding hydrazine (e.g., by treatment with sodium nitrite and aqueous acid), treating the hydrazine with a suitable ethyl 2,4-dioxoalkanoate (EtOC(O)C(O)$CH_2$C(O)$R^1$) to afford a pyrazole carboxylate ethyl ester intermediate, and converting the ester to the amide 10. The ester may be converted directly to the amide (e.g., by treatment with ammonia gas in dry methanol), or conversion may be accomplished by hydrolysis of the ester (e.g., by treatment with LiOH in methanol), followed by amide formation (e.g., by treatment with ammonia in the presence of HATU and a base). Conversion to the triazole (X=N) can be accomplished by converting compound 9 to the corresponding hydrazine (e.g., by treatment with sodium nitrite and aqueous acid), treating the hydrazine with a suitably substituted diethyl amidomalonate (EtOC(O)CH(NHC(O)$R_1$)C(O)OEt) to afford a triazole carboxylate ethyl ester intermediate, and converting the ester to the amide 10. The ester may be converted directly to the amide (e.g., by treatment with ammonia gas in dry methanol), or conversion may be accomplished by hydrolysis of the ester (e.g., by treatment with LiOH in methanol), followed by amide formation (e.g., by treatment with ammonia in the presence of HATU and a base).

In general, the compounds of formula (I) can be synthesized from intermediates 5 and 10 by following the general procedure described in General Scheme 3.

General Scheme 3. Synthesis of Compounds of Formula (I)

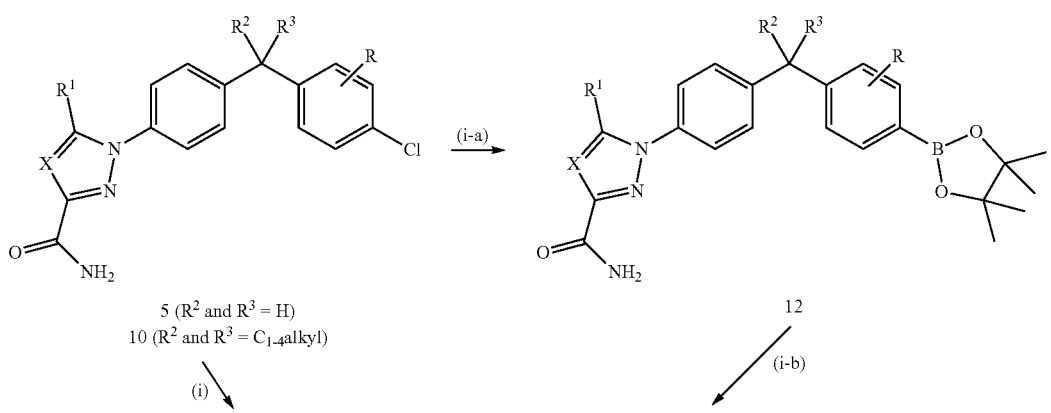

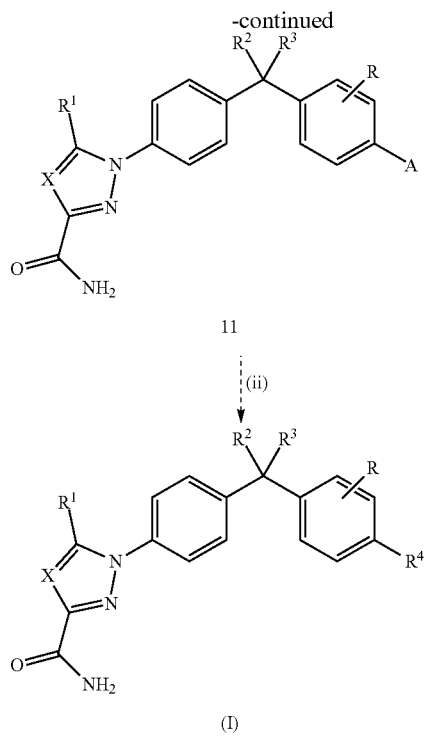

The starting materials for the synthesis described in General Scheme 3, i.e., intermediates 5 and 10, can be prepared as described in General Schemes 1 and 2, respectively. In general, the compounds of formula (I) are prepared from intermediates 5 and 10 as described in General Scheme 3 as follows:

In step (i), cross-coupling of aryl chloride 5 or 10 (e.g., Suzuki coupling with an aryl, heteroaryl, or vinyl boronic acid or boronate ester of formula A-B(OR)$_2$) affords compound 11, wherein A is a precursor to the $R^4$ substituents in the desired compound of formula (I).

Alternatively, in step (i-a), Miyaura borylation of compound 5 or 10 affords boronate ester intermediate 12 (step (i-a)), followed by Suzuki coupling of intermediate 12 with an aryl, heteroaryl, or vinyl halide or triflate of formula A-L (where L is Cl, Br, I, or OTf) affords compound 11.

In step (ii), further modification of the A substituent in compound 11 according to well-known methods, such as cross-coupling (e.g., Suzuki coupling, Sonogashira coupling), amide coupling, reductive amination, hydrogenation, and the like, to arrive at the desired $R^4$ substituent affords the compound of formula (I). For some $R^4$ substituents, it is possible to couple the $R^4$ substituent directly to compound 5 or 10 in step (i), such that step (ii) is unnecessary. In such cases, A is $R^4$, and compound 11 is the compound of formula (I).

The disclosure further includes any variants of the processes described in General Schemes 1-3 in which an intermediate product obtainable at any stage thereof is used as starting material, and the remaining steps are carried out.

In the synthetic schemes and chemical structures described herein, compounds may be drawn with one particular configuration (e.g., with or without a particular stereoisomer indicated) for simplicity. Such particular configurations or lack thereof are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

EXAMPLES

General Conditions

The following examples are intended to illustrate the disclosure and are not to be construed as being limitations thereon. Temperatures are given in degrees Celsius. If not otherwise specified, all evaporations were performed under reduced pressure, typically between about 15 mm Hg and 100 mm Hg (=20-133 mbar). The structure of final products, intermediates and starting materials was confirmed by standard analytical methods, e.g., microanalysis and spectroscopic characteristics, e.g., MS, NMR. Abbreviations used are those conventional in the art.

All starting materials, building blocks, reagents, acids, bases, dehydrating agents, solvents, and catalysts utilized in the following examples are commercially available or can be produced by methods known to one of ordinary skill in the art.

Mass spectra were acquired on LC-MS or SFC-MS systems using electrospray, chemical and electron impact ionization methods.

NMR spectra were run on Bruker AVANCE 400 MHz or 500 MHz NMR spectrometers using ICON-NMR, under TopSpin program control. Spectra were measured at 298K, unless indicated otherwise, and were referenced relative to the solvent resonance.

Instrumentation

Liquid Chromatography-Mass Spectrometry (LC-MS)

The following instrumentation and conditions were used for LC-MS analysis.

Instrumentation and Materials for LC-MS conditions A, B, C, E and Q:

| | |
|---|---|
| Pump | Waters AcQuity UPLC Binary Solvent Manager |
| Sample Manager | Waters AcQuity UPLC Sample Manager |
| Column Compartment | Waters AcQuity UPLC Column Manager |
| Detector | Waters AcQuity UPLC PDA |
| ELSD | Waters ELSD |
| Mass Spec | Waters SQD |
| Eluent A1 | 0.1% Formic Acid in Water |
| Eluent B1 | 0.1% Formic Acid in Acetonitrile |
| Eluent A2 | 5 mM Ammonium Hydroxide in Water (0.05% TFA instead of Ammonium Hydroxide on CA_SQD) |
| Eluent B2 | 5 mM Ammonium Hydroxide in Acetonitrile (0.05% TFA instead of Ammonium Hydroxide on CA_SQD) |
| Columns | AcQuity UPLC BEH C18 1.7 μm 2.1 × 30 mm<br>AcQuity UPLC BEH C18 1.7 μm 2.1 × 50 mm<br>AcQuity UPLC CSH C18 1.7 μm 2.1 × 50 mm |
| Column Temperature | 50° C. |

LC-MS condition A:

| | |
|---|---|
| Flow | 1.0 mL/min |
| Stop Time | 5.20 min |
| pH | 2.6 |

| Gradient | Time | % A (Eluent A1) | % B (Eluent B1) |
|---|---|---|---|
| | 0.00 | 98 | 2 |
| | 4.40 | 2 | 98 |
| | 5.15 | 2 | 98 |
| | 5.19 | 98 | 2 |

| | | |
|---|---|---|
| Column | AcQuity UPLC BEH C18 1.7 μm 2.1 × 50 mm | |
| Column Temperature | 50° C. | |
| UV | 210-400 nm | |
| Mass Range | 120-1600 m/z SQD | 120-1250 m/z QDa |
| Scan Time | 0.3 sec | |

LC-MS Condition B:

| | |
|---|---|
| Flow | 1.0 mL/min |
| Stop Time | 2.00 min |
| pH | 2.6 |

| Gradient | Time | % A (Eluent A1) | % B (Eluent B1) |
|---|---|---|---|
| | 0.00 | 98 | 2 |
| | 0.10 | 98 | 2 |
| | 1.50 | 2 | 98 |
| | 1.80 | 2 | 98 |
| | 1.90 | 98 | 2 |
| | 2.00 | 98 | 2 |

| | | |
|---|---|---|
| Column | AcQuity UPLC BEH C18 1.7 μm 2.1 × 30 mm | |
| Column Temperature | 50° C. | |
| UV | 210-400 nm | |
| Mass Range | 120-1600 m/z SQD | 120-1250 m/z QDa |
| Scan Time | 0.3 sec | |

LC-MS Condition C:

| | |
|---|---|
| Flow | 1.0 mL/min |
| Stop Time | 2.00 min |
| pH | 10.2 |

| Gradient | Time | % A (Eluent A2) | % B (Eluent B2) |
|---|---|---|---|
| | 0.00 | 98 | 2 |
| | 0.10 | 98 | 2 |
| | 1.50 | 2 | 98 |
| | 1.80 | 2 | 98 |
| | 1.90 | 98 | 2 |
| | 2.00 | 98 | 2 |

| | | |
|---|---|---|
| Column | AcQuity UPLC BEH C18 1.7 μm 2.1 × 30 mm | |
| Column Temperature | 50° C. | |
| UV | 210-400 nm | |
| Mass Range | 120-1600 m/z SQD | 120-1250 m/z QDa |
| Scan Time | 0.3 sec | |

LC-MS Condition D:

| | |
|---|---|
| LC Method | INERTSIL333_C18_Neutral pH |
| Column | Xbridge C18, 3.5 μm, 3.0 × 30 mm |
| Column Temperature | 50° C. |
| UV | 220-600 nm |
| Mass Range | 80-1160 m/z Da |
| Eluent A | Water (+5 mM Ammonium formate, 2% Acetonitrile) |
| Eluent B | Acetonitrile |
| Flow Rate | 2 mL/min |
| Gradient | 0 min of 10% B; 10-95% B in 1.70 min; 0.3 min, 95% B; 2.1 min of 10% B |
| Scan Time | 0.3 sec |

LC-MS Condition Q:

Waters Acquity UPLC system
Waters Acquity UPLC BEH C18 1.7 um, 2.1 × 30 mm (Part# 186002349)
Flow rate: 1 mL/min
Temperature: 55° C. (column temp)
Mobile phase compositions:
0.05% formic acid in water
0.04% formic acid in methanol

| Gradient | Time | % A (Eluent A1) | % B (Eluent B1) |
|---|---|---|---|
| | 0.00 | 95 | 5 |
| | 0.10 | 95 | 5 |
| | 0.50 | 20 | 80 |
| | 0.60 | 5 | 95 |
| | 0.80 | 5 | 95 |
| | 0.90 | 95 | 5 |
| | 1.15 | 95 | 5 |

LC-MS condition E:

| | |
|---|---|
| Flow | 1.0 mL/min |
| Stop Time | 5.20 min |
| pH | 2.6 |

| Gradient | Time | % A (Eluent A2) | % B (Eluent B2) |
|---|---|---|---|
| | 0.00 | 98 | 2 |
| | 4.40 | 2 | 98 |
| | 5.15 | 2 | 98 |
| | 5.19 | 98 | 2 |

| | | |
|---|---|---|
| Column | AcQuity UPLC BEH C18 1.7 μm 2.1 × 50 mm | |
| Column Temperature | 50° C. | |
| UV | 210-400 nm | |
| Mass Range | 120-1600 m/z SQD | 120-1250 m/z QDa |
| Scan Time | 0.4 sec | |

Abbreviations

Unless otherwise noted, or where the context dictates otherwise, the following abbreviations shall be understood to have the following meanings:

| Abbreviation | Meaning |
| --- | --- |
| First generation Xphos Precatalyst | (2-Dicyclohexylphosphino-2',4',6'-triisopropyl-1,1'-biphenyl)[2-(2-aminoethyl)phenyl)]palladium(II) chloride (CAS# 1028206-56-5) |
| Second generation Xphos Precatalyst (Pd-Xphos G2) | Chloro(2-dicyclohexylphosphino-2',4',6'-triisopropyl-1,1'-biphenyl)[2-(2'-amino-1,1'-biphenyl)]palladium(II) (CAS# 1310584-14-5) |
| $PdCl_2(dppf) \cdot DCM$ (adduct) | CAS# 95464-05-4 |
| 10% Pd/C | Palladium on carbon: 10 wt. % loading (dry basis), matrix activated carbon, wet support, Degussa type E101 NE/W |
| OTf | trifluoromethanesulfonate |
| $Pd_2(dba)_3$ | Tris(dibenzylideneacetone)dipalladium(0) |
| $PCy_3$-$HBF_3$ | Tricyclohexylphosphine tetrafluoroborate |
| [Rh(COD)$Cl_2$] | Chloro(1,5-cyclooctadiene)rhodium(I) dimer |
| mm | Millimeters |
| mbar | Millibars |
| MS | Mass spectrometry |
| IR | Infrared (spectroscopy) |
| NMR | Nuclear magnetic resonance (spectroscopy) |
| LC-MS/LCMS | Liquid chromatography - mass spectrometry |
| SFC-MS | Supercritical Fluid Chromatography-mass spectrometry |
| GC-MS | Gas chromatography - mass spectrometry |
| MHz | Megahertz |
| ICON-NMR | Bruker NMR automation software |
| K | Kelvin |
| UPLC | Ultra Performance Liquid Chromatography |
| HPLC | High-Performance Liquid Chromatography |
| PDA | Photodiode Array Detector |
| ELSD | Evaporative light scattering detector |
| SQD | Single Quadrupole Detector |
| mM | Millimolar |
| μM | Micromolar |
| TFA | Trifluoroacetic acid |
| BEH | Waters ® brand Ethylene Bridged Hybrid Silica column technology |
| CSH | Waters ® brand Charged Surface Hybrid Silica column technology |
| mL | Milliliters |
| min | Minute(s) |
| μm | Micrometers |
| UV | Ultraviolet |
| nm | Nanometers |
| QDa | Waters ® brand Single Quad Detector |
| m/z | Mass-to-charge ratio |
| sec | Seconds |
| THF | Tetrahydrofuran |
| DMSO | Dimethylsulfoxide |
| HPLC | High performance liquid chromatograph |
| ACN/MeCN | Acetonitrile |
| M | Molar |
| EtOAc | Ethyl acetate |
| SCX-BSA | Agilent BondElute SCX-Benzylsulfonic acid cartridge |
| MeOH | Methanol |
| EtOH | Ethanol |
| DCM | Dichloromethane |
| N | Normal (concentration) |
| LiHMDS | Lithium bis(trimethylsilyl)amide |
| Boc | Tert-butoxy carbonyl |
| h | Hours |
| mg | Milligrams |
| mmol | Millimoles |
| eq | Equivalents |
| g | Grams |
| $Et_2O$ | Diethyl ether |
| HATU | 1-[Bis(dimethylamino)methylene]-1H-1,2,3-triazolo[4,5-b]pyridinium 3-oxid hexafluorophosphate |
| DMF | N,N-dimethylformamide |
| PhMe | Toluene |
| DIPEA | Diisopropyl ethyl amine |
| TEA | Triethylamine |
| DEA | Diethylamine |
| SFC | Supercritical Fluid Chromatography |
| HBTU | (2-(1H-benzotriazol-1-yl)-1,1,3,3-tetramethyluronium |

-continued

| Abbreviation | Meaning |
|---|---|
| | hexafluorophosphate) |
| PTFE | Polytetrafluoroethylene |
| DMAP | 4-(N,N-dimethylamino)pyridine |
| BINAP | 2,2'-Bis(diphenylphosphino)-1,1'-binaphthyl |
| FCC | Flash Column Chromatography, normal phase |
| TLC | Thin layer chromatography |
| FBS | Fetal bovine serum |
| GFP | Green Fluorescent Protein |
| AKT | Protein Kinase B |
| $^1$H NMR | Proton nuclear magnetic resonance |
| RT | Room temperature |
| Rt | Retention time |
| psi | Pounds per square inch |
| IPA | Isopropanol |
| 4A | 4 Ångström |
| $AC_{50}$ | Concentration that results in 50% activation or inhibition |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate (CAS# 1445085-55-1) |
| NMM | N-methymorpholine |
| HOBt | Hydroxybenzotriazole |
| EDC•HCL | N-(3-Dimethylaminopropyl)-N'-ethylcarbodiimide hydrochloride |
| $NaBH(OAc)_3$ | Sodium triacetoxyborohydride |
| AcOH | Acetic acid |
| $SOCl_2$ | Thionyl chloride |
| DCE | Dichloroethane |
| 9-BBN | 9-Borabicyclo[3.3.1]nonane |
| DIAD | Diisopropyl azodicarboxylate |

General Methods

General Method I

Representative Procedure for Suzuki Coupling

A microwave vial was charged with aryl halide (1 equivalent), boronic ester (1.5 equivalents), $K_3PO_4$ (3 equivalents), and 5:1 THF:Water (0.1 M in aryl halide) and the mixture was evacuated and filled with $N_2$ (3×). Then XPhos-Pd-Cycle G1 (0.1 equivalents) was added and the mixture was heated in the microwave at 120° C. for 40 min, cooled to ambient temperature, filtered through a 0.45 micron syringe filter and concentrated in vacuo. The crude product was taken up in 90:10 DMSO:Water and purified by preparative HPLC (ACN/Water+0.05% ammonium hydroxide modifier) to provide the desired product.

General Method II

Representative Procedure for Suzuki Coupling

To a stirred solution of aryl boronate ester (1 equivalent) in THF:Water (5:1, 0.1M) was added halide or triflate (1.5 equivalents) and sodium carbonate (3 equivalents), and the mixture was evacuated and filled with $N_2$ (3×). Then $PdCl_2$ (dppf). DCM (0.1 equivalents) was added at ambient temperature. The suspension was again degassed with $N_2$, then sealed and heated at 80° C. for 16 h. The reaction mixture was cooled to ambient temperature and diluted with excess EtOAc. The organic layer was washed with water (3×) and brine (3×), dried over anhydrous sodium sulfate, and concentrated in vacuo. The crude material was purified by silica gel in EtOAc:Heptane (0-100%) to provide the desired product.

General Method III

Representative Procedure for SCX Cartridge Purification

The crude material was taken up in MeOH and loaded onto the appropriate sized Agilent BondElute SCX-Benzylsulfonic acid cartridge, prewashed with 1:1 MeOH:DCM. The cartridge was then washed with excess 1:1 MeOH:DCM. Then the product was eluted in a 1:1 mixture of DCM:(7N $NH_3$ in MeOH). The basic eluent was concentrated under reduced pressure to afford the desired compound.

General Method IV

Representative Procedure for Suzuki Coupling

A reaction vial was charged with aryl halide (1.0 equiv), bronoate ester (1.2 equiv), XPhos Pd G3 (0.05 equiv) and $K_3PO_4$ (2 equiv). The vial was sealed and evacuated under hi-vac and backfilled with $N_2$ (×3). Degassed 1-butanol: degassed water (5:1, 0.2M) was added, and the reaction was heated to 80° C. for 4 h or until LCMS analysis indicated full conversion of the starting material. The reaction mixture was allowed to cool to RT and diluted with EtOAc and water. The layers were separated and the aqueous layer was extracted with EtOAc (×3). The combined organic layers were washed with brine, dried over sodium sulfate, filtered and concentrated. The crude material was purified by Preparative HPLC or FCC.

Preparation of Intermediates

Preparation 1

Intermediate I: ethyl 1-(4-bromophenyl)-5-methyl-1H-pyrazole-3-carboxylate

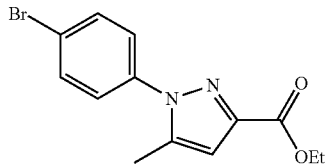 [SMILES: CCOC(=O)c1cc(C)n(-c2ccc(Br)cc2)n1]

To ethyl 2,4-dioxopentanoate (141.2 g, 892.8 mmol) in AcOH (2.3 L) was added (4-bromophenyl)hydrazine hydrochloride (200 mg, 894.9 mmol). The suspension was heated at 100° C. for 3 h. The mixture was then cooled to ambient temperature and exacted with EtOAc. The organic extract was washed with water, then brine, dried over anhydrous sodium sulfate and concentrated in vacuo. The crude product was purified on silica gel (12-20% EtOAc in diethyl ether) to afford ethyl 1-(4-bromophenyl)-5-methyl-1H-pyrazole-3-carboxylate (170 g, 61%) (Intermediate I): LCMS Rt=2.35 min (condition A), MS (M+1)=309.04. $^1$H NMR (400 MHz, DMSO-$d_6$) δ 7.81-7.68 (m, 2H), 7.64-7.47 (m, 2H), 6.85-6.72 (m, 1H), 4.29 (q, J=7.1 Hz, 2H), 2.34 (s, 3H), 1.29 (t, J=7.1 Hz, 3H).

Preparation 2

Intermediate II: 1-(4-(4-chlorobenzyl)phenyl)-5-methyl-1H-pyrazole-3-carboxamide

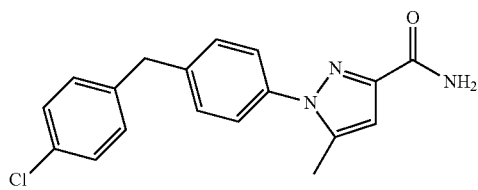 [SMILES: Cc1cc(C(N)=O)nn1-c1ccc(Cc2ccc(Cl)cc2)cc1]

Step 1: ethyl 1-(4-(4-chlorobenzyl)phenyl)-5-methyl-1H-pyrazole-3-carboxylate

To a suspension of zinc powder (66.8 g, 1022 mmol) in dry THF (700 mL) was added 1,2-dibromoethane (3.7 g, 19.70 mmol) and trimethylsilylchloride (10.6 g, 97.56 mmol). The suspension was stirred at 70° C. for 0.5 h, then 1-(bromomethyl)4-chlorobenzene (200 mg, 973 mmol) in dry THF (270 mL) was added dropwise and the resulting mixture was heated for another 1 h. The crude organozinc solution was used in the next step without further purification.

To a degassed solution of ethyl 1-(4-bromophenyl)-5-methyl-1H-pyrazole-3-carboxylate (Intermediate I) in dry THF (830 mL) was added triphenylphosphine (8.44 g, 32.17 mmol) and Pd$_2$(dba)$_3$. The resulting solution was heated to 60° C. then the prepared organozinc reagent was added dropwise and the resulting mixture was stirred at 60° C. for 12 h. The mixture was then cooled to ambient temperature and extracted with EtOAc. The organic extract was washed with water and brine, dried with over sodium sulfate and concentrated. The crude product was purified by silica gel chromatography (gradient 12-20% EtOAc in diethyl ether) to afford ethyl 1-(4-(4-chlorobenzyl)phenyl)-5-methyl-1H-pyrazole-3-carboxylate (55.0 g, 48%): LCMS Rt=2.97 min (condition A), MS (M+1)=355.0. $^1$H NMR (400 MHz, DMSO-$d_6$) δ 7.53-7.45 (m, 2H), 7.44-7.35 (m, 4H), 7.35-7.28 (m, 2H), 6.77-6.69 (m, 1H), 4.27 (q, J=7.1 Hz, 2H), 4.04 (s, 2H), 2.36-2.24 (m, 3H), 1.28 (t, J=7.1 Hz, 3H).

Step 2: 1-(4-(4-chlorobenzyl)phenyl)-5-methyl-1H-pyrazole-3-carboxylic acid

To ethyl 1-(4-(4-chlorobenzyl)phenyl)-5-methyl-1H-pyrazole-3-carboxylate (33.8 g, 95 mmol) in THF (300 mL) and MeOH (75 mL) was added LiOH.H$_2$O (20 g, 476 mmol) and water (75 mL). The mixture was stirred at 50° C. for 1 h then cooled to ambient temperature and filtered through celite. The filtrate was concentrated in vacuo. To the resulting grey slurry was added excess water. The suspension was adjusted to pH=2 with 6N HCl aq (80 mL) and cooled to 0° C. for 0.5 h. The white precipitate was filtered off and washed with excess water, then dried under high vacuum to afford 1-(4-(4-chlorobenzyl)phenyl)-5-methyl-1H-pyrazole-3-carboxylic acid (30.5 g, 98%): LCMS Rt=2.47 min (condition A), MS (M+1)=327.1. $^1$H NMR (400 MHz, DMSO-$d_6$) δ 7.51-7.43 (m, 2H), 7.43-7.35 (m, 4H), 7.35-7.24 (m, 2H), 6.71-6.60 (m, 1H), 4.04 (s, 2H), 2.30 (m, 3H).

Step 3: 1-(4-(4-chlorobenzyl)phenyl)-5-methyl-1H-pyrazole-3-carboxamide

To 1-(4-(4-chlorobenzyl)phenyl)-5-methyl-1H-pyrazole-3-carboxylic acid and HATU (42.5 g, 112 mmol) in DCM (400 mL) and DMF (40 mL) was added DIPEA (48.8 mL, 280 mmol) followed by 0.5 M NH$_3$ in 1,4-dioxane (298 mL, 149 mmol). The mixture was stirred at ambient temperature overnight at which time the reaction was quenched with excess saturated aqueous NH$_4$Cl. The mixture was diluted with brine and extracted with DCM (3x). The organic extracts were filtered through celite and concentrated in vacuo. The crude material was diluted with MeOH (100 mL) and stirred at ambient temperature while water (200 mL) was added dropwise, resulting in a while precipitate. The suspension was cooled for 0.5 h then the solids were collected by vacuum filtration. The solids were washed with cold MeOH/Water (1:2), then diethyl ether and dried under high vacuum to afford 1-(4-(4-chlorobenzyl)phenyl)-5-methyl-1H-pyrazole-3-carboxamide (26.7 g, 88%) (Intermediate II): LCMS Rt=2.40 min (condition A), MS (M+1) =326.1. $^1$H NMR (400 MHz, Chloroform-d) δ 7.43-7.36 (m, 2H), 7.34-7.29 (m, 4H), 7.21-7.11 (m, 2H), 6.77 (d, J=0.7 Hz, 1H), 4.04 (s, 2H), 2.35 (m, 3H).

Preparation 3

Intermediate III: 5-methyl-1-(4-(4-(4,4,5,5-tetramethyl-1,3,2-dioxaborolan-2-yl)benzyl)phenyl)-1H-pyrazole-3-carboxamide

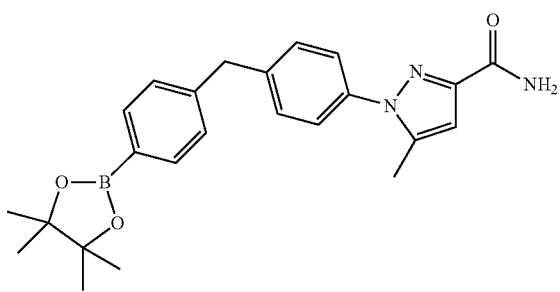 [SMILES: Cc1cc(C(N)=O)nn1-c1ccc(Cc2ccc(B3OC(C)(C)C(C)(C)O3)cc2)cc1]

To 1-(4-(4-chlorobenzyl)phenyl)-5-methyl-1H-pyrazole-3-carboxamide (Intermediate II) in 1,4-dioxane (7.7 mL) was added bis(pinacolato)diboron (1.17 g, 4.60 mmol), potassium acetate (0.904 g, 9.21 mmol) and XPhos (0.110 g, 0.230 mmol). The suspension was degassed with nitrogen for 5 min then $Pd_2(dba)_3$ (0.105 g, 0.115 mmol) was added and the resulting mixture was heated at 110° C. for 3 h. The mixture was then cooled to ambient temperature, diluted with excess EtOAc, washed with water, dried over anhydrous sodium sulfate and concentrated in vacuo. The crude material was then purified by column chromatography (gradient 0-100% EtOAc in Heptane) to afford 5-methyl-1-(4-(4-(4,4,5,5-tetramethyl-1,3,2-dioxaborolan-2-yl)benzyl)phenyl)-1H-pyrazole-3-carboxamide (943 mg, 98%) (Intermediate III): LCMS Rt=1.15 min (condition B), MS (M+1)=418.3. $^1$H NMR (400 MHz, DMSO-d6) δ 7.62 (d, J=7.9 Hz, 2H), 7.48 (d, J=8.4 Hz, 3H), 7.38 (d, J=8.4 Hz, 2H), 7.35-6.87 (m, 3H), 6.60 (s, 1H), 4.05 (s, 2H), 2.31 (m, 3H), 1.33-1.13 (m, 12H).

Preparation 4

Intermediate IV: 4-(2-(4-chlorophenyl)propan-2-yl)aniline

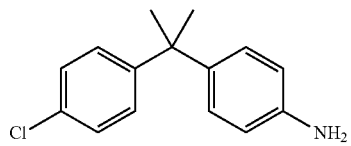 [SMILES: CC(C)(c1ccc(N)cc1)c1ccc(Cl)cc1]

Step 1: (4-aminophenyl)(3-chlorophenyl)methanol

A solution of 4-bromo-N,N-bis(trimethylsily)aniline (3.22 mL, 11.38 mmol) in THF (50 mL) was cooled to −78° C., and degassed with nitrogen. 2.5M n-butyllithium in hexanes (5.27 mL, 13.18 mmol) was added dropwise and the resulting mixture was stirred at −78° C. for 0.5 h. 4-chlorobenzaldehyde (2.0 g, 14.23 mmol) in THF (18 mL) was added dropwise, and the mixture was again stirred at −78° C. for 1 h. The resulting mixture was quenched with saturated aqueous $NH_4Cl$ solution and extracted with EtOAc. The EtOAc layer was concentrated and the crude material was purified by column chromatography (gradient 0-80% EtOAc in heptane) to afford (4-aminophenyl)(3-chlorophenyl)methanol (1.8 g, 54%): LCMS Rt=1.10 min (condition C), MS (M+1)=234.2.

Step 2: (4-aminophenyl)(4-chlorophenyl)methanone

To (4-aminophenyl)(3-chlorophenyl)methanol (751 mg, 3.21 mmol) in toluene (23 mL) was added $MnO_2$ (657 mg, 6.43 mmol). The suspension was stirred at 110° C. for 2 h then cooled to ambient temperature. The mixture was filtered through celite, washing with toluene, and the resulting filtrate was concentrated in vacuo to afford (4-aminophenyl)(4-chlorophenyl)methanone (200 mg, 27%): LCMS Rt=1.17 min (condition C), MS (M+1)=247.2.

Step 3: 4-(2-(4-chlorophenyl)propan-2-yl)aniline

To a solution of 1M $TiCl_4$ in DCM (2.59 mL, 2.59 mmol) cooled to −30° C. was added 2M dimethylzinc in toluene (1.30 mL, 2.59 mmol). After stirring the mixture at −30° C. for 20 min, (4-aminophenyl)(4-chlorophenyl)methanone (100 mg, 0.432 mmol) in DCM (3 mL) was added dropwise. The resulting mixture was stirred at −30° C. for 15 min then at ambient temperature for 1.5 h. Then the reaction mixture was poured into ice/methanol, stirred for 2 h, and then extracted with DCM. The organic layer was concentrated in vacuo and purified by column chromatography (gradient 0-20% EtOAc in heptane) to afford 4-(2-(4-chlorophenyl)propan-2-yl)aniline (23.7 mg, 22%) (Intermediate IV): $^1$H NMR (400 MHz, Chloroform-d) δ 7.17-7.13 (m, 2H), 7.12-7.00 (m, 4H), 6.67-6.59 (m, 2H), 3.72 (s, 2H), 1.64 (s, 6H).

Preparation 5

Intermediate V: 1-(4-(2-(4-chlorophenyl)propan-2-yl)phenyl)-5-methyl-1H-pyrazole-3-carboxamide

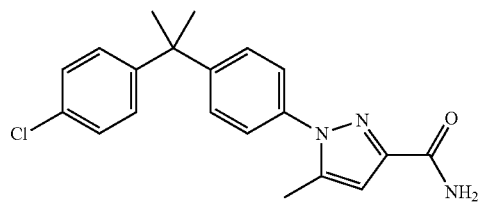 [SMILES: Cc1cc(C(N)=O)nn1-c1ccc(C(C)(C)c2ccc(Cl)cc2)cc1]

Step 1: (4-(2-(4-chlorophenyl)propan-2-yl)phenyl)hydrazine

To a solution of 4-(2-(4-chlorophenyl)propan-2-yl)aniline (Intermediate IV) in 12N aq HCl (11.7 mL, 141 mmol) at 00° C., was added sodium nitrite (390 mg, 5.65 mmol) in water (2.6 mL) dropwise over 10 min. Then a solution of $SnCl_2$ (2.25 g, 11.85 mmol) in 12N aq. HCl (2.6 mL) was added dropwise over 5 min. The resulting mixture was stirred for 30 min at 0° C. and then the precipitate was collected by vacuum filtration and washed with water, then ether to afford (4-(2-(4-chlorophenyl)propan-2-yl)phenyl)hydrazine (1.3 g, 100%): LCMS Rt=1.44 min (condition C), MS (M+1)=261.0.

Step 2: ethyl 1-(4-(2-(4-chlorophenyl)propan-2-yl)phenyl)-5-methyl-1H-pyrazole-3-carboxylate To ethyl 2,4-dioxopentanoate (0.812 mL, 5.75 mmol) in AcOH (15 mL) was added (4-(2-(4-chlorophenyl)propan-2- yl)phenyl)hydrazine (1.5 g, 5.75 mmol). The resulting mixture was heated to 100° C. for 2 h. The mixture was then cooled to ambient temperature, diluted with water and extracted with EtOAc. The organic extract was washed with water and saturated aqueous sodium bicarbonate, then concentrated in vacuo. The resulting crude material was purified by column chromatography (gradient 0-20% EtOAc in heptane) to afford ethyl 1-(4-(2-(4-chlorophenyl)propan-2-yl)phenyl)-5-methyl-1H-pyrazole-3-carboxylate (615 mg, 28%): LCMS Rt=1.80 min (condition C), MS (M+1)=383.2.

Step 3: 1-(4-(2-(4-chlorophenyl)propan-2-yl)phenyl)-5-methyl-1H-pyrazole-3-carboxamide To ethyl 1-(4-(2-(4-chlorophenyl)propan-2-yl)phenyl)-5-methyl-1H-pyrazole-3-carboxylate (1.04 g, 2.72 mmol) was added 7N NH₃ in MeOH (11.64 mL, 81 mmol). The resulting solution was stirred at ambient temperature for 3 days then concentrated in vacuo. The crude material was purified by column chromatography (gradient 50-80% EtOAc in heptane) to afford ethyl 1-(4-(2-(4-chlorophenyl)propan-2-yl)phenyl)-5-methyl-1H-pyrazole-3-carboxamide (1.6 g, 97%) (Intermediate V): LCMS Rt=1.52 min (condition C), MS (M+1)=354.2. $^1$H NMR (400 MHz, Chloroform-d) δ 7.43-7.32 (m, 4H), 7.32-7.24 (m, 2H), 7.24-7.16 (m, 2H), 6.81 (s, 1H), 6.76 (s, 1H), 5.37 (s, 1H), 2.36 (s, 3H), 1.72 (s, 6H).

Preparation 6

Intermediate VI: 5-methyl-1-(4-(2-(4-(4,4,5,5-tetramethyl-1,3,2-dioxaborolan-2-yl)phenyl)propan-2-yl)phenyl)-1H-pyrazole-3-carboxamide

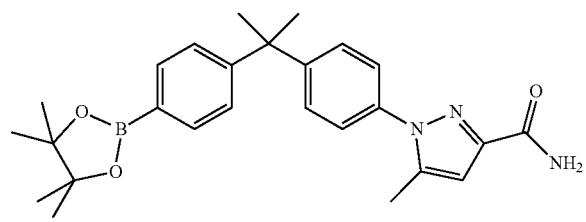 [SMILES: Cc1cc(C(N)=O)nn1-c1ccc(C(C)(C)c2ccc(B3OC(C)(C)C(C)(C)O3)cc2)cc1]

Ethyl 1-(4-(2-(4-chlorophenyl)propan-2-yl)phenyl)-5-methyl-1H-pyrazole-3-carboxamide (Intermediate V) (0.5 g, 1.413 mmol), bis(pinacolato)diboron (1.076 g, 4.24 mmol), potassium acetate (0.555 g, 5.65 mmol) and Xphos (0.067 g, 0.141 mmol) were taken up in 1,4-dioxane (4.71 mL) and degassed with nitrogen for 5 min. Pd₂(dba)₃ (0.065 g, 0.071 mmol) was added, and the mixture was heated at 110° C. for 2 h. The reaction mixture was cooled to ambient temperature, diluted with EtOAc and filtered through celite, washing with excess EtOAc. The filtrate was concentrated to afford 5-methyl-1-(4-(2-(4-(4,4,5,5-tetramethyl-1,3,2-dioxaborolan-2-yl)phenyl)propan-2-yl)phenyl)-1H-pyrazole-3-carboxamide (629 mg) (Intermediate VI): LCMS Rt=1.67 min (condition B), MS (M+1)=446.4.

Preparation 7

Intermediate VII: 1-(4-(4-chlorobenzyl)phenyl)-5-methyl-1H-1,2,4-triazole-3-carboxamide

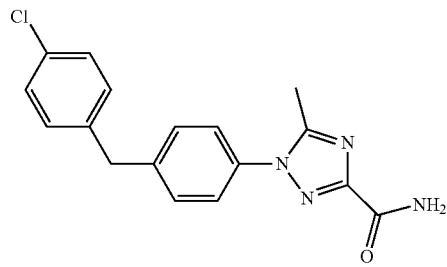 [SMILES: Cc1nc(C(N)=O)nn1-c1ccc(Cc2ccc(Cl)cc2)cc1]

Step 1: Preparation of ethyl 1-(4-bromophenyl)-5-methyl-1H-1,2,4-triazole-3-carboxylate A mixture of 4-bromophenyl hydrazine.HCl (30 g, 268 mmol), ethyl 2-amino-2-thioxoacetate (42.9 g, 322 mmol), DIPEA (34.7 g, 268 mmol), acetic acid (32.5 g, 54 mmol) in toluene (420 mL) was stirred at ambient temperature for 1 h under nitrogen. Acetic anhydride (82.3 mL, 806 mmol) was added and the mixture was heated at 100° C. for 3 h. The mixture was cooled to ambient temperature and concentrated in vacuo to remove toluene. Water (500 mL) was added to the resulting slurry, which was then neutralized with saturated aqueous sodium bicarbonate and extracted with EtOAc (2×200 mL). The combined organic layer was dried over anhydrous sodium sulfate, filtered and concentrated in vacuo. The crude material obtained was purified by column chromatography to afford ethyl 1-(4-bromophenyl)-5-methyl-1H-1,2,4-triazole-3-carboxylate (50.8 g, 48%): $^1$H NMR (400 MHz, CDCl₃) δ 7.69 (d, J=8.7 Hz, 2H), 7.40 (d, J=8.7 Hz, 2H), 4.52 (q, J=7.1 Hz, 2H), 2.60 (s, 3H), 1.48-1.41 (m, 3H).

Step 2: Preparation of 1-(4-bromophenyl)-5-methyl-1H-1,2,4-triazole-3-carboxamide To a stirred solution of ethyl 1-(4-bromophenyl)-5-methyl-1H-1,2,4-triazole-3-carboxylate (50 g, 161 mmol) in dry MeOH (500 mL) was passed NH₃ gas for 1 h, and then the mixture was allowed to stir at ambient temperature for 18 h. After completion, the reaction mixture was concentrated in vacuo. The crude material was triturated in ether, and the resulting solid was collected by vacuum filtration, washing with diethyl ether to afford 1-(4-bromophenyl)-5-methyl-1H-1,2,4-triazole-3-carboxamide (29 g, 79%): $^1$H NMR (400 MHz, DMSO-d6) δ 7.90 (s, 1H), 7.85-7.75 (m, 2H), 7.71-7.53 (m, 3H), 2.50 (m, 3H).

Step 3: Preparation of 1-(4-(4-chlorobenzyl)phenyl)-5-methyl-1H-1,2,4-triazole-3carboxamide To 1-(4-bromophenyl)-5-methyl-1H-1,2,4-triazole-3-carboxamide (29 g, 103 mmol) in dry THF (300 mL) was added 1M (4-chlorobenzyl)zinc(II) bromide in THF (266 mL) followed by triphenylphosphine (2.8 g, 10.6 mmol). The reaction mixture was degassed by purging with N₂ for 0.5 h, and then Pd(OAc)₂ (1.2 g, 5.2 mmol) was added, and the mixture was heated at 60° C. for 4 h. The reaction mixture was concentrated in vacuo. The material was taken up in EtOAc (400 mL), washed with water (150 mL×3) and brine solution (50 mL×2), then dried over anhydrous sodium sulfate, filtered and concentrated in vacuo. The resulting crude material was purified by column chromatography to afford 1-(4-(4-chlorobenzyl)phenyl)-5-methyl-1H-1,2,4-triazole-3-carboxamide (25 g, 74%) (Intermediate VIII): $^{1}$H NMR (400 MHz, DMSO-d6) δ 7.85 (s, 1H), 7.58 (dd, J=22.6, 11.7 Hz, 4H), 7.44 (d, J=8.5 Hz, 2H), 7.38 (d, J=8.5 Hz, 2H), 7.33 (s, 1H), 4.05 (s, 2H), 2.46 (s, 3H).

Preparation 8

Intermediate VIII: 1-(4-((4'-formyl-[1,1'-biphenyl]-4-yl)methyl)phenyl)-5-methyl-1H-pyrazole-3-carboxamide

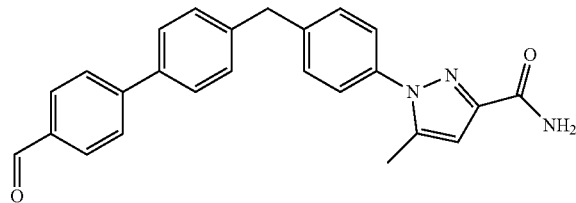 [SMILES: Cc1cc(C(N)=O)nn1-c1ccc(Cc2ccc(-c3ccc(C=O)cc3)cc2)cc1]

To a stirred solution of Intermediate II (1.0 g, 3.07 mmol) in THF\Water (10:2) was added 4-(4,4,5,5-tetramethyl-1,3,2-dioxaborolan-2-yl)benzaldehyde (0.713 g, 3.07 mmol) and K$_3$PO$_4$ (1.95 g, 9.23 mmol), and the mixture was degassed with nitrogen for 5 min. XPhos-Pd-Cycle G1 (0.217 g, 0.30 mmol) was added and the mixture was again degassed with nitrogen for 5 min and heated at 120° C. for 4 h. The mixture was then diluted with EtOAc (50 mL) and washed with water (15 mL×3) and brine solution (5 mL×3), dried over anhydrous Na$_2$SO$_4$, and concentrated in vacuo. The crude material was purified by column chromatography to afford 1-(4-((4'-formyl-[1,1'-biphenyl]-4-yl)methyl)phenyl)-5-methyl-1H-pyrazole-3-carboxamide (0.94 g, 77%). $^{1}$H NMR (400 MHz, DMSO-d6) δ 10.01 (m, 1H), 7.96 (d, J=8.2 Hz, 2H), 7.88 (d, J=8.1 Hz, 2H), 7.71 (d, J=8.1 Hz, 2H), 7.52-7.38 (m, 5H), 7.22 (s, 1H), 6.57 (d, J=14.6 Hz, 1H), 4.08 (s, 2H), 2.28 (s, 3H).

Preparation 9

Intermediate IX: 5-methyl-1-(4-(4-(4,4,5,5-tetramethyl-1,3,2-dioxaborolan-2-yl)benzyl)phenyl)-1H-1,2,4-triazole-3-carboxamide

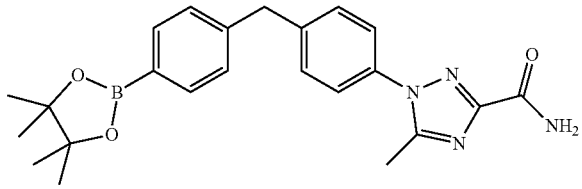 [SMILES: Cc1nc(C(N)=O)nn1-c1ccc(Cc2ccc(B3OC(C)(C)C(C)(C)O3)cc2)cc1]

A 40 mL vial was charged with XPhos Pd G2 (110 mg, 0.140 mmol), bis(pinacolato)diboron (1.06 g, 4.19 mmol), potassium acetate (822 mg, 8.37 mmol) and Intermediate VII (456 mg, 1.4 mmol). The vial was sealed and evacuated under hi-vac and backfilled with N$_2$ (×3). Dry, degassed 1,4-dioxane (6.9 mL) was added and the reaction was heated to 100° C. for 3 h. The reaction was allowed to cool to RT, then was diluted with EtOAc (30 mL) and filtered through celite, washing the filter cake with EtOAc. The filtrate was concentrated and purified by FCC (2-10% MeOH in DCM) to afford 5-methyl-1-(4-(4-(4,4,5,5-tetramethyl-1,3,2-dioxaborolan-2-yl)benzyl)phenyl)-1H-1,2,4-triazole-3-carboxamide (435 mg, 63%) as a light brown powder. LC-MS Rt=2.43 min (Condition E), MS (M+1)=419.3.

Preparation 10

Intermediate X: 4'-(4-(3-carbamoyl-5-methyl-1H-pyrazol-1-yl)benzyl)-[1,1'-biphenyl]-4-carboxylic acid

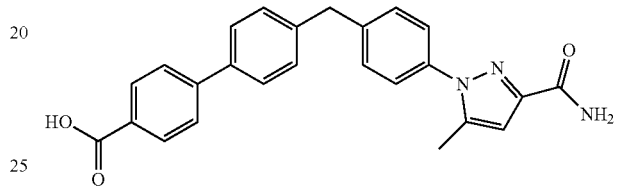

Step 1: Preparation of tert-butyl 4'-(4-(3-carbamoyl-5-methyl-1H-pyrazol-1-yl)benzyl)-[1,1'-biphenyl]-4-carboxylate 1-(4-(4-Chlorobenzyl)phenyl)-5-methyl-1H-pyrazole-3-carboxamide (Intermediate II) (6.7 g, 20.56 mmol) and tert-butyl 4-(4,4,5,5-tetramethyl-1,3,2-dioxaborolan-2-yl)benzoate (6.9 g, 22.62 mmol) were taken up in THF (60 mL) and water (20 mL). To the mixture was added potassium phosphate (13.0 g, 61.69 mmol). The reaction was then purged with nitrogen for 15 minutes followed by the addition of First generation Xphos Precatalyst (0.91 g, 1.23 mmol). The resulting mixture was heated for 16 h at 100° C. Then the reaction mixture was diluted with water (200 mL) and ethyl acetate (200 mL), then filtered through celite. The organic layer was separated and the aqueous layer was extracted with ethyl acetate (3×100 mL). The combined organic extracts were dried over sodium sulfate and concentrated in vacuo. The crude material was purified by column chromatography to afford tert-butyl 4'-(4-(3-carbamoyl-5-methyl-1H-pyrazol-1-yl)benzyl)-[1,1'-biphenyl]-4-carboxylate (6.5 g, 68%). $^{1}$H NMR (400 MHz, DMSO-D6) δ 7.96-7.68 (d, J=8.4 Hz, 2H), 7.80-7.78 (d, J=8.4 Hz, 2H), 7.70-7.68 (d, J=8.0 Hz, 2H), 7.52-7.41 (m, 7H), 7.25 (s, 1H), 6.62 (s, 1H), 4.10 (s, 2H), 2.31 (s, 3H), 1.57 (s, 9H).

Step 2: Preparation of 4'-(4-(3-carbamoyl-5-methyl-1H-pyrazol-1-yl)benzyl)-[1,1'-biphenyl]-4-carboxylic acid tert-Butyl 4'-(4-(3-carbamoyl-5-methyl-1H-pyrazol-1-yl)benzyl)-[1,1'-biphenyl]-4-carboxylate (6.5 g, 13.9 mmol) was taken up in dichloromethane (58.5 mL). The resulting mixture was cooled to 00° C. followed by the dropwise addition of 4M HCl in 1,4-dioxane (19.5 mL). The reaction mixture was allowed to warm to RT and stirred for 16 h. Then the mixture was concentrated in vacuo and triturated in diethyl ether to afford 4'-(4-(3-carbamoyl-5-methyl-1H-pyrazol-1-yl)benzyl)-[1,1'-biphenyl]-4-carboxylic acid (5.6 g, 98%). LCMS Rt=0.96 min (condition B), MS (M+1)= 412.2. $^1$H NMR (400 MHz, DMSO-d$_6$) δ 12.91 (s, 1H), 8.00 (d, J=8.4 Hz, 2H), 7.78 (d, J=8.5 Hz, 2H), 7.69 (d, J=8.2 Hz, 2H), 7.53-7.47 (m, 3H), 7.43 (dd, J=13.1, 8.4 Hz, 4H), 7.23 (s, 1H), 6.60 (s, 1H), 4.09 (s, 2H), 2.30 (s, 3H).

Preparation 11

Intermediate XI: 4'-(4-(3-carbamoyl-5-methyl-1H-1,2,4-triazol-1-yl)benzyl)-[1,1'-biphenyl]-4-carboxylic acid

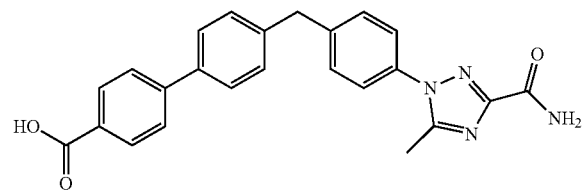 [SMILES: Cc1nc(C(N)=O)nn1-c1ccc(Cc2ccc(-c3ccc(C(=O)O)cc3)cc2)cc1]

Step 1: Preparation of tert-butyl 4'-(4-(3-carbamoyl-5-methyl-1H-1,2,4-triazol-1-yl)benzyl)-[1,1'-biphenyl]-4-carboxylate To the stirred solution of Intermediate IX (0.3 g, 0.92 mmol) in THF:Water (5:1) was added tert-butyl 4-(4,4,5,5-tetramethyl-1,3,2-dioxaborolan-2-yl)benzoate (0.31 g, 0.10 mmol) and K$_3$PO$_4$ (0.59 g, 0.27 mmol), then the reaction was degassed with nitrogen for 5 min. First generation Xphos Precatalyst (0.39 g, 0.83 mmol) was then added and again degassed with nitrogen for 5 min. The reaction vessel was then sealed and heated at 120° C. for 1 h. Progress of reaction was monitored by LCMS and TLC. After the completion, the reaction was diluted with EtOAc (20 mL) and washed with water (3×5 mL) and brine solution (3×5 mL). The organic layers were dried over sodium sulfate, filtered and concentrated. The crude material was purified by FCC to afford tert-butyl 4'-(4-(3-carbamoyl-5-methyl-1H-1,2,4-triazol-1-yl)benzyl)-[1,1'-biphenyl]-4-carboxylate (0.25 g, 52%).

Step 2: Preparation of 4'-(4-(3-carbamoyl-5-methyl-1H-1,2,4-triazol-1-yl)benzyl)-[1,1'-biphenyl]-4-carboxylic acid To the stirred solution of tert-butyl 4'-(4-(3-carbamoyl-5-methyl-1H-1,2,4-triazol-1-yl)benzyl)-[1,1'-biphenyl]-4-carboxylate (0.23 g, 0.36 mmol) in dry DCM (4 mL) was added 4M HCl in 1,4-dioxane (0.01 mL) at 00° C. Then reaction was allowed to stir for 2 h at RT. The progress of reaction was monitored by LCMS and TLC. At completion the reaction was concentrated and triturated with Et$_2$O to afford 4'-(4-(3-carbamoyl-5-methyl-1H-1,2,4-triazol-1-yl)benzyl)-[1,1'-biphenyl]-4-carboxylic acid (0.17 g, 98%). LC-MS Rt=0.88 min (condition B), MS (M+1)=413.3. $^1$H NMR (400 MHz, DMSO-d6) δ 8.00 (d, J=8.3 Hz, 2H), 7.84 (s, 1H), 7.78 (d, J=8.3 Hz, 2H), 7.70 (d, J=8.1 Hz, 2H), 7.57 (d, J=8.4 Hz, 3H), 7.49 (d, J=8.4 Hz, 2H), 7.42 (d, J=8.1 Hz, 2H), 4.11 (s, 2H), 2.47 (s, 3H).

Preparation 12

Intermediate XII: 1-(4-(4-bromobenzyl)phenyl)-5-methyl-1H-1,2,4-triazole-3-carboxamide

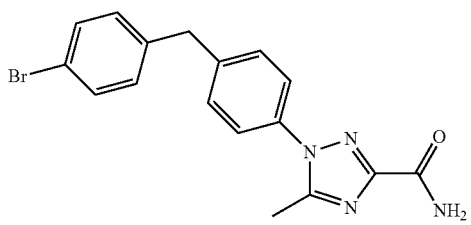 [SMILES: Cc1nc(C(N)=O)nn1-c1ccc(Cc2ccc(Br)cc2)cc1]

To the stirred solution of 1-(4-bromophenyl)-5-methyl-1H-1,2,4-triazole-3-carboxamide (8 g, 28.5 mmol), as prepared in the synthesis of Intermediate VII, and 4-bromobenzylzinc bromide (0.5 M in THF) (142 mL, 71.1 mmol) in dry THF (100 mL) was added triphenylphosphine (0.746 g, 2.85 mmol). The reaction mixture was stirred at RT for 30 min, then Pd(OAc)$_2$ (0.319 g, 1.423 mmol) was added and the reaction was heated at 60° C. overnight. After completion, the solvent was removed under reduced pressure and the resulting crude product was diluted with EtOAc. The solid was filtered off, and the organic solution was washed with water, separated and concentrated in vacuo. The resulting materials were diluted with DCM to precipitate the solid from solution. After the solid was filtered, the organic layers were concentrated in vacuo. The resulting crude product was purified by column chromatography (gradient 2%-10% MeOH in DCM) to afford 1-(4-(4-bromobenzyl)phenyl)-5-methyl-1H-1,2,4-triazole-3-carboxamide (6.4 g, 61%): LCMS Rt=0.97 min (condition B), MS (M+1)=371.2.

Preparation of Compounds

Example 1

1-(4-(2-(4-chlorophenyl)propan-2-yl)phenyl)-5-methyl-1H-1,2,4-triazole-3-carboxamide

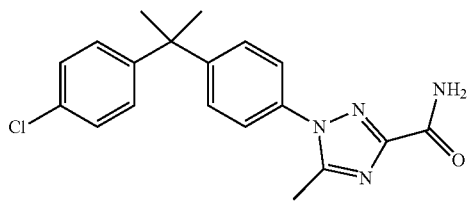 [SMILES: Cc1nc(C(N)=O)nn1-c1ccc(C(C)(C)c2ccc(Cl)cc2)cc1]

To 4-(2-(4-chlorophenyl)propan-2-yl)aniline (Intermediate IV) (1.1 g, 4.03 mmol) in MeOH (15 mL) and water (8 mL) was added 12N HCl (aqueous) (1.18 mL, 14.1 mmol). The mixture was cooled to 0° C. and sodium nitrite (278 mg, 4.03 mmol) was added portionwise. The resulting mixture was stirred for 0.5 h at 0° C. Diethyl 2-acetamidomalonate (0.8 g, 4.23 mmol) was added followed by sodium acetate (991 mg, 12.08 mmol). The resulting mixture was stirred for 1 h at 00° C., then diluted with water and extracted with EtOAc (3×). The organic extracts were then washed with water and brine, dried over anhydrous sodium sulfate, and concentrated in vacuo. To this product was added 7N NH$_3$ in MeOH (0.09 mL, 4.03 mmol). The solution was stirred at ambient temperature for 1 h then concentrated in vacuo. The crude material was purified by column chromatography (gradient 0-100% EtOAc in heptane) to afford 1-(4-(2-(4-chlorophenyl)propan-2-yl)phenyl)-5-methyl-1H-1,2,4-triazole-3-carboxamide (373 mg, 30%): LCMS Rt=1.39 min (condition D), MS (M+1)=355.1. $^1$H NMR (400 MHz, Chloroform-d) δ 7.47-7.33 (m, 4H), 7.32-7.25 (m, 3H), 7.24-7.11 (m, 2H), 6.96 (s, 1H), 2.58 (s, 3H), 1.73 (s, 6H). Ethyl 1-(4-(2-(4-chlorophenyl)propan-2-yl)phenyl)-5-methyl-1H-1,2,4-triazole-3-carboxylate (484 mg, 36%) was obtained as a side product.

Example 2

1-(4-((6H-benzo[c]chromen-3-yl)methyl)phenyl)-5-methyl-1H-pyrazole-3-carboxamide

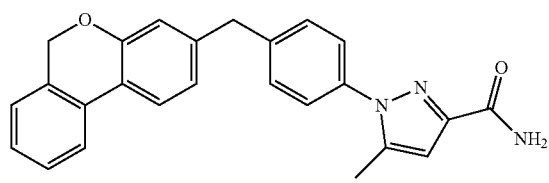 [SMILES: Cc1cc(C(N)=O)nn1-c1ccc(Cc2ccc3c(c2)OCc2ccccc2-3)cc1]

Step 1: Preparation of methyl 3-((2-bromobenzyl)oxy)benzoate

1-Bromo-2-(bromomethyl)benzene (1.0 g, 4.00 mmol), methyl 3-hydroxybenzoate (1.2 g, 8.00 mmol), $K_2CO_3$ (1.7 g, 12.00 mmol), and NaI (0.06 g, 0.40 mmol) were combined in acetone (13.3 mL) and stirred at 50° C. for 18 h. The mixture was cooled to ambient temperature, diluted with water and extracted with EtOAc (2×). The organic layer was washed with brine, dried over anhydrous sodium sulfate and concentrated in vacuo to afford (1.25 g, 78%) of methyl 3-((2-bromobenzyl)oxy)benzoate: 1H NMR (400 MHz, Chloroform-d) δ 7.63-7.56 (m, 2H), 7.56-7.44 (m, 2H), 7.33-7.21 (m, 2H), 7.18-7.08 (m, 2H), 5.09 (s, 2H), 3.85 (s, 3H), 3.83 (s, 1H).

Step 2: Preparation of methyl 6H-benzo[c]chromene-3-carboxylate

Methyl 3-((2-bromobenzyl)oxy)benzoate (1.25 g, 3.89 mmol), $K_2CO_3$ (1.1 g, 7.78 mmol) and $PCy_3$-$HBF_4$ (0.143 g, 0.389 mmol) were combined in DMA (19.4 mL) and the mixture was degassed with $N_2$. Pd(OAc)$_2$ (0.044 g, 0.195 mmol) was added and the mixture was heated at 130° C. for 24 h. The reaction was then cooled to ambient temperature and concentrated in vacuo. The crude material was diluted with DCM and filtered through celite. The filtrate was purified by column chromatography (gradient 0-50% EtOAc in heptane) to afford methyl 6H-benzo[c]chromene-3-carboxylate (378 mg, 40%): LCMS Rt=1.53 min (condition B), MS (M+1)=241.1

Step 3: Preparation of (6H-benzo[c]chromen-3-yl)methanol

To methyl 6H-benzo[c]chromene-3-carboxylate (378 mg, 1.57 mmol) in THF (7.2 mL) was added NaBH$_4$ (357 mg, 9.44 mmol). The mixture was heated to 65° C. and MeOH (0.72 mL) was added dropwise. The resulting reaction mixture was stirred at 65° C. for 4 h. The reaction was then diluted with saturated aqueous NH$_4$Cl and extracted with EtOAc. The organic layer was dried over anhydrous sodium sulfate and concentrated in vacuo to afford crude (6H-benzo[c]chromen-3-yl)methanol (334 mg): 1H NMR (400 MHz, DMSO-d6) δ 7.86-7.76 (m, 2H), 7.43-7.36 (m, 1H), 7.35-7.24 (m, 2H), 7.06-6.98 (m, 1H), 6.96-6.89 (m, 1H), 5.11 (s, 2H), 4.49 (s, 2H).

Step 4: Preparation of 3-(bromomethyl)-6H-benzo[c]chromene

To (6H-benzo[c]chromen-3-yl)methanol (334 mg, 1.57 mmol) in DCM (5.8 mL) was added 33% HBr in AcOH (0.43 mL, 2.36 mmol). The mixture was stirred at ambient temperature for 3 h then quenched with water. The mixture was then extracted with DCM and the organic layer was dried over anhydrous sodium sulfate and concentrated in vacuo. The crude material was purified by column chromatography (gradient 0-30% EtOAc in heptane) to afford 3-(bromomethyl)-6H-benzo[c]chromene (190 mg, 42%): $^1$H NMR (400 MHz, DMSO-d6) δ 7.91-7.79 (m, 2H), 7.41 (td, J=7.6, 1.4 Hz, 1H), 7.34 (td, J=7.4, 1.2 Hz, 1H), 7.31-7.25 (m, 1H), 7.15 (dd, J=8.0, 1.8 Hz, 1H), 7.07 (d, J=1.7 Hz, 1H), 5.14 (s, 2H), 4.70 (s, 2H).

Step 5: Preparation of ethyl 1-(4-((6H-benzo[c]chromen-3-yl)methyl)phenyl)-5-methyl-1H-pyrazole-3-carboxylate Flask 1: To a suspension of Zinc powder (47 mg, 0.725 mmol) in anhydrous THF (0.5 mL) at 60° C. was added 1,2-dibromoethane (0.001 mL, 0.014 mmol) and trimethylsilylchloride (0.009 mL, 0.069 mmol). The resulting mixture was heated for 0.5 h, then 3-(bromomethyl)-6H-benzo[c]chromene (190 mg, 0.691 mmol) in dry THF (0.5 mL) was added dropwise. The mixture was stirred at 60° C. for 1 h and cooled to ambient temperature.

Flask 2: To (Intermediate I) (190 mg, 0.615 mmol) in THF (3.1 mL) was added tris(dibenzylideneacetone)dipalladium (0) (56 mg, 0.061 mmol) and triphenylphosphine (32 mg, 0.123 mmol) and the mixture was heated to 60° C. Then the contents of flask 1 were added dropwise and the resulting suspension was heated at 60° C. for 3 days. The reaction mixture was cooled to ambient temperature and then filtered through celite, washing with DCM and MeOH. The filtrate was concentrated in vacuo and redissolved in DCM. The mixture was then washed with water and brine, dried over anhydrous sodium sulfate and concentrated in vacuo to afford crude ethyl 1-(4-((6H-benzo[c]chromen-3-yl)methyl)phenyl)-5-methyl-1H-pyrazole-3-carboxylate (261 mg): LCMS Rt=1.77 min (condition B), MS (M+1)=425.3.

Step 6: Preparation of 1-(4-((6H-benzo[c]chromen-3-yl)methyl)phenyl)-5-methyl-1H-pyrazole-3-carboxylic acid To ethyl 1-(4-((6H-benzo[c]chromen-3-yl)methyl)phenyl)-5-methyl-1H-pyrazole-3-carboxylate (293 mg, 0.690 mmol) in THF (3.4 mL) was added 1M LiOH (aqueous) (2.8 mL, 2.76 mmol) and MeOH (0.86 mL). The resulting mixture was stirred at ambient temperature 1 h, acidified with 1N HCl (aq) and extracted with EtOAc (2×). The combined organic extracts were dried over anhydrous sodium sulfate and concentrated in vacuo to afford crude 1-(4-((6H-benzo[c]chromen-3-yl)methyl)phenyl)-5-methyl-1H-pyrazole-3-carboxylic acid (275 mg): LCMS Rt=1.56 min (condition B), MS (M+1)=397.3.

Step 7: Preparation of 1-(4-((6H-benzo[c]chromen-3-yl)methyl)phenyl)-5-methyl-1H-pyrazole-3-carboxamide To 1-(4-((6H-benzo[c]chromen-3-yl)methyl)phenyl)-5-methyl-1H-pyrazole-3-carboxylic acid (275 mg, 0.694 mmol) in DMF (2.3 mL) was added DIPEA (0.36 mL, 2.08 mmol) and HATU (290 mg, 0.763 mmol). NH$_4$Cl (74 mg, 1.39 mmol) was added and the resulting mixture was stirred at ambient temperature for 1 h. The reaction mixture was purified by preparative HPLC. The isolated product fractions were dried under lyophilization, taken up in MeOH:DCM (1:1) and loaded onto a 500 mg PL-carbonate cartridge. The product was eluted with 10 mL MeOH:DCM (1:1) and the product fractions were concentrated to afford the free base 1-(4-((6H-benzo[c]chromen-3-yl)methyl)phenyl)-5-methyl-1H-pyrazole-3-carboxamide (12.8 mg, 4.4%): LCMS Rt=2.61 min (condition A), MS (M+1)=396.2. $^1$H NMR (400 MHz, DMSO-d6) δ 7.79 (t, J=8.0 Hz, 2H), 7.52-7.21 (m, 9H), 6.99 (dd, J=7.9, 1.5 Hz, 1H), 6.88 (d, J=1.5 Hz, 1H), 6.60 (s, 1H), 5.11 (s, 2H), 4.02 (s, 2H), 2.30 (s, 3H).

Example 3-1

5-methyl-1-(4-((4'-(pyrrolidin-1-ylmethyl)-[1,1'-biphenyl]-4-yl)methyl)phenyl)-1H-pyrazole-3-carboxamide

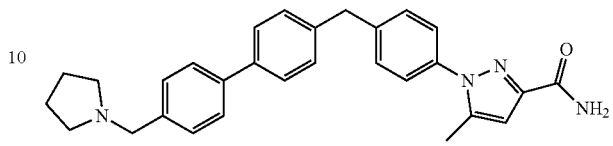

A microwave vial was charged with 1-(4-(4-chlorobenzyl)phenyl)-5-methyl-1H-pyrazole-3-carboxamide (Intermediate II) (250 mg, 0.767 mmol), 1-(4-(4,4,5,5-tetramethyl-1,3,2-dioxaborolan-2-yl)benzyl)pyrrolidine (331 mg, 1.151 mmol), K$_3$PO$_4$ (489 mg, 2.302 mmol), water (1.2 mL) and THF (6.4 mL), and the vial was evacuated and filled with N$_2$ (3×). Then First generation Xphos Precatalyst (56.7 mg, 0.077 mmol) was added, and the mixture was heated in a microwave at 120° C. for 40 min, cooled to RT, filtered through a 0.45 micron syringe filter and concentrated in vacuo. The crude product was taken up in 90:10 DMSO:Water and purified by preparative HPLC to provide 5-methyl-1-(4-((4'-(pyrrolidin-1-ylmethyl)-[1,1'-biphenyl]-4-yl)methyl)phenyl)-1H-pyrazole-3-carboxamide (102 mg, 28%): LCMS Rt=1.56 min (condition A), MS (M+1)=451.2. $^1$H NMR (400 MHz, DMSO-d6) δ 7.64-7.53 (m, 4H), 7.53-7.41 (m, 5H), 7.41-7.31 (m, 4H), 7.23 (s, 1H), 6.60 (d, J=0.7 Hz, 1H), 4.07 (s, 2H), 3.60 (s, 2H), 2.49-2.38 (m, 4H), 2.34-2.27 (s, 3H), 1.81-1.59 (m, 4H).

Examples 3-2 to 3-15

The following compounds were prepared using a similar procedure as in Example 3-1:

| Example | Compound | LCMS M + 1, Rt, conditions | $^1$H NMR, 400 MHz |
|---|---|---|---|
| 3-2 | 1-(4-((4'-((diethylamino)methyl)-[1,1'-biphenyl]-4-yl)methyl)phenyl)-5-methyl-1H-pyrazole-3-carboxamide | 453.3 1.59 min A | (DMSO-d6) δ 7.64-7.54 (m, 4H), 7.54-7.41 (m, 5H), 7.41-7.31 (m, 4H), 7.23 (s, 1H), 6.61 (d, J = 0.7 Hz, 1H), 4.07 (s, 2H), 3.54 (s, 2H), 2.46 (t, J = 7.1 Hz, 4H), 2.33-2.28 (m, 3H), 0.98 (t, J = 7.1 Hz, 6H). |
| 3-3 | 5-methyl-1-(4-(4-(2-methyl-1,2,3,4-tetrahydroisoquinolin-6-yl)benzyl)phenyl)-1H-pyrazole-3-carboxamide | 437.0 0.78 min A | (DMSO-d6) δ 7.62-7.53 (m, 2H), 7.52-7.31 (m, 9H), 7.23 (s, 1H), 7.11 (d, J = 8.6 Hz, 1H), 6.60 (d, J = 0.7 Hz, 1H), 4.06 (s, 2H), 3.49 (s, 2H), 2.87 (t, J = 5.8 Hz, 2H), 2.60 (t, J = 5.9 Hz, 2H), 2.34 (s, 3H), 2.32-2.28 (m, 3H). |
| 3-4 | 1-(4-(4-(isoindolin-5-yl)benzyl)phenyl)-5-methyl-1H-pyrazole-3-carboxamide | 409.3 1.52 min A | (DMSO-d6) δ 7.66-7.18 (m, 14H), 6.60 (d, J = 0.7 Hz, 1H), 4.20-4.00 (m, 6H), 2.30 (s, 3H). |

-continued

| Example | Compound | LCMS M + 1, Rt, conditions | ¹H NMR, 400 MHz |
|---|---|---|---|
| 3-5 | 5-methyl-1-(4-(4-(pyridin-4-yl)benzyl)phenyl)-1H-pyrazole-3-carboxamide | 369.1<br>1.30 min<br>A | (DMSO-d6) δ 8.67-8.56 (m, 2H), 7.76 (d, J = 8.2 Hz, 2H), 7.73-7.66 (m, 2H), 7.54-7.39 (m, 7H), 7.23 (s, 1H), 6.60 (s, 1H), 4.10 (s, 2H), 2.30 (s, 3H). |
| 3-6 | 5-methyl-1-(4-((4'-(methylsulfonyl)-[1,1'-biphenyl]-4-yl)methyl)phenyl)-1H-pyrazole-3-carboxamide | 446.2<br>2.14 min<br>A | (DMSO-d6) δ 8.01-7.89 (m, 4H), 7.71 (d, J = 8.3 Hz, 2H), 7.55-7.41 (m, 7H), 7.23 (s, 1H), 6.63-6.57 (m, 1H), 4.10 (s, 2H), 3.25 (s, 3H), 2.30 (s, 3H). |
| 3-7 | 5-methyl-1-(4-((3'-(5-methyl-1,3,4-oxadiazol-2-yl)-[1,1'-biphenyl]-4-yl)methyl)phenyl)-1H-pyrazole-3-carboxamide | 450.3<br>2.34 min<br>A | (DMSO-d6) δ 8.21-8.14 (m, 1H), 8.00-7.92 (m, 1H), 7.92-7.86 (m, 1H), 7.78-7.62 (m, 3H), 7.47 (dt, J = 26.3, 8.5 Hz, 7H), 7.23 (s, 1H), 6.61 (s, 1H), 4.10 (s, 2H), 2.60 (s, 3H), 2.30 (s, 3H). |
| 3-8 | 1-(4-([1,1'-biphenyl]-4-ylmethyl)phenyl)-5-methyl-1H-pyrazole-3-carboxamide | 368.2<br>2.70 min<br>A | (DMSO-d6) δ 7.68-7.58 (m, 4H), 7.55-7.41 (m, 7H), 7.40-7.30 (m, 3H), 7.23 (s, 1H), 6.60 (d, J = 0.7 Hz, 1H), 4.08 (s, 2H), 2.30 (s, 3H). |
| 3-9 | 5-methyl-1-(4-((4'-(5-methyl-1,3,4-oxadiazol-2-yl)-[1,1'-biphenyl]-4-yl)methyl)phenyl)-1H-pyrazole-3-carboxamide | 450.3<br>2.31 min<br>A | (DMSO-d6) δ 8.08-8.00 (m, 2H), 7.92-7.85 (m, 2H), 7.72 (d, J = 8.3 Hz, 2H), 7.55-7.39 (m, 7H), 7.23 (s, 1H), 6.61 (d, J = 0.7 Hz, 1H), 4.10 (s, 2H), 2.60 (s, 3H), 2.32-2.28 (m, 3H). |
| 3-10 | 5-methyl-1-(4-(4-(pyridin-3-yl)benzyl)phenyl)-1H-pyrazole-3-carboxamide | 369.1<br>1.49 min<br>A | (DMSO-d6) δ 8.89-8.85 (m, 1H), 8.55 (dd, J = 4.7, 1.6 Hz, 1H), 8.05 (ddd, J = 8.0, 2.3, 1.7 Hz, 1H), 7.72-7.65 (m, 2H), 7.54-7.37 (m, 8H), 7.23 (s, 1H), 6.60 (d, J = 0.7 Hz, 1H), 4.09 (s, 2H), 2.32-2.27 (m, 3H). |

| Example | Compound | LCMS M + 1, Rt, conditions | ¹H NMR, 400 MHz |
|---|---|---|---|
| 3-11 | 1-(4-(4-(1-(dimethylglycyl)-1,2,3,6-tetrahydropyridin-4-yl)benzyl)phenyl)-5-methyl-1H-pyrazole-3-carboxamide | 458.2 0.72 min B | (Methanol-d4) δ 7.45 (d, J = 8.5 Hz, 2H), 7.40 (d, J = 9.6 Hz, 4H), 7.24 (d, J = 8.3 Hz, 2H), 6.69 (d, J = 0.5 Hz, 1H), 6.11 (d, J = 10.5 Hz, 1H), 4.27 (d, J = 2.9 Hz, 1H), 4.20 (d, J = 2.8 Hz, 1H), 4.07 (s, 2H), 3.80 (dt, J = 8.4, 5.8 Hz, 2H), 3.28 (d, J = 15.0 Hz, 2H), 2.59 (d, J = 30.2 Hz, 2H), 2.40-2.28 (m, 9H). |
| 3-12 | 5-methyl-1-(4-((4'-((4-methylpiperazin-1-yl)methyl)-[1,1'-biphenyl]-4-yl)methyl)phenyl)-1H-pyrazole-3-carboxamide | 480.0 1.47 min A | (DMSO-d6) δ 7.59 (dd, J = 8.1, 5.8 Hz, 4H), 7.53-7.41 (m, 5H), 7.40-7.31 (m, 4H), 7.23 (s, 1H), 6.60 (s, 1H), 4.07 (s, 2H), 3.47 (s, 2H), 2.30 (s, 11H), 2.14 (s, 3H). |
| 3-13 | 5-methyl-1-(4-(4-(2-methylisoindolin-5-yl)benzyl)phenyl)-1H-pyrazole-3-carboxamide | 423.2 1.54 min A | (DMSO-d6) δ 7.63-7.55 (m, 2H), 7.53-7.40 (m, 7H), 7.35 (d, J = 8.3 Hz, 2H), 7.31-7.17 (m, 2H), 6.60 (d, J = 0.8 Hz, 1H), 4.06 (s, 2H), 3.83 (d, J = 8.6 Hz, 4H), 2.49 (s, 3H), 2.30 (d, J = 0.6 Hz, 3H). |
| 3-14 | 5-methyl-1-(4-(4-(1,2,3,4-tetrahydroisoquinolin-6-yl)benzyl)phenyl)-1H-pyrazole-3-carboxamide | 423.1 1.43 min A | (DMSO-d6) δ 7.60-7.54 (m, 2H), 7.54-7.30 (m, 9H), 7.23 (s, 1H), 7.07 (d, J = 7.9 Hz, 1H), 6.60 (d, J = 0.7 Hz, 1H), 4.06 (s, 2H), 3.86 (s, 2H), 2.96 (t, J = 5.9 Hz, 2H), 2.74 (t, J = 5.7 Hz, 2H), 2.31-2.27 (m, 3H). |
| 3-15 | 5-methyl-1-(4-(4-(1-methyl-1,2,3,6-tetrahydropyridin-4-yl)benzyl)phenyl)-1H-pyrazole-3-carboxamide | 387.3 1.33 min A | (DMSO-d6) δ 7.53-7.45 (m, 3H), 7.43 - 7.32 (m, 4H), 7.26-7.18 (m, 3H), 6.62-6.57 (m, 1H), 6.15-6.08 (m, 1H), 4.01 (s, 2H), 3.04-2.95 (m, 2H), 2.54 (t, J = 5.7 Hz, 2H), 2.48-2.41 (m, 2H), 2.31-2.23 (m, 6H). |

Example 4

5-methyl-1-(4-(4-(1-methylpiperidin-4-yl)benzyl)phenyl)-1H-pyrazole-3-carboxamide

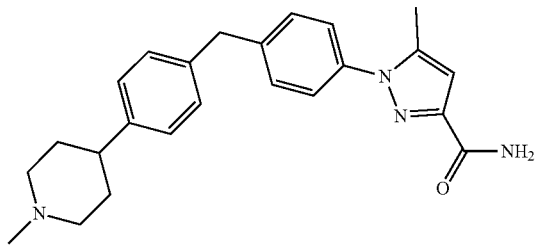 [SMILES: Cc1cc(C(N)=O)nn1-c1ccc(Cc2ccc(C3CCN(C)CC3)cc2)cc1]

To the stirred solution of Example 3-15 (0.09 g, 0.233 mmol) in MeOH (2 mL) was added 10% Pd/C (43 mg, 0.023 mmol). The mixture was stirred under hydrogen atmosphere with 50 psi pressure and room temperature for 4 h. The suspension was filtered through celite, washing with excess methanol. The filtrate was concentrated in vacuo and purified by Prep-HPLC to afford 5-methyl-1-(4-(4-(1-methyl piperidin-4-yl)benzyl)phenyl)-1H-pyrazole-3-carboxamide (0.03 g, 33%), LC-MS Rt=0.68 min (condition B), MS (M+1)=389.2, $^1$H NMR (400 MHz, Methanol-d4) δ 7.42 (dd, J=22.2, 8.3 Hz, 4H), 7.20 (s, 4H), 6.69 (s, 1H), 4.04 (s, 2H), 3.01 (s, 2H), 2.55-2.49 (m, 1H), 2.29 (t, J=32.4 Hz, 8H), 1.83 (s, 4H).

Examples 5-1 and 5-2

Enantiomers of 5-methyl-1-(4-(4-(1-methylpyrrolidin-3-yl)benzyl)phenyl)-1H-pyrazole-3-carboxamide

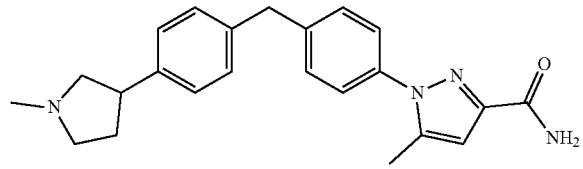 [SMILES: Cc1cc(C(N)=O)nn1-c1ccc(Cc2ccc(C3CCN(C)C3)cc2)cc1]

Step 1. Preparation of tert-butyl 3-(4-(4-(3-carbamoyl-5-methyl-1H-pyrazol-1-yl)benzyl)phenyl)-2,5-dihydro-1H-pyrrole-1-carboxylate Intermediate III (1.2 g, 2.88 mmol) and tert-butyl 3-(((trifluoromethyl)sulfonyl)oxy)-2,5-dihydro-1H-pyrrole-1-carboxylate (1.14 g, 3.6 mmol) were reacted according to General Method II for Suzuki coupling to afford tert-butyl 3-(4-(4-(3-carbamoyl-5-methyl-1H-pyrazol-1-yl)benzyl)phenyl)-2,5-dihydro-1H-pyrrole-1-carboxylate (0.7 g, 63%).

Step 2. Preparation of 1-(4-(4-(2,5-dihydro-1H-pyrrol-3-yl)benzyl)phenyl)-5-methyl-1H-pyrazole-3-carboxamide To a stirred solution of tert-butyl 3-(4-(4-(3-carbamoyl-5-methyl-1H-pyrazol-1-yl)benzyl)phenyl)-2,5-dihydro-1H-pyrrole-1-carboxylate (0.7 g, 1.53 mmol) in dry DCM (5 mL) was added TFA (3 mL) at 00° C. Then reaction was allowed to stir for 1 h at ambient temperature. The reaction mixture was evaporated in vacuo and the crude material was triturated with diethyl ether and filtered to afford crude 1-(4-(4-(2,5-dihydro-1H-pyrrol-3-yl)benzyl)phenyl)-5-methyl-1H-pyrazole-3-carboxamide which was taken on to the next step without further purification (0.45 g).

Step 3. Preparation of 5-methyl-1-(4-(4-(1-methyl-2,5-dihydro-1H-pyrrol-3-yl)benzyl)phenyl)-1H-pyrazole-3-carboxamide To a stirred solution of 1-(4-(4-(2,5-dihydro-1H-pyrrol-3-yl)benzyl)phenyl)-5-methyl-1H-pyrazole-3-carboxamide (0.43 g, 1.20 mmol) in MeOH (10 mL) was added 37% aqueous formaldehyde (72 mg, 2.40 mmol) and Na(OAc)$_3$BH (0.509 g, 2.40 mmol) at ambient temperature. The reaction was allowed to stir at ambient temperature for 3 h and evaporated in vacuo. The crude material was diluted with EtOAc (50 mL), the organic layer was separated, dried over anhydrous sodium sulfate, and evaporated in vacuo. The resulting crude material was purified by silica gel chromatography to obtain 5-methyl-1-(4-(4-(1-methyl-2,5-dihydro-1H-pyrrol-3-yl)benzyl)phenyl)-1H-pyrazole-3-carboxamide (0.40 g, 89%): 1H NMR (400 MHz, DMSO) δ 7.47-7.49 (d, 3H), 7.33-7.39 (m, 4H), 7.19-7.35 (m, 3H), 6.60 (s, 1H), 6.229 (s, 1H), 4.018 (s, 2H), 3.705 (m, 2H), 3.527 (s, 2H), 2.429 (s, 3H), 2.26 (s, 3H).

Step 4. Preparation of 5-methyl-1-(4-(4-(1-methylpyrrolidin-3-yl)benzyl)phenyl)-1H-pyrazole-3-carboxamide To a stirred solution of 5-methyl-1-(4-(4-(1-methyl-2,5-dihydro-1H-pyrrol-3-yl)benzyl)phenyl)-1H-pyrazole-3-carboxamide (0.4 g, 1.08 mmol) in dry MeOH (20 mL) was added 10% Pd/C (200 mg, 0.108 mmol) at ambient temperature. The reaction was allowed to stir for 4 h at ambient temperature under H$_2$ gas at atmospheric pressure. The reaction mixture was filtered through celite, washing with MeOH. The filtrate was concentrated in vacuo and purified by Chiral HPLC to afford the pure enantiomers.

| CHIRAL PREP HPLC METHOD | | | |
|---|---|---|---|
| Mobile Phase | (A) | 0.1% DEA IN HEXANE | |
| | (B) | 0.1% DEA IN IPA:MEOH(50:50) | |
| Column | | CHIRALPAK AD-H (250 × 21) mm, 5μ | |
| Column Flow | 18 | ml/min | |
| Isocratic | | Time (min) | % B |
| | | 0.01 | 22 |
| | | 25.00 | 22 |

Example 5-1: Enantiomer 1

5-methyl-1-(4-(4-(1-methylpyrrolidin-3-yl)benzyl)phenyl)-1H-pyrazole-3-carboxamide (9 mg, 2.3%): Chiral Rt=14.47 min. LC-MS Rt=0.63 min (condition B), MS (M+1)=375.1. 1H NMR (400 MHz, Methanol-d4) δ 7.46-7.34 (m, 4H), 7.29-7.18 (m, 4H), 6.70-6.65 (m, 1H), 4.04 (s, 2H), 3.54-3.46 (m, 1H), 3.42-3.35 (m, 1H), 3.24-3.14 (m, 1H), 3.13-3.01 (m, 1H), 2.94-2.82 (m, 1H), 2.68 (s, 3H), 2.50-2.36 (m, 1H), 2.32 (s, 3H), 2.13-1.98 (m, 1H).

Example 5-2: Enantiomer 2

5-methyl-1-(4-(4-(1-methylpyrrolidin-3-yl)benzyl)phenyl)-1H-pyrazole-3-carboxamide (9 mg, 2.3%): Chiral Rt=15.57 min. LC-MS Rt=0.63 min (condition B), MS (M+1)=375.1. 1H NMR (400 MHz, Methanol-d4) δ 7.47-7.35 (m, 4H), 7.29-7.16 (m, 4H), 6.71-6.67 (m, 1H), 4.04 (s, 2H), 3.54-3.39 (m, 1H), 3.27-3.17 (m, 1H), 3.14-2.98 (m, 1H), 2.96-2.82 (m, 1H), 2.76-2.61 (m, 1H), 2.55 (s, 3H), 2.38 (s, 1H), 2.32 (s, 3H), 2.08-1.92 (m, 1H).

Examples 5-3 to 5-8

The following compounds were prepared using a similar procedure as in Example 5-1

| Example | Compound | LCMS M + 1, Rt, conditions | $^1$H NMR, 400 MHz |
|---|---|---|---|
| 5-3 | 1-(4-(4-(6-((dimethylamino)methyl)pyridin-3-yl)benzyl)phenyl)-5-methyl-1H-pyrazole-3-carboxamide | 426.6 1.34 min A | (DMSO-d6) δ 8.77 (d, J = 1.9 Hz, 1H), 8.03 (dd, J = 8.1, 2.2 Hz, 1H), 7.67 (d, J = 8.1 Hz, 2H), 7.51-7.41 (m, 6H), 7.20 (s, 1H), 6.61 (s, 1H), 4.10 (s, 2H), 3.55 (s, 2H), 2.31 (s, 3H), 2.22 (s, 6H). |
| 5-4 | 1-(4-(4-(2-((dimethylamino)methyl)pyridin-4-yl)benzyl)phenyl)-5-methyl-1H-pyrazole-3-carboxamide | 426.2 0.69 min B | (DMSO-d6) δ 8.52 (d, J = 5.2 Hz, 1H), 7.74 (d, J = 8.1 Hz, 2H), 7.67 (s, 1H), 7.50 (dd, J = 25.8, 17.4 Hz, 6H), 7.24 (s, 1H), 6.61 (s, 1H), 4.11 (s, 2H), 3.57 (s, 2H), 2.30 (s, 3H), 2.21 (s, 6H). |
| 5-5 | 5-methyl-1-(4-(4-(6-(pyrrolidin-1-ylmethyl)pyridin-3-yl)benzyl)phenyl)-1H-pyrazole-3-carboxamide | 452.2 1.46 min A | (Methanol-d4) δ 8.76 (d, J = 2.0 Hz, 1H), 8.06 (dd, J = 8.1, 2.3 Hz, 1H), 7.62 (d, J = 8.2 Hz, 2H), 7.56 (d, J = 8.1 Hz, 1H), 7.46-7.37 (m, 6H), 6.68 (s, 1H), 4.13 (s, 2H), 3.95 (s, 2H), 2.86-2.66 (m, 4H), 2.33 (s, 3H), 1.96-1.83 (m, 4H). |
| 5-6 | 1-(4-(4-(5-((dimethylamino)methyl)pyridin-3-yl)benzyl)phenyl)-5-methyl-1H-pyrazole-3-carboxamide | 426.2 1.22 min A | (DMSO-d6) δ 8.73 (s, 1H), 8.43 (s, 1H), 7.92 (s, 1H), 7.66 (d, J = 7.6 Hz, 2H), 7.43 (dd, J = 19.5, 10.0 Hz, 5H), 7.18 (s, 1H), 6.61 (s, 1H), 4.08 (s, 2H), 3.42 (s, 2H), 2.28 (s, 3H), 2.16 (s, 6H). |
| 5-7 | 5-methyl-1-(4-(4-(1-methyl-2,3,6,7-tetrahydro-1H-azepin-4-yl)benzyl)phenyl)-1H-pyrazole-3-carboxamide | 401.1 1.32 min A | (Methanol-d4) δ 7.42 (dd, J = 21.9, 8.3 Hz, 4H), 7.33 (d, J = 7.9 Hz, 2H), 7.22 (d, J = 8.1 Hz, 2H), 6.69 (s, 1H), 5.99 (d, J = 6.5 Hz, 1H), 4.07 (s, 2H), 3.41 (s, 2H), 3.02 (s, 2H), 2.76 (d, J = 10.7 Hz, 2H), 2.47 (s, 3H), 2.34 (s, 3H), 1.91 (d, J = 7.4 Hz, 2H). |

| Example | Compound | LCMS M + 1, Rt, conditions | ¹H NMR, 400 MHz |
|---|---|---|---|
| 5-8 | (S)-5-methyl-1-(4-((4'-(1-methylpyrrolidin-2-yl)-[1,1'-biphenyl]-4-yl)methyl)phenyl)-1H-pyrazole-3-carboxamide (prepared from commercially available (S)-2-(4-bromophenyl)pyrrolidine) | 451.4 1.60 min A | (DMSO-d6) δ 7.59 (dd, J = 8.3, 6.5 Hz, 4H), 7.53-7.31 (m, 9H), 7.23 (s, 1H), 6.60 (d, J = 0.7 Hz, 1H), 4.07 (s, 2H), 3.20-3.12 (m, 1H), 3.12-3.02 (m, 1H), 2.32- 2.28 (m, 3H), 2.27-2.04 (m, 5H), 1.93-1.69 (m, 2H), 1.68-1.48 (m, 1H). |

Example 6-1

5-methyl-1-(4-(2-(4'-(pyrrolidin-1-ylmethyl)-[1,1'-biphenyl]-4-yl)propan-2-yl)phenyl)-1H-pyrazole-3-carboxamide

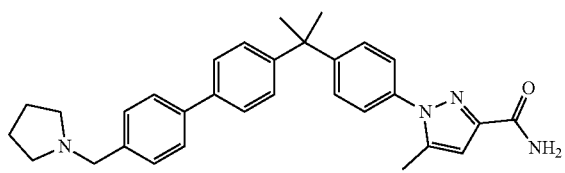 [SMILES: Cc1cc(C(N)=O)nn1-c1ccc(C(C)(C)c2ccc(-c3ccc(CN4CCCC4)cc3)cc2)cc1]

A microwave vial was charged with 1-(4-(2-(4-chlorophenyl)propan-2-yl)phenyl)-5-methyl-1H-pyrazole-3-carboxamide (Intermediate V) (100 mg, 0.283 mmol), 1-(4-(4,4,5,5-tetramethyl-1,3,2-dioxaborolan-2-yl)benzyl)pyrrolidine (89 mg, 0.311 mmol), K₃PO₄ (180 mg, 0.848 mmol), water (0.47 mL) and THF (2.36 mL) and the mixture was evacuated and filled with N₂ (3×). Then First generation Xphos Precatalyst (20.9 mg, 0.028 mmol) was added and the mixture was heated in the microwave at 120° C. for 40 min, cooled to RT, filtered through a 0.45 micron syringe filter and concentrated in vacuo. The crude product was purified by HPLC to afford 5-methyl-1-(4-(2-(4'-(pyrrolidin-1-ylmethyl)-[1,1'-biphenyl]-4-yl)propan-2-yl)phenyl)-1H-pyrazole-3-carboxamide (49.4 mg, 36%): LCMS Rt=1.80 min (condition A), MS (M+1)=479.1. ¹H NMR (400 MHz, DMSO-d6) δ 7.63-7.55 (m, 4H), 7.53-7.47 (m, 3H), 7.46-7.39 (m, 2H), 7.39-7.30 (m, 4H), 7.24 (s, 1H), 6.65-6.57 (m, 1H), 3.59 (s, 2H), 2.48-2.39 (m, 4H), 2.32 (s, 3H), 1.80-1.63 (m, 10H).

Examples 6-2 to 6-6

The following compounds were prepared using a similar procedure as in Example 6-1:

| Example | Compound | LCMS M + 1, Rt, conditions | ¹H NMR, 400 MHz |
|---|---|---|---|
| 6-2 | 5-methyl-1-(4-(2-(3'-(methylsulfonyl)-[1,1'-biphenyl]-4-yl)propan-2-yl)phenyl)-1H-pyrazole-3-carboxamide | 474.2 2.43 min A | (DMSO-d6) δ 8.13 (t, J = 1.7 Hz, 1H), 8.06-7.98 (m, 1H), 7.94-7.84 (m, 1H), 7.79-7.66 (m, 3H), 7.55-7.46 (m, 3H), 7.46-7.37 (m, 4H), 7.23 (s, 1H), 6.61 (d, J = 0.7 Hz, 1H), 3.29 (s, 3H), 2.32 (d, J = 0.6 Hz, 3H), 1.74 (s, 6H). |
| 6-3 | 5-methyl-1-(4-(2-(4-(pyridin-4-yl)phenyl)propan-2-yl)phenyl)-1H-pyrazole-3-carboxamide | 397.4 1.54 min A | (DMSO-d6) δ 8.68-8.57 (m, 2H), 7.75 (d, J = 8.4 Hz, 2H), 7.72-7.66 (m, 2H), 7.55-7.46 (m, 3H), 7 46-7.35 (m, 4H), 7.23 (s, 1H), 6.61 (s, 1H), 2.32 (s, 3H), 1.74 (s, 6H). |

| Example | Compound | LCMS M + 1, Rt, conditions | ¹H NMR, 400 MHz |
|---|---|---|---|
| 6-4 | 1-(4-(2-(4-(1H-indazol-5-yl)phenyl)propan-2-yl)phenyl)-5-methyl-1H-pyrazole-3-carboxamide | 436.3 2.42 min A | (DMSO-d6) δ 13.10 (s, 1H), 8.15-8.06 (m, 1H), 8.04-7.94 (m, 1H), 7.69-7.58 (m, 4H), 7.55-7.39 (m, 5H), 7.39-7.31 (m, 2H), 7.24 (s, 1H), 6.61 (d, J = 0.9 Hz, 1H), 2.32 (s, 3H), 1.74 (s, 6H). |
| 6-5 | 1-(4-(2-(4-(2-aminopyridin-4-yl)phenyl)propan-2-yl)phenyl)-5-methyl-1H-pyrazole-3-carboxamide | 412.3 1.49 min A | (DMSO-d6) δ 7.95 (d, J = 5.3 Hz, 1H), 7.58 (d, J = 8.4 Hz, 2H), 7.53-7.45 (m, 3H), 7.45-7.31 (m, 4H), 7.23 (s, 1H), 6.76 (dd, J = 5.4, 1.6 Hz, 1H), 6.70-6.65 (m, 1H), 6.63-6.57 (m, 1H), 5.94 (s, 2H), 2.32 (s, 3H), 1.73 (s, 6H). |
| 6-6 | 5-methyl-1-(4-(2-(4'-(5-methyl-1,3,4-oxadiazol-2-yl)-[1,1'-biphenyl]-4-yl)propan-2-yl)phenyl)-1H-pyrazole-3-carboxamide | 478.3 2.57 min A | (DMSO-d6) δ 8.04 (d, J = 8.4 Hz, 2H), 7.89 (d, J = 8.4 Hz, 2H), 7.72 (d, J = 8.4 Hz, 2H), 7.55-7.35 (m, 7H), 7.23 (s, 1H), 6.61 (s, 1H), 2.60 (s, 3H), 2.32 (s, 3H), 1.74 (s, 6H). |

Example 7

5-methyl-1-(4-(2-(4'-(pyrrolidin-1-ylmethyl)-[1,1'-biphenyl]-4-yl)propan-2-yl)phenyl)-1H-pyrazole-3-carboxamide

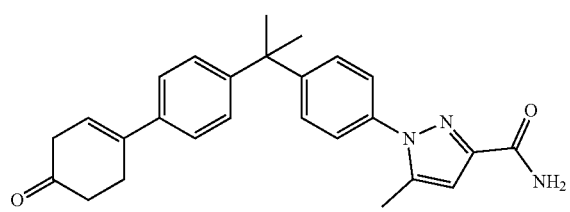 [SMILES: Cc1cc(C(N)=O)nn1-c1ccc(C(C)(C)c2ccc(C3=CCC(=O)CC3)cc2)cc1]

Step 1: Preparation of 1-(4-(2-(4-(1,4-dioxaspiro[4.5]dec-7-en-8-yl)phenyl)propan-2-yl)phenyl)-5-methyl-1H-pyrazole-3-carboxamide Intermediate V (0.5 g, 1.41 mmol) and 4,4,5,5-tetramethyl-2-(1,4-dioxaspiro[4.5]dec-7-en-8-yl)-1,3,2-dioxaborolane (0.38 g, 1.41 mmol) were reacted according to General Method I for Suzuki coupling to afford crude 1-(4-(2-(4-(1,4-dioxaspiro[4.5]dec-7-en-8-yl)phenyl)propan-2-yl)phenyl)-5-methyl-1H-pyrazole-3-carboxamide (0.65 g): LCMS Rt=1.26 min (condition B), MS (M+1)= 458.3.

Step 2: Preparation of 5-methyl-1-(4-(2-(4'-oxo-2',3',4',5'-tetrahydro-[1,1'-biphenyl]-4-yl)propan-2-yl)phenyl)-1H-pyrazole-3-carboxamide To 1-(4-(2-(4-(1,4-dioxaspiro[4.5]dec-7-en-8-yl)phenyl)propan-2-yl)phenyl)-5-methyl-1H-pyrazole-3-carboxamide (0.65 g, 1.41 mmol) in DCM (2.8 mL) was added TFA (2.2 mL, 28.3 mmol) followed by water (0.1 mL, 5.66 mmol). The resulting solution was stirred at ambient temperature for 1 h and concentrated in vacuo. The crude material was purified by silica gel chromatography in EtOAc:Heptanes (0-100%) to afford 5-methyl-1-(4-(2-(4'-oxo-2',3',4',5'-tetrahydro-[1,1'-biphenyl]-4-yl)propan-2-yl)phenyl)-1H-pyrazole-3-carboxamide (0.42 g, 71%): LC-MS Rt=2.47 min (condition A), MS (M+1)=414.2. ¹H NMR (400 MHz, DMSO-d6) δ 7.51-7.44 (m, 3H), 7.44-7.34 (m, 4H), 7.29-7.18 (m, 3H), 6.60 (d, J=0.7 Hz, 1H), 6.20-6.08 (m, 1H), 3.04-2.98 (m, 2H), 2.87-2.78 (m, 2H), 2.54 (t, J=6.9 Hz, 2H), 2.33-2.29 (m, 3H), 1.69 (s, 6H).

Example 8

5-methyl-1-(4-(2-(4'-morpholino-2',3',4',5'-tetrahydro-[1,1'-biphenyl]-4-yl)propan-2-yl)phenyl)-1H-pyrazole-3-carboxamide

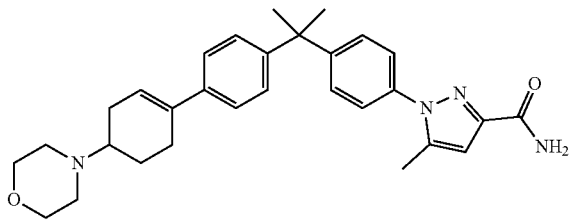 [SMILES: Cc1cc(C(N)=O)nn1-c1ccc(C(C)(C)c2ccc(C3=CCC(N4CCOCC4)CC3)cc2)cc1]

To 5-methyl-1-(4-(2-(4'-oxo-2',3',4',5'-tetrahydro-[1,1'-biphenyl]-4-yl)propan-2-yl)phenyl)-1H-pyrazole-3-carboxamide (100 mg, 0.242 mmol) in DCM (1.2 mL) was added morpholine (32 mg, 0.363 mmol), sodium cyanoborohydride (45 mg, 0.725 mmol) and acetic acid (15 mg, 0.242 mmol). The resulting mixture was stirred at ambient temperature for 1 h, then quenched with excess saturated NH$_4$Cl (aq). The suspension was then extracted with DCM and the organic layer was washed with water and brine, dried over anhydrous sodium sulfate and concentrated in vacuo. The crude material was purified by preparative HPLC to afford 5-methyl-1-(4-(2-(4'-morpholino-2',3',4',5'-tetrahydro-[1,1'-biphenyl]-4-yl)propan-2-yl)phenyl)-1H-pyrazole-3-carboxamide (8.7 mg, 7.4%): LC-MS Rt=1.73 min (condition A), MS (M+1)=485.4. $^1$H NMR (400 MHz, DMSO-d6) δ 7.47 (d, J=8.6 Hz, 3H), 7.40-7.30 (m, 4H), 7.29-7.16 (m, 3H), 6.60 (s, 1H), 6.13-6.03 (m, 1H), 3.58 (t, J=4.6 Hz, 4H), 2.61-2.27 (m, 11H), 2.19-1.99 (m, 2H), 1.68 (s, 6H), 1.52-1.37 (m, 1H).

Example 9

1-(4-(2-(4'-hydroxy-2',3',4',5'-tetrahydro-[1,1'-biphenyl]-4-yl)propan-2-yl)phenyl)-5-methyl-1H-pyrazole-3-carboxamide

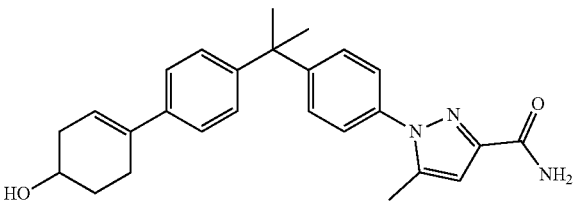 [SMILES: Cc1cc(C(N)=O)nn1-c1ccc(C(C)(C)c2ccc(C3=CCC(O)CC3)cc2)cc1]

To 5-methyl-1-(4-(2-(4'-oxo-2',3',4',5'-tetrahydro-[1,1'-biphenyl]-4-yl)propan-2-yl)phenyl)-1H-pyrazole-3-carboxamide (50 mg, 0.121 mmol) in MeOH (1.2 mL) was added NaBH$_4$ (9.2 mg, 0.242 mmol). The resulting mixture was stirred at ambient temperature for 10 min., diluted with MeOH and purified by HPLC to afford 1-(4-(2-(4'-hydroxy-2',3',4',5'-tetrahydro-[1,1'-biphenyl]-4-yl)propan-2-yl)phenyl)-5-methyl-1H-pyrazole-3-carboxamide (19.2 mg, 37%): LCMS Rt=2.31 min (condition A), MS (M+1)=416.3. $^1$H NMR (400 MHz, DMSO-d6) δ 7.52-7.43 (m, 3H), 7.40-7.29 (m, 4H), 7.27-7.16 (m, 3H), 6.63-6.57 (m, 1H), 6.03-5.96 (m, 1H), 4.65 (d, J=3.9 Hz, 1H), 3.85-3.70 (m, 1H), 2.48-2.35 (m, 3H), 2.30 (s, 3H), 2.10-1.98 (m, 1H), 1.95-1.81 (m, 1H), 1.68 (s, 6H), 1.63-1.51 (m, 1H).

Example 10

5-methyl-1-(4-(2-(4-(pyridin-2-yl)phenyl)propan-2-yl)phenyl)-1H-pyrazole-3-carboxamide

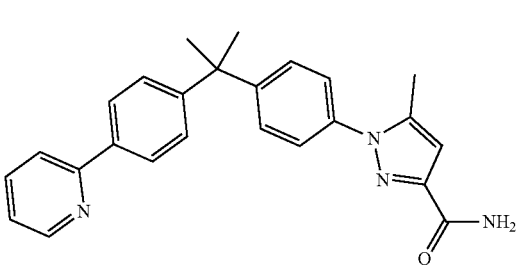 [SMILES: Cc1cc(C(N)=O)nn1-c1ccc(C(C)(C)c2ccc(-c3ccccn3)cc2)cc1]

A mixture of Xphos (13.2 mg, 0.028 mmol) and Pd$_2$(dba)$_3$ (12.9 mg, 0.014 mmol) in THF (0.94 mL) was degassed with nitrogen, then heated to 65° C. for 10 min. Intermediate V (100 mg, 0.283 mmol) was added and stirred another 15 min., then 0.5M pyridin-2-ylzinc(II) bromide in THF (0.85 mL, 0.424 mmol) was added dropwise, and the resulting mixture was stirred at 65° C. for 48 h. The reaction was cooled to ambient temperature, diluted with excess MeOH, filtered through celite and the filtrate was concentrated. The crude material was purified by preparative HPLC to afford 5-methyl-1-(4-(2-(4-(pyridin-2-yl)phenyl)propan-2-yl)phenyl)-1H-pyrazole-3-carboxamide (23 mg, 20%): LCMS Rt=1.92 min (condition A), MS (M+1)=397.4. $^1$H NMR (400 MHz, DMSO-d6) δ 8.64 (s, 1H), 8.02 (d, J=7.9 Hz, 2H), 7.90 (dd, J=21.3, 7.7 Hz, 2H), 7.54-7.27 (m, 8H), 7.22 (s, 1H), 6.60 (s, 1H), 2.31 (s, 3H), 1.74 (s, 6H).

Example 11

1-(4-(2-(4'-(3-(aminomethyl)oxetan-3-yl)-[1,1'-biphenyl]-4-yl)propan-2-yl)phenyl)-5-methyl-1H-pyrazole-3-carboxamide

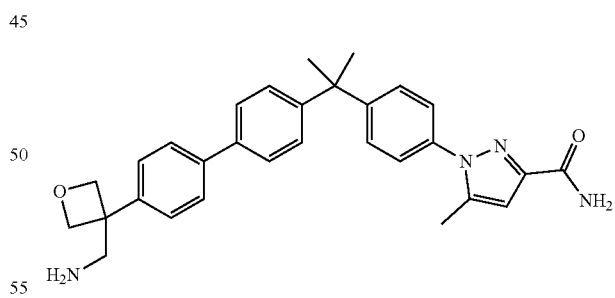

Step 1: Preparation of ethyl 2-(3-(4-bromophenyl)oxetan-3-yl)acetate

To ethyl 2-(oxetan-3-ylidene)acetate (0.6 g, 4.22 mmol) and [Rh(COD)Cl]$_2$ (0.104 g, 0.211 mmol) in 1,4-dioxane (20 mL) was added 1M KOH (aqueous) (2.11 mL, 5.49 mmol). Then a suspension of (4-bromophenyl)boronic acid (1.70 g, 8.44 mmol) was added portionwise and the resulting mixture was stirred at ambient temperature for 48 h. The reaction was then diluted with brine and extracted with EtOAc (2×). The combined organic extracts were dried over anhydrous sodium sulfate and concentrated in vacuo. The crude material was purified by column chromatography (gradient 0-40% EtOAc in heptane) to afford ethyl 2-(3-(4-bromophenyl)oxetan-3-yl)acetate (474 mg, 38%): LCMS Rt=1.07 min (condition B), MS (M+3)=300.9.

Step 2: Preparation of 2-(3-(4-bromophenyl)oxetan-3-yl)acetic acid

To ethyl 2-(3-(4-bromophenyl)oxetan-3-yl)acetate (0.45 g, 1.59 mmol) in MeOH (60 mL) at 00° C. was added 1M NaOH (aq) (1.63 mL, 3.25 mmol). The resulting mixture was stirred at ambient temperature for 18 h. The mixture was acidified to pH=1-2 with 1M HCl (aq), diluted with excess water and extracted with EtOAc (3×). The combined organic extracted were dried over anhydrous sodium sulfate and concentrated to afford 2-(3-(4-bromophenyl)oxetan-3-yl) acetic acid (339 mg, 79%): LC-MS Rt=1.09 min (condition B), MS (M+3)=273.1. $^1$H NMR (400 MHz, DMSO-d6) δ 12.20 (s, 1H), 7.66-7.45 (m, 2H), 7.38-7.17 (m, 2H), 4.89-4.67 (m, 4H), 3.06 (s, 2H).

Step 3: Preparation of tert-butyl ((3-(4-bromophenyl)oxetan-3-yl)methyl)carbamate To 2-(3-(4-bromophenyl)oxetan-3-yl)acetic acid (339 mg, 1.25 mmol) in t-BuOH (6.3 mL) and TEA (0.17 mL, 1.25 mmol) was added diphenylphosphinyl azide (0.24 mL, 1.25 mmol). The resulting mixture was heated at 80° C. for 20 h. The reaction was then cooled to ambient temperature, diluted with EtOAc (50 mL), and washed with 10% citric acid (aq), saturated sodium bicarbonate (aq), and brine. The organic extract was then dried over anhydrous sodium sulfate and concentrated in vacuo. The crude material was purified by column chromatography (gradient 0-50% EtOAc in heptane) to afford tert-butyl ((3-(4-bromophenyl)oxetan-3-yl)methyl)carbamate (164 mg, 38%): LC-MS Rt=1.11 min (condition B), MS (M+1)=342.0.

Step 4: Preparation of tert-butyl ((3-(4'-(2-(4-(3-carbamoyl-5-methyl-1H-pyrazol-1-yl)phenyl)propan-2-yl)-[1,1'-biphenyl]-4-yl)oxetan-3-yl)methyl)carbamate Intermediate VI and tert-butyl ((3-(4-bromophenyl)oxetan-3-yl)methyl)carbamate reacted according to General Method II to afford crude tert-butyl ((3-(4'-(2-(4-(3-carbamoyl-5-methyl-1H-pyrazol-1-yl)phenyl)propan-2-yl)-[1,1'-biphenyl]-4-yl)oxetan-3-yl)methyl)carbamate: LCMS Rt=1.60 min (condition B), MS (M-55)=525.5.

Step 5: Preparation of 1-(4-(2-(4'-(3-(aminomethyl) oxetan-3-yl)-[1,1'-biphenyl]-4-yl)propan-2-yl)phenyl)-5-methyl-1H-pyrazole-3-carboxamide To tert-butyl ((3-(4'-(2-(4-(3-carbamoyl-5-methyl-1H-pyrazol-1-yl)phenyl)propan-2-yl)-[1,1'-biphenyl]-4-yl)oxetan-3-yl)methyl)carbamate (278 mg, 0.479 mmol) in DCM (1 mL) was added TFA (0.9 mL, 11.97 mmol). The mixture was stirred at ambient temperature for 3 h and concentrated in vacuo. The crude material was taken up in MeOH and purified by SCX-BSA according to General Method III. The isolated product was purified by preparative HPLC to afford 1-(4-(2-(4'-(3-(aminomethyl)oxetan-3-yl)-[1,1'-biphenyl]-4-yl)propan-2-yl)phenyl)-5-methyl-1H-pyrazole-3-carboxamide (7.3 mg, 3.1%): LCMS Rt=1.72 min (condition A), MS (M-55)=481.4. $^1$H NMR (400 MHz, Chloroform-d) δ 7.49 (d, J=8.2 Hz, 2H), 7.42 (d, J=8.4 Hz, 2H), 7.36-7.20 (m, 6H), 7.03 (d, J=8.2 Hz, 2H), 6.71 (s, 1H), 6.64 (s, 1H), 5.36 (s, 1H), 4.92 (d, J=6.0 Hz, 2H), 4.73 (d, J=6.0 Hz, 2H), 3.29 (s, 2H), 2.25 (s, 3H), 1.67 (s, 6H).

Example 12

1-(4-(2-(4'-(3-aminooxetan-3-yl)-[1,1'-biphenyl]-4-yl)propan-2-yl)phenyl)-5-methyl-1H-pyrazole-3-carboxamide

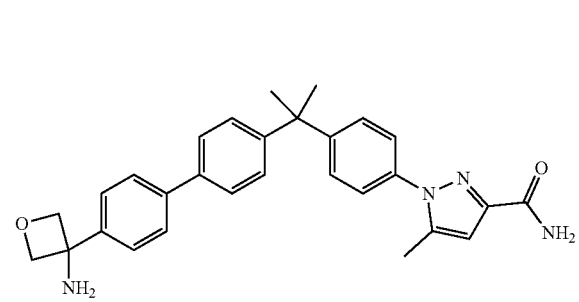 [SMILES: Cc1cc(C(N)=O)nn1-c1ccc(C(C)(C)c2ccc(-c3ccc(C4(N)COC4)cc3)cc2)cc1]

Step 1: Preparation of N-(3-(4-bromophenyl)oxetan-3-yl)-2-methylpropane-2-sulfinamide To 1,4-dibromobenzene (0.5 g, 2.12 mmol) in dry THF (8.8 mL) at −78° C. was added a solution of n-butyllithium (1.2 mL, 2.97 mmol). The resulting mixture was stirred for 1 h, then 2-methyl-N-(oxetan-3-ylidene)propane-2-sulfinamide (0.371 g, 2.12 mmol) in dry THF (1.8 mL) was added dropwise. The reaction was allowed to warm to ambient temperature and stirred another 1 h. The mixture was then quenched with saturated NH$_4$Cl (aq) and extracted with EtOAc. The organic phase was washed with saturated sodium bicarbonate (aq), dried over anhydrous sodium sulfate and concentrated in vacuo. The crude material was purified by column chromatography (gradient 0-100% EtOAc in heptane) to afford N-(3-(4-bromophenyl)oxetan-3-yl)-2-methylpropane-2-sulfinamide (284 mg, 36%): LCMS Rt=0.95 min (condition B), MS (M+3)=334.0.

Step 2: Preparation of 1-(4-(2-(4'-(3-(1,1-dimethyl-ethylsulfinamido)oxetan-3-yl)-[1,1'-biphenyl]-4-yl)propan-2-yl)phenyl)-5-methyl-1H-pyrazole-3-carboxamide Intermediate VI (0.16 g, 0.352 mmol) and N-(3-(4-bromophenyl)oxetan-3-yl)-2-methylpropane-2-sulfinamide (0.09 g, 0.271 mmol) were reacted according to General Method II for Suzuki coupling to afford crude 1-(4-(2-(4'-(3-(1,1-dimethylethylsulfinamido)oxetan-3-yl)-[1,1'-biphenyl]-4-yl)propan-2-yl)phenyl)-5-methyl-1H-pyrazole-3-carboxamide (155 mg): LCMS Rt=1.46 min (condition B), MS (M+1)=571.3.

Step 3: Preparation of 1-(4-(2-(4'-(3-aminooxetan-3-yl)-[1,1'-biphenyl]-4-yl)propan-2-yl)phenyl)-5-methyl-1H-pyrazole-3-carboxamide To 1-(4-(2-(4'-(3-(1,1-dimethylethylsulfinamido)oxetan-3-yl)-[1,1'-biphenyl]-4-yl)propan-2-yl)phenyl)-5-methyl-1H-pyrazole-3-carboxamide (155 mg, 0.272 mmol) in DCM (0.91 mL) was added 4N HCl in 1,4-dioxane (0.27 mL, 1.09 mmol). The resulting mixture was stirred at ambient temperature for 0.5 h then concentrated under reduced pressure. The crude material was purified on a 5 g SCX-BSA cartridge according to General Method III. The isolated product was purified by preparative HPLC to afford 1-(4-(2-(4'-(3-aminooxetan-3-yl)-[1,1'-biphenyl]-4-yl)propan-2-yl)phenyl)-5-methyl-1H-pyrazole-3-carboxamide (9.1 mg, 6.8%): LCMS Rt=0.87 min (condition B), MS (M+1)=467.3. $^1$H NMR (400 MHz, Chloroform-d) δ 7.51-7.46 (m, 2H), 7.45-7.35 (m, 4H), 7.34-7.20 (m, 6H), 6.71 (s, 1H), 6.65 (s, 1H), 5.35 (s, 1H), 3.97-3.73 (m, 2H), 2.26 (s, 3H), 2.18-1.84 (m, 4H), 1.67 (s, 6H).

Example 13-1

5-methyl-1-(4-(2-(4'-(pyrrolidin-1-ylmethyl)-[1,1'-biphenyl]-4-yl)propan-2-yl)phenyl)-1H-1,2,4-triazole-3-carboxamide

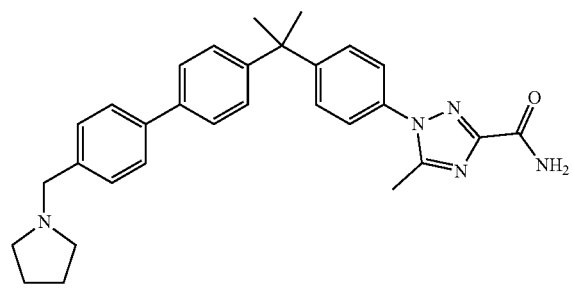 [SMILES: Cc1nc(C(N)=O)nn1-c1ccc(C(C)(C)c2ccc(-c3ccc(CN4CCCC4)cc3)cc2)cc1]

Example 1 and 1-(4-(4,4,5,5-tetramethyl-1,3,2-dioxaborolan-2-yl)benzyl)pyrrolidine were reacted according to General Method I for Suzuki coupling to afford crude 5-methyl-1-(4-(2-(4'-(pyrrolidin-1-ylmethyl)-[1,1'-biphenyl]-4-yl)propan-2-yl)phenyl)-1H-1,2,4-triazole-3-carboxamide: LCMS Rt=1.62 min (condition A), MS (M+1)=480.9. $^1$H NMR (400 MHz, DMSO-d6) δ 7.85 (s, 1H), 7.68-7.52 (m, 7H), 7.52-7.42 (m, 2H), 7.42-7.27 (m, 4H), 3.59 (s, 2H), 2.49 (s, 3H), 2.47-2.38 (m, 4H), 1.81-1.62 (m, 10H).

Examples 13-2 to 13-16

The following compounds were prepared using a similar procedure as in Example 13-1:

| Example | Compound | LCMS M + 1, Rt, conditions | 1H NMR, 400 MHz |
|---------|----------|----------------------------|-----------------|
| 13-2 | 1-(4-(2-(4'-(N,N-dimethylsulfamoyl)-[1,1'-biphenyl]-4-yl)propan-2-yl)phenyl)-5-methyl-1H-1,2,4-triazole-3-carboxamide | 504.3 0.64 min Q | (DMSO-d6) δ 7.96-7.89 (m, 2H), 7.87-7.76 (m, 3H), 7.75-7.67 (m, 2H), 7.62-7.52 (m, 3H), 7.51-7.44 (m, 2H), 7.44-7.38 (m, 2H), 2.64 (s, 6H), 2.49 (s, 3H), 1.75 (s, 6H). |

-continued

| Example | Compound | LCMS M + 1, Rt, conditions | 1H NMR, 400 MHz |
|---|---|---|---|
| 13-3 | 5-methyl-1-(4-(2-(4-(quinolin-6-yl)phenyl)propan-2-yl)phenyl)-1H-1,2,4-triazole-3-carboxamide | 448.3 0.65 min Q | (DMSO-d6) δ 8.90 (dd, J = 4.2, 1.7 Hz, 1H), 8.42 (dd, J = 8.4, 1.7 Hz, 1H), 8.27 (s, 1H), 8.10-8.08 (m, 2H), 7.84 (s, 1H), 7.82-7.77 (m, 2H), 7.61-7.53 (m, 4H), 7.52-7.46 (m, 2H), 7.46-7.40 (m, 2H), 2.50, (s, 3H), 1.76 (s, 6H). |
| 13-4 | 5-methyl-1-(4-(2-(4-(quinoxalin-6-yl)phenyl)propan-2-yl)phenyl)-1H-1,2,4-triazole-3-carboxamide | 449.2 0.66 min Q | (DMSO-d6) δ 8.98 (d, J = 1.8 Hz, 1H), 8.94 (d, J = 1.8 Hz, 1H), 8.35 (d, J = 1.8 Hz, 1H), 8.25-8.14 (m, 2H), 7.91-7.81 (m, 3H), 7.62-7.54 (m, 3H), 7.53-7.42 (m, 4H), 2.50 (s, 3H), 1.77 (s, 6H). |
| 13-5 | 1-(4-(2-(4-(isoquinolin-7-yl)phenyl)propan-2-yl)phenyl)-5-methyl-1H-1,2,4-triazole-3-carboxamide | 448.3 0.63 min Q | N/A |
| 13-6 | 1-(4-(2-(4'-(dimethylcarbamoyl)-[1,1'-biphenyl]-4-yl)propan-2-yl)phenyl)-5-methyl-1H-1,2,4-triazole-3-carboxamide | 468.3 0.64 min Q | (DMSO-d6) δ 7.83 (s, 1H), 7.74-7.68 (m, 2H), 7.68-7.63 (m, 2H), 7.60-7.54 (m, 3H), 7.50-7.45 (m, 4H), 7.37 (d, J = 8.5 Hz, 2H), 3.32 (s, 3H), 2.99 (s, 3H), 2.49 (s, 3H), 1.74 (s, 6H). |

| Example | Compound | LCMS M + 1, Rt, conditions | 1H NMR, 400 MHz |
|---|---|---|---|
| 13-7 | 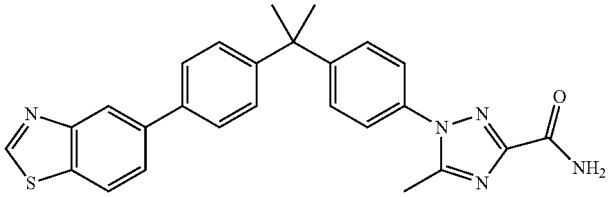<br>1-(4-(2-(4-(benzo[d]thiazol-5-yl)phenyl)propan-2-yl)phenyl)-5-methyl-1H-1,2,4-triazole-3-carboxamide | 454.2<br>0.67 min<br>Q | (DMSO-d6) δ 9.43 (s, 1H), 8.35 (d, J = 1.6 Hz, 1H), 8.24 (d, J = 8.4 Hz, 1H), 7.89-7.70 (m, 4H), 7.64-7.52 (m, 3H), 7.52-7.45 (m, 2H), 7.43-7.35 (m, 2H), 1.76 (s, 6H). (CH$_3$—Me believed to be under DMSO) |
| 13-8 | 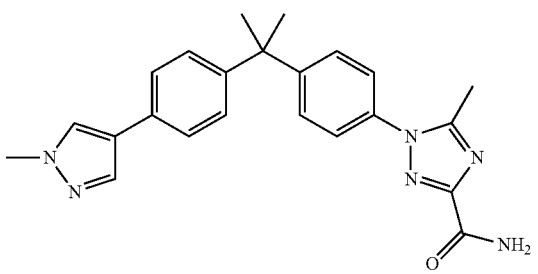<br>5-methyl-1-(4-(2-(4-(1-methyl-1H-pyrazol-4-yl)phenyl)propan-2-yl)phenyl)-1H-1,2,4-triazole-3-carboxamide | 401.2<br>0.61 min<br>Q | (DMSO-d6) δ 8.07 (s, 1H), 7.83 (s, 1H), 7.80 (s, 1H), 7.58 (s, 1H), 7.56-7.52 (m, 2H), 7.50-7.46 (m, 2H), 7.46-7.42 (m, 2H), 7.27-7.21 (m, 2H), 3.85 (s, 3H), 2.48 (s, 3H), 1.70 (s, 6H). |
| 13-9 | 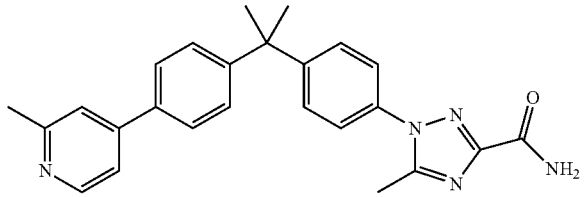<br>5-methyl-1-(4-(2-(4-(2-methylpyridin-4-yl)phenyl)propan-2-yl)phenyl)-1H-1,2,4-triazole-3-carboxamide | 412.2<br>0.53 min<br>Q | (DMSO-d6) δ 8.48 (d, J = 5.3 Hz, 1H), 7.83 (s, 1H), 7.77-7.69 (m, 2H), 7.63-7.51 (m, 4H), 7.50-7.43 (m, 3H), 7.43-7.36 (m, 2H), 2.52 (s, 3H), 2.49 (s, 3H), 1.74 (s, 6H). |
| 13-10 | 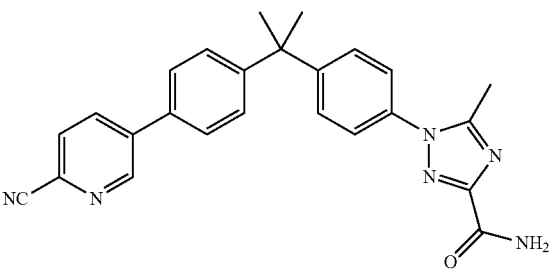<br>1-(4-(2-(4-(6-cyanopyridin-3-yl)phenyl)propan-2-yl)phenyl)-5-methyl-1H-1,2,4-triazole-3-carboxamide | 423.2<br>0.62 min<br>Q | (DMSO-d6) δ 9.10 (d, J = 1.8 Hz, 1H), 8.34 (dd, J = 8.2, 2.3 Hz, 1H), 8.12 (d, J = 8.2 Hz, 1H), 7.83 (s, 1H), 7.79 (d, J = 8.5 Hz, 2H), 7.61-7.53 (m, 3H), 7.51-7.40 (m, 4H), 2.49 (s, 3H), 1.75 (s, 6H). |

-continued

| Example | Compound | LCMS M + 1, Rt, conditions | 1H NMR, 400 MHz |
|---|---|---|---|
| 13-11 | 5-methyl-1-(4-(2-(4-(4-methyl-3,4-dihydro-2H-pyrido[3,2-b][1,4]oxazin-7-yl)phenyl)propan-2-yl)phenyl)-1H-1,2,4-triazole-3-carboxamide | 469.3 0.61 min Q | (DMSO-d$_6$) δ 7.99 (d, J = 2.1 Hz, 1H), 7.83 (s, 1H), 7.57 (s, 1H), 7.57-7.50 (m, 4H), 7.46 (d, J = 8.7 Hz, 2H), 7.31-7.26 (m, 2H), 7.22 (d, J = 2.1 Hz, 1H), 4.29-4.18 (m, 2H), 3.47-3.42 (m, 2H), 3.05 (s, 3H), 2.49 (s, 3H), 1.71 (s, 6H). |
| 13-12 | 5-methyl-1-(4-(2-(4'-(morpholinomethyl)-[1,1'-biphenyl]-4-yl)propan-2-yl)phenyl)-1H-1,2,4-triazole-3-carboxamide | 496.4 0.54 min Q | (DMSO-d6) δ 7.83 (s, 1H), 7.65-7.51 (m, 7H), 7.50-7.42 (m, 2H), 7.42-7.28 (m, 4H), 3.62-3.53 (m, 4H), 3.49 (s, 2H), 2.49 (s, 3H), 2.40-2.34 (m, 4H), 1.73 (s, 6H). |
| 13-13 | 5-methyl-1-(4-(2-(3'-(5-methyl-1,3,4-oxadiazol-2-yl)-[1,1'-biphenyl]-4-yl)propan-2-yl)phenyl)-1H-1,2,4-triazole-3-carboxamide | 479.2 0.67 min Q | (DMSO-d6) δ 8.17 (t, J = 1.6 Hz, 1H), 7.98-7.87 (m, 2H), 7.83 (s, 1H), 7.73-7.65 (m, 3H), 7.62-7.53 (m, 3H), 7.52-7.44 (m, 2H), 7.43-7.37 (m, 2H), 2.60 (s, 3H), 2.49 (s, 3H), 1.75 (s, 6H). |
| 13-14 | 5-methyl-1-(4-(2-(4-(6-(pyrrolidin-1-yl)pyridin-3-yl)phenyl)propan-2-yl)phenyl)-1H-1,2,4-triazole-3-carboxamide | 467.3 0.54 min Q | (DMSO-d6) δ 8.39 (d, J = 2.3 Hz, 1H), 7.83 (s, 1H), 7.78 (dd, J = 8.8, 2.5 Hz, 1H), 7.60-7.51 (m, 5H), 7.49-7.44 (m, 2H), 7.33-7.26 (m, 2H), 6.51 (d, J = 8.8 Hz, 1H), 3.47-3.36 (m, 4H), 2.49 (s, 3H), 2.00-1.91 (m, 4H), 1.72 (s, 6H). |

| Example | Compound | LCMS M + 1, Rt, conditions | 1H NMR, 400 MHz |
|---|---|---|---|
| 13-15 | 5-methyl-1-(4-(2-(4-(6-morpholinopyridin-3-yl)phenyl)propan-2-yl)phenyl)-1H-1,2,4-triazole-3-carboxamide | 483.3 0.62 min Q | (DMSO-d6) δ 8.45 (d, J = 2.5 Hz, 1H), 7.90-7.82 (m, 2H), 7.61-7.50 (m, 5H), 7.46 (d, J = 8.7 Hz, 2H), 7.31 (d, J = 8.5 Hz, 2H), 6.91 (d, J = 9.0 Hz, 1H), 3.74-3.67 (m, 4H), 3.52-3.44 (m, 4H), 2.49 (s, 3H), 1.72 (s, 6H). |
| 13-16 | 5-methyl-1-(4-(2-(4-(thiophen-3-yl)phenyl)propan-2-yl)phenyl)-1H-1,2,4-triazole-3-carboxamide | 403.2 0.67 min Q | (DMSO-d6) δ 7.88-7.78 (m, 2H), 7.68-7.60 (m, 3H), 7.60-7.50 (m, 4H), 7.48-7.42 (m, 2H), 7.33-7.26 (m, 2H), 2.48 (s, 3H), 1.72 (s, 6H). |

Example 14

1-(4-(2-(4'-(1-amino-2,2,2-trifluoroethyl)-[1,1'-biphenyl]-4-yl)propan-2-yl)phenyl)-5-methyl-1H-1,2,4-triazole-3-carboxamide

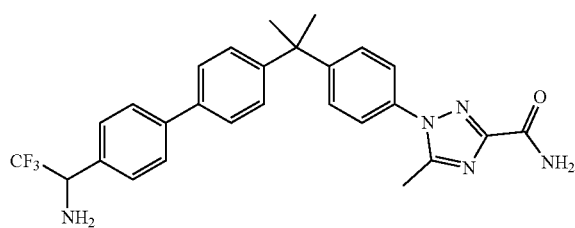 [SMILES: Cc1nc(C(N)=O)nn1-c1ccc(C(C)(C)c2ccc(-c3ccc(C(N)C(F)(F)F)cc3)cc2)cc1]

Example 1 (75 mg, 0.211 mmol) and racemic (4-(1-((tert-butoxycarbonyl)amino)-2,2,2-trifluoroethyl)phenyl)boronic acid (0.67 mg, 0.211 mmol) were reacted according to General Method I for Suzuki coupling to afford crude tert-butyl (1-(4'-(2-(4-(3-carbamoyl-5-methyl-1H-1,2,4-triazol-1-yl)phenyl)propan-2-yl)-[1,1'-biphenyl]-4-yl)-2,2,2-trifluoroethyl)carbamate. This crude material was immediately taken up in 4N HCl in 1,4-dioxane (5 mL) and the mixture was stirred at ambient temperature for 2 h. The reaction mixture was diluted with MeOH and purified directly by preparative HPLC to afford 1-(4-(2-(4'-(1-amino-2,2,2-trifluoroethyl)-[1,1'-biphenyl]-4-yl)propan-2-yl)phenyl)-5-methyl-1H-1,2,4-triazole-3-carboxamide (36.2 mg, 34%): LC-MS Rt=0.98 min (condition A), MS (M+1)= 494.4. $^1$H NMR (400 MHz, DMSO-d6) δ 7.83 (s, 1H), 7.69-7.59 (m, 4H), 7.59-7.52 (m, 5H), 7.51-7.44 (m, 2H), 7.39-7.31 (m, 2H), 4.66-4.40 (m, 1H), 2.49 (s, 3H), 1.74 (s, 6H).

Example 15-1

5-methyl-1-(4-((4'-((4-methylpiperazin-1-yl)methyl)-[1,1'-biphenyl]-4-yl)methyl)phenyl)-1H-1,2,4-triazole-3-carboxamide

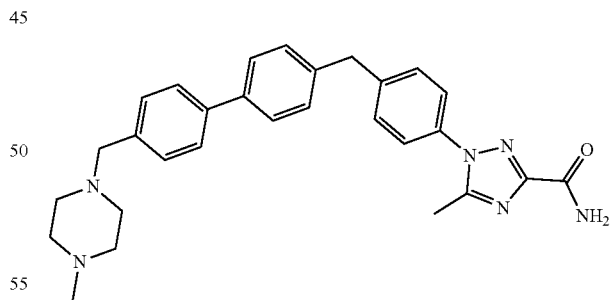

Intermediate VII and 1-methyl-4-(4-(4,4,5,5-tetramethyl-1,3,2-dioxaborolan-2-yl)benzyl)piperazine were reacted according to General Method I for Suzuki coupling to afford 5-methyl-1-(4-((4'-((4-methylpiperazin-1-yl)methyl)-[1,1'-biphenyl]-4-yl)methyl)phenyl)-1H-1,2,4-triazole-3-carboxamide: LCMS Rt=1.30 min (condition A), MS (M+1)= 481.4. $^1$H NMR (400 MHz, DMSO-d6) δ 7.83 (s, 1H), 7.70-7.52 (m, 7H), 7.48 (d, J=8.4 Hz, 2H), 7.36 (dd, J=8.0, 6.3 Hz, 4H), 4.09 (s, 2H), 3.47 (s, 2H), 2.49-2.19 (m, 11H), 2.16 (s, 3H).

Examples 15-2 to 15-4

The following compounds were prepared using a similar procedure as in Example 15-1

| Example | Compound | LCMS M + 1, Rt, conditions | $^1$H NMR, 400 MHz |
|---|---|---|---|
| 15-2 | 5-methyl-1-(4-(4-(pyridin-3-yl)benzyl)phenyl)-1H-1,2,4-triazole-3-carboxamide | 370.2<br>1.19 min<br>A | (DMSO-d6) δ 8.88 (s, 1H), 8.55 (d, J = 4.2 Hz, 1H), 8.05 (d, J = 8.0 Hz, 1H), 7.84 (s, 1H), 7.69 (d, J = 8.1 Hz, 2H), 7.57 (d, J = 8.5 Hz, 3H), 7.53-7.39 (m, 5H), 4.11 (s, 2H), 2.47 (s, 3H). |
| 15-3 | 5-methyl-1-(4-((4'-(4-methylpiperazine-1-carbonyl)-[1,1'-biphenyl]-4-yl)methyl)phenyl)-1H-1,2,4-triazole-3-carboxamide | 495.4<br>1.28 min<br>A | (Methanol-d$_4$) δ 7.62 (d, J = 8.2 Hz, 2H), 7.52 (d, J = 8.2 Hz, 2H), 7.45-7.32 (m, 6H), 7.27 (d, J = 8.2 Hz, 2H), 4.03 (s, 2H), 3.88-3.27 (m, 4H), 2.53-2.28 (m, 7H), 2.24 (s, 3H). |
| 15-4 | 5-methyl-1-(4-((4'-(pyrolidin-1-ylmethyl)-[1,1'-biphenyl]-4-yl)methyl)phenyl)-1H-1,2,4-triazole-3-carboxamide | 452.4<br>1.34 min<br>A | (DMSO-d6) δ 7.83 (s, 1H), 7.67-7.52 (m, 7H), 7.48 (d, J = 8.5 Hz, 2H), 7.42-7.32 (m, 4H), 4.09 (s, 2H), 3.59 (s, 2H), 2.48-2.40 (m, 7H), 1.76-1.64 (m, 4H). |

To a stirred solution of Intermediate VIII (0.25 g, 0.63 mmol) in 1,2-dichloroethane (5 mL) were added AcOH (3 mg, 0.063 mmol) and L-prolinol (0.070 g, 0.69 mmol). The reaction was allowed to stir for 4 h at 25° C. Then NaBH$_3$CN (0.043 g, 0.069 mmol) was added, and the reaction was allowed to stir for 1 h at 25° C. The mixture was concentrated in vacuo and purified by prep HPLC to afford (S)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide (26 mg, 9%). LC-MS Rt=0.53 min (condition Q), MS (M+1)=481.2. 1H NMR (400 MHz, Methanol-d4) δ 7.63-7.56 (m, 4H), 7.52-7.41 (m, 6H), 7.34 (d, J=8.2 Hz, 2H), 6.70 (s, 1H), 4.17-4.10 (m, 3H), 3.63 (dd, J=10.9, 4.6 Hz, 1H), 3.53 (dd, J=11.0, 6.0 Hz, 2H), 2.97 (m, 1H), 2.74 (m, 1H), 2.44-2.30 (m, 4H), 2.09-1.94 (m, 1H), 1.85-1.63 (m, 3H).

Example 16-1

(S)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide

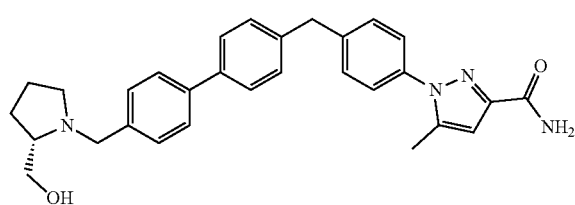 [SMILES: Cc1cc(C(N)=O)nn1-c1ccc(Cc2ccc(-c3ccc(CN4CCC[C@H]4CO)cc3)cc2)cc1]

Examples 16-2 to 16-8

The following compounds were prepared using a similar procedure as in Example 16-1:

| Example | Compound | LCMS M + 1, Rt, conditions | ¹H NMR, 400 MHz |
|---|---|---|---|
| 16-2 | 1-(4-((4'-(((2-hydroxyethyl)amino)methyl)-[1,1'-biphenyl]-4-yl)methyl)phenyl)-5-methyl-1H-pyrazole-3-carboxamide | 441.2 0.52 min Q | (DMSO-d6) δ 7.60 (t, J = 8.0 Hz, 3H), 7.51 (d, J = 8.1 Hz, 3H), 7.44 (d, J = 8.4 Hz, 2H), 7.38 (dd, J = 12.5, 8.1 Hz, 3H), 7.26 (s, 1H), 6.61 (s, 1H), 4.49 (t, J = 5.3 Hz, 1H), 4.07 (s, 2H), 3.73 (s, 2H), 3.49-3.44 (m, 2H), 2.57 (d, J = 6.1 Hz, 2H), 2.31 (s, 3H). |
| 16-3 | 1-(4-((4'-((cyclobutylamino)methyl)-[1,1'-biphenyl]-4-yl)methyl)phenyl)-5-methyl-1H-pyrazole-3-carboxamide | 451.2 0.54 min Q | (DMSO-d6) δ 7.63-7.56 (m, 3H), 7.49 (t, J = 11.0 Hz, 3H), 7.44 (d, J = 8.2 Hz, 2H), 7.37 (t, J = 8.6 Hz, 3H), 7.26 (s, 1H), 6.61 (s, 1H), 4.07 (s, 2H), 3.64 (s, 2H), 3.18 (s, 1H), 2.30 (s, 3H), 2.07 (d, J = 7.0 Hz, 2H), 1.78-1.60 (m, 4H). |
| 16-4 | 5-methyl-1-(4-((4'-((oxetan-3-ylamino)methyl)-[1,1'-biphenyl]-4-yl)methyl)phenyl)-1H-pyrazole-3-carboxamide | 453.3 0.52 min Q | (DMSO-d6) δ 7.59 (t, J = 8.3 Hz, 4H), 7.53-7.46 (m, 3H), 7.43 (d, J = 8.4 Hz, 2H), 7.37 (t, J = 8.5 Hz, 4H), 7.23 (s, 1H), 6.60 (s, 1H), 4.56 (t, J = 6.6 Hz, 2H), 4.31 (t, J = 6.2 Hz, 2H), 4.07 (s, 2H), 3.95-3.81 (m, 1H), 3.65 (s, 2H), 2.30 (s, 3H). |
| 16-5 | 5-methyl-1-(4-((4'-((5-methylhexahydropyrrolo[3,4-c]pyrrol-2(1H)-yl)methyl)-[1,1'-biphenyl]-4-yl)methyl)phenyl)-1H-pyrazole-3-carboxamide | 506.2 0.49 min Q | (DMSO-d₆) δ 7.62-7.52 (m, 5H), 7.50-7.40 (m, 4H), 7.40-7.31 (m, 4H), 7.23 (s, 1H), 6.62 (s, 1H), 4.04 (s, 2H), 3.53 (s, 2H), 2.58-2.55 (m, 3H), 2.44-2.41 (m, 2H), 2.27 (s, 3H), 2.26-2.18 (m, 5H), 2.17 (s, 3H). |

| Example | Compound | LCMS M + 1, Rt, conditions | $^1$H NMR, 400 MHz |
|---|---|---|---|
| 16-6 | 5-methyl-1-(4-((4'-(piperidin-1-ylmethyl)-[1,1'-biphenyl]-4-yl)methyl)phenyl)-1H-pyrazole-3-carboxamide | 465.3 0.53 min Q | (DMSO-d6) δ 7.57 (t, J = 7.5 Hz, 3H), 7.48 (d, J = 7.9 Hz, 3H), 7.41 (d, J = 8.2 Hz, 2H), 7.33 (d, J = 7.6 Hz, 3H), 7.22 (s, 1H), 6.58 (s, 1H), 4.05 (s, 2H), 3.42 (s, 2H), 2.29 (d, J = 9.3 Hz, 4H), 2.28 (s, 3H), 1.47 (d, J = 4.6 Hz, 4H), 1.36 (s, 2H). |
| 16-7 | (R)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide | 481.2 0.52 min Q | (Chloroform-d) δ 7.54 (dd, J = 8.2, 2.5 Hz, 4H), 7.42-7.33 (m, 6H), 7.28 (d, J = 8.3 Hz, 2H), 6.80 (s, 1H), 6.73 (s, 1H), 5.37 (s, 1H), 4.09 (s, 2H), 4.00 (d, J = 13.0 Hz, 1H), 3.69 (dd, J = 10.7, 3.5 Hz, 1H), 3.50-3.42 (m, 1H), 3.40 (d, J = 13.1 Hz, 1H), 3.09-2.96 (m, 1H), 2.76 (m, 1H), 2.38-2.26 (m, 4H), 2.03-1.79 (m, 2H), 1.79-1.69 (m, 2H). |
| 16-8 | 1-(4-((4'-(azetidin-1-ylmethyl)-[1,1'-biphenyl]-4-yl)methyl)phenyl)-5-methyl-1H-pyrazole-3-carboxamide | 437.2 0.52 min Q | (Methanol-d4) δ 7.63-7.55 (m, 4H), 7.51-7.41 (m, 4H), 7.41-7.31 (m, 4H), 6.70 (s, 1H), 4.13 (s, 2H), 3.71 (s, 2H), 3.39 (t, J = 7.2 Hz, 4H), 2.39-2.31 (m, 3H), 2.17 (p, J = 7.2 Hz, 2H). |

Example 17

1-(4-((4'-((2-hydroxyethyl)sulfonyl)-[1,1'-biphenyl]-4-yl)methyl)phenyl)-5-methyl-1H-pyrazole-3-carboxamide

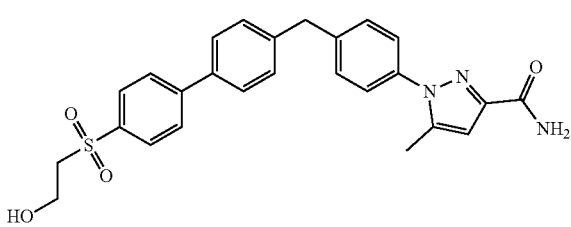 [SMILES: Cc1cc(C(N)=O)nn1-c1ccc(Cc2ccc(-c3ccc(S(=O)(=O)CCO)cc3)cc2)cc1]

Step 1: Preparation of 2-((4-bromophenyl)thio)ethan-1-ol

To 4-bromobenzenethiol (1.0 g, 5.29 mmol) was added dropwise a solution of NaOH (1.06 g, 26 mmol) in water (2 mL). After 10 min, 2-bromoethanol (0.656 g, 5.29 mmol) was added over 10 min. The solution was stirred at room temperature for 2 h, then diluted with EtOAc (50 mL) and washed with water (3×5 mL) and brine (3×5 mL). The organic layer was dried over sodium sulfate, filtered and concentrated. The crude material was purified by FCC to afford 2-((4-bromophenyl)thio)ethan-1-ol (1.1 g, 89%). $^1$H NMR (400 MHz, DMSO-d6) δ 7.85 (q, J=8.8 Hz, 4H), 4.88 (t, J=5.4 Hz, 1H), 3.69 (q, J=6.0 Hz, 2H), 3.49 (t, J=6.1 Hz, 2H).

Step 2: Preparation of 2-((4-bromophenyl)sulfonyl)ethan-1-ol 2-((4-Bromophenyl)thio)ethan-1-ol (1.1 g, 4.7 mmol) was dissolved in MeCN (10 mL) in a 3-neck RBF. Water (10 mL) was added then oxone (1.44 g, 9.4 mmol) portion-wise. The reaction was stirred at 60° C. for 2 h, then was diluted with EtOAc (50 mL) and washed with water (3×5 mL) and brine (3×5 mL). The organic layer was dried over sodium sulfate, filtered and concentrated. The crude material was purified by FCC to afford 2-((4-bromophenyl)sulfonyl)ethan-1-ol (0.65 g, 51%). $^1$H NMR (400 MHz, DMSO-d6) δ 7.86 (q, J=8.7 Hz, 4H), 4.89 (t, J=5.4 Hz, 1H), 3.70 (q, J=5.9 Hz, 2H), 3.50 (t, J=6.2 Hz, 2H).

Step 3: Preparation of 1-(4-((4'-((2-hydroxyethyl)sulfonyl)-[1,1'-biphenyl]-4-yl)methyl)phenyl)-5-methyl-1H-pyrazole-3-carboxamide Intermediate III and 2-((4-bromophenyl)sulfonyl)ethan-1-ol were reacted according to General Method I for Suzuki Coupling. The crude material was purified by preparative HPLC to afford 1-(4-((4'-((2-hydroxyethyl)sulfonyl)-[1,1'-biphenyl]-4-yl)methyl)phenyl)-5-methyl-1H-pyrazole-3-carboxamide (0.2 g, 88%). LC-MS Rt=0.60 min (Condition Q), MS (M+1)=476.2. $^1$H NMR (400 MHz, DMSO-d6) δ 7.99-7.88 (m, 4H), 7.73 (d, J=7.9 Hz, 2H), 7.58-7.44 (m, 4H), 7.47-7.40 (m, 3H), 7.25 (s, 1H), 6.61 (s, 1H), 4.92 (s, 1H), 4.11 (s, 2H), 3.71 (q, J=6.1 Hz, 2H), 3.49 (t, J=6.4 Hz, 2H), 2.31 (s, 3H).

Example 18

(R)-1-(4-((4'-((4,4-difluoro-2-(hydroxymethyl)pyrrolidin-1-yl)methyl)-[1,1'-biphenyl]-4-yl)methyl)phenyl)-5-methyl-1H-pyrazole-3-carboxamide

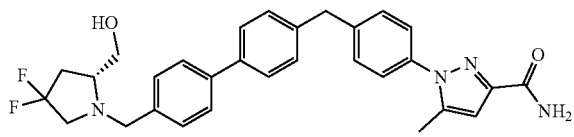 [SMILES: Cc1cc(C(N)=O)nn1-c1ccc(Cc2ccc(-c3ccc(CN4CC(F)(F)C[C@@H]4CO)cc3)cc2)cc1]

Intermediate VIII (200 mg, 0.51 mmol) was dissolved in THF (5.0 mL) in a 20 mL vial. AcOH (2.90 μl, 0.051 mmol) and (R)-(4,4-difluoropyrrolidin-2-yl)methanol (139 mg, 1.0 mmol) were added and stirred at RT for 1 h. NaBH(OAc)$_3$ (214 mg, 1.0 mmol) was added and the reaction was stirred at RT for 4 h. The reaction was quenched with saturated aqueous sodium bicarbonate, and the aqueous layer was extracted with DCM (3×20 mL). The combined organic layers were dried over sodium sulfate, filtered and concentrated, then dissolved in MeOH/water and purified by preparative HPLC. After concentration, the product was dissolved in THF and free-based by filtering through a 3 g Si-carbonate cartridge (Silicycle, 40-63 um, 0.49 mmol/g) pre-quilibrated with THF to afford (R)-1-(4-((4'-((4,4-difluoro-2-(hydroxymethyl)pyrrolidin-1-yl)methyl)-[1,1'-biphenyl]-4-yl)methyl)phenyl)-5-methyl-1H-pyrazole-3-carboxamide (67 mg, 25%) as a white powder. LC-MS Rt=1.91 min (Condition A), MS (M+1)=517.2. $^1$H NMR (400 MHz, Methanol-d$_4$) δ 7.57 (dd, J=8.3, 2.2 Hz, 4H), 7.47-7.37 (m, 6H), 7.32 (d, J=8.2 Hz, 2H), 6.69-6.65 (m, 1H), 4.16 (d, J=13.1 Hz, 1H), 4.10 (s, 2H), 3.66 (dq, J=11.4, 6.2, 5.3 Hz, 2H), 3.43 (d, J=13.2 Hz, 1H), 3.24-3.13 (m, 1H), 3.04-2.93 (m, 1H), 2.68 (td, J=16.3, 11.2 Hz, 1H), 2.46-2.35 (m, 1H), 2.33 (s, 3H), 2.28-2.12 (m, 1H).

Example 19

1-(4-(4-(5-(2-hydroxypropan-2-yl)pyridin-2-yl)benzyl)phenyl)-5-methyl-1H-pyrazole-3-carboxamide

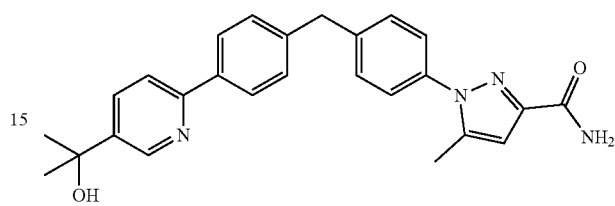

Intermediate III (292 mg, 0.7 mmol) and 2-(6-chloropyridin-3-yl)propan-2-ol (100 mg, 0.58 mmol) were reacted according to General Method IV for Suzuki coupling. This crude material was purified by FCC (0-5% MeOH in DCM) to afford 1-(4-(4-(5-(2-hydroxypropan-2-yl)pyridin-2-yl)benzyl)phenyl)-5-methyl-1H-pyrazole-3-carboxamide (168 mg, 67%) as white powder. LC-MS Rt=1.54 min (condition A), MS (M+1)=427.4. $^1$H NMR (400 MHz, DMSO-d6) δ 8.74 (d, J=1.7 Hz, 1H), 8.01 (d, J=8.3 Hz, 2H), 7.90 (dd, J=8.3, 2.3 Hz, 1H), 7.85 (d, J=8.0 Hz, 1H), 7.53-7.46 (m, 3H), 7.44 (d, J=8.4 Hz, 2H), 7.38 (d, J=8.3 Hz, 2H), 7.23 (s, 1H), 6.60 (s, 1H), 5.22 (s, 1H), 4.09 (s, 2H), 2.30 (s, 3H), 1.48 (s, 6H).

Example 20

1-(4-(4-(5-(2-hydroxypropan-2-yl)-6-methylpyridin-2-yl)benzyl)phenyl)-5-methyl-1H-pyrazole-3-carboxamide

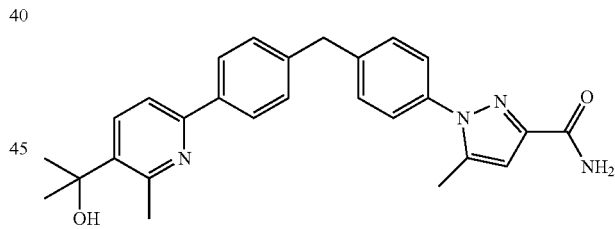

Step 1: Preparation of methyl 6-chloro-2-methylnicotinate

6-Chloro-2-methylnicotinic acid (1.0 g, 5.83 mmol) was dissolved in MeOH (30 mL) in a 100 mL RBF. SOCl$_2$ (2.13 mL, 29.1 mmol) was added and the reaction was stirred at RT overnight. The reaction was cooled to 0° C. and quenched with saturated aqueous NaHCO$_3$, then the aqueous layer was extracted with EtOAc (3×100 mL). The combined organic layers were dried over sodium sulfate, filtered and concentrated. This material was used in the subsequent step without further purification.

Step 2: Preparation of 2-(6-chloro-2-methylpyridin-3-yl)propan-2-ol

Methyl 6-chloro-2-methylnicotinate (900 mg, 4.85 mmol) was dissolved in dry THF (24 mL) in a 100 mL RBF under N₂. The solution was cooled to 0° C. and MeMgBr (3.0 M in Et₂O) (4.85 mL, 14.55 mmol) was added dropwise. The reaction warmed to RT of its own accord and continued stirring for 3 h. The reaction was cooled to 0° C. and quenched slowly with 1M HCl aq. (1 mL) followed by water (20 mL). The mixture was diluted with EtOAc (30 mL) and stirred for 10 min. The layers were separated and the aqueous layer was extracted with EtOAc (3×20 mL), and the combined organic layers were dried over sodium sulfate, filtered and concentrated to afford a yellow oil. This material was used in the subsequent step without further purification. LC-MS Rt=1.26 min (Condition A), MS (M+1)=182.2.

Step 3: Preparation of 1-(4-(4-(5-(2-hydroxypropan-2-yl)-6-methylpyridin-2-yl)benzyl)phenyl)-5-methyl-1H-pyrazole-3-carboxamide 2-(6-chloro-2-methylpyridin-3-yl)propan-2-ol (100 mg, 0.54 mmol) and Intermediate III (539 mg, 0.65 mmol) were reacted according to General Method IV for Suzuki Coupling. The crude material was purified by preparative HPLC to afford 1-(4-(4-(5-(2-hydroxypropan-2-yl)-6-methylpyridin-2-yl)benzyl)phenyl)-5-methyl-1H-pyrazole-3-carboxamide (84 mg, 34%) as a white powder. LC-MS Rt=0.57 min (Condition Q), MS (M+1)=441.4. 1H NMR (400 MHz, Methanol-d4) δ 7.93-7.85 (m, 2H), 7.56 (d, J=8.3 Hz, 1H), 7.48-7.11 (m, 7H), 6.67 (s, 1H), 4.12 (s, 2H), 2.81 (s, 3H), 2.32 (s, 3H), 1.65 (s, 6H).

Example 21

1-(4-(4-(5-(2-hydroxypropan-2-yl)pyridin-2-yl)benzyl)phenyl)-5-methyl-1H-1,2,4-triazole-3-carboxamide

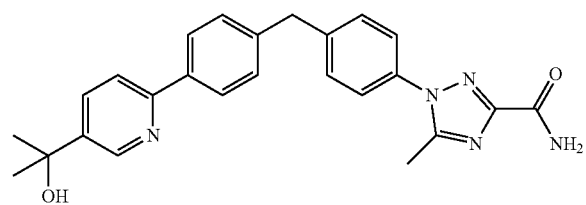 [SMILES: Cc1nc(C(N)=O)nn1-c1ccc(Cc2ccc(-c3ccc(C(C)(C)O)cn3)cc2)cc1]

Intermediate IX (632 mg, 1.5 mmol) and 2-(6-chloropyridin-3-yl)propan-2-ol (216 mg, 1.26 mmol) were reacted according to General Method IV for Suzuki Coupling. The crude material was purified by FCC (0-5% MeOH in DCM) then reverse phase column chromatography (10-100% MeCN in water with 0.1% NH₄OH) to afford 1-(4-(4-(5-(2-hydroxypropan-2-yl)pyridin-2-yl)benzyl)phenyl)-5-methyl-1H-pyrazole-3-carboxamide (82 mg, 15%) as a white powder. LC-MS Rt=1.78 min (condition E), MS (M+1)=428.2. ¹H NMR (400 MHz, DMSO-d6) δ 8.74 (d, J=1.7 Hz, 1H), 8.01 (d, J=8.3 Hz, 2H), 7.90 (dd, J=8.3, 2.3 Hz, 1H), 7.88-7.81 (m, 2H), 7.61-7.53 (m, 3H), 7.49 (d, J=8.5 Hz, 2H), 7.39 (d, J=8.3 Hz, 2H), 5.22 (s, 1H), 4.11 (s, 2H), 2.47 (s, 3H), 1.48 (s, 6H).

Example 22

1-(4-(4-(6-(3-hydroxyoxetan-3-yl)pyridin-3-yl)benzyl)phenyl)-5-methyl-1H-pyrazole-3-carboxamide

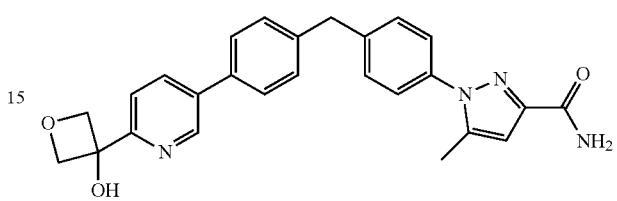

Step 1: Preparation of 3-(5-bromopyridin-2-yl)oxetan-3-ol 2,5-Dibromopyridine (0.5 g, 2.1 mmol) was dissolved in toluene (10 mL) and cooled to −78° C. n-Butyllithium (2.5M in hexane, 0.92 mL, 2.32 mmol) was added dropwise at −78° C. The reaction was stirred for 1 h at −78° C. and a solution of oxetan-3-one (167 mg, 2.32 mmol) in toluene (5 mL) was added dropwise at −78° C. and stirred at that temperature for 2 h. The reaction was quenched with saturated aqueous ammonium chloride solution, diluted with water (20 mL) and extracted with EtOAc (3×15 mL). The combined organic layers were dried over sodium sulfate, filtered and concentrated to afford 3-(5-bromopyridin-2-yl)oxetan-3-ol (185 mg, 38%), which was used in the subsequent step without further purification.

Step 2: Preparation of 1-(4-(4-(6-(3-hydroxyoxetan-3-yl)pyridin-3-yl)benzyl)phenyl)-5-methyl-1H-pyrazole-3-carboxamide Intermediate III (0.3 g, 0.77 mmol) and 3-(5-bromopyridin-2-yl)oxetan-3-ol (0.15 g, 0.65 mmol) were taken up in 1,4-dioxane (3 mL) and water (1.2 mL). Sodium bicarbonate (0.27 g, 2.60 mmol) was added and the mixture was purged with N₂ for 15 minutes. PdCl₂(dppf) (33 mg, 0.04 mmol) was added and the mixture was heated at 80° C. for 18 h. After completion, the reaction mixture was diluted with water (15 mL) and extracted with EtOAc (3×15 mL). The combined organic layers were dried over sodium sulfate, filtered and concentrated. The crude material was purified by preparative HPLC to afford 1-(4-(4-(6-(3-hydroxyoxetan-3-yl)pyridin-3-yl)benzyl)phenyl)-5-methyl-1H-pyrazole-3-carboxamide (130 mg, 45%). LC-MS Rt=0.60 min (Condition Q), MS (M+1)=441.3. ¹H NMR (400 MHz, DMSO-d₆) δ 8.93 (d, J=2.3 Hz, 1H), 8.09 (dd, J=8.2, 2.4 Hz, 1H), 7.74-7.69 (m, 2H), 7.66 (d, J=8.2 Hz, 1H), 7.54-7.49 (m, 3H), 7.49-7.41 (m, 4H), 7.29-7.24 (m, 1H), 6.61 (s, 1H), 6.60 (s, 1H), 4.95 (d, J=6.0 Hz, 2H), 4.68 (d, J=6.0 Hz, 2H), 4.10 (s, 2H), 2.31 (s, 3H).

Example 23

1-(4-(4-(2-(2-hydroxypropan-2-yl)pyridin-4-yl)benzyl)phenyl)-5-methyl-1H-pyrazole-3-carboxamide

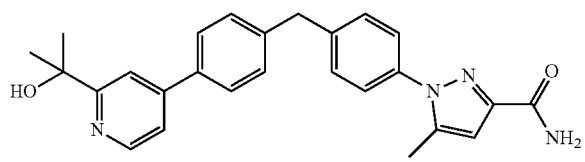 [SMILES: Cc1cc(C(N)=O)nn1-c1ccc(Cc2ccc(-c3ccnc(C(C)(C)O)c3)cc2)cc1]

Step 1: Preparation of ethyl 4-chloropicolinate

To 4-chloropicolinic acid (1.0 g, 6.35 mmol) was added SOCl$_2$ (10 mL) at RT. The reaction mixture was heated at 100° C. for 6 h then concentrated to remove excess SOCl$_2$. To the resulting residue was added EtOH (10 mL) dropwise at 0° C. and the reaction mixture was stirred at RT for 8 h. After completion, the reaction mixture was concentrated and diluted with EtOAc (50 mL). The organic phase was washed with water (2×25 mL), saturated sodium bicarbonate solution (2×25 mL) and brine (25 mL). The organic layer was dried over sodium sulfate and concentrated to afford ethyl 4-chloropicolinate (1.0 g, 85%). $^1$H NMR (400 MHz, DMSO-d6) δ 8.71-8.72 (d, J=8.8 Hz, 1H), 8.09 (s, 1H), 7.84-7.85 (m, 1H), 4.34-4.39 (q, J=7.2 Hz, 2H), 1.33-1.36 (t, 3H).

Step 2: Preparation of 2-(4-chloropyridin-2-yl)propan-2-ol

Ethyl 4-chloropicolinate (1.0 g, 5.38 mmol) was dissolved in THF (50 mL) and the solution was cooled to 00° C. Methyl magnesium bromide (3.0 M in Et$_2$O, 5.4 mL, 16.2 mmol) was added dropwise at 0° C. The reaction was stirred at RT for 1 h. After completion, the reaction mixture was quenched with saturated sodium bicarbonate solution (10 mL) at 0° C. Ethyl acetate (150 mL) was added and the reaction mixture was stirred at room temperature for 30 minutes. The resulting mixture was filtered through celite and the desired compound was partitioned between two layers. The organic layer was washed with saturated sodium bicarbonate solution (2×25 mL) and brine (2×25 mL), then dried over sodium sulfate, filtered and concentrated to afford 2-(4-chloropyridin-2-yl)propan-2-ol (0.67 g, 73%). $^1$H NMR (400 MHz, DMSO-d6) δ 8.49-8.48 (d, J=5.2 Hz, 1H), 7.70-7.69 (d, J=1.6 Hz, 1H), 7.40-7.39 (m, 1H), 7.85-7.84 (m, 1H), 5.49 (s, 1H), 1.44 (s, 6H).

Step 3: Preparation of 1-(4-(4-(2-(2-hydroxypropan-2-yl)pyridin-4-yl)benzyl)phenyl)-5-methyl-1H-pyrazole-3-carboxamide Intermediate III (0.26 g, 0.64 mmol) and 2-(4-chloropyridin-2-yl)propan-2-ol (0.1 g, 0.58 mmol) were taken up in 1,4-dioxane (2 mL) and water (0.8 mL). Sodium bicarbonate (0.24 g, 2.33 mmol) was added to the reaction mixture which was then purged with N$_2$ for 15 minutes. PdCl$_2$(dppf) (29.7 mg, 0.04 mmol) was added and the reaction mixture was heated at 80° C. for 18 h. After completion, the reaction mixture was diluted with water (15 mL) and extracted with EtOAc (3×15 mL). The combined organic layers were dried over sodium sulfate, filtered and concentrated. The crude material was purified by preparative HPLC to afford 1-(4-(4-(2-(2-hydroxypropan-2-yl)pyridin-4-yl)benzyl)phenyl)-5-methyl-1H-pyrazole-3-carboxamide (130 mg, 45%). LC-MS Rt=0.55 min (Condition Q), MS (M+1)=427.3. $^1$H NMR (400 MHz, DMSO-d6) δ 8.53-8.52 (d, J=4.8 Hz, 1H), 7.91 (d, J=0.8 Hz, 1H), 7.74-7.72 (d, J=8.0 Hz, 2H), 7.52-7.43 (m, 8H), 7.25 (s, 1H), 6.61 (s, 1H), 5.29 (s, 1H), 4.11 (s, 2H), 2.33 (s, 3H), 1.47 (s, 6H).

Example 24

5-methyl-1-(4-((4'-(piperazine-1-carbonyl)-[1,1'-biphenyl]-4-yl)methyl)phenyl)-1H-pyrazole-3-carboxamide

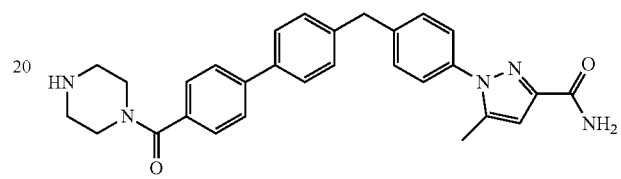

Step 1: Preparation of tert-butyl 4-(4'-(4-(3-carbamoyl-5-methyl-1H-pyrazol-1-yl)benzyl)-[1,1'-biphenyl]-4-carbonyl)piperazine-1-carboxylate A solution of Intermediate X (52 mg 0.13 mmol) and N-Boc-piperazine in dry DCM (5 mL) was cooled to 0° C. and DIPEA (0.067 mL, 0.38 mmol), HOBT (0.025 g, 0.189 mmol) and EDC.HCL (36 mg, 0.19 mmol) were added. The reaction was allowed to stir for 12 h at RT. The progress of reaction was monitored by TLC and LCMS. At completion, the reaction mixture was diluted with EtOAc (10 mL) and the organic layer was washed with ice water (3×10 mL) and brine (3×5 mL). The organic layer was dried over sodium sulfate, filtered and concentrated. The crude material was purified by FCC to afford tert-butyl 4-(4'-(4-(3-carbamoyl-5-methyl-1H-pyrazol-1-yl)benzyl)-[1,1'-biphenyl]-4-carbonyl)piperazine-1-carboxylate (50 mg, 68%).

Step 3: Preparation of 5-methyl-1-(4-((4'-(piperazine-1-carbonyl)-[1,1'-biphenyl]-4-yl)methyl)phenyl)-1H-pyrazole-3-carboxamide To a stirred solution of tert-butyl 4-(4'-(4-(3-carbamoyl-5-methyl-1H-pyrazol-1-yl)benzyl)-[1,1'-biphenyl]-4-carbonyl)piperazine-1-carboxylate (50 mg, 0.09 mmol) in dry DCM (5 mL) was added TFA (5 mL) at 0° C. The reaction was stirred for 2 h at RT and progress was monitored by LCMS and TLC. After the completion, the reaction mixture was evaporated under vacuum and the crude material was diluted with EtOAc (10 mL) and the organic layer was washed with ice water (3×10 mL) and brine (3×5 mL). The organic layer was dried over sodium sulfate, filtered and concentrated. The crude material was purified by preparative HPLC to afford 5-methyl-1-(4-((4'-(piperazine-1-carbonyl)-[1,1'-biphenyl]-4-yl)methyl)phenyl)-1H-pyrazole-3-carboxamide (37 mg, 41%). LC-MS Rt=1.87 min (condition E), MS (M+1)=480.4. $^1$H NMR (400 MHz, DMSO-d$_6$) δ 7.70 (d, J=8.3 Hz, 2H), 7.65 (d, J=8.2 Hz, 2H), 7.54-7.42 (m, 7H), 7.39 (d, J=8.2 Hz, 2H), 7.23 (s, 1H), 6.60 (s, 1H), 4.09 (s, 2H), 3.53 (apparent s, 4H), 2.71 (apparent s, 4H), 2.30 (s, 3H).

Example 25

5-methyl-1-(4-((4'-(piperazine-1-carbonyl)-[1,1'-biphenyl]-4-yl)methyl)phenyl)-1H-1,2,4-triazole-3-carboxamide

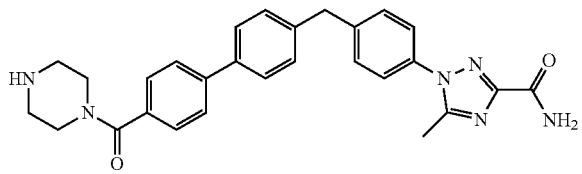 [SMILES: Cc1nc(C(N)=O)nn1-c1ccc(Cc2ccc(-c3ccc(C(=O)N4CCNCC4)cc3)cc2)cc1]

Step 1: Preparation of tert-butyl 4-(4'-(4-(3-carbamoyl-5-methyl-1H-1,2,4-triazol-1-yl)benzyl)-[1,1'-biphenyl]-4-carbonyl)piperazine-1-carboxylate To a solution of Intermediate XI (150 mg, 0.36 mmol) and tert-butyl piperazine-1-carboxylate (81 mg, 0.43 mmol) in MeCN (1.5 mL) was added DIPEA (141 mg, 1.09 mmol), HOBT (74 mg, 0.54 mmol) and EDC.HCL (105 mg, 0.54 mmol). The reaction was stirred at RT overnight. After completion, the reaction was diluted with water (10 mL) and EtOAc (10 mL). The layers were separated and the aqueous layer was extracted with EtOAc (3×10 mL). The combined organic layers were washed with brine (10 mL), dried over sodium sulfate, filtered and concentrated to afford tert-butyl 4-(4'-(4-(3-carbamoyl-5-methyl-1H-1,2,4-triazol-1-yl)benzyl)-[1,1'-biphenyl]-4-carbonyl)piperazine-1-carboxylate (110 mg, 52%), which was used without further purification.

Step 2: Preparation of 5-methyl-1-(4-((4'-(piperazine-1-carbonyl)-[1,1'-biphenyl]-4-yl)methyl)phenyl)-1H-1,2,4-triazole-3-carboxamide tert-Butyl-4-(4'-(4-(3-carbamoyl-5-methyl-1H-1,2,4-triazol-1-yl)benzyl)-[1,1'-biphenyl]-4-carbonyl)piperazine-1-carboxylate (110 mg, 0.18 mmol) was taken up in dry DCM (3 mL). 4M HCl in 1,4-dioxane (3 mL) was added at 00° C. The reaction was stirred at RT for 3 h and concentrated in vacuo. The crude mixture was purified by preparative HPLC to afford 5-methyl-1-(4-((4'-(piperazine-1-carbonyl)-[1,1'-biphenyl]-4-yl)methyl)phenyl)-1H-1,2,4-triazole-3-carboxamide (90 mg, 99%). LC-MS Rt=0.49 min (Condition Q), MS (M+1)=481.4. $^1$H NMR (400 MHz, Methanol-$d_4$) δ 7.75-7.69 (m, 2H), 7.64-7.60 (m, 2H), 7.54-7.44 (m, 6H), 7.40-7.33 (m, 2H), 4.13 (s, 2H), 3.83-3.43 (m, 4H), 2.86 (d, J=30.6 Hz, 4H), 2.52 (s, 3H).

Example 26

5-methyl-1-(4-(4-(6-(piperazine-1-carbonyl)pyridin-3-yl)benzyl)phenyl)-1H-pyrazole-3-carboxamide

Step 1: Preparation of tert-butyl 4-(5-bromopicolinoyl)piperazine-1-carboxylate tert-Butyl piperazine-1-carboxylate (1 g, 5.37 mmol), 5-bromopicolinic acid (1.09 g, 5.37 mmol) and HATU (2.45 g, 6.44 mmol) were dissolved in DMF (10.7 mL) in a 40 mL vial. NMM (1.77 mL, 16.11 mmol) was added and the reaction was stirred at RT overnight. The reaction mixture was diluted with EtOAc (30 mL) and the organic layer was washed with water (3×20 mL) and brine (1×20 mL). The organic layer was dried over sodium sulfate, filtered and concentrated, then purified using FCC [0-50% (3:1 EtOAc:EtOH) in heptane] to afford tert-butyl 4-(5-bromopicolinoyl)piperazine-1-carboxylate (1.88 g, 95%) as a white solid. LC-MS Rt=0.76 min (Condition C), MS (M+1)=316.0. $^1$H NMR (400 MHz, CDCl$_3$) δ 8.66 (d, J=2.1 Hz, 1H), 7.97 (dd, J=8.3, 2.3 Hz, 1H), 7.64 (d, J=8.3 Hz, 1H), 3.84-3.73 (m, 2H), 3.67-3.61 (m, 2H), 3.59-3.52 (m, 2H), 3.51-3.44 (m, 2H), 1.50 (s, 9H).

Step 2: Preparation of tert-butyl 4-(5-(4-(4-(3-carbamoyl-5-methyl-1H-pyrazol-1-yl)benzyl)phenyl)picolinoyl)piperazine-1-carboxylate tert-Butyl 4-(5-bromopicolinoyl)piperazine-1-carboxylate 290 mg, 0.78 mmol) and Intermediate III (392 mg, 0.94 mmol) were reacted according to General Method IV replacing 1-butanol for 1,4-dioxane as solvent. The crude mixture was purified by FCC [0-50% (3:1 EtOAc:EtOH) in heptane] to afford tert-butyl 4-(5-(4-(4-(3-carbamoyl-5-methyl-1H-pyrazol-1-yl)benzyl)phenyl)picolinoyl)piperazine-1-carboxylate (253 mg, 56%) as a white solid. LC-MS Rt=2.43 min (condition E), MS (M+1)=581.0.

Step 3: Preparation of 5-methyl-1-(4-(4-(6-(piperazine-1-carbonyl)pyridin-3-yl)benzyl)phenyl)-1H-pyrazole-3-carboxamide tert-Butyl 4-(5-(4-(4-(3-carbamoyl-5-methyl-1H-pyrazol-1-yl)benzyl)phenyl)picolinoyl)piperazine-1-carboxylate (253 mg, 0.44 mmol) was dissolved in DCM (1.4 mL) in a 100 mL RBF. TFA (0.73 mL) was added and the reaction was stirred at RT for 1 h. The reaction was concentrated and purified according to General Method III to afford 5-methyl-1-(4-(4-(6-(piperazine-1-carbonyl)pyridin-3-yl)benzyl)phenyl)-1H-pyrazole-3-carboxamide (175 mg, 81%). LC-MS Rt=1.29 min (Condition A), MS (M+1)=481.1. $^1$H NMR (400 MHz, DMSO-d6) δ 8.90-8.83 (m, 1H), 8.17 (dd, J=8.2, 2.3 Hz, 1H), 7.73 (d, J=8.2 Hz, 2H), 7.63 (d, J=8.3 Hz, 1H), 7.53-7.49 (m, 2H), 7.49-7.41 (m, 5H), 7.23 (s, 1H), 6.60 (d, J=0.7 Hz, 1H), 4.10 (s, 2H), 3.64-3.53 (m, 2H), 3.40-3.33 (m, 2H), 2.80-2.71 (m, 2H), 2.71-2.62 (m, 2H), 2.30 (s, 3H).

Example 27

5-methyl-1-(4-(4-(5-(piperazine-1-carbonyl)pyridin-2-yl)benzyl)phenyl)-1H-pyrazole-3-carboxamide

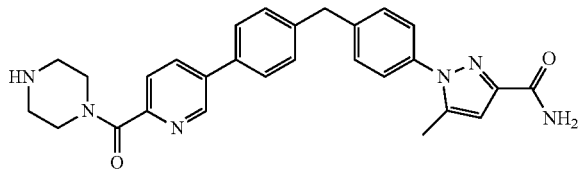 [SMILES: Cc1cc(C(N)=O)nn1-c1ccc(Cc2ccc(-c3ccc(C(=O)N4CCNCC4)nc3)cc2)cc1]

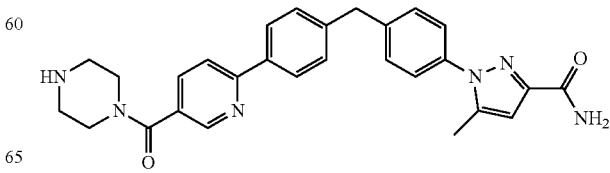

Step 1: Preparation of tert-butyl 4-(6-bromonicotinoyl)piperazine-1-carboxylate N-Boc-piperazine (2 g, 10.7 mmol), 6-bromonicotinic acid (2.17 g, 10.7 mmol) and HATU (4.9 g, 12.9 mmol) were dissolved in DMF (21.5 mL) in a 100 mL RBF. NMM (2.36 mL, 21.5 mmol) was added and the reaction was stirred at RT overnight. The reaction was diluted with EtOAc (30 mL) and the organic layer was washed with water (3×20 mL) and brine (1×20 mL), then dried over sodium sulfate, filtered and concentrated. The crude mixture was purified by FCC (0-6% MeOH in DCM) to afford crude tert-butyl 4-(6-bromonicotinoyl)piperazine-1-carboxylate (4.1 g). LC-MS Rt=1.85 min (Condition A), MS (M+1)=314.1.

Step 2: Preparation of tert-butyl 4-(6-(4-(4-(3-carbamoyl-5-methyl-1H-pyrazol-1-yl)benzyl)phenyl)nicotinoyl)piperazine-1-carboxylate tert-Butyl 4-(6-bromonicotinoyl)piperazine-1-carboxylate (150 mg, 0.41 mmol, 70% purity) and Intermediate III (203 mg, 0.49 mmol) were reacted according to General Method IV, replacing 1-butanol for 1,4-dioxane. The crude mixture was purified by FCC (10-100% EtOAc in heptane) to afford tert-butyl 4-(6-(4-(4-(3-carbamoyl-5-methyl-1H-pyrazol-1-yl)benzyl)phenyl)nicotinoyl)piperazine-1-carboxylate (92 mg, 23%, 60% purity) as a light yellow oil. LC-MS Rt=2.39 min (condition E), MS (M+1)=581.1.

Step 3: Preparation of 5-methyl-1-(4-(4-(5-(piperazine-1-carbonyl)pyridin-2-yl)benzyl)phenyl)-1H-pyrazole-3-carboxamide tert-Butyl 4-(6-(4-(4-(3-carbamoyl-5-methyl-1H-pyrazol-1-yl)benzyl)phenyl)nicotinoyl)piperazine-1-carboxylate (92 mg, 0.1 mmol, 60% purity) was dissolved in DCM (0.3 mL). TFA (0.3 mL) was added and the reaction was stirred at RT for 1 h. The reaction was concentrated and purified by preparative HPLC to afford 5-methyl-1-(4-(4-(5-(piperazine-1-carbonyl)pyridin-2-yl)benzyl)phenyl)-1H-pyrazole-3-carboxamide (9 mg, 20%) as a white powder. LC-MS Rt=1.66 min (condition E), MS (M+1)=481.2. $^1$H NMR (400 MHz, DMSO-d6) δ 8.66 (d, J=1.6 Hz, 1H), 8.07 (d, J=8.4 Hz, 2H), 8.00 (d, J=8.2 Hz, 1H), 7.89 (dd, J=8.2, 2.2 Hz, 1H), 7.53-7.49 (m, 2H), 7.48 (s, 1H), 7.46-7.40 (m, 4H), 7.23 (s, 1H), 6.60 (s, 1H), 4.11 (s, 2H), 3.58 (s, 2H), 2.71 (d, J=28.0 Hz, 4H), 2.30 (s, 3H).

Example 28

(R)-1-(4-((4'-(3-(hydroxymethyl) piperazine-1-carbonyl)-[1,1'-biphenyl]-4-yl)methyl)phenyl)-5-methyl-1H-pyrazole-3-carboxamide

Step 1: Preparation of tert-butyl (R)-4-(4-bromobenzoyl)-2-(hydroxymethyl)piperazine-1-carboxylate 4-Bromobenzoic acid (541 mg, 2.69 mmol), HATU (1.2 g, 3.23 mmol) and (R)-tert-butyl 2-(hydroxymethyl)piperazine-1-carboxylate (582 mg, 2.69 mmol) were dissolved in DMF (8.9 mL) in a 40 mL vial. NMM (0.59 mL, 5.38 mmol) was added and the reaction was stirred at RT for 12 h then diluted with water (20 mL) and EtOAc (20 mL). The layers were separated and the organic layer was washed with water (2×10 mL) and brine (1×10 mL), then dried over sodium sulfate, filtered and concentrated. The crude mixture was purified by FCC (0-7% MeOH in DCM) to afford tert-butyl (R)-4-(4-bromobenzoyl)-2-(hydroxymethyl)piperazine-1-carboxylate (961 mg, 89%). LC-MS Rt=1.99 min (Condition C), MS (M-54)=345.1.

Step 2: Preparation of tert-butyl (R)-4-(4'-(4-(3-carbamoyl-5-methyl-1H-pyrazol-1-yl)benzyl)-[1,1'-biphenyl]-4-carbonyl)-2-(hydroxymethyl) piperazine-1-carboxylate (R)-4-(4-Bromobenzoyl)-2-(hydroxymethyl)piperazine-1-carboxylate (100 mg, 0.25 mmol) and Intermediate III (125 mg, 0.301 mmol) were reacted according to General Method IV for Suzuki Coupling. The crude mixture was purified by FCC (0-7% MeOH in DCM) to afford tert-butyl (R)-4-(4'-(4-(3-carbamoyl-5-methyl-1H-pyrazol-1-yl)benzyl)-[1,1'-biphenyl]-4-carbonyl)-2-(hydroxymethyl)piperazine-1-carboxylate (41 mg, 27%) as a colorless oil. LC-MS Rt=2.34 min (Condition A), MS (M+1)=610.9.

Step 3: Preparation of (R)-1-(4-((4'-(3-(hydroxymethyl)piperazine-1-carbonyl)-[1,1'-biphenyl]-4-yl)methyl)phenyl)-5-methyl-1H-pyrazole-3-carboxamide tert-Butyl (R)-4-(4'-(4-(3-carbamoyl-5-methyl-1H-pyrazol-1-yl)benzyl)-[1,1'-biphenyl]-4-carbonyl)-2-(hydroxymethyl)piperazine-1-carboxylate (41 mg, 0.067 mmol) was dissolved in 2:1 DCM:TFA (1.5 mL) and stirred at RT overnight. The reaction mixture was concentrated and purified by preparative HPLC to afford (R)-1-(4-((4'-(3-(hydroxymethyl)piperazine-1-carbonyl)-[1,1'-biphenyl]-4-yl)methyl)phenyl)-5-methyl-1H-pyrazole-3-carboxamide (10 mg, 8%) as a white powder. LC-MS Rt=1.39 min (Condition A), MS (M+1)=510.4. $^1$H NMR (400 MHz, Methanol-d4) δ 7.74 (d, J=8.4 Hz, 2H), 7.64 (d, J=8.3 Hz, 2H), 7.54-7.42 (m, 6H), 7.38 (d, J=8.3 Hz, 2H), 6.70 (s, 1H), 4.38 (s, 1H), 4.14 (s, 2H), 2.98 (s, 2H), 2.79 (s, 3H), 2.35 (d, J=0.6 Hz, 3H).

Example 29

(S)-5-methyl-1-(4-((4'-(3-methylpiperazine-1-carbonyl)-[1,1'-biphenyl]-4-yl)methyl)phenyl)-1H-1,2,4-triazole-3-carboxamide

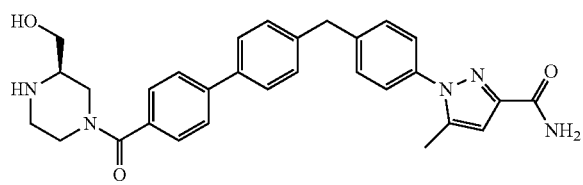 [SMILES: Cc1cc(C(N)=O)nn1-c1ccc(Cc2ccc(-c3ccc(C(=O)N4CCN[C@@H](CO)C4)cc3)cc2)cc1]

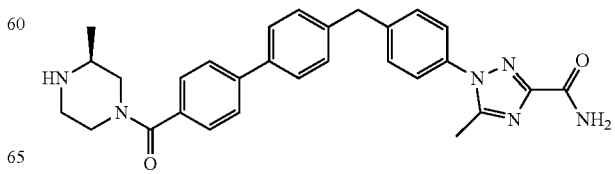

Step 1: Preparation of tert-butyl (S)-4-(4-bromobenzoyl)-2-methylpiperazine-1-carboxylate 4-Bromobenzoic acid (502 mg, 2.5 mmol), HATU (1.1 g, 3.00 mmol) and (S)-tert-butyl 2-methylpiperazine-1-carboxylate (500 mg, 2.5 mmol) were dissolved in DMF (12.5 mL) in a 40 mL vial. NMM (0.55 mL, 5.0 mmol) was added and the mixture was stirred at RT for 12 h. The reaction was diluted with water (30 mL) and EtOAc (30 mL) and the layers were separated. The organic layer was washed with water (2×20 mL) and brine (1×20 mL) then dried over sodium sulfate, filtered and concentrated. The crude material was purified by FCC (0-7% MeOH in DCM) to afford tert-butyl (S)-4-(4-bromobenzoyl)-2-methylpiperazine-1-carboxylate as a white solid. LC-MS Rt=2.47 min (condition E), MS (M-54)=329.1.

Step 2: Preparation of tert-butyl (S)-4-(4'-(4-(3-carbamoyl-5-methyl-1H-1,2,4-triazol-1-yl)benzyl)-[1,1'-biphenyl]-4-carbonyl)-2-methylpiperazine-1-carboxylate A 20 mL vial was charged with tert-butyl (S)-4-(4-bromobenzoyl)-2-methylpiperazine-1-carboxylate (75 mg, 0.2 mmol), Intermediate IX (98 mg, 0.23 mmol), XPhos Pd G2 (15.4 mg, 0.02 mmol) and K₃PO₄ (125 mg, 0.59 mmol). The vial was sealed and evacuated under hi-vacuum/backfilled with N₂ (×3). Degassed 1,4-dioxane (0.82 mL) and degassed water (0.16 mL) were added and the reaction was heated to 100° C. overnight. The reaction mixture was diluted with EtOAc (10 mL) and water (10 mL) and the layers were separated. The organic layer was washed with brine (1×10 mL), dried over sodium sulfate, filtered and concentrated. The crude material was used is the subsequent step without further purification.

Step 3: Preparation of (S)-5-methyl-1-(4-((4'-(3-methylpiperazine-1-carbonyl)-[1,1'-biphenyl]-4-yl)methyl)phenyl)-1H-1,2,4-triazole-3-carboxamide tert-Butyl (S)-4-(4'-(4-(3-carbamoyl-5-methyl-1H-1,2,4-triazol-1-yl)benzyl)-[1,1'-biphenyl]-4-carbonyl)-2-methylpiperazine-1-carboxylate was dissolved in 1:1 DCM:TFA (4 mL) and stirred at RT for 2 h. The reaction mixture was concentrated and purified using preparative HPLC to afford (S)-5-methyl-1-(4-((4'-(3-methylpiperazine-1-carbonyl)-[1,1'-biphenyl]-4-yl)methyl)phenyl)-1H-1,2,4-triazole-3-carboxamide (68 mg, 70%) as a white powder. LC-MS Rt=1.74 min (condition E), MS (M-54)=495.3. ¹H NMR (400 MHz, DMSO-d6) δ 7.83 (s, 1H), 7.71 (d, J=8.3 Hz, 2H), 7.66 (d, J=8.2 Hz, 2H), 7.61-7.55 (m, 3H), 7.49 (d, J=8.5 Hz, 2H), 7.44 (d, J=8.3 Hz, 2H), 7.40 (d, J=8.3 Hz, 2H), 4.44-4.20 (m, 1H), 4.10 (s, 2H), 3.58-3.40 (m, 1H), 3.13-2.71 (m, 2H), 2.66-2.57 (m, 2H), 2.47 (s, 3H), 2.44-2.32 (m, 1H), 0.93 (d, J=57.7 Hz, 3H).

Example 30

1-(4-((4'-(azetidin-3-ylcarbamoyl)-[1,1'-biphenyl]-4-yl)methyl)phenyl)-5-methyl-1H-pyrazole-3-carboxamide

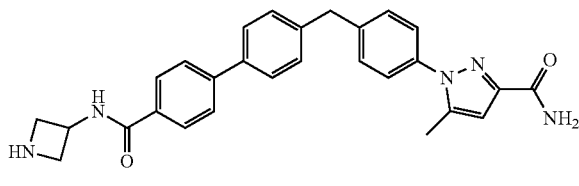 [SMILES: Cc1cc(C(N)=O)nn1-c1ccc(Cc2ccc(-c3ccc(C(=O)NC4CNC4)cc3)cc2)cc1]

Step 1: Preparation of tert-butyl 3-(4'-(4-(3-carbamoyl-5-methyl-1H-pyrazol-1-yl)benzyl)-[1,1'-biphenyl]-4-carboxamido)azetidine-1-carboxylate tert-Butyl 3-aminoazetidine-1-carboxylate (50 mg, 0.29 mmol), Intermediate X (119 mg, 0.290 mmol) and HATU (132 mg, 0.35 mmol) were dissolved in DMF (1.5 mL) in a 20 mL vial. Then NMM (0.096 mL, 0.87 mmol) was added and the mixture was stirred at RT overnight, then diluted with water (20 mL) and EtOAc (30 mL). The layers were separated then the organic layer was washed with water (2×20 mL) and brine (1×20 mL), dried over sodium sulfate, filtered and concentrated. The crude material was used in the next step without further purification.

Step 2: Preparation of 1-(4-((4'-(azetidin-3-ylcarbamoyl)-[1,1'-biphenyl]-4-yl)methyl)phenyl)-5-methyl-1H-pyrazole-3-carboxamide tert-Butyl 3-(4'-(4-(3-carbamoyl-5-methyl-1H-pyrazol-1-yl)benzyl)-[1,1'-biphenyl]-4-carboxamido)azetidine-1-carboxylate was dissolved in 1:1 TFA:DCM (4 mL) and stirred at RT for 2 h. The reaction was concentrated then purified with preparative HPLC to afford 1-(4-((4'-(azetidin-3-ylcarbamoyl)-[1,1'-biphenyl]-4-yl)methyl)phenyl)-5-methyl-1H-pyrazole-3-carboxamide (60 mg, 41%) as a white powder. LC-MS Rt=1.95 min (condition E), MS (M+1)=466.7. ¹H NMR (400 MHz, DMSO-d6) δ 9.06 (d, J=6.9 Hz, 1H), 7.95 (d, J=8.4 Hz, 2H), 7.78 (d, J=8.5 Hz, 2H), 7.69 (d, J=8.2 Hz, 2H), 7.51 (d, J=8.5 Hz, 2H), 7.47 (s, 1H), 7.42 (dd, J=12.5, 8.4 Hz, 4H), 7.24 (s, 1H), 6.61 (s, 1H), 4.91-4.67 (m, 1H), 4.09 (s, 2H), 4.05-3.87 (m, 4H), 2.30 (s, 3H).

Example 31-1

5-methyl-1-(4-(4-(6-(piperazin-1-ylmethyl)pyridin-3-yl)benzyl)phenyl)-1H-pyrazole-3-carboxamide

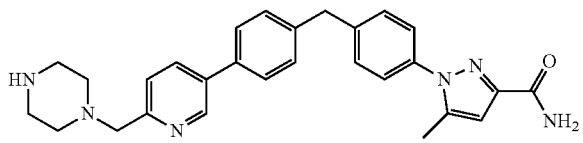 [SMILES: Cc1cc(C(N)=O)nn1-c1ccc(Cc2ccc(-c3ccc(CN4CCNCC4)nc3)cc2)cc1]

Step 1: Preparation of tert-butyl 4-((5-bromopyridin-2-yl)methyl)piperazine-1-carboxylate A mixture of 5-bromopicolinaldehyde (0.3 g, 1.6 mmol) and tert-butyl piperazine-1-carboxylate (0.19 g, 1.0 mmol)

in DCM (10 mL) was treated with acetic acid (0.2 mL). The mixture was stirred at RT for 15 min. Then NaBH(OAc)$_3$ (0.899 g, 4.24 mmol) was added and the reaction was stirred overnight. The reaction was washed with sat. NaHCO$_3$ (20 mL), and the wash was back extracted with DCM (2×20 mL). The combined organic layers were washed with brine (1×20 mL), dried over sodium sulfate, filtered and concentrated. The crude material was purified by FCC (0-10% MeOH in DCM) to afford tert-butyl 4-((5-bromopyridin-2-yl)methyl)piperazine-1-carboxylate (120 mg).

Step 2: Preparation of tert-butyl 4-((5-(4-(4-(3-carbamoyl-5-methyl-1H-pyrazol-1-yl)benzyl)phenyl)pyridin-2-yl)methyl)piperazine-1-carboxylate tert-Butyl 4-((5-bromopyridin-2-yl)methyl)piperazine-1-carboxylate (0.3 g, 0.9 mmol) and Intermediate III (0.2 g, 0.47 mmol) were reacted according to General Method I for Suzuki Coupling. The crude material was purified by FCC to afford tert-butyl 4-((5-(4-(4-(3-carbamoyl-5-methyl-1H-pyrazol-1-yl)benzyl)phenyl)pyridin-2-yl)methyl)piperazine-1-carboxylate (0.14 g, 60%).

Step 3: Preparation of 5-methyl-1-(4-(4-(6-(piperazin-1-ylmethyl)pyridin-3-yl)benzyl)phenyl)-1H-pyrazole-3-carboxamide To a stirred solution of tert-butyl 4-((5-(4-(4-(3-carbamoyl-5-methyl-1H-pyrazol-1-yl)benzyl)phenyl)pyridin-2-yl)methyl)piperazine-1-carboxylate (0.14 g, 0.25 mmol) in dry DCM (1.3 mL) was added TFA (0.2 mL) at 0° C. The reaction was stirred for 2 h at RT, monitoring progress by LCMS and TLC. Upon completion, the reaction was concentrated, diluted with EtOAc (10 mL) and washed with water (3×10 mL) and brine (3×5 mL). The organic layer was dried over sodium sulfate, filtered and concentrated and the crude product was purified by preparative HPLC to afford 5-methyl-1-(4-(4-(6-(piperazin-1-ylmethyl)pyridin-3-yl)benzyl)phenyl)-1H-pyrazole-3-carboxamide (80 mg, 69%). LC-MS Rt=0.51 min (Condition Q), MS (M+1)=467.3. $^1$H NMR (400 MHz, DMSO-d6) δ 8.79 (d, J=2.3 Hz, 1H), 8.30 (s, 1H), 8.03 (dd, J=8.1, 2.4 Hz, 1H), 7.67 (d, J=7.9 Hz, 2H), 7.51-7.43 (m, 7H), 7.25 (s, 1H), 6.61 (s, 1H), 4.09 (s, 2H), 3.63 (s, 2H), 2.86 (s, 8H), 2.31 (s, 3H).

Examples 31-2 and 31-3

The following compounds were prepared using a similar procedure as in Example 31-1:

| Example | Compound | LCMS M + 1, Rt, conditions | $^1$H NMR, 400 MHz |
|---|---|---|---|
| 31-2 | 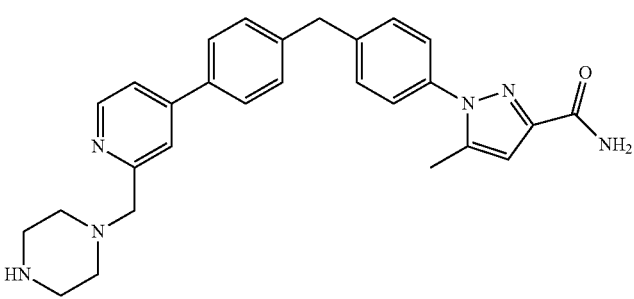<br>5-methyl-1-(4-(4-(2-(piperazin-1-ylmethyl)pyridin-4-yl)benzyl)phenyl)-1H-pyrazole-3-carboxamide | 467.3<br>0.49 min<br>Q | (DMSO-d6) δ 8.60-8.50 (m, 1H), 8.39-8.29 (m, 2H), 7.80-7.70 (m, 2H), 7.69 (s, 1H), 7.60-7.40 (m, 6H), 7.25 (s, 1H), 6.61 (s, 1H), 4.11 (s, 2H), 3.67 (s, 2H), 2.98-2.89 (m, 4H), 2.58-2.40 (m, 4H), 2.30 (s, 3H). |
| 31-3 | 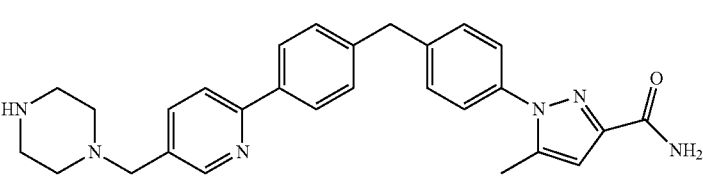<br>5-methyl-1-(4-(4-(5-(piperazin-1-ylmethyl)pyridin-2-yl)benzyl)phenyl)-1H-pyrazole-3-carboxamide | 467.4<br>0.5 min<br>Q | (DMSO-d6) δ 8.55 (s, 1H), 8.04 (d, J = 8.0 Hz, 2H), 7.90 (d, J = 8.1 Hz, 1H), 7.78 (d, J = 7.9 Hz, 1H), 7.52-7.43 (m, 8H), 7.25 (s, 1H), 6.62 (s, 1H), 4.11 (s, 2H), 3.50 (s, 2H), 2.71 (t, J = 4.9 Hz, 4H), 2.56 (d, J = 4.2 Hz, 4H), 2.32 (s, 3H). |

Example 32

1-(4-(4-(6-((4-(2-hydroxyethyl)piperazin-1-yl)methyl)pyridin-3-yl)benzyl)phenyl)-5-methyl-1H-pyrazole-3-carboxamide

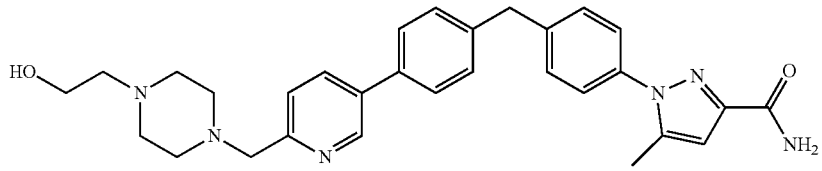 [SMILES: Cc1cc(C(N)=O)nn1-c1ccc(Cc2ccc(-c3ccc(CN4CCN(CCO)CC4)nc3)cc2)cc1]

To a solution of 5-methyl-1-(4-(4-(6-(piperazin-1-ylmethyl)pyridin-3-yl)benzyl)phenyl)-1H-pyrazole-3-carboxamide (Example 31-1) (25 mg, 0.053 mmol) in MeCN:DMF (1:1, 0.25 mL) was added potassium carbonate (14.7 mg, 0.11 mmol) and 2-bromoethan-1-ol (6.6 mg, 0.053 mmol). The reaction mixture and heated at 90° C. for 18 h. After completion, the reaction was filtered, and the filtrate was diluted with water (10 mL) and extracted with ethyl acetate (3×10 mL). The combined organic layers were washed with brine solution (10 mL), dried over sodium sulfate, filtered and concentrated. The crude material was purified by preparative HPLC to afford 1-(4-(4-(6-((4-(2-hydroxyethyl)piperazin-1-yl)methyl)pyridin-3-yl)benzyl)phenyl)-5-methyl-1H-pyrazole-3-carboxamide. LC-MS Rt=0.51 min (Condition Q), MS (M+1)=511.4. $^1$H NMR (400 MHz, MeOD) δ 8.78 (s, 1H), 8.12-8.10 (m, 1H), 7.66-7.62 (m, 3H), 7.50-7.42 (m, 6H), 6.71 (s, 1H), 4.2 (s, 2H), 3.83 (s, 2H), 3.71-3.58 (m, 2H), 3.14 (m, 2H), 3.02 (m, 2H), 2.72 (m, 4H), 2.36 (s, 3H), 2.06-2.00 (m, 2H).

Example 33

5-methyl-1-(4-(4-(5-((4-(oxetan-3-yl)piperazin-1-yl)methyl)pyridin-2-yl)benzyl)phenyl)-1H-pyrazole-3-carboxamide

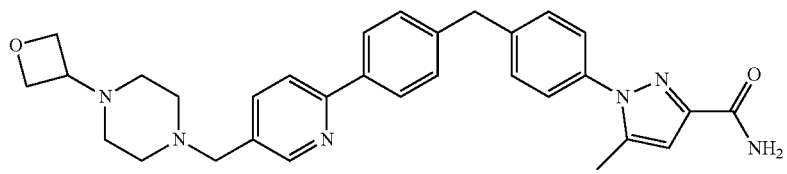 [SMILES: Cc1cc(C(N)=O)nn1-c1ccc(Cc2ccc(-c3ccc(CN4CCN(C5COC5)CC4)cn3)cc2)cc1]

To a solution of 5-methyl-1-(4-(4-(5-(piperazin-1-ylmethyl)pyridin-2-yl)benzyl)phenyl)-1H-pyrazole-3-carboxamide (Example 31-3) (55 mg, 0.12 mmol) and oxetan-3-one (16 mg, 0.24 mmol) in DCE (1 mL) was added acetic acid (2 drops) and the reaction was stirred for 2 h at RT. NaBH(OAc)$_3$ (0.062 g, 0.295 mmol) was added to the reaction portion-wise at RT. The reaction was stirred at RT for 16 hours. The reaction was concentrated, dissolved in water and basified to pH 8-9 using saturated aqueous NaHCO$_3$ solution. The compound was extracted with EtOAc (2×25 mL) and the combined organic layers were washed with water and brine, then dried over sodium sulfate, filtered and concentrated. The crude mixture was purified by preparative HPLC to afford 5-methyl-1-(4-(4-(5-((4-(oxetan-3-yl)piperazin-1-yl)methyl)pyridin-2-yl)benzyl)phenyl)-1H-pyrazole-3-carboxamide. LC-MS Rt=0.50 min (Condition Q), MS (M+1)=523.4. $^1$H NMR (400 MHz, Methanol-d$_4$) δ 8.58 (s, 1H), 7.89 (dt, J=19.9, 8.2 Hz, 4H), 7.45 (dd, J=24.0, 6.2 Hz, 6H), 6.71 (s, 1H), 4.71 (t, J=6.7 Hz, 2H), 4.61 (t, J=6.2 Hz, 2H), 4.17 (s, 2H), 3.70-3.63 (m, 2H), 3.58-3.53 (m, 2H), 3.29-3.39 (m, 2H), 2.69 (m, 3H), 2.48-2.41 (m, 2H), 2.37 (s, 3H).

Example 34

5-methyl-1-(4-(4-(6-((4-methylpiperazin-1-yl)methyl)pyridin-3-yl)benzyl)phenyl)-1H-1,2,4-triazole-3-carboxamide

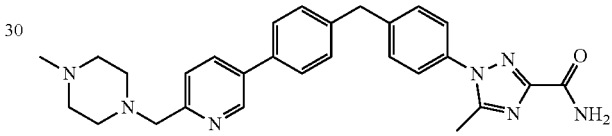

Step 1: Preparation of 1-((5-chloropyridin-2-yl)methyl)-4-methylpiperazine

5-Chloropicolinaldehyde (1.0 g, 7.1 mmol) was dissolved in DCE (10 mL) and 4 drops of acetic acid was added followed by NaBH(OAc)$_3$ (3.0 g, 14.1 mmol) and 1-methylpiperazine (0.71 g, 7.1 mmol). The reaction was stirred at RT for 18 h. After completion, the reaction mixture was diluted with water (20 mL) and extracted with EtOAc (3×20 mL). The combined organic layers were washed with brine (1×10 mL), dried over sodium sulfate, filtered and concentrated to afford 1-((5-chloropyridin-2-yl)methyl)-4-methylpiperazine (530 mg, 33%).

Step 2: Preparation of 5-methyl-1-(4-(4-(6-((4-methylpiperazin-1-yl)methyl)pyridin-3-yl)benzyl)phenyl)-1H-1,2,4-triazole-3-carboxamide Intermediate IX (200 mg, 0.48 mmol) and 1-((5-chloropyridin-2-yl)methyl)-4-methylpiperazine (107 mg, 0.48 mmol) were suspended in THF (1.8 mL) and water (0.6 mL).

Then K$_3$PO$_4$ (304 mg, 1.4 mmol) was added and the mixture was purged with nitrogen for 15 min. Then First generation Xphos Precatalyst (35 mg, 0.04 mmol) was added and the mixture was heated at 100° C. for 3 h. The reaction mixture was then filtered through ceilite and the filtrate was diluted with water (10 mL) and extracted with EtOAc (3×10 mL). The organic layer was dried over sodium sulfate, filtered and concentrated in vacuo. The crude material was purified by preparative HPLC to afford 5-methyl-1-(4-(4-(6-((4-methylpiperazin-1-yl)methyl)pyridin-3-yl)benzyl)phenyl)-1H-1,2,4-triazole-3-carboxamide. LC-MS Rt=1.01 min (Condition A), MS (M+1)=482.4.1H NMR (400 MHz, Methanol-d4) δ 8.75 (d, J=1.8 Hz, 1H), 8.08 (dd, J=8.1, 2.3 Hz, 1H), 7.68-7.59 (m, 3H), 7.57-7.52 (m, 2H), 7.49 (d, J=8.6 Hz, 2H), 7.42 (d, J=8.3 Hz, 2H), 4.17 (s, 2H), 3.74 (s, 2H), 2.82-2.42 (m, 11H), 2.34 (s, 3H).

Example 35

5-methyl-1-(4-(4-(5-(piperazin-1-ylmethyl)pyridin-2-yl)benzyl)phenyl)-1H-1,2,4-triazole-3-carboxamide

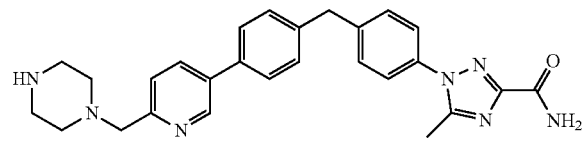

Step 1: Preparation of tert-butyl 4-((6-chloropyridin-3-yl)methyl)piperazine-1-carboxylate To a solution of 6-chloronicotinaldehyde (0.5 g, 2.68 mmol) and tert-butyl piperazine-1-carboxylate (0.6 g, 3.22 mmol) in DCE was added acetic acid (0.1 mL) and the reaction was stirred for 2 h at RT. Then NaBH(OAc)$_3$ (1.7 g, 8.1 mmol) was added to the reaction portion-wise at RT. The reaction was stirred at RT for 16 hours. The reaction mixture was then concentrated. The crude material was dissolved in water and basified to pH 8-9 using saturated aqueous NaHCO$_3$ solution. The mixture was extracted with EtOAc (2×25 mL). The combined organic layers were washed with water and brine, dried over sodium sulfate, filtered and concentrated in vacuo. The crude material was purified by preparative HPLC to afford tert-butyl 4-((6-chloropyridin-3-yl)methyl)piperazine-1-carboxylate (300 mg, 31% yield).

Step 2: Preparation of tert-butyl 4-((6-(4-(4-(3-carbamoyl-5-methyl-1H-1,2,4-triazol-1-yl)benzyl)phenyl)pyridin-3-yl)methyl)piperazine-1-carboxylate Intermediate IX (300 mg, 0.72 mmol) and tert-butyl 4-((5-chloropyridin-2-yl)methyl)piperazine-1-carboxylate (220 mg, 0.72 mmol) were taken up in THF (2.7 mL) and water (0.9 mL). Then K$_3$PO$_4$ (220 mg, 1.1 mmol) was added to the reaction mixture and purged with nitrogen for 15 min. First generation Xphos Precatalyst (53 mg, 0.07 mmol) was then added to reaction mixture and heated for 18 hours at 10° C. After completion, the reaction mixture was filtered through celite. The filtrate was diluted with water (20 mL) and ethyl acetate (50 mL). The layers were separated and the aqueous layer was extracted with ethyl acetate (3×30 mL). The combined organic layers were dried over sodium sulfate, filtered and concentrated. The crude product was purified by FCC to afford tert-butyl 4-((6-(4-(4-(3-carbamoyl-5-methyl-1H-1,2,4-triazol-1-yl)benzyl)phenyl)pyridin-3-yl)methyl)piperazine-1-carboxylate.

Step 3: Preparation of 5-methyl-1-(4-(4-(5-(piperazin-1-ylmethyl)pyridin-2-yl)benzyl)phenyl)-1H-1,2,4-triazole-3-carboxamide To the solution of tert-butyl 4-((5-(4-(4-(3-carbamoyl-5-methyl-1H-1,2,4-triazol-1-yl)benzyl)phenyl)pyridin-2-yl)methyl)piperazine-1-carboxylate (110 mg, 0.19 mmol) in dry DCM (10 mL) was added 4.0M HCl in 1,4-dioxane (1.0 mL) drop-wise at 0° C. under nitrogen atmosphere. The reaction was then stirred at 0° C. for 2-3 hours and progress was monitored on TLC. The reaction was concentrated and the crude material was purified by preparative HPLC to afford 5-methyl-1-(4-(4-(6-(piperazin-1-ylmethyl)pyridin-3-yl)benzyl)phenyl)-1H-1,2,4-triazole-3-carboxamide (50 mg, 30% yield). LC-MS Rt=0.47 min (Condition Q), MS (M+1)=468.3. $^1$H NMR (400 MHz, DMSO-d6) δ 8.80 (d, J=2.3 Hz, 1H), 8.05 (dd, J=8.2, 2.5 Hz, 1H), 7.86 (s, 1H), 7.68 (d, J=7.9 Hz, 2H), 7.63-7.56 (m, 3H), 7.55-7.48 (m, 3H), 7.44 (d, J=7.9 Hz, 2H), 4.12 (s, 2H), 3.65 (s, 2H), 2.92-2.87 (m, 4H), 2.48 (s, 3H).

Example 36

(S)-5-methyl-1-(4-(4-(6-((3-methylpiperazin-1-yl)methyl)pyridin-3-yl)benzyl)phenyl)-1H-1,2,4-triazole-3-carboxamide

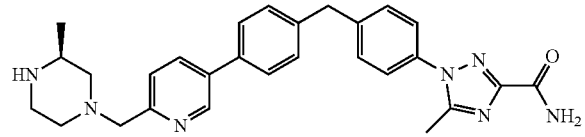 [SMILES: Cc1nc(C(N)=O)nn1-c1ccc(Cc2ccc(-c3ccc(CN4CCN[C@@H](C)C4)nc3)cc2)cc1]

Step 1: Preparation of tert-butyl (S)-4-((5-chloropyridin-2-yl)methyl)-2-methylpiperazine-1-carboxylate 5-Chloropicolinaldehyde (500 mg, 3.53 mmol) was dissolved in DCM (5 mL) and AcOH (0.5 mL, catalytic) and sodium cyanoborohydride (555 mg, 8.83 mmol) were added followed by tert-butyl (S)-2-methylpiperazine-1-carboxylate (706 mg, 3.53 mmol). The reaction mixture was stirred at RT for 2 h. The reaction was diluted with water (20 mL) and extracted with EtOAc (3×20 mL). The combined organic layers were washed with brine (20 mL), dried over sodium sulfate, filtered and concentrated. The crude material was purified by FCC to afford tert-butyl (S)-4-((5-chloropyridin-2-yl)methyl)-2-methylpiperazine-1-carboxylate (350 mg, 30%).

Step 2: Preparation of tert-butyl (S)-4-((5-(4-(4-(3-carbamoyl-5-methyl-1H-1,2,4-triazol-1-yl)benzyl)phenyl)pyridin-2-yl)methyl)-2-methylpiperazine-1-carboxylate Intermediate IX (0.2 mg, 0.47 mmol) and tert-butyl (S)-4-((5-chloropyridin-2-yl) methyl)-2-methyl piperazine-1-carboxylate (155 mg, 0.47 mmol) were suspended in THF (1.8 mL) and water (0.6 mL). K₃PO₄ (304 mg, 1.43 mmol) was added and the reaction mixture was purged with N₂ for 15 min. First generation Xphos Precatalyst (35 mg, 0.04 mmol) was added and the mixture was heated for 3 h at 10° C. After completion, the reaction mixture was filtered through celite and the filtrate was diluted with water (10 mL). The mixture was extracted with EtOAc (3×10 mL) and the combined organic layers were dried over sodium sulfate, filtered and concentrated to afford tert-butyl (S)-4-((5-(4-(4-(3-carbamoyl-5-methyl-1H-1,2,4-triazol-1-yl)benzyl)phenyl)pyridin-2-yl)methyl)-2-methyl piperazine-1-carboxylate (180 mg, 64%), which was used without further purification.

Step 3: Preparation of (S)-5-methyl-1-(4-(4-(6-((3-methylpiperazin-1-yl)methyl)pyridin-3-yl)benzyl)phenyl)-1H-1,2,4-triazole-3-carboxamide To the stirred solution of tert-butyl (S)-4-((5-(4-(4-(3-carbamoyl-5-methyl-1H-1,2,4-triazol-1-yl)benzyl)phenyl)pyridin-2-yl)methyl)-2-methylpiperazine-1-carboxylate (180 mg, 0.30 mmol) in dry DCM (5 mL) was added 4M HCl in 1,4-dioxane (5 mL) at 0° C. Then reaction was allowed to stir for 3 h at RT. Progress of reaction was monitored by TLC and LCMS. Upon completion, the reaction was concentrated and the crude material was purified by preparative HPLC to afford (S)-5-methyl-1-(4-(4-(6-((3-methylpiperazin-1-yl)methyl)pyridin-3-yl)benzyl)phenyl)-1H-1,2,4-triazole-3-carboxamide (25 mg). LC-MS Rt=0.48 min (Condition Q), MS (M+1)=482.4. ¹H NMR (400 MHz, DMSO-d6) δ 8.78 (s, 1H), 8.04-8.02 (d, J=8.0 Hz, 1H), 7.85 (s, 1H), 7.69-7.67 (d, J=8 Hz, 2H), 7.59-7.56 (d, J=12 Hz, 3H), 7.51-7.49 (d, J=12 Hz, 3H), 7.44-7.42 (d, J=8.0 Hz, 2H), 4.12 (s, 2H), 3.60 (s, 2H), 2.85-2.83 (m, 1H), 2.80-2.65 (m, 4H), 2.21-2.17 (m, 3H), 2.10-1.95 (m, 1H), 1.75-1.65 (m, 1H), 0.94-0.92 (m, 3H).

Example 37

(S)-1-(4-(4-(6-((3,4-dimethylpiperazin-1-yl)methyl)pyridin-3-yl)benzyl)phenyl)-5-methyl-1H-1,2,4-triazole-3-carboxamide (S)-5-Methyl-1-(4-(4-(6-((3-methylpiperazin-1-yl)methyl)pyridin-3-yl)benzyl)phenyl)-1H-1,2,4-triazole-3-carboxamide (Example 36) (50 mg, 0.01 mmol) was dissolved in MeOH (2 mL) and formaldehyde (0.02 mL, 0.02 mmol) was added. The reaction was stirred for 1-2 h at RT. NaBH(OAc)₃ (60 mg, 0.031 mmol) was added portion-wise at RT and stirred at RT for the 16 h. Progress of the reaction was monitored by TLC. The reaction was concentrated, dissolved in water and basified to pH 8-9 using saturated aqueous NaHCO₃ solution. The compound was extracted with EtOAc (2×25 mL). The combined organic layers were washed with water, brine, dried over sodium sulfate, filtered and concentrated. The crude material was purified by preparative HPLC to afford ((S)-1-(4-(4-(6-((3,4-dimethylpiperazin-1-yl)methyl)pyridin-3-yl)benzyl)phenyl)-5-methyl-1H-1,2,4-triazole-3-carboxamide. LC-MS Rt=0.48 min (Condition Q), MS (M+1)=496.3. ¹H NMR (400 MHz, Methanol-d₄) δ 8.75 (d, J=2.6 Hz, 1H), 8.08 (dd, J=6.6, 4.2 Hz, 1H), 7.66-7.60 (m, 3H), 7.56-7.51 (m, 3H), 7.49-7.42 (m, 3H), 4.18 (s, 2H), 3.72 (s, 2H), 2.91-2.75 (m, 3H), 2.60-48 (m, 3H), 2.41-2.32 (m, 5H), 2.15-1.98 (m, 2H), 1.25-1.00 (m, 3H).

Example 38-1

1-(4-((4'-((2-oxa-6-azaspiro[3.4]octan-6-yl)methyl)-[1,1'-biphenyl]-4-yl)methyl)phenyl)-5-methyl-1H-1,2,4-triazole-3-carboxamide

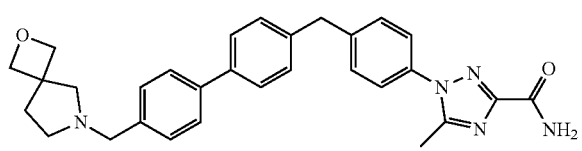 [SMILES: Cc1nc(C(N)=O)nn1-c1ccc(Cc2ccc(-c3ccc(CN4CCC5(COC5)C4)cc3)cc2)cc1]

Step 1: Preparation of 6-(4-bromobenzyl)-2-oxa-6-azaspiro[3.4]octane

To a solution of 4-bromobenzyl bromide (44 mg, 1.76 mmol) and 2-oxa-6-azaspiro[3.4]octane (100 mg, 0.884 mmol) in THF (4.0 mL) was added TEA (268 mg, 2.654 mmol). The reaction mixture was heated at 80° C. for 4 hours. The reaction was filtered and the filtrate was diluted with water (10 mL) and extracted with EtOAc (3×10 mL). The combined organic layers were washed with brine (10 mL) then dried over sodium sulfate, filtered and concentrated to afford 6-(4-bromobenzyl)-2-oxa-6-azaspiro[3.4]octane (168 mg, 67%), which was used without further purification.

Step 2: Preparation of 1-(4-((4'-((2-oxa-6-azaspiro[3.4]octan-6-yl)methyl)-[1,1'-biphenyl]-4-yl)methyl)phenyl)-5-methyl-1H-1,2,4-triazole-3-carboxamide 6-(4-Bromobenzyl)-2-oxa-6-azaspiro[3.4]octane (168 mg, 0.59 mmol), Intermediate IX (250 mg, 0.59 mmol) and K₃PO₄ (380 mg, 1.79 mmol) were suspended in THF (2.2 mL) and water (0.75 mL). The mixture was purged with N₂ for 15 min. followed by addition of PdCl₂.dppf.DCM (adduct) (49 mg, 0.05 mmol). The reaction was heated for 18 h at 100° C. After completion, the reaction mixture was filtered through celite. The filtrate was diluted with water (20 mL) and EtOAc (20 mL) and the layers were separated. The aqueous layer was extracted with EtOAc (3×20 mL), dried over sodium sulfate, filtered and concentrated. The crude material was purified by preparative HPLC to afford 1-(4-((4'-((2-oxa-6-azaspiro[3.4]octan-6-yl)methyl)-[1,1'-biphenyl]-4-yl)methyl)phenyl)-5-methyl-1H-1,2,4-triazole-3-carboxamide (30 mg). LC-MS Rt=0.49 min (Condition Q), MS (M+1)=494.5. ¹H NMR (400 MHz, DMSO-d₆) δ 8.17 (s, 1H), 7.85 (s, 1H), 7.63-7.56 (m, 6H), 7.51-7.48 (m, 2H), 7.39-7.36 (m, 4H), 4.50-4.46 (m, 4H), 4.10 (s, 2H), 3.59 (s, 2H), 2.75 (s, 2H), 2.56-2.51 (m, 5H), 2.48-2.46 (m, 2H).

Examples 38-2 to 38-10

The following compounds were prepared using a similar procedure to Example 38-1.

| Example | Compound | LCMS M + 1, Rt, conditions | ¹H NMR, 400 MHz |
|---|---|---|---|
| 38-2 | 1-(4-((4'-((3,3-difluoropyrrolidin-1-yl)methyl-[1,1'-biphenyl]-4-yl)methyl)phenyl)-5-methyl-1H-1,2,4-triazole-3-carboxamide | 488.4<br>0.61 min<br>Q | (DMSO-d6) δ 7.86 (s, 1H), 7.68-7.55 (m, 7H), 7.52-7.45 (m, 2H), 7.41-7.32 (m, 4H), 4.10 (s, 2H), 3.66 (s, 2H), 2.88 (t, J = 13.3 Hz, 2H), 2.72 (t, J = 7.0 Hz, 2H), 2.48 (s, 3H), 2.32-2.20 (m, 2H). |
| 38-3 | 5-methyl-1-(4-((4'-(((3aR,6aS)-5-methylhexahydropyrrolo[3,4-c]pyrrol-2(1H)-yl)methyl-[1,1'-biphenyl]-4-yl)methyl)phenyl)-1H-1,2,4-triazole-3-carboxamide | 507.4<br>0.45 min<br>Q | (DMSO-d6) δ 7.87 (s, 1H), 7.66-7.55 (m, 7H), 7.50 (d, J = 8.2 Hz, 2H), 7.38 (dd, J = 8.3, 2.8 Hz, 4H), 4.10 (s, 2H), 3.57 (s, 2H), 2.65-2.56 (m, 4H), 2.49 (s, 3H), 2.26 (d, J = 4.4 Hz, 7H). |
| 38-4 | 1-(4-((4'-((2-oxa-6-azaspiro[3.3]heptan-6-yl)methyl)-[1,1'-biphenyl]-4-yl)methyl)phenyl)-5-methyl-1H-1,2,4-triazole-3-carboxamide | 480.5<br>0.48 min<br>Q | (DMSO-d6) δ 7.84 (s, 1H), 7.63-7.53 (m, 7H), 7.49 (d, J = 8.3 Hz, 2H), 7.34 (dd, J = 26.9, 7.9 Hz, 2H), 7.31-7.29 (m, 2H), 4.61 (s, 4H), 4.09 (s, 2H), 3.51 (s, 2H), 3.29 (s, 4H), 2.47 (s, 3H). |
| 38-5 | (R)-1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide | 482.4<br>0.49 min<br>Q | (Methanol-d4) δ 7.60 (d, J = 7.8 Hz, 4H), 7.54 (d, J = 8.4 Hz, 4H), 7.47 (dd, J = 17.3, 8.1 Hz, 2H), 7.36 (d, J = 8.0 Hz, 2H), 4.20-4.10 (m, 4H), 3.68-3.63 (m, 1H), 3.59-3.47 (m, 2H), 3.02-2.93 (m, 1H), 2.80-2.70 (m, 1H), 2.55 (s, 3H), 2.45-2.30 (m, 1H), 2.05-1.95 (m, 1H), 1.81-1.65 (m, 2H). |
| 38-6 | 1-(4-((4'-((2-oxa-6-azaspiro[3.5]nonan-6-yl)methyl)-[1,1'-biphenyl]-4-yl)methyl)phenyl)-5-methyl-1H-1,2,4-triazole-3-carboxamide | 508.4<br>0.50 min<br>Q | (DMSO-d6) δ 7.85 (s, 1H), 7.63-7.56 (m, 7H), 7.51-7.48 (m, 2H), 7.39-7.36 (m, 4H), 4.50-4.46 (m, 4H), 4.10 (s, 2H), 3.59 (s, 2H), 2.52-2.48 (s, 3H), 2.35-2.25 (m, 2H), 1.70-1.59 (m, 2H), 1.50-1.40 (m, 2H). |

| Example | Compound | LCMS M + 1, Rt, conditions | ¹H NMR, 400 MHz |
|---|---|---|---|
| 38-7 | 1-(4-((4'-((3,3-dimethylpyrrolidin-1-yl)methyl)-[1,1'-biphenyl]-4-yl)methyl)phenyl)-5-methyl-1H-1,2,4-triazole-3-carboxamide | 480.5 0.52 min Q | (DMSO-d6) δ 7.86 (s, 1H), 7.63-7.59 (m, 7H), 7.51-7.49 (d, J = 8 Hz, 2H), 7.39-7.37 (m, 4H), 4.10 (s, 2H), 3.58 (s, 2H), 2.65-2.28 (m, 5H), 2.34-2.26 (s, 2H), 1.60 (s, 6H), 1.55-1.52 (t, 2H). |
| 38-8 | 1-(4-((4'-((2-oxa-7-azaspiro[3.5]nonan-7-yl)methyl)-[1,1'-biphenyl]-4-yl)methyl)phenyl)-5-methyl-1H-1,2,4-triazole-3-carboxamide | 508.4 0.49 min Q | (DMSO-d6) δ 7.87 (s, 1H), 7.63-7.59 (m, 7H), 7.51-7.48 (d, J = 8.2 Hz, 2H), 7.39-7.35 (t, J = 8.2 Hz, 4H), 4.28 (s, 4H), 4.10 (s, 2H), 3.43-3.41 (d, J = 16.1 Hz, 2H), 2.48 (s, 3H), 2.40-2.15 (m, 4H), 1.85-1.70 (m, 4H). |
| 38-9 | 1-(4-((4'-((3,3-difluoropiperidin-1-yl)methyl)-[1,1'-biphenyl]-4-yl)methyl)phenyl)-5-methyl-1H-1,2,4-triazole-3-carboxamide | 502.4 0.60 min Q | (DMSO-d6) δ 7.86 (s, 1H), 7.66-7.53 (m, 5H), 7.49 (d, J = 8.3 Hz, 4H), 7.38 (dd, J = 8.2, 4.2 Hz, 4H), 4.10 (s, 2H), 3.60 (s, 2H), 2.63 (t, J = 11.7 Hz, 2H), 2.48 (s, 5H), 1.88 (dt, J = 14.1, 7.4 Hz, 2H), 1.66 (s, 2H). |
| 38-10 | 1-(4-((4'-((4,4-dimethylpiperidin-1-yl)methyl)-[1,1'-biphenyl]-4-yl)methyl)phenyl)-5-methyl-1H-1,2,4-triazole-3-carboxamide | 494.5 0.53 min Q | (DMSO-d6) δ 7.87 (s, 1H), 7.63-7.57 (m, 7H), 7.51-7.49 (m, 2H), 7.39-7.35 (m, 4H), 4.10 (s, 2H), 3.50 (s, 2H), 2.48 (s, 3H), 2.35-2.25 (m, 4H), 1.35-1.25 (m, 4H), 0.90 (s, 6H). |

Example 39-1

1-(4-((4'-((4-((dimethylamino)methyl)piperidin-1-yl)methyl)-[1,1'-biphenyl]-4-yl)methyl)phenyl)-5-methyl-1H-1,2,4-triazole-3-carboxamide

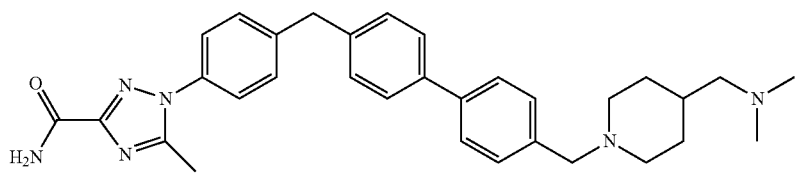 [SMILES: Cc1nc(C(N)=O)nn1-c1ccc(Cc2ccc(-c3ccc(CN4CCC(CN(C)C)CC4)cc3)cc2)cc1]

Step 1: Preparation of 1-(4-((4'-(hydroxymethyl)-[1,1'-biphenyl]-4-yl)methyl)phenyl)-5-methyl-1H-1,2,4-triazole-3-carboxamide 1-(4-(4-Bromobenzyl)phenyl)-5-methyl-1H-1,2,4-triazole-3-carboxamide, Intermediate XII, (1.0 g, 2.69 mmol) and (4-(hydroxymethyl)phenyl)boronic acid (0.491 g, 3.23 mmol) were reacted according to General Method I for Suzuki coupling to afford crude 1-(4-((4'-(hydroxymethyl)-[1,1'-biphenyl]-4-yl)methyl)phenyl)-5-methyl-1H-1,2,4-triazole-3-carboxamide (1.01 g) LC-MS Rt=0.86 min (Condition B), MS (M+3)=299.3.

Step 2: Preparation of 1-(4-((4'-(bromomethyl)-[1,1'-biphenyl]-4-yl)methyl)phenyl)-5-methyl-1H-1,2,4-triazole-3-carboxamide To a solution of 1-(4-((4'-(hydroxymethyl)-[1,1'-biphenyl]-4-yl)methyl)phenyl)-5-methyl-1H-1,2,4-triazole-3-carboxamide (2.15 g, 5.40 mmol) in THF (10.8 mL) at 00° C. was added phosphorus tribromide (0.51 mL, 5.40 mmol) dropwise. The resulting mixture was stirred at 00° C. for 2 h. The reaction was quenched with water and extracted with ethyl acetate. The organic layer was separated, dried over sodium sulfate and concentrated in vacuo. The resulting crude material was purified by FCC to afford 1-(4-((4'-(bromomethyl)-[1,1'-biphenyl]-4-yl)methyl)phenyl)-5-methyl-1H-1,2,4-triazole-3-carboxamide (2.0 g, 80%) LC-MS Rt=1.13 min (Condition A), MS (M+3)=463.3.

Step 3: Preparation of 1-(4-((4'-((4-((dimethylamino)methyl)piperidin-1-yl)methyl)-[1,1'-biphenyl]-4-yl)methyl)phenyl)-5-methyl-1H-1,2,4-triazole-3-carboxamide To a mixture of N,N-dimethyl-1-(piperidin-4-yl)methanamine (14.5 mg, 0.102 mmol) in DMF (0.43 mL) was added 1-(4-((4'-(bromomethyl)-[1,1'-biphenyl]-4-yl)methyl)phenyl)-5-methyl-1H-1,2,4-triazole-3-carboxamide (39 mg, 0.085 mmol) and potassium carbonate (35 mg, 0.255 mmol). The resulting suspension was heated at 75° C. for 18 h. The reaction mixture was then diluted with acetonitrile (3 mL) and filtered through a solid phase extraction filter. The filtrate was concentrated in vacuo to afford crude product which was purified by preparative HPLC to afford 1-(4-((4'-((4-((dimethylamino)methyl)piperidin-1-yl)methyl)-[1,1'-biphenyl]-4-yl)methyl)phenyl)-5-methyl-1H-1,2,4-triazole-3-carboxamide (9.6 mg, 21%) LC-MS Rt=0.99 min (Condition A), MS (M+1)=523.2. $^1$H NMR (400 MHz, DMSO-$d_6$) δ 7.83 (s, 1H), 7.64-7.32 (m, 13H), 4.09 (s, 2H), 3.46 (s, 2H), 2.83-2.76 (m, 2H), 2.48-2.46 (m, 3H), 2.15-2.06 (m, 6H), 2.06-2.00 (m, 2H), 1.91 (t, J=11.3 Hz, 2H), 1.68-1.61 (m, 2H), 1.48-1.34 (m, 1H), 1.18-1.01 (m, 2H).

Example 39-2 to 39-38

The following compounds were prepared using a similar procedure to Example 39-1

| Example | Compound | LCMS M + 1, Rt, conditions | $^1$H NMR, 400 MHz |
|---|---|---|---|
| 39-2 | 1-(4-((4'-((4-(dimethylamino)piperidin-1-yl)methyl)-[1,1'-biphenyl]-4-yl)methyl)phenyl)-5-methyl-1H-1,2,4-triazole-3-carboxamide | 509.4<br>0.98 min<br>A | (DMSO-d6) δ 7.83 (s, 1H), 7.63-7.33 (m, 13H), 4.09 (s, 2H), 3.45 (s, 2H), 2.87-2.79 (m, 2H), 2.47 (s, 3H), 2.14 (s, 6H), 2.06-1.96 (m, 1H), 1.96-1.88 (m, 2H), 1.74-1.65 (m, 2H), 1.38 (td, J = 12.0, 3.6 Hz, 2H). |
| 39-3 | 1-(4-((4'-((4-(2-hydroxypropan-2-yl)piperidin-1-yl)methyl-[1,1'-biphenyl]-4-yl)methyl)phenyl)-5-methyl-1H-1,2,4-triazole-3-carboxamide | 524.5<br>0.51 min<br>Q | (DMSO-d6) δ 7.83 (s, 1H), 7.64-7.52 (m, 7H), 7.52-7.45 (m, 2H), 7.41-7.31 (m, 4H), 4.09 (s, 2H), 3.44 (s, 2H), 2.95-2.81 (m, 2H), 2.47 (s, 3H), 1.92-1.77 (m, 2H), 1.70-1.57 (m, 2H), 1.32-1.10 (m, 3H), 1.02 (s, 6H). |

-continued

| Example | Compound | LCMS M + 1, Rt, conditions | ¹H NMR, 400 MHz |
|---|---|---|---|
| 39-4 | 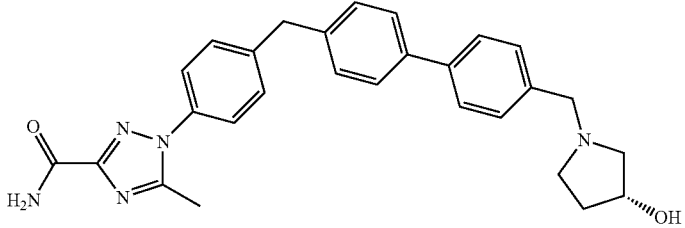<br>(R)-1-(4-((4'-((3-hydroxypyrrolidin-1-yl)methyl)-[1,1'-biphenyl]-4-yl)methyl)phenyl)-5-methyl-1H-1,2,4-triazole-3-carboxamide | 468.4<br>0.50 min<br>Q | (DMSO-d6) δ 7.83 (s, 1H), 7.66-7.32 (m, 13H), 4.80-4.59 (m, 1H), 4.26-4.14 (m, 1H), 4.09 (s, 2H), 3.73-3.46 (m, 2H), 3.29 (s, 1H), 2.76-2.65 (m, 1H), 2.65-2.54 (m, 1H), 2.47 (s, 3H), 2.39-2.29 (m, 1H), 2.09-1.92 (m, 1H), 1.63-1.46 (m, 1H). |
| 39-5 | 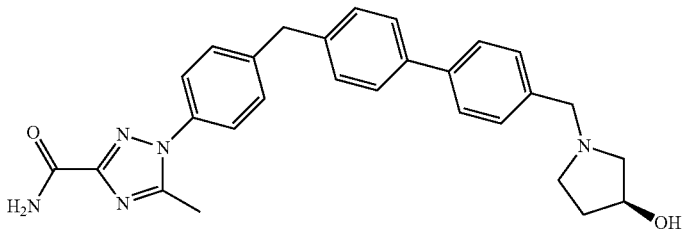<br>(S)-1-(4-((4'-((3-hydroxypyrrolidin-1-yl)methyl)-[1,1'-biphenyl]-4-yl)methyl)phenyl)-5-methyl-1H-1,2,4-triazole-3-carboxamide | 468.4<br>0.49 min<br>Q | (DMSO-d6) δ 7.83 (s, 1H), 7.63-7.33 (m, 13H), 4.67 (d, J = 4.4 Hz, 1H), 4.24-4.15 (m, 1H), 4.09 (s, 2H), 3.64-3.51 (m, 2H), 2.72-2.64 (m, 1H), 2.64-2.53 (m, 1H), 2.47 (s, 3H), 2.44-2.37 (m, 1H), 2.36-2.27 (m, 1H), 2.05-1.93 (m, 1H), 1.59-1.47 (m, 1H). |
| 39-6 | 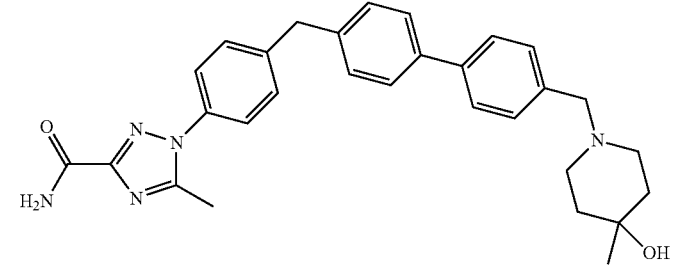<br>1-(4-((4'-((4-hydroxy-4-methylpiperidin-1-yl)methyl)-[1,1'-biphenyl]-4-yl)methyl)phenyl)-5-methyl-1H-1,2,4-triazole-3-carboxamide | 496.5<br>0.49 min<br>Q | N/A |
| 39-7 | 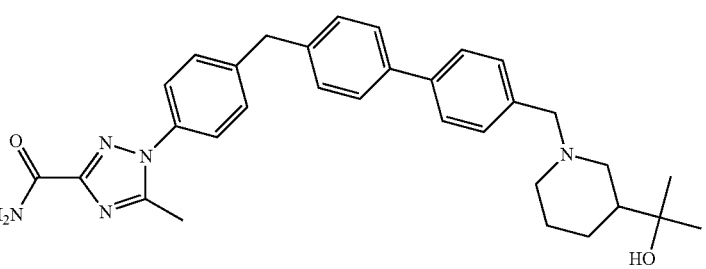<br>1-(4-((4'-((3-(2-hydroxypropan-2-yl)piperidin-1-yl)methyl-[1,1'-biphenyl]-4-yl)methyl)phenyl)-5-methyl-1H-1,2,4-triazole-3-carboxamide | 524.5<br>0.51 min<br>Q | N/A |

| Example | Compound | LCMS M + 1, Rt, conditions | ¹H NMR, 400 MHz |
|---|---|---|---|
| 39-8 | 1-(4-((4'-((3-hydroxyazetidin-1-yl)methyl)-[1,1'-biphenyl]-4-yl)methyl)phenyl)-5-methyl-1H-1,2,4-triazole-3-carboxamide | 454.4<br>0.49 min<br>Q | N/A |
| 39-9 | 1-(4-((4'-(((3R,5R)-3,5-dimethylpiperazin-1-yl)methyl)-[1,1'-biphenyl]-4-yl)methyl)phenyl)-5-methyl-1H-1,2,4-triazole-3-carboxamide | 495.4<br>0.54 min<br>Q | N/A |
| 39-10 | 1-(4-((4'-((3-hydroxy-3-methylpyrrolidin-1-yl)methyl)-[1,1'-biphenyl]-4-yl)methyl)phenyl)-5-methyl-1H-1,2,4-triazole-3-carboxamide | 482.4<br>0.50 min<br>Q | N/A |

-continued

| Example | Compound | LCMS M + 1, Rt, conditions | ¹H NMR, 400 MHz |
|---|---|---|---|
| 39-11 | 1-(4-((4'-((5-oxa-2-azaspiro[3.4]octan-2-yl)methyl)-[1,1'-biphenyl]-4-yl)methyl)phenyl)-5-methyl-1H-1,2,4-triazole-3-carboxamide | 494.4 0.51 min Q | N/A |
| 39-12 | (R)-1-(4-((4'-((3-(hydroxymethyl)piperazin-1-yl)methyl)-[1,1'-biphenyl]-4-yl)methyl)phenyl)-5-methyl-1H-1,2,4-triazole-3-carboxamide | 497.4 0.51 min Q | N/A |
| 39-13 | (R)-1-(4-((4'-((3-fluoropyrrolidin-1-yl)methyl)-[1,1'-biphenyl]-4-yl)methyl)phenyl)-5-methyl-1H-1,2,4-triazole-3-carboxamide | 470.4 0.50 min Q | N/A |

| Example | Compound | LCMS M + 1, Rt, conditions | ¹H NMR, 400 MHz |
|---|---|---|---|
| 39-14 | 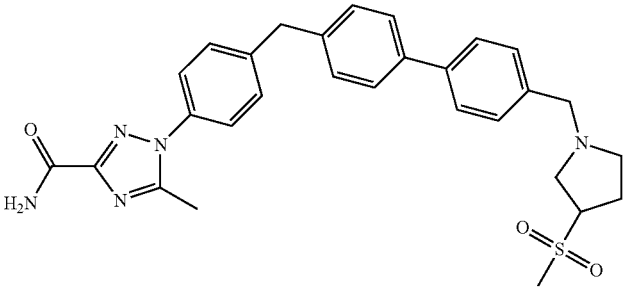<br>5-methyl-1-(4-((4'-((3-(methylsulfonyl)pyrrolidin-1-yl)methyl)-[1,1'-biphenyl]-4-yl)methyl)phenyl)-1H-1,2,4-triazole-3-carboxamide | 530.4<br>0.50 min<br>Q | N/A |
| 39-15 | 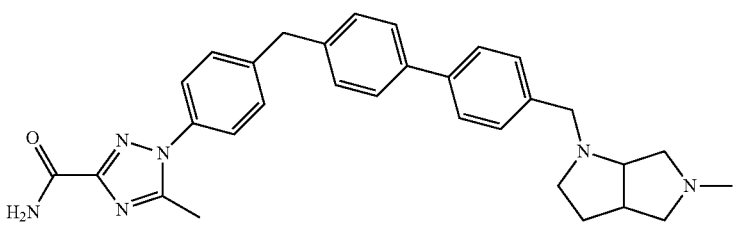<br>5-methyl-1-(4-((4'-((5-methylhexahydropyrrolo[3,4-b]pyrrol-1(2H)-yl)methyl)-[1,1'-biphenyl]-4-yl)methyl)phenyl)-1H-1,2,4-triazole-3-carboxamide | 507.4<br>0.52 min<br>Q | N/A |
| 39-16 | 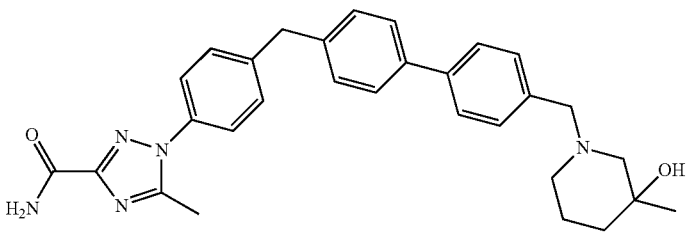<br>1-(4-((4'-((3-hydroxy-3-methylpiperidin-1-yl)methyl)-[1,1'-biphenyl]-4-yl)methyl)phenyl)-5-methyl-1H-1,2,4-triazole-3-carboxamide | 496.4<br>0.50 min<br>Q | (Methanol-d4) δ 7.56 (d, J = 8.2 Hz, 4H), 7.53-7.49 (m, 2H), 7.46 (d, J = 8.5 Hz, 2H), 7.40 (d, J = 8.1 Hz, 2H), 7.32 (d, J = 8.2 Hz, 2H), 4.12 (s, 2H), 3.56 (s, 2H), 2.58 (s, 1H), 2.52 (s, 3H), 2.46-2.12 (m, 3H), 1.80 (s, 1H), 1.66-1.37 (m, 3H), 1.17 (s, 3H). |

-continued

| Example | Compound | LCMS M + 1, Rt, conditions | ¹H NMR, 400 MHz |
|---|---|---|---|
| 39-17 | 1-(4-((4'-((4-(tert-butyl)piperazin-1-yl)methyl)-[1,1'-biphenyl]-4-yl)methyl)phenyl)-5-methyl-1H-1,2,4-triazole-3-carboxamide | 523.5 0.53 min Q | (Methanol-d4) δ 7.60-7.54 (m, 4H), 7.53-7.48 (m, 2H), 7.45 (d, J = 8.5 Hz, 2H), 7.39 (d, J = 8.2 Hz, 2H), 7.32 (d, J = 8.2 Hz, 2H), 4.11 (s, 2H), 3.56 (s, 2H), 2.77-2.45 (m, 8H), 2.51 (s, 3H), 1.09 (s, 9H). |
| 39-18 | 1-(4-((4'-((3,3-dimethylpiperazin-1-yl)methyl)-[1,1'-biphenyl]-4-yl)methyl)phenyl)-5-methyl-1H-1,2,4-triazole-3-carboxamide | 495.5 0.54 min Q | (Methanol-d4) δ 7.58-7.53 (m, 4H), 7.53-7.49 (m, 2H), 7.46 (d, J = 8.5 Hz, 2H), 7.38 (d, J = 8.2 Hz, 2H), 7.32 (d, J = 8.2 Hz, 2H), 4.11 (s, 2H), 3.49 (s, 2H), 2.89 (d, J = 4.9 Hz, 2H), 2.51 (s, 3H), 2.30 (d, J = 92.1 Hz, 4H), 1.15 (s, 6H). |
| 39-19 | 1-(4-((4'-(((3R,5R)-3,5-dimethylpiperazin-1-yl)methyl)-[1,1'-biphenyl]-4-yl)methyl)phenyl)-5-methyl-1H-1,2,4-triazole-3-carboxamide | 495.4 0.53 min Q | (Methanol-d4) δ 7.57 (dd, J = 8.3, 2.3 Hz, 4H), 7.51 (d, J = 8.5 Hz, 2H), 7.46 (d, J = 8.5 Hz, 2H), 7.38 (d, J = 8.2 Hz, 2H), 7.32 (d, J = 8.2 Hz, 2H), 4.11 (s, 2H), 3.55 (s, 2H), 2.97-2.85 (m, 2H), 2.81 (d, J = 11.6 Hz, 2H), 2.51 (s, 3H), 1.68 (t, J = 10.9 Hz, 2H), 1.04 (d, J = 6.4 Hz, 6H). |

| Example | Compound | LCMS M + 1, Rt, conditions | ¹H NMR, 400 MHz |
|---|---|---|---|
| 39-20 | 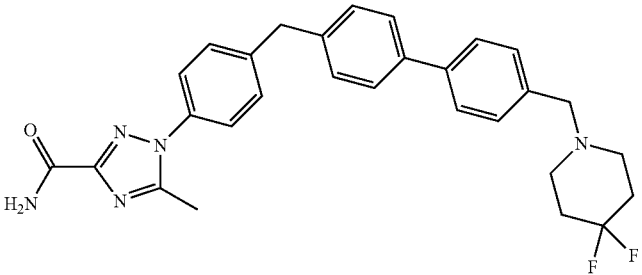<br>1-(4-((4'-((4,4-difluoropiperidin-1-yl)methyl)-[1,1'-biphenyl]-4-yl)methyl)phenyl)-5-methyl-1H-1,2,4-triazole-3-carboxamide | 502.5<br>0.53 min<br>Q | (Methanol-d4) δ 7.60-7.54 (m, 4H), 7.54-7.49 (m, 2H), 7.46 (d, J = 8.6 Hz, 2H), 7.40 (d, J = 8.2 Hz, 2H), 7.32 (d, J = 8.2 Hz, 2H), 4.12 (s, 2H), 3.60 (s, 2H), 2.58 (d, J = 5.6 Hz, 4H), 2.51 (s, 3H), 1.98-2.01 (m, 4H). |
| 39-21 | 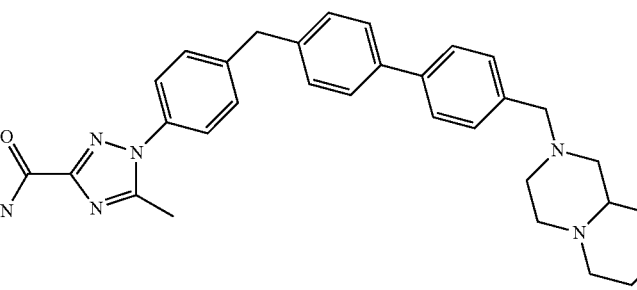<br>5-methyl-1-(4-((4'-((octahydro-2H-pyrido[1,2-a]pyrazin-2-yl)methyl)-[1,1'-biphenyl]-4-yl)methyl)phenyl)-1H-1,2,4-triazole-3-carboxamide | 521.5<br>0.53 min<br>Q | (Methanol-d4) δ 7.59-7.54 (m, 4H), 7.52-7.48 (m, 2H), 7.45 (d, J = 8.5 Hz, 2H), 7.38 (d, J = 8.2 Hz, 2H), 7.32 (d, J = 8.2 Hz, 2H), 4.11 (s, 2H), 3.55 (s, 2H), 2.83 (t, J = 9.5 Hz, 2H), 2.76-2.69 (m, 2H), 2.51 (s, 3H), 2.39-2.21 (m, 2H), 2.13-2.01 (m, 2H), 1.90 (t, J = 10.8 Hz, 1H), 1.80-1.43 (m, 4H), 1.41-1.12 (m, 2H). |
| 39-22 | 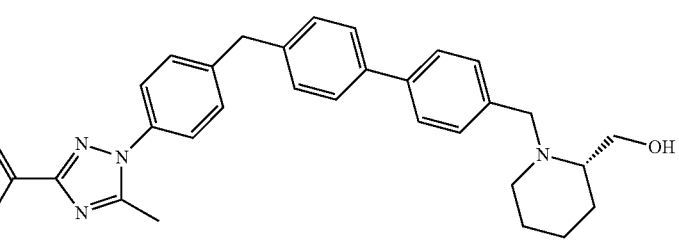<br>(S)-1-(4-((4'-((2-(hydroxymethyl)piperidin-1-yl)methyl)-[1,1'-biphenyl]-4-yl)methyl)phenyl)-5-methyl-1H-1,2,4-triazole-3-carboxamide | 496.4<br>0.50 min<br>Q | (Methanol-d4) δ 7.60-7.37 (m, 10H), 7.35-7.28 (m, 2H), 4.16 (d, J = 13.3 Hz, 1H), 4.11 (s, 2H), 3.86-3.66 (m, 2H), 3.38 (d, J = 13.3 Hz, 1H), 2.88-2.78 (m, 1H), 2.51 (s, 3H), 2.42-2.32 (m, 1H), 2.14-2.03 (m, 1H), 1.84-1.67 (m, 2H), 1.63-1.24 (m, 4H). |

| Example | Compound | LCMS M + 1, Rt, conditions | ¹H NMR, 400 MHz |
|---|---|---|---|
| 39-23 | 1-(4-((4'-((4-(hydroxymethyl)piperidin-1-yl)methyl)-[1,1'-biphenyl]-4-yl)methyl)phenyl)-5-methyl-1H-1,2,4-triazole-3-carboxamide | 496.4 0.49 min Q | N/A |
| 39-24 | 1-(4-((4'-((3-hydroxy-3-methylazetidin-1-yl)methyl)-[1,1'-biphenyl]-4-yl)methyl)phenyl)-5-methyl-1H-1,2,4-triazole-3-carboxamide | 468.4 0.49 min Q | N/A |
| 39-25 | 1-(4-((4'-((4-hydroxypiperidin-1-yl)methyl)-[1,1'-biphenyl]-4-yl)methyl)phenyl)-5-methyl-1H-1,2,4-triazole-3-carboxamide | 482.4 0.49 min Q | N/A |

| Example | Compound | LCMS M + 1, Rt, conditions | ¹H NMR, 400 MHz |
|---|---|---|---|
| 39-26 | 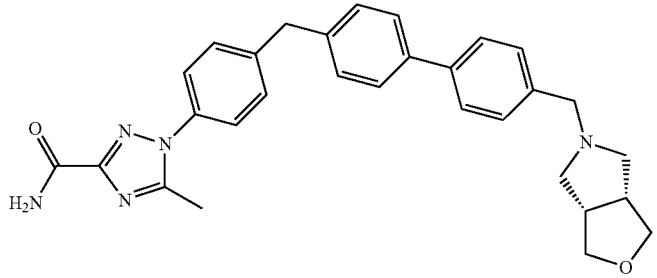
5-methyl-1-(4-((4'-(((3aR,6aS)-tetrahydro-1H-furo[3,4-c]pyrrol-5(3H)-yl)methyl-[1,1'-biphenyl]-4-yl)methyl)phenyl)-1H-1,2,4-triazole-3-carboxamide | 494.4
0.49 min
Q | N/A |
| 39-27 | 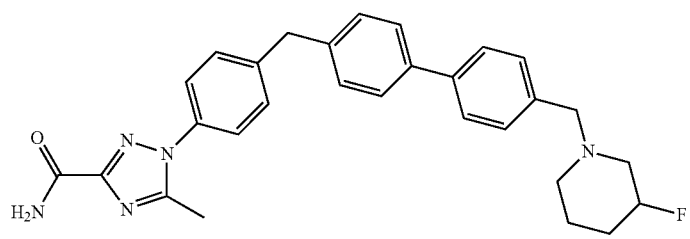
1-(4-((4'-((3-fluoropiperidin-1-yl)methyl)-[1,1'-biphenyl]-4-yl)methyl)phenyl)-5-methyl-1H-1,2,4-triazole-3-carboxamide | 484.4
0.50 min
Q | N/A |
| 39-28 | 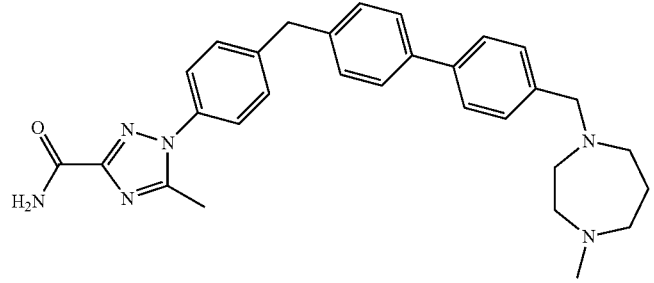
5-methyl-1-(4-((4'-((4-methyl-1,4-diazepan-1-yl)methyl)-[1,1'-biphenyl]-4-yl)methyl)phenyl)-1H-1,2,4-triazole-3-carboxamide | 495.4
0.48 min
Q | N/A |

| Example | Compound | LCMS M + 1, Rt, conditions | ¹H NMR, 400 MHz |
|---|---|---|---|
| 39-29 | 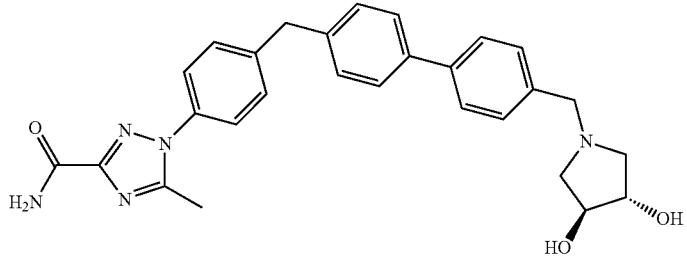<br>1-(4-((4'-(((3S,4S)-3,4-dihydroxypyrrolidin-1-yl)methyl)-[1,1'-biphenyl]-4-yl)methyl)phenyl)-5-methyl-1H-1,2,4-triazole-3-carboxamide | 484.4<br>0.49 min<br>Q | N/A |
| 39-30 | 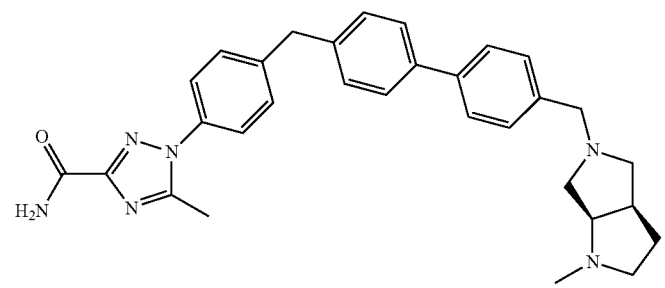<br>5-methyl-1-(4-((4'-(((3aR,6aR)-1-methylhexahydropyrrolo[3,4-b]pyrrol-5-(1H)-yl)methyl)-[1,1'-biphenyl]-4-yl)methyl)phenyl)-1H-1,2,4-triazole-3-carboxamide | 507.4<br>0.52 min<br>Q | N/A |
| 39-31 | 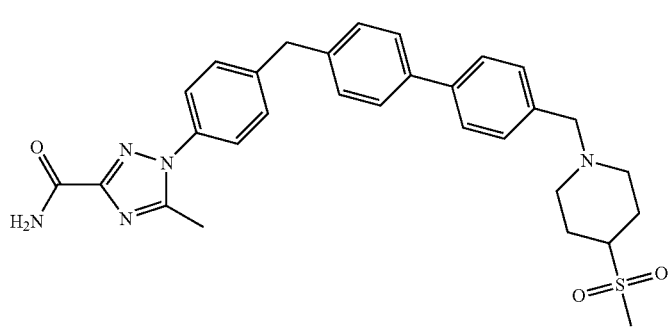<br>5-methyl-1-(4-((4'-((4-(methylsulfonyl)piperidin-1-yl)methyl)-[1,1'-biphenyl]-4-yl)methyl)phenyl)-1H-1,2,4-triazole-3-carboxamide | 544.4<br>0.49 min<br>Q | N/A |

| Example | Compound | LCMS M + 1, Rt, conditions | ¹H NMR, 400 MHz |
|---|---|---|---|
| 39-32 | 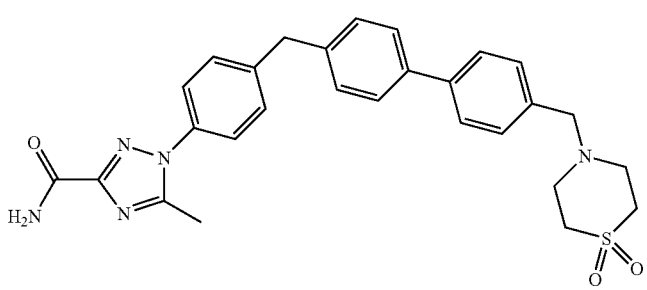<br>1-(4-((4'-((1,1-dioxidothiomorpholino)methyl)-[1,1'-biphenyl]-4-yl)methyl)phenyl)-5-methyl-1H-1,2,4-triazole-3-carboxamide | 516.3<br>0.61 min<br>Q | N/A |
| 39-33 | 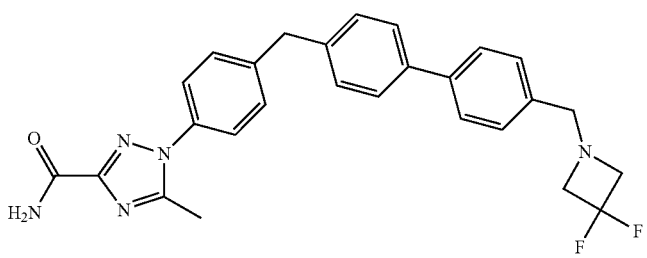<br>1-(4-((4'-((3,3-difluoroazetidin-1-yl)methyl)-[1,1'-biphenyl]-4-yl)methyl)phenyl)-5-methyl-1H-1,2,4-triazole-3-carboxamide | 474.4<br>0.59 min<br>Q | N/A |
| 39-34 | 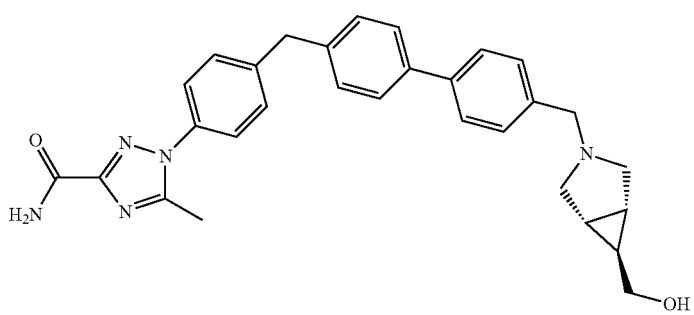<br>1-(4-((4'-(((1R,5S,6r)-6-(hydroxymethyl)-3-azabicyclo[3.1.0]hexan-3-yl)methyl)-[1,1'-biphenyl]-4-yl)methyl)phenyl)-5-methyl-1H-1,2,4-triazole-3-carboxamide | 494.4<br>0.49 min<br>Q | N/A |

| Example | Compound | LCMS M + 1, Rt, conditions | ¹H NMR, 400 MHz |
|---------|----------|----------------------------|-----------------|
| 39-35 | 5-methyl-1-(4-((4'-((4-(trifluoromethyl)piperidin-1-yl)methyl)-[1,1'-biphenyl]-4-yl)methyl)phenyl)-1H-1,2,4-triazole-3-carboxamide | 534.5 0.53 min Q | N/A |
| 39-36 | 1-(4-((4'-((3-(hydroxymethyl)azetidin-1-yl)methyl)-[1,1'-biphenyl]-4-yl)methyl)phenyl)-5-methyl-1H-1,2,4-triazole-3-carboxamide | 468.4 0.49 min Q | N/A |
| 39-37 | 1-(4-((4'-((1-oxa-7-azaspiro[3.5]nonan-7-yl)methyl)-[1,1'-biphenyl]-4-yl)methyl)phenyl)-5-methyl-1H-1,2,4-triazole-3-carboxamide | 508.4 1.37 min A | (DMSO-d6) δ 7.83 (s, 1H), 7.64-7.52 (m, 7H), 7.52-7.45 (m, 2H), 7.42-7.30 (m, 4H), 4.35 (t, J = 7.7 Hz, 2H), 4.09 (s, 2H), 3.45 (s, 2H), 2.48-2.39 (m, 5H), 2.35-2.11 (m, 4H), 1.87-1.66 (m, 4H). |
| 39-38 | (S)-1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide | 482.4 2.14 min A | (DMSO-d6) δ 7.83 (s, 1H), 7.64-7.52 (m, 7H), 7.52-7.44 (m, 2H), 7.43-7.34 (m, 4H), 4.49-4.33 (m, 1H), 4.16-4.01 (m, 3H), 3.54-3.44 (m, 1H), 3.42-3.33 (m, 1H), 2.87-2.75 (m, 1H), 2.62-2.54 (m, 1H), 2.47 (s, 3H), 2.24-2.08 (m, 1H), 1.94-1.77 (m, 1H), 1.70-1.49 (m, 3H), 1.33-1.19 (m, 1H). |

Example 40

1-(4-((4'-((4-(dimethylamino)piperidin-1-yl)methyl)-[1,1'-biphenyl]-4-yl)methyl)phenyl)-5-methyl-1H-pyrazole-3-carboxamide

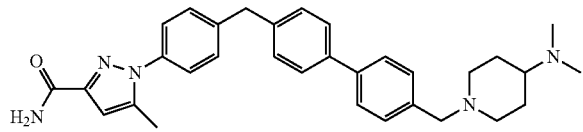 [SMILES: Cc1cc(C(N)=O)nn1-c1ccc(Cc2ccc(-c3ccc(CN4CCC(N(C)C)CC4)cc3)cc2)cc1]

To a stirred solution of Intermediate VIII (150 mg, 0.379 mmol) in THF was added N,N-dimethylpiperidin-4-amine (48.6 mg, 0.379 mmol) and Acetic Acid (2.171 µL, 0.038 mmol). After 1 h at RT, NaBH(OAc)$_3$ (161 mg, 0.759 mmol) was added and the mixture was stirred at RT for 3 days. The mixture was neutralized with saturated aq. sodium bicarbonate and extracted with EtOAc. The organic layer was washed with water, dried over anhydrous sodium sulfate and concentrated in vacuo. The crude material was purified by column chromatography to afford 1-(4-((4'-((4-(dimethylamino)piperidin-1-yl)methyl)-[1,1'-biphenyl]-4-yl)methyl)phenyl)-5-methyl-1H-pyrazole-3-carboxamide (12.9 mg, 6.6%). LC-MS RT=1.48 min (condition A), MS (M+1)= 508.1. $^1$H NMR (400 MHz, DMSO-d6) δ 7.70-7.15 (m, 14H), 6.60 (d, J=0.9 Hz, 1H), 4.07 (s, 2H), 3.45 (s, 2H), 2.83 (d, J=11.2 Hz, 2H), 2.67 (d, J=2.0 Hz, 1H), 2.33 (t, J=1.9 Hz, 1H), 2.30 (d, J=0.8 Hz, 3H), 2.15 (s, 5H), 1.92 (t, J=11.3 Hz, 2H), 1.70 (d, J=12.3 Hz, 2H), 1.37 (d, J=12.0 Hz, 2H).

Example 41

5-methyl-1-(4-((4'-(((3aR,6aS)-2-methyloctahydrocyclopenta[c]pyrrol-5-yl)methyl)-[1,1'-biphenyl]-4-yl)methyl)phenyl)-1H-1,2,4-triazole-3-carboxamide

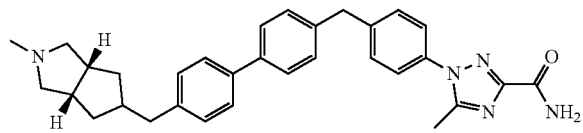 [SMILES: Cc1nc(C(N)=O)nn1-c1ccc(Cc2ccc(-c3ccc(CC4C[C@@H]5CN(C)C[C@@H]5C4)cc3)cc2)cc1]

Step 1. Preparation of (3aR,6aS)-tert-butyl 5-methylenehexahydrocyclopenta[c]pyrrole-2(1H)-carboxylate n-Butyllithium (3.55 mL, 8.88 mmol) was added slowly to a suspension of methyltriphenylphosphonium bromide (3.33 g, 9.32 mmol) in THF (11.1 mL) at 0° C. The resulting mixture was stirred for 20 min at 00° C. Then a solution of (3aR,6aS)-tert-butyl 5-oxohexahydrocyclopenta[c]pyrrole-2(1H)-carboxylate (1 g, 4.44 mmol) in THF (11.1 mL) was slowly added and the mixture was stirred at RT for 18 h. The reaction mixture was then quenched with saturated aq. ammonium chloride and extracted with EtOAc. The organic layer was washed with water and brine, dried over sodium sulfate and concentrated in vacuo. The crude material was purified by FCC to afford (3aR,6aS)-tert-butyl 5-methylenehexahydrocyclopenta[c]pyrrole-2(1H)-carboxylate (336 mg, 33%). $^1$H NMR (400 MHz, Chloroform-d) δ 4.98-4.77 (m, 2H), 3.53 (dt, J=12.0, 5.8 Hz, 2H), 3.13 (dd, J=11.2, 4.4 Hz, 2H), 2.69 (dq, J=8.0, 4.9 Hz, 2H), 2.63-2.43 (m, 2H), 2.31-2.11 (m, 2H), 1.47 (s, 9H).

Step 2. Preparation of (3aR,6aS)-tert-butyl 5-(4-chlorobenzyl)hexahydrocyclopenta[c]pyrrole-2(1H)-carboxylate To (3aR,6aS)-tert-butyl 5-methylenehexahydrocyclopenta[c]pyrrole-2(1H)-carboxylate (100 mg, 0.448 mmol) was added 9-BBN in THF (1.4 mL, 0.694 mmol) dropwise. The resulting solution was heated at 65° C. for 1 h. The mixture was then cooled to RT and added to a mixture of 1-bromo-4-chlorobenzene (86 mg, 0.448 mmol), K$_2$CO$_3$ (186 mg, 1.343 mmol) and PdCl$_2$(dppf).DCM (adduct) (36.6 mg, 0.045 mmol) in 1,4-dioxane (0.93 mL) and water (0.19 mL). The resulting mixture was heated to 65° C. for 48 h. The reaction was then cooled to RT, diluted with EtOAc and washed with water and brine. The organic layer was then dried over sodium sulfate and concentrated in vacuo. The crude material was purified by FCC to afford (3aR,6aS)-tert-butyl 5-(4-chlorobenzyl)hexahydrocyclopenta[c]pyrrole-2(1H)-carboxylate (150 mg, 100%). LC-MS Rt=1.41 min (Condition B), MS (M-55.6)=280.3.

Step 3. Preparation of (3aR,6aS)-tert-butyl 5-((4'-(4-(3-carbamoyl-5-methyl-1H-1,2,4-triazol-1-yl)benzyl)-[1,1'-biphenyl]-4-yl)methyl) hexahydrocyclopenta[c]pyrrole-2(1H)-carboxylate 5-Methyl-1-(4-(4-(4,4,5,5-tetramethyl-1,3,2-dioxaborolan-2-yl)benzyl)phenyl)-1H-1,2,4-triazole-3-carboxamide, Intermediate IX, (100 mg, 0.239 mmol), (3aR,6aS)-tert-butyl 5-(4-chlorobenzyl)hexahydrocyclopenta[c]pyrrole-2(1H)-carboxylate (168 mg, 0.500 mmol), and K$_3$PO$_4$ (152 mg, 0.717 mmol) were combined in Water (0.4 mL) and THF (2.0 mL). The resulting suspension was degassed with nitrogen for 5 min. Then First generation Xphos Precatalyst (17.7 mg, 0.024 mmol) was added and the mixture was degassed another 5 min followed by heating in the microwave at 120° C. for 40 min. The reaction mixture was then diluted with water and extracted with EtOAc. The organic layer was then washed with brine, dried over sodium sulfate and concentrated in vacuo to afford crude (3aR,6aS)-tert-butyl 5-((4'-(4-(3-carbamoyl-5-methyl-1H-1,2,4-triazol-1-yl)benzyl)-[1,1'-biphenyl]-4-yl)methyl)hexahydrocyclopenta[c]pyrrole-2(1H)-carboxylate (141 mg) LC-MS Rt=1.35 min (Condition B), MS (M-100)=491.5.

Step 4. Preparation of 5-methyl-1-(4-((4'-(((3aR,6aS)-octahydrocyclopenta[c]pyrrol-5-yl)methyl)-[1,1'-biphenyl]-4-yl)methyl)phenyl)-1H-1,2,4-triazole-3-carboxamide Crude (3aR,6aS)-tert-butyl 5-((4'-(4-(3-carbamoyl-5-methyl-1H-1,2,4-triazol-1-yl)benzyl)-[1,1'-biphenyl]-4-yl)methyl)hexahydrocyclopenta[c]pyrrole-2(1H)-carboxylate (141 mg, 0.238 mmol) was taken up in DCM (1.2 mL). To this mixture was added TFA (367 µl, 4.77 mmol) and the resulting reaction mixture was stirred at RT for 1 h. The mixture was then diluted with toluene and concentrated in vacuo to afford crude 5-methyl-1-(4-((4'-(((3aR,6aS)-octahydrocyclopenta[c]pyrrol-5-yl)methyl)-[1,1'-biphenyl]-4-yl)methyl)phenyl)-1H-1,2,4-triazole-3-carboxamide as a TFA salt (117 mg). LC-MS Rt=1.30 min (Condition B), MS (M+1)=492.4.

Step 5. Preparation of 5-methyl-1-(4-((4'-(((3aR, 6aS)-2-methyloctahydrocyclopenta[c]pyrrol-5-yl) methyl)-[1,1'-biphenyl]-4-yl)methyl)phenyl)-1H-1,2, 4-triazole-3-carboxamide The TFA salt of 5-methyl-1-(4-((4'-(((3aR,6aS)-octahydrocyclopenta[c]pyrrol-5-yl)methyl)-[1,1'-biphenyl]-4-yl) methyl)phenyl)-1H-1,2,4-triazole-3-carboxamide (117 mg, 0.238 mmol) was taken up in MeOH (2.4 mL). To the solution was added 37% aqueous formaldehyde (35.4 µl, 0.476 mmol) and NaBH(OAc)³ (101 mg, 0.476 mmol). The resulting mixture was stirred for 10 min. The reaction mixture was then diluted with water and extracted with EtOAC. The organic layer was washed with brine, dried over sodium sulfate and concentrated in vacuo. The crude material was purified by preparative HPLC followed by preparative SFC to afford 5-methyl-1-(4-((4'-(((3aR,6aS)-2-methyloctahydrocyclopenta[c]pyrrol-5-yl)methyl)-[1,1'-biphenyl]-4-yl)methyl)phenyl)-1H-1,2,4-triazole-3-carboxamide (9.2 mg, 7.5%). LC-MS Rt=1.66 min (Condition A), MS (M+1)=506.4. $^1$H NMR (400 MHz, DMSO-d6) δ 7.83 (s, 1H), 7.61-7.50 (m, 7H), 7.51-7.45 (m, 2H), 7.36 (d, J=8.2 Hz, 2H), 7.23 (d, J=8.2 Hz, 2H), 4.08 (s, 2H), 2.61 (d, J=6.4 Hz, 2H), 2.47 (s, 3H), 2.45-2.37 (m, 2H), 2.21 (s, 3H), 2.12-1.99 (m, 2H), 1.96-1.82 (m, 3H), 1.08-0.93 (m, 2H).

Example 42

5-methyl-1-(4-(4-(4-(piperazine-1-carbonyl)bicyclo [2.2.2]octan-1-yl)benzyl)phenyl)-1H-pyrazole-3-carboxamide

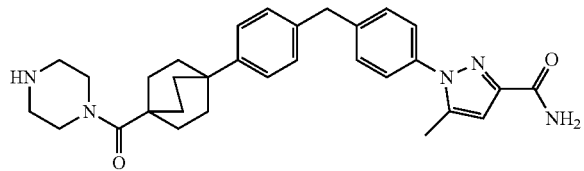 [SMILES: Cc1cc(C(N)=O)nn1-c1ccc(Cc2ccc(C34CCC(C(=O)N5CCNCC5)(CC3)CC4)cc2)cc1]

Step 1. Preparation of methyl 4-phenylbicyclo [2.2.2]octane-1-carboxylate

To a suspension of aluminum chloride (809 mg, 6.07 mmol) in Benzene (4.0 mL) at −10° C. was added methyl 4-bromobicyclo[2.2.2]octane-1-carboxylate (300 mg, 1.214 mmol) in Benzene (2.0 mL). The resulting mixture was stirred at RT for 18 h, then slowly poured into ice water and extracted with EtOAc. The organic layer was washed with brine, dried over sodium sulfate and concentrated in vacuo to afford crude methyl 4-phenylbicyclo[2.2.2]octane-1-carboxylate (317 mg). $^1$H NMR (400 MHz, Chloroform-d) δ 7.37-7.28 (m, 4H), 7.26-7.18 (m, 1H), 3.71 (s, 3H), 2.00-1.87 (m, 12H).

Step 2. methyl 4-(4-bromophenyl)bicyclo[2.2.2] octane-1-carboxylate

Crude methyl 4-phenylbicyclo[2.2.2]octane-1-carboxylate (317 mg, 1.297 mmol) and silver trifluoroacetate (330 mg, 1.492 mmol) were taken up in chloroform (1 mL). Then bromine (70.2 µl, 1.362 mmol) in chloroform (1 mL) was added dropwise over 10 min. The resulting mixture was stirred at RT for 18 h. The reaction mixture was then filtered through celite and concentrated in vacuo. The crude material was purified by FCC to afford methyl 4-(4-bromophenyl) bicyclo[2.2.2]octane-1-carboxylate (263 mg). 1H NMR (400 MHz, Chloroform-d) b 7.43 (d, J=8.6 Hz, 2H), 7.20 (d, J=8.7 Hz, 2H), 3.69 (s, 3H), 2.00-1.77 (m, 12H).

Step 3. Preparation of 4-(4-bromophenyl)bicyclo [2.2.2]octane-1-carboxylic acid

Methyl 4-(4-bromophenyl)bicyclo[2.2.2]octane-1-carboxylate (263 mg, 0.814 mmol) was taken up in THF (3.3 mL). To the mixture was added 2M aq. LiOH (2.0 mL, 4.07 mmol) followed by MeOH (0.8 mL). The resulting mixture was stirred at RT for 18 h. The reaction mixture was then acidified with 1N aq. HCl and extracted with EtOAc. The organic layer was washed with brine, dried over sodium sulfate and concentrated in vacuo to afford crude 4-(4-bromophenyl)bicyclo[2.2.2]octane-1-carboxylic acid (252 mg). LC-MS Rt=1.15 min (Condition B), MS (M-1)=307.1.

Step 4. Preparation of tert-butyl 4-(4-(4-bromophenyl)bicyclo[2.2.2]octane-1-carbonyl)piperazine-1-carboxylate Crude 4-(4-bromophenyl)bicyclo[2.2.2]octane-1-carboxylic acid (252 mg, 0.815 mmol), tert-butyl piperazine-1-carboxylate (152 mg, 0.815 mmol), DIPEA (569 µl, 3.26 mmol), and HATU (341 mg, 0.897 mmol) were taken up in DMF (4.1 mL) and the resulting mixture was stirred at RT for 18 h. The reaction mixture was then diluted with water and extracted with EtOAc. The organic layer was washed with brine, dried over sodium sulfate and concentrated in vacuo. The crude material was purified by FCC to afford tert-butyl 4-(4-(4-bromophenyl)bicyclo[2.2.2]octane-1-carbonyl)piperazine-1-carboxylate (315 mg). LC-MS Rt=1.32 min (Condition B), MS (M+1)=477.3.

Step 5. Preparation of ethyl 1-(4-((benzyloxy) methyl)phenyl)-5-methyl-1H-pyrazole-3-carboxylate Potassium benzyloxytrifluoroborate (2.0 g, 8.73 mmol), Intermediate I, (2.7 g, 8.73 mmol), Cs$_2$CO$_3$ (8.54 g, 26.2 mmol), and s-BINAP (0.544 g, 0.873 mmol) were taken up in 1,4-dioxane (32 mL) and Water (3.2 mL). The resulting suspension was degassed with nitrogen for 5 min then Pd(OAc)$_2$ (98 mg, 0.437 mmol) was added and the mixture was heated at 100° C. for 24 h. The reaction mixture was then cooled to RT, diluted with EtOAC, washed with water and brine, dried over sodium sulfate and concentrated in vacuo. The crude material was purified by FCC to afford ethyl 1-(4-((benzyloxy)methyl)phenyl)-5-methyl-1H-pyrazole-3-carboxylate (2.15 g, 70.3%). LC-MS Rt=1.16 min (Condition B), MS (M+1)=351.3.

Step 6. Preparation of ethyl 1-(4-(hydroxymethyl) phenyl)-5-methyl-1H-pyrazole-3-carboxylate To a mixture of ethyl 1-(4-((benzyloxy)methyl)phenyl)-5-methyl-1H-pyrazole-3-carboxylate (2.15 g, 6.14 mmol) in MeOH (31 mL) was added 10% Pd/C (0.653 g, 0.614 mmol). The resulting suspension was stirred under an atmosphere of hydrogen at RT for 18 h. The reaction mixture was then filtered through celite and concentrated in vacuo to afford crude ethyl 1-(4-(hydroxymethyl)phenyl)-5-methyl-1H-pyrazole-3-carboxylate (1.6 g). LC-MS Rt=0.76 min (Condition B), MS (M+2)=262.1.

Step 7: Preparation of ethyl 1-(4-(bromomethyl) phenyl)-5-methyl-1H-pyrazole-3-carboxylate To a solution of crude ethyl 1-(4-(hydroxymethyl)phenyl)-5-methyl-1H-pyrazole-3-carboxylate (1.6 g, 6.15 mmol) in THF (12.3 mL) at 0° C. was added dropwise phosphorus tribromide (0.58 mL, 6.15 mmol). The resulting mixture was stirred 0° C. for 2 h. The reaction mixture was diluted with water and extracted with EtOAc. The organic layer was dried over sodium sulfate and concentrated in vacuo. The crude material was purified by FCC to afford ethyl 1-(4-(bromomethyl)phenyl)-5-methyl-1H-pyrazole-3-carboxylate (1.6 g, 64%) LC-MS Rt=1.04 min (Condition B), MS (M+1)=323.0.

Step 8. Preparation of ethyl 5-methyl-1-(4-((4,4,5,5-tetramethyl-1,3,2-dioxaborolan-2-yl)methyl)phenyl)-1H-pyrazole-3-carboxylate Ethyl 1-(4-(bromomethyl)phenyl)-5-methyl-1H-pyrazole-3-carboxylate (267 mg, 0.826 mmol), potassium acetate (243 mg, 2.478 mmol), and bis(pinacolato)diboron (210 mg, 0.826 mmol) were taken up in 1,4-dioxane (4.1 mL). The resulting suspension was degassed with nitrogen for 5 min then $PdCl_2$.dppf-DCM (adduct) (68 mg, 0.083 mmol) was added and the resulting mixture degassed with nitrogen an additional 5 min and then heated to 95° C. for 18 h. The reaction mixture was cooled to RT, diluted with EtOAc, filtered through celite and concentrated in vacuo. The crude material was purified by FCC to afford ethyl 5-methyl-1-(4-((4,4,5,5-tetramethyl-1,3,2-dioxaborolan-2-yl)methyl)phenyl)-1H-pyrazole-3-carboxylate (239 mg, 78%). LC-MS Rt=1.13 min (Condition B), MS (M+1)=371.2.

Step 9. Preparation of tert-butyl 4-(4-(4-(4-(3-(ethoxycarbonyl)-5-methyl-1H-pyrazol-1-yl)benzyl) phenyl)bicyclo[2.2.2]octane-1-carbonyl)piperazine-1-carboxylate tert-Butyl 4-(4-(4-bromophenyl)bicyclo[2.2.2]octane-1-carbonyl)piperazine-1-carboxylate (308 mg, 0.646 mmol), ethyl 5-methyl-1-(4-((4,4,5,5-tetramethyl-1,3,2-dioxaborolan-2-yl)methyl)phenyl)-1H-pyrazole-3-carboxylate (239 mg, 0.646 mmol), and $K_2CO_3$ (268 mg, 1.937 mmol) were taken up in 1,4-dioxane (0.54 mL), water (0.54 mL) and toluene (5.4 mL). The resulting suspension was degassed with nitrogen for 5 min then $PdCl_2$.dppf-DCM (adduct) (53 mg, 0.065 mmol) was added and the resulting mixture degassed with nitrogen an additional 5 min and then heated to 90° C. for 4 h. The reaction mixture was cooled to RT, diluted with water and extracted with EtOAc. The organic layer was washed with saturated aq. sodium bicarbonate and brine, then dried over sodium sulfate and concentrated in vacuo to afford crude tert-butyl 4-(4-(4-(4-(3-(ethoxycarbonyl)-5-methyl-1H-pyrazol-1-yl)benzyl)phenyl)bicyclo[2.2.2]octane-1-carbonyl)piperazine-1-carboxylate (414 mg). LC-MS Rt=1.35 min (Condition B), MS (M+1)=641.5.

Step 10: Preparation of tert-butyl 4-(4-(4-(4-(3-carbamoyl-5-methyl-1H-pyrazol-1-yl)benzyl)phenyl)bicyclo[2.2.2]octane-1-carbonyl)piperazine-1-carboxylate Crude tert-butyl 4-(4-(4-(4-(3-(ethoxycarbonyl)-5-methyl-1H-pyrazol-1-yl)benzyl)phenyl)bicyclo[2.2.2]octane-1-carbonyl)piperazine-1-carboxylate (0.514 g, 0.802 mmol) was taken up in 7N $NH_3$ in MeOH (15 mL) and stirred in a sealed vial at RT for 72 h. The reaction mixture was concentrated in vacuo to afford crude tert-butyl 4-(4-(4-(4-(3-carbamoyl-5-methyl-1H-pyrazol-1-yl)benzyl)phenyl)bicyclo[2.2.2]octane-1-carbonyl)piperazine-1-carboxylate (0.491 g). LC-MS Rt=1.15 min (Condition B), MS (M+1)=612.5.

Step 11: Preparation of 5-methyl-1-(4-(4-(4-(piperazine-1-carbonyl)bicyclo[2.2.2]octan-1-yl)benzyl) phenyl)-1H-pyrazole-3-carboxamide Crude tert-butyl 4-(4-(4-(4-(3-carbamoyl-5-methyl-1H-pyrazol-1-yl)benzyl)phenyl)bicyclo[2.2.2]octane-1-carbonyl)piperazine-1-carboxylate (491 mg, 0.803 mmol) was taken up in DCM (4.0 mL). TFA (1.2 mL, 16.05 mmol) was added and the resulting mixture was stirred at RT for 2 h. The reaction mixture was then concentrated in vacuo. The crude material was purified by SCX-BSA according to General Method III. The resulting product was purified by preparative HPLC followed by a second SCX-BSA purification according to General Method III to afford 5-methyl-1-(4-(4-(4-(piperazine-1-carbonyl)bicyclo[2.2.2]octan-1-yl)benzyl)phenyl)-1H-pyrazole-3-carboxamide (13.9 mg, 3.3%). LC-MS Rt=1.55 min (Condition A), MS (M+2)=513.5. $^1$H NMR (400 MHz, DMSO-d6) δ 7.47 (d, J=8.3 Hz, 3H), 7.38 (d, J=8.3 Hz, 2H), 7.31-7.11 (m, 5H), 6.60 (s, 1H), 3.97 (s, 2H), 3.76-3.45 (m, 4H), 2.96-2.68 (m, 4H), 2.29 (s, 3H), 1.97-1.68 (m, 12H).

Example 43

5-methyl-1-(4-(4-(4-(4-methylpiperazine-1-carbonyl)bicyclo[2.2.2]octan-1-yl)benzyl)phenyl)-1H-pyrazole-3-carboxamide

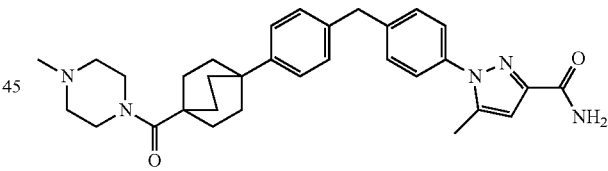

To 5-methyl-1-(4-(4-(4-(piperazine-1-carbonyl)bicyclo[2.2.2]octan-1-yl)benzyl)phenyl)-1H-pyrazole-3-carboxamide (Example 42) (200 mg, 0.391 mmol) in MeOH (7.8 mL) was added 37% aqueous formaldehyde (58.2 µl, 0.782 mmol) followed by $NaBH(OAc)_3$ (166 mg, 0.782 mmol). The resulting mixture was stirred at RT for 20 min. The reaction mixture was purified by SCX-BSA according to General Method Ill. The resulting product was purified by preparative HPLC followed by a second SCX-BSA purification according to General Method III to afford 5-methyl-1-(4-(4-(4-(4-methylpiperazine-1-carbonyl)bicyclo[2.2.2]octan-1-yl)benzyl)phenyl)-1H-pyrazole-3-carboxamide (26.5 mg, 12.6%). LC-MS Rt=1.57 min (Condition A), MS (M+1)=526.4. $^1$H NMR (400 MHz, DMSO-d6) δ 7.47 (d, J=8.4 Hz, 3H), 7.42-7.35 (m, 2H), 7.24 (t, J=6.9 Hz, 3H), 7.18 (d, J=8.4 Hz, 2H), 6.60 (s, 1H), 3.97 (s, 2H), 3.77-3.36 (m, 4H), 2.40-2.06 (m, 10H), 1.93-1.71 (m, 12H).

Example 44

5-methyl-1-(4-(4-(6-(piperazine-1-carbonyl)spiro[3.3]heptan-2-yl)benzyl)phenyl)-1H-1,2,4-triazole-3-carboxamide

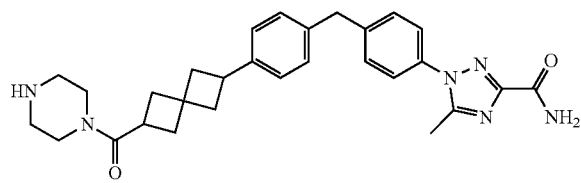 [SMILES: Cc1nc(C(N)=O)nn1-c1ccc(Cc2ccc(C3CC4(CC(C(=O)N5CCNCC5)C4)C3)cc2)cc1]

Step 1. Preparation of methyl 6-(((trifluoromethyl)sulfonyl)oxy)spiro[3.3]hept-5-ene-2-carboxylate To a solution of methyl 6-oxospiro[3.3]heptane-2-carboxylate (0.5 g, 2.97 mmol) in THF (14.9 mL) at −78° C. was added LiHMDS (3.0 ml, 2.97 mmol) dropwise over 5 min. The resulting mixture was stirred at −78° C. for 30 min. Then 1,1,1-trifluoro-N-phenyl-N-((trifluoromethyl)sulfonyl)methanesulfonamide (1.06 g, 2.97 mmol) in THF (14.8 mL) was added dropwise over 15 min. The mixture was stirred at −78° C. for 30 min then removed from the bath and allowed to warm to RT while stirring for 1 h. The reaction mixture was then quenched with water and brine and extracted with EtOAc. The organic layer was then washed with brine, dried over sodium sulfate and concentrated in vacuo to afford crude methyl 6-(((trifluoromethyl)sulfonyl)oxy)spiro[3.3]hept-5-ene-2-carboxylate (0.893 g). $^1$H NMR (400 MHz, DMSO-d6) δ 5.71 (s, 1H), 3.60 (s, 3H), 2.99 (s, 2H), 2.88 (s, 1H), 2.42-2.38 (m, 4H).

Step 2. Preparation of methyl 6-(4,4,5,5-tetramethyl-1,3,2-dioxaborolan-2-yl)spiro[3.3]hept-5-ene-2-carboxylate Crude methyl 6-(((trifluoromethyl)sulfonyl)oxy)spiro[3.3]hept-5-ene-2-carboxylate (0.9 g, 3.00 mmol), potassium acetate (0.883 g, 8.99 mmol), and bis(pinacolato)diboron (0.761 g, 3.00 mmol) were taken up in 1,4-dioxane (15 mL). The resulting suspension was degassed with nitrogen for 5 min then PdCl$_2$.dppf.DCM (adduct) (245 mg, 0.300 mmol) was added and the resulting mixture degassed with nitrogen an additional 5 min and then heated to 70° C. for 2 h. The reaction mixture was cooled to RT and diluted with water and EtOAc. The organic layer was washed with brine, dried over sodium sulfate and concentrated in vacuo. The crude material was purified by FCC to afford ethyl 5-methyl-1-(4-((4,4,5,5-tetramethyl-1,3,2-dioxaborolan-2-yl)methyl)phenyl)-1H-pyrazole-3-carboxylate (239 mg). $^1$H NMR (400 MHz, Chloroform-d) δ 3.13-3.01 (m, 1H), 2.62 (d, J=43.3 Hz, 2H), 1.28 (s, 12H), 6.93 (d, J=82.3 Hz, 1H), 3.69 (s, 3H), 2.56-2.30 (m, 4H).

Step 3. Preparation of methyl 6-(4-(4-(3-carbamoyl-5-methyl-1H-1,2,4-triazol-1-yl)benzyl)phenyl)spiro[3.3]hept-5-ene-2-carboxylate Crude ethyl 5-methyl-1-(4-((4,4,5,5-tetramethyl-1,3,2-dioxaborolan-2-yl)methyl)phenyl)-1H-pyrazole-3-carboxylate (210 mg, 0.754 mmol), K$_3$PO$_4$ (172 mg, 0.808 mmol), and Intermediate XII (100 mg, 0.269 mmol) were taken up in 1,4-dioxane (1.1 mL) and water (0.27 mL). The resulting suspension was degassed with nitrogen for 5 min then PdCl$_2$.dppf.DCM (adduct) (22 mg, 0.027 mmol) was added and the resulting mixture degassed with nitrogen an additional 5 min and then heated at 80° C. for 18 hr. The reaction mixture was then diluted with EtOAc and filtered through celite. The filtrate was washed with saturated aq. sodium bicarbonate, water and brine, dried over sodium sulfate and concentrated in vacuo to afford crude methyl 6-(4-(4-(3-carbamoyl-5-methyl-1H-1,2,4-triazol-1-yl)benzyl)phenyl)spiro[3.3]hept-5-ene-2-carboxylate (119 mg). LC-MS Rt=1.06 min (Condition B), MS (M+1)=443.3.

Step 4. Preparation of methyl 6-(4-(4-(3-carbamoyl-5-methyl-1H-1,2,4-triazol-1-yl)benzyl)phenyl)spiro[3.3]heptane-2-carboxylate To a solution of crude methyl 6-(4-(4-(3-carbamoyl-5-methyl-1H-1,2,4-triazol-1-yl)benzyl)phenyl)spiro[3.3]hept-5-ene-2-carboxylate (119 mg, 0.269 mmol) in MeOH (2.7 mL) was added 10% Pd/C (57 mg, 0.054 mmol). The resulting suspension was stirred under an atmosphere of hydrogen at RT for 18 h. The reaction mixture was then filtered through celite and concentrated in vacuo to afford crude methyl 6-(4-(4-(3-carbamoyl-5-methyl-1H-1,2,4-triazol-1-yl)benzyl)phenyl)spiro[3.3]heptane-2-carboxylate (120 mg). LC-MS Rt=1.08 min (Condition B), MS (M+1)=445.2.

Step 5. Preparation of 6-(4-(4-(3-carbamoyl-5-methyl-1H-1,2,4-triazol-1-yl)benzyl)phenyl)spiro[3.3]heptane-2-carboxylic acid To a solution of crude methyl 6-(4-(4-(3-carbamoyl-5-methyl-1H-1,2,4-triazol-1-yl)benzyl)phenyl)spiro[3.3]heptane-2-carboxylate (120 mg, 0.270 mmol) in THF (1.1 mL) was added 2N aq. LiOH (675 μl, 1.350 mmol) followed by MeOH (270 μl). The resulting mixture was stirred at RT for 2 h. The reaction mixture was then diluted with water, acidified to pH=1 with 1N aq. HCl, and extracted with EtOAc. The organic layer was washed with water and brine, dried over sodium sulfate and concentrated in vacuo to afford crude 6-(4-(4-(3-carbamoyl-5-methyl-1H-1,2,4-triazol-1-yl)benzyl)phenyl)spiro[3.3]heptane-2-carboxylic acid (116 mg) LC-MS Rt=0.91 min (Condition B), MS (M+1)=431.3.

Step 6. Preparation of tert-butyl 4-(6-(4-(4-(3-carbamoyl-5-methyl-1H-1,2,4-triazol-1-yl)benzyl)phenyl)spiro[3.3]heptane-2-carbonyl)piperazine-1-carboxylate A mixture of crude 6-(4-(4-(3-carbamoyl-5-methyl-1H-1,2,4-triazol-1-yl)benzyl)phenyl)spiro[3.3]heptane-2-carboxylic acid (116 mg, 0.269 mmol), tert-butyl piperazine-1-carboxylate (60.2 mg, 0.323 mmol), DIPEA (188 μL, 1.078 mmol), and HATU (113 mg, 0.296 mmol) in DMF (1.4 mL) was stirred at RT for 18 h. The reaction mixture was then quenched with water and extracted with EtOAc. The organic layer was washed with saturated aq. sodium bicarbonate, 10% aq. citric acid, and brine, dried over sodium sulfate and concentrated in vacuo to afford crude tert-butyl 4-(6-(4-(4-(3-carbamoyl-5-methyl-1H-1,2,4-triazol-1-yl)benzyl)phenyl)spiro[3.3]heptane-2-carbonyl)piperazine-1-carboxylate (116 mg). LC-MS Rt=1.05 min (Condition B), MS (M+1)=599.4.

Step 7. Preparation of 5-methyl-1-(4-(4-(6-(piperazine-1-carbonyl)spiro[3.3]heptan-2-yl)benzyl)phenyl)-1H-1,2,4-triazole-3-carboxamide To a solution of crude tert-butyl 4-(6-(4-(4-(3-carbamoyl-5-methyl-1H-1,2,4-triazol-1-yl)benzyl)phenyl)spiro[3.3]heptane-2-carbonyl)piperazine-1-carboxylate (160 mg, 0.267 mmol) in DCM (1.3 mL) was added TFA (412 μl, 5.34 mmol). The resulting mixture was stirred at RT for 1 h then concentrated in vacuo. The crude was purified by SCX-BSA according to General Method III, then purified by preparative HPLC to afford 5-methyl-1-(4-(4-(6-(piperazine-1-carbonyl)spiro[3.3]heptan-2-yl)benzyl)phenyl)-1H-1,2,4-triazole-3-carboxamide (9.5 mg, 6.8%) LC-MS Rt=1.40 min (Condition A), MS (M+1)=499.2. $^1$H NMR (400 MHz, Methanol-d4) δ 7.50-7.43 (m, 2H), 7.41-7.36 (m, 2H), 7.17-7.09 (m, 4H), 4.01 (s, 2H), 3.57-3.48 (m, 2H), 3.44-3.32 (m, 3H), 3.30-3.21 (m, 1H), 2.76 (q, J=4.9 Hz, 4H), 2.56-2.47 (m, 4H), 2.43-1.98 (m, 7H).

Example 45

5-methyl-1-(4-((4'-(piperazin-1-ylmethyl)-[1,1'-biphenyl]-4-yl)methyl)phenyl)-1H-1,2,4-triazole-3-carboxamide

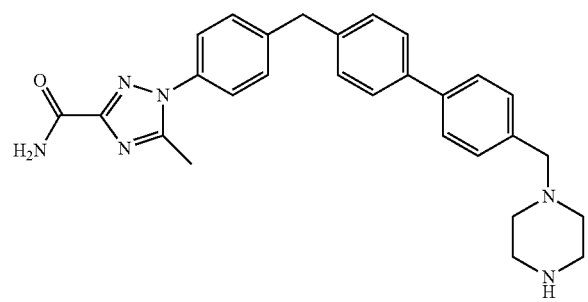 [SMILES: Cc1nc(C(N)=O)nn1-c1ccc(Cc2ccc(-c3ccc(CN4CCNCC4)cc3)cc2)cc1]

Step 1. Preparation of tert-butyl 4-((4'-(4-(3-carbamoyl-5-methyl-1H-1,2,4-triazol-1-yl)benzyl)-[1,1'-biphenyl]-4-yl)methyl)piperazine-1-carboxylate Intermediate XII (0.5 g, 1.35 mmol) and tert-butyl 4-(4-(4,4,5,5-tetramethyl-1,3,2-dioxaborolan-2-yl)benzyl)piperazine-1-carboxylate (0.542 g, 1.35 mmol) were reacted according to General Method I for Suzuki coupling and purified by FCC to afford tert-butyl 4-((4'-(4-(3-carbamoyl-5-methyl-1H-1,2,4-triazol-1-yl)benzyl)-[1,1'-biphenyl]-4-yl)methyl) piperazine-1-carboxylate (0.65 g): LCMS Rt=1.18 min (condition B), MS (M+1)=567.5.

Step 2. Preparation of 5-methyl-1-(4-((4'-(piperazin-1-ylmethyl)-[1,1'-biphenyl]-4-yl)methyl)phenyl)-1H-1,2,4-triazole-3-carboxamide To a solution of tert-butyl 4-((4'-(4-(3-carbamoyl-5-methyl-1H-1,2,4-triazol-1-yl)benzyl)-[1,1'-biphenyl]-4-yl) methyl) piperazine-1-carboxylate (100 mg, 0.176 mmol) in DCM (1.03 mL) was added TFA (150 μL, 1.941 mmol). The resulting mixture was stirred at RT for 1 h and then concentrated in vacuo. The crude material was purified by preparative HPLC to afford 5-methyl-1-(4-((4'-(piperazin-1-ylmethyl)-[1,1'-biphenyl]-4-yl)methyl)phenyl)-1H-1,2,4-triazole-3-carboxamide (18.2 mg, 21%). LC-MS Rt=1.21 min (Condition A), MS (M+1)=467.3. $^1$H NMR (400 MHz, DMSO-d6) δ 7.83 (s, 1H), 7.64-7.52 (m, 7H), 7.52-7.45 (m, 2H), 7.36 (dd, J=8.1, 6.1 Hz, 4H), 4.09 (s, 2H), 3.44 (s, 2H), 2.68 (t, J=4.8 Hz, 4H), 2.47 (s, 3H), 2.35-2.23 (m, 4H).

Example 46

1-(4-(4-(6-(2-hydroxypropan-2-yl)pyridin-3-yl)benzyl)phenyl)-5-methyl-1H-1,2,4-triazole-3-carboxamide

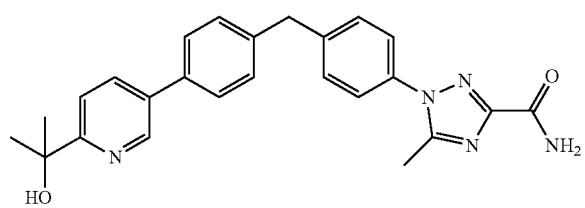 [SMILES: Cc1nc(C(N)=O)nn1-c1ccc(Cc2ccc(-c3ccc(C(C)(C)O)nc3)cc2)cc1]

A microwave vial was charged with methyl-1-(4-(2-(4-(4,4,5,5-tetramethyl-1,3,2-dioxaborolan-2-yl)phenyl)propan-2-yl)phenyl)-1H-pyrazole-3-carboxamide (Intermediate IX) (60 mg, 0.143 mmol), 2-(5-Bromopyridin-2-yl)propan-2-ol) (31 mg, 0.143 mmol), K$_3$PO$_4$ (91 mg, 0.430 mmol), second generation Xphos Precatalyst (11.29 mg, 0.014 mmol), water (0.5 mL) and THF (2 mL). The mixture was evacuated and degassed with N$_2$ for 5 min, and then heated in the microwave at 100° C. for 1 h. After cooling to RT, the mixture was concentrated in vacuo. The resulting crude material was purified by preparative HPLC to afford 1-(4-(4-(6-(2-hydroxypropan-2-yl)pyridin-3-yl)benzyl)phenyl)-5-methyl-1H-1,2,4triazole-3-carboxamide (15 mg, 23%): LCMS Rt=1.33 min (condition A), MS (M+1)=428.3. $^1$H NMR (400 MHz, Methanol-d$_4$) δ 8.70 (dd, J=2.3, 0.9 Hz, 1H), 8.03 (dd, J=8.3, 2.4 Hz, 1H), 7.74 (dd, J=8.3, 0.9 Hz, 1H), 7.68-7.57 (m, 2H), 7.57-7.43 (m, 4H), 7.43-7.30 (m, 2H), 4.14 (s, 2H), 2.52 (s, 3H), 1.57 (s, 6H).

Example 47

5-methyl-1-(4-((4'-((1-methylpiperidin-4-yl)oxy)-[1,1'-biphenyl]-4-yl)methyl)phenyl)-1H-1,2,4-triazole-3-carboxamide

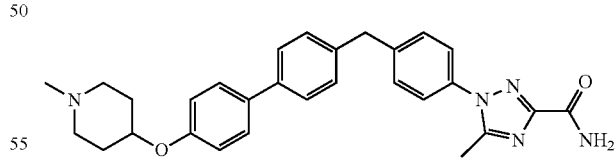

Step 1: Preparation of 4-(4-chlorophenoxy)-1-methylpiperidine

To a solution of 4-(4-chlorophenoxy)piperidine (0.5 g, 2.362 mmol) in MeOH (4 mL) was added 37% aqueous formaldehyde (0.528 mL, 7.09 mmol), followed by NaBH(OAc)$_3$ (1.502 g, 7.09 mmol). The mixture was stirred at RT overnight, and then concentrated in vacuo. The resulting crude product was purified by column chromatography (gradient 2%-10% MeOH in DCM) to afford 4-(4-chlorophenoxy)-1-methylpiperidine. LCMS Rt=0.51 min (condition B), MS (M+1)=226.3.

Step 2: Preparation of 5-methyl-1-(4-((4'-((1-methylpiperidin-4-yl)oxy)-[1,1'-biphenyl]-4-yl)methyl)phenyl)-1H-1,2,4-triazole-3-carboxamide A microwave vial was charged with methyl-1-(4-(2-(4-(4,4,5,5-tetramethyl-1,3,2-dioxaborolan-2-yl)phenyl)propan-2-yl)phenyl)-1H-pyrazole-3-carboxamide (Intermediate IX) (60 mg, 0.143 mmol), 4-(4-chlorophenoxy)-1-methylpiperidine (38.9 mg, 0.172 mmol), K$_3$PO$_4$ (91 mg, 0.430 mmol), second generation Xphos Precatalyst (11.29 mg, 0.014 mmol), water (0.5 mL), THF (2 mL), and was evacuated and degassed with N$_2$ for 5 min. The mixture was heated in the microwave at 10° C. for 1 hr, cooled to RT, and concentrated in vacuo. The resulting crude product was purified by preparative HPLC to afford 1-(4-(4-(6-(2-hydroxypropan-2-yl)pyridin-3-yl)benzyl)phenyl)-5-methyl-1H-1,2,4triazole-3-carboxamide (9 mg, 12%): LCMS Rt=1.48 min (condition A), MS (M+1)=482.4. $^1$H NMR (400 MHz, Methanol-d$_4$) δ 7.55-7.48 (m, 6H), 7.47-7.42 (m, 2H), 7.32-7.25 (m, 2H), 7.02-6.94 (m, 2H), 4.44 (s, 1H), 4.09 (s, 2H), 2.80-2.65 (m, 2H), 2.45-2.34 (m, 2H), 2.31 (s, 3H), 2.08-1.95 (m, 2H), 1.89-1.75 (m, 2H).

Example 48

1-(4-((4'-(1-hydroxy-2-methylpropan-2-yl)-[1,1'-biphenyl]-4-yl)methyl)phenyl)-5-methyl-1H-1,2,4-triazole-3-carboxamide

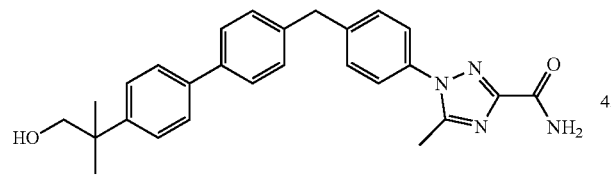

A microwave vial was charged with methyl-1-(4-(2-(4-(4,4,5,5-tetramethyl-1,3,2-dioxaborolan-2-yl)phenyl)propan-2-yl)phenyl)-1H-pyrazole-3-carboxamide (Intermediate IX) (100 mg, 0.239 mmol), 2-(4-bromo-phenyl)-2-methyl-propan-1-ol (110 mg, 0.478 mmol), K$_3$PO$_4$ (254 mg, 1.195 mmol), second generation Xphos Precatalyst (18.81 mg, 0.024 mmol), water (0.5 mL), THF (2 mL), and was evacuated and degassed with N2 for 5 min. The mixture was heated in the microwave at 100° C. for 1 hr, cooled to RT, and concentrated in vacuo. The resulting crude product was purified by preparative HPLC to afford 1-(4-((4'-(1-hydroxy-2-methylpropan-2-yl)-[1,1'-biphenyl]-4-yl)methyl)phenyl)-5-methyl-1H-1,2,4-triazole-3-carboxamide (30 mg, 27%): LCMS Rt=2.28 min (condition A), MS (M+1)=441.3. $^1$H NMR (400 MHz, MeOD-d4) δ 7.57-7.53 (m, 4H), 7.52-7.50 (m, 2H), 7.47-7.44 (m, 4H), 7.32-7.30 (m, 2H), 4.11 (s, 2H), 3.59 (s, 2H), 2.51 (s, 3H), 1.33 (s, 6H).

Example 49

1-(4-(4-(4-(2-hydroxypropan-2-yl)piperidin-1-yl)benzyl)phenyl)-5-methyl-1H-1,2,4-triazole-3-carboxamide

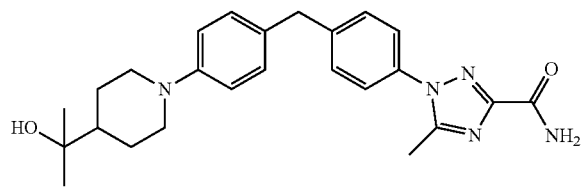 [SMILES: Cc1nc(C(N)=O)nn1-c1ccc(Cc2ccc(N3CCC(C(C)(C)O)CC3)cc2)cc1]

To a solution of methyl-1-(4-(2-(4-(4,4,5,5-tetramethyl-1,3,2-dioxaborolan-2-yl)phenyl)propan-2-yl)phenyl)-1H-pyrazole-3-carboxamide (Intermediate IX) (100 mg, 0.239 mmol) in DMSO (2 mL) was added 2-(4-Piperidyl)-2-propanol (51.4 mg, 0.359 mmol), K$_2$CO$_3$ (99 mg, 0.717 mmol), L-proline (5.5 mg, 0.048 mmol), and copper iodide (4.55 mg, 0.024 mmol). The reaction was heated in microwave at 80° C. for 1 hr, followed by heating at 80° C. overnight. The mixture was cooled to ambient temperature and concentrated in vacuo. The resulting crude product was purified by FCC (gradient 2%-10% MeOH in DCM) firstly, and then purified by preparative HPLC to afford 1-(4-(4-(4-(2-hydroxypropan-2-yl)piperidin-1-yl)benzyl)phenyl)-5-methyl-1H-1,2,4-triazole-3-carboxamide (5 mg, 4%): LCMS Rt=1.05 min (condition A), MS (M+1)=434.4. $^1$H NMR (400 MHz, Methanol-d$_4$) δ 7.53-7.43 (m, 2H), 7.39 (d, J=8.4 Hz, 2H), 7.12 (d, J=8.6 Hz, 2H), 7.02-6.88 (m, 2H), 3.98 (s, 2H), 3.70 (d, J=12.0 Hz, 2H), 2.58 (t, J=11.9 Hz, 2H), 2.50 (s, 3H), 1.86 (d, J=12.1 Hz, 2H), 1.63-1.26 (m, 3H), 1.17 (s, 6H).

Example 50

1-(4-((4'-(N-(2-hydroxy-2-methylpropyl)sulfamoyl)-[1,1'-biphenyl]-4-yl)methyl)phenyl)-5-methyl-1H-1,2,4-triazole-3-carboxamide

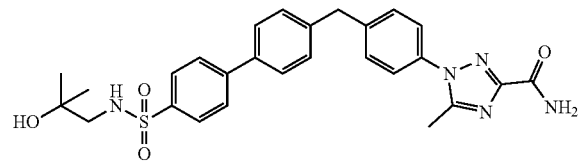 [SMILES: Cc1nc(C(N)=O)nn1-c1ccc(Cc2ccc(-c3ccc(S(=O)(=O)NCC(C)(C)O)cc3)cc2)cc1]

Step 1: Preparation of 4-bromo-N-(2-hydroxy-2-methylpropyl)benzenesulfonamide

To a stirring solution of 1-amino-2-methylpropan-2-ol (0.5 g, 5.61 mmol) in THF (5 mL), was added DIPEA (1.176 mL, 6.73 mmol), followed by 4-bromobenzenesulfonyl chloride (1.433 g, 5.61 mmol). The reaction was stirred at RT for 45 min. The solvent was removed under reduced pressure. The resulting crude product was diluted in EtOAc and washed with 0.1M HCl, brine, and concentrated to afford 4-bromo-N-(2-hydroxy-2-methylpropyl)benzenesulfonamide (1.7 g, 98%): LCMS Rt=1.05 min (condition B), MS (M+1)=309.1.

Step 2: Preparation of 1-(4-((4'-(N-(2-hydroxy-2-methylpropyl)sulfamoyl)-[1,1'-biphenyl]-4-yl)methyl)phenyl)-5-methyl-1H-1,2,4-triazole-3-carboxamide A microwave vial was charged with methyl-1-(4-(2-(4-(4,4,5,5-tetramethyl-1,3,2-dioxaborolan-2-yl)phenyl)propan-2-yl)phenyl)-1H-pyrazole-3-carboxamide (Intermediate IX) (60 mg, 0.143 mmol), 4-bromo-N-(2-hydroxy-2-methylpropyl)benzenesulfonamide (53 mg, 0.172 mmol), $K_3PO_4$ (91 mg, 0.43 mmol), second generation Xphos Precatalyst (11.29 mg, 0.014 mmol), water (0.5 mL), THF (2 mL), and was evacuated and degassed with N2 for 5 min. The mixture was heated in the microwave at 100° C. for 90 min, cooled to RT, and concentrated in vacuo. The resulting crude product was purified by column chromatography (gradient 2%-10% MeOH in DCM) firstly, and then purified by preparative HPLC to afford 1-(4-((4'-(N-(2-hydroxy-2-methylpropyl)sulfamoyl)-[1,1'-biphenyl]-4-yl)methyl)phenyl)-5-methyl-1H-1,2,4-triazole-3-carboxamide (18 mg, 23%): LCMS Rt=1.92 min (condition A), MS (M+1)=520.3. $^1$H NMR (400 MHz, Methanol-$d_4$) δ 7.97-7.85 (m, 2H), 7.85-7.74 (m, 2H), 7.71-7.58 (m, 2H), 7.58-7.42 (m, 4H), 7.42-7.31 (m, 2H), 4.14 (s, 2H), 2.80 (s, 2H), 2.52 (s, 3H), 1.17 (s, 6H).

Example 51

1-(4-((4'-((2-hydroxy-2-methylpropyl)carbamoyl)-[1,1'-biphenyl]-4-yl)methyl)phenyl)-5-methyl-1H-1,2,4-triazole-3-carboxamide

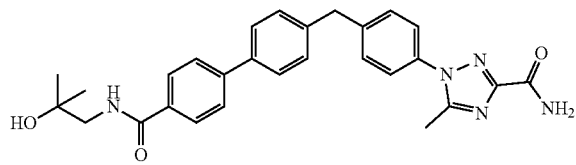 [SMILES: Cc1nc(C(N)=O)nn1-c1ccc(Cc2ccc(-c3ccc(C(=O)NCC(C)(C)O)cc3)cc2)cc1]

Step 1: Preparation of 4-bromo-N-(2-hydroxy-2-methylpropyl)benzamide

To a stirring solution of 1-amino-2-methylpropan-2-ol (0.5 g, 5.61 mmol) in THF (5 mL), was added DIPEA (1.176 mL, 6.73 mmol), followed by 4-bromobenzoyl chloride (1.231 g, 5.61 mmol). The reaction was stirred at RT for 45 min. The solvent was removed under reduced pressure. The resulting crude product was diluted in EtOAc and washed with 0.1M HCl, brine, and concentrated to afford 4-bromo-N-(2-hydroxy-2-methylpropyl)benzamide (1.5 g, 98%): LCMS Rt=0.71 min (condition B), MS (M+1)=274.1.

Step 2: Preparation of 1-(4-((4'-((2-hydroxy-2-methylpropyl)carbamoyl)-[1,1'-biphenyl]-4-yl)methyl)phenyl)-5-methyl-1H-1,2,4-triazole-3-carboxamide A microwave vial was charged with methyl-1-(4-(2-(4-(4,4,5,5-tetramethyl-1,3,2-dioxaborolan-2-yl)phenyl)propan-2-yl)phenyl)-1H-pyrazole-3-carboxamide (Intermediate IX) (60 mg, 0.143 mmol), 4-bromo-N-(2-hydroxy-2-methylpropyl)benzamide (46.8 mg, 0.172 mmol), $K_3PO_4$ (91 mg, 0.43 mmol), second generation Xphos Precatalyst (11.29 mg, 0.014 mmol), water (0.5 mL), THF (2 mL), and was evacuated and degassed with $N_2$ for 5 min. The mixture was heated in the microwave at 100° C. for 90 min, cooled to RT, and concentrated in vacuo. The resulting crude product was purified by FCC (gradient 2%-10% MeOH in DCM) then purified by preparative HPLC to afford 1-(4-((4'-((2-hydroxy-2-methylpropyl)carbamoyl)-[1,1'-biphenyl]-4-yl)methyl)phenyl)-5-methyl-1H-1,2,4-triazole-3-carboxamide (15 mg, 20%): LCMS Rt=1.79 min (condition A), MS (M+1)=484.4. $^1$H NMR (400 MHz, Methanol-$d_4$) δ 7.97-7.86 (m, 2H), 7.77-7.68 (m, 2H), 7.68-7.58 (m, 2H), 7.58-7.42 (m, 4H), 7.42-7.29 (m, 2H), 4.13 (s, 2H), 3.43 (s, 2H), 2.52 (s, 3H), 1.25 (s, 6H).

Example 52

1-(4-(4-(5-(N-(2-hydroxy-2-methylpropyl)sulfamoyl)pyridin-2-yl)benzyl)phenyl)-5-methyl-1H-1,2,4-triazole-3-carboxamide

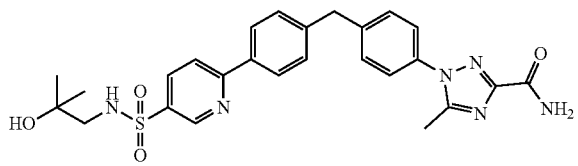 [SMILES: Cc1nc(C(N)=O)nn1-c1ccc(Cc2ccc(-c3ccc(S(=O)(=O)NCC(C)(C)O)cn3)cc2)cc1]

Step 1: Preparation of 6-chloro-N-(2-hydroxy-2-methylpropyl)pyridine-3-sulfonamide To a stirring solution of 1-amino-2-methylpropan-2-ol (0.2 g, 2.244 mmol) in THF (5 mL) was added DIPEA (0.47 mL, 2.69 mmol), followed by 2-chloro-5-pyridinesulfonyl chloride (0.476 g, 2.244 mmol). The reaction was stirred at RT for 45 min. The solvent was removed under reduced pressure. The resulting crude product was diluted in EtOAc and washed with 0.1M aq. HCl, brine, and concentrated to afford 6-chloro-N-(2-hydroxy-2-methylpropyl)pyridine-3-sulfonamide (0.5 g, 84%): LCMS Rt=0.63 min (condition B), MS (M+1)=265.2.

Step 2: Preparation of 1-(4-(4-(5-(N-(2-hydroxy-2-methylpropyl)sulfamoyl)pyridin-2-yl)benzyl)phenyl)-5-methyl-1H-1,2,4-triazole-3-carboxamide A microwave vial was charged with methyl-1-(4-(2-(4-(4,4,5,5-tetramethyl-1,3,2-dioxaborolan-2-yl)phenyl)propan-2-yl)phenyl)-1H-pyrazole-3-carboxamide (Intermediate IX) (90 mg, 0.215 mmol), 6-chloro-N-(2-hydroxy-2-methylpropyl)pyridine-3-sulfonamide (68.4 mg, 0.258 mmol), $K_3PO_4$ (137 mg, 0.645 mmol), second generation Xphos Precatalyst (16.93 mg, 0.022 mmol), water (0.5 mL), THF (2 mL), and was evacuated and degassed with $N_2$ for 5 min. The mixture was heated in the microwave at 100° C. for 90 min, cooled to RT, and concentrated in vacuo. The resulting crude product was purified by FCC and then purified by preparative HPLC to afford 1-(4-(4-(5-(N-(2-hydroxy-2-methylpropyl)sulfamoyl)pyridin-2-yl)benzyl)phenyl)-5-methyl-1H-1,2,4-triazole-3-carboxamide (4 mg, 3%): LCMS Rt=1.77 min (condition A), MS (M+1)=521.3. $^1$H NMR (400 MHz, Methanol-$d_4$) δ 9.01 (m, 1H), 8.26-8.24 (m, 1H), 8.06-8.03 (m, 3H), 7.54-7.46 (m, 4H), 7.44-7.41 (m, 2H), 4.17 (s, 2H), 2.86 (s, 2H), 2.52 (s, 3H), 1.19 (s, 6H).

Example 53

1-(4-(4-(4-(2-hydroxypropan-2-yl)pyridin-2-yl)benzyl)phenyl)-5-methyl-1H-1,2,4-triazole-3-carboxamide

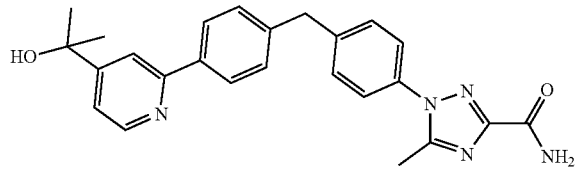 [SMILES: Cc1nc(C(N)=O)nn1-c1ccc(Cc2ccc(-c3cc(C(C)(C)O)ccn3)cc2)cc1]

A microwave vial was charged with 5-methyl-1-(4-(4-(4,4,5,5-tetramethyl-1,3,2-dioxaborolan-2-yl)benzyl)phenyl)-1H-1,2,4-triazole-3-carboxamide, (Intermediate IX) (60 mg, 0.143 mmol), 2-(2-chloropyridine-4-yl)propane-2-ol (36.9 mg, 0.215 mmol), K$_3$PO$_4$ (91 mg, 0.43 mmol), second generation Xphos Precatalyst (11.29 mg, 0.014 mmol), water 0.5 mL), THF (2 mL), and was evacuated and degassed with N$_2$ for 5 min. The mixture was heated in the microwave at 100° C. for 2 hr, cooled to RT, and concentrated in vacuo. The resulting crude product was purified by FCC (gradient 2%-10% MeOH in DCM) firstly, and then purified by preparative HPLC to afford 1-(4-(4-(4-(2-hydroxypropan-2-yl)pyridin-2-yl)benzyl)phenyl)-5-methyl-1H-1,2,4-triazole-3-carboxamide (6 mg, 9%): LCMS Rt=1.2 min (condition A), MS (M+1)=428.1. $^1$H NMR (400 MHz, Methanol-d$_4$) δ 8.51 (dd, J=5.3, 0.8 Hz, 1H), 7.92 (dd, J=1.8, 0.8 Hz, 1H), 7.90-7.86 (m, 2H), 7.55-7.45 (m, 4H), 7.44 (dd, J=5.3, 1.8 Hz, 1H), 7.41-7.37 (m, 2H), 4.15 (s, 2H), 2.52 (s, 3H), 1.56 (s, 6H).

Example 54

5-methyl-1-(4-(4-((1-methylpiperidin-4-yl)ethynyl)benzyl)phenyl)-1H-1,2,4-triazole-3-carboxamide

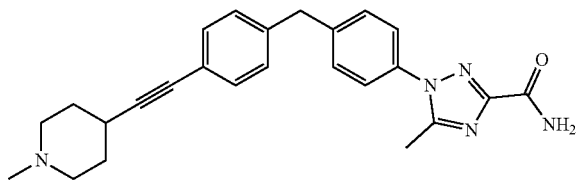 [SMILES: Cc1nc(C(N)=O)nn1-c1ccc(Cc2ccc(C#CC3CCN(C)CC3)cc2)cc1]

Step 1: Preparation of tert-butyl 4-((4-(4-(3-carbamoyl-5-methyl-1H-1,2,4-triazol-1-yl)benzyl)phenyl)ethynyl)piperidine-1-carboxylate To a degassed solution of 1-(4-(4-bromobenzyl)phenyl)-5-methyl-1H-1,2,4-triazole-3-carboxamide (Intermediate XII) (100 mg, 0.269 mmol) in DMF (2 mL) was added 1-boc-4-ethynylpiperidine (67.7 mg, 0.323 mmol), copper(I) iodide (5.13 mg, 0.027 mmol), TEA (0.112 mL, 0.808 mmol), and tetrakis(triphenylphosphine)palladium (31.1 mg, 0.027 mmol) at RT. The reaction mixture was slowly heated to 100° C. then stirred at this temperature for 2 days. The mixture was concentrated in vacuo. The resulting crude product was purified by FCC (gradient 2%-10% MeOH in DCM) to afford tert-butyl 4-((4-(4-(3-carbamoyl-5-methyl-1H-1,2,4-triazol-1-yl)benzyl)phenyl)ethynyl)piperidine-1-carboxylate (90 mg, 67%): LCMS Rt=1.16 min (condition B), MS (M+1)=500.3.

Step 2: Preparation of 5-methyl-1-(4-(4-(piperidin-4-ylethynyl)benzyl)phenyl)-1H-1,2,4-triazole-3-carboxamide To a solution of tert-butyl 4-((4-(4-(3-carbamoyl-5-methyl-1H-1,2,4-triazol-1-yl)benzyl)phenyl)ethynyl)piperidine-1-carboxylate (90 mg, 0.18 mmol) in DCM (2 mL) was added TFA (0.139 mL, 1.801 mmol) at RT. The reaction mixture was stirred at RT for 1 hr, and concentrated in vacuo to afford 5-methyl-1-(4-(4-(piperidin-4-ylethynyl)benzyl)phenyl)-1H-1,2,4-triazole-3-carboxamide (70 mg, 97%): LCMS Rt=0.7 min (condition B), MS (M+1)=400.3.

Step 3: Preparation of 5-methyl-1-(4-(4-((1-methylpiperidin-4-yl)ethynyl)benzyl)phenyl)-1H-1,2,4-triazole-3-carboxamide To a solution of 5-methyl-1-(4-(4-(piperidin-4-ylethynyl)benzyl)phenyl)-1H-1,2,4-triazole-3-carboxamide (60 mg, 0.15 mmol) in MeOH (2 mL) was added formaldehyde (0.034 mL, 0.451 mmol), followed by NaBH(OAc)$_3$ (95 mg, 0.451 mmol) at RT. The reaction mixture was stirred at RT overnight, and concentrated in vacuo. The resulting crude product was purified by FCC (gradient 2%-10% MeOH in DCM) then purified by preparative HPLC to afford 5-methyl-1-(4-(4-((1-methylpiperidin-4-yl)ethynyl)benzyl)phenyl)-1H-1,2,4-triazole-3-carboxamide (12 mg, 18%): LCMS Rt=1.22 min (condition A), MS (M+1)=414.5. $^1$H NMR (400 MHz, Methanol-d$_4$) δ 7.54-7.47 (m, 2H), 7.45-7.38 (m, 2H), 7.34-7.27 (m, 2H), 7.23-7.15 (m, 2H), 4.06 (s, 2H), 2.84-2.71 (m, 2H), 2.70-2.57 (m, 1H), 2.51 (s, 3H), 2.40-2.14 (m, 5H), 2.00-1.90 (m, 2H), 1.79-1.68 (m, 2H).

Example 55

1-(4-(4-((1-hydroxycyclohexyl)ethynyl)benzyl)phenyl)-5-methyl-1H-1,2,4-triazole-3-carboxamide

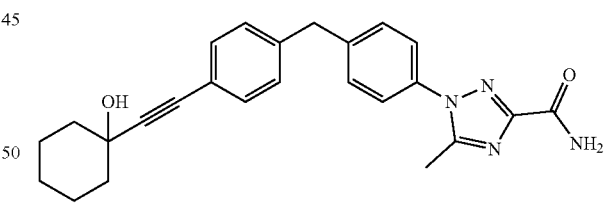

To a degassed solution of 1-(4-(4-bromobenzyl)phenyl)-5-methyl-1H-1,2,4-triazole-3-carboxamide (Intermediate XII) (100 mg, 0.269 mmol) in DMF (2 mL) was added 1-ethynyl-1-cyclohexanol (40.1 mg, 0.323 mmol), copper(I) iodide (5.13 mg, 0.027 mmol), TEA (0.112 mL, 0.808 mmol), and tetrakis(triphenylphosphine)palladium (31.1 mg, 0.027 mmol) at RT. The reaction mixture was slowly heated to 100° C. and then stirred at this temperature overnight. The mixture was concentrated in vacuo. The resulting crude product was purified by FCC (gradient 2%-10% MeOH in DCM) to afford 1-(4-(4-((1-hydroxycyclohexyl)ethynyl)benzyl)phenyl)-5-methyl-1H-1,2,4-triazole-3-carboxamide (18 mg, 15%): LCMS Rt=2.21 min (condition A), MS (M+1)=415.4. $^1$H NMR (400 MHz, Methanol-d$_4$) δ 7.57-7.46 (m, 2H), 7.46-7.39 (m, 2H), 7.39-7.29 (m, 2H), 7.29-7.13 (m, 2H), 4.07 (s, 2H), 2.51 (s, 3H), 2.20-1.91 (m, 2H), 1.91-1.51 (m, 8H).

Example 56

1-(4-(4-(5-(1-hydroxy-2-methylpropan-2-yl)pyridin-2-yl)benzyl)phenyl)-5-methyl-1H-1,2,4-triazole-3-carboxamide

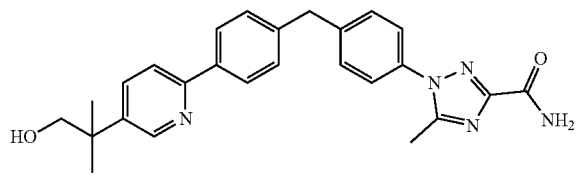 [SMILES: Cc1nc(C(N)=O)nn1-c1ccc(Cc2ccc(-c3ccc(C(C)(C)CO)cn3)cc2)cc1]

A microwave vial was charged with methyl-1-(4-(2-(4-(4,4,5,5-tetramethyl-1,3,2-dioxaborolan-2-yl)phenyl)propan-2-yl)phenyl)-1H-pyrazole-3-carboxamide (Intermediate IX) (100 mg, 0.239 mmol), 2-(6-chloropyridine-3-yl)-2-methylpropan-1-ol (53.3 mg, 0.287 mmol), K$_3$PO$_4$ (152 mg, 0.717 mmol), second generation Xphos Precatalyst (18.81 mg, 0.024 mmol), water (0.5 mL), THF (2 mL), and was evacuated and degassed with N$_2$ for 5 min. The mixture was heated in the microwave at 100° C. for 2 hr, cooled to RT, and concentrated in vacuo. The resulting crude product was purified by FCC (gradient 2%-10% MeOH in DCM) firstly, and then purified by preparative HPLC to afford 1-(4-(4-(5-(1-hydroxy-2-methylpropan-2-yl)pyridin-2-yl)benzyl)phenyl)-5-methyl-1H-1,2,4-triazole-3-carboxamide (14 mg, 12%): LCMS Rt=1.32 min (condition A), MS (M+1)=442.3. $^1$H NMR (400 MHz, Methanol-d$_4$) δ 8.63 (dd, J=2.5, 0.8 Hz, 1H), 7.97-7.81 (m, 3H), 7.77 (dd, J=8.4, 0.8 Hz, 1H), 7.58-7.42 (m, 4H), 7.42-7.30 (m, 2H), 4.14 (s, 2H), 3.62 (s, 2H), 2.51 (s, 3H), 1.37 (s, 6H).

Example 57

1-(4-(4-(5-(1-hydroxy-2-methylpropan-2-yl)pyridin-2-yl)benzyl)phenyl)-5-methyl-1H-pyrazole-3-carboxamide

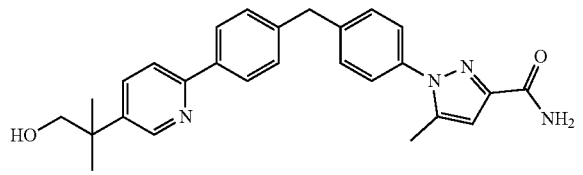 [SMILES: Cc1cc(C(N)=O)nn1-c1ccc(Cc2ccc(-c3ccc(C(C)(C)CO)cn3)cc2)cc1]

A microwave vial was charged with Intermediate III (100 mg, 0.24 mmol), 2-(6-Chloropyridine-3-yl)-2-methylpropan-1-ol (53.4 mg, 0.288 mmol), K$_3$PO$_4$ (153 mg, 0.719 mmol), second generation Xphos Precatalyst (18.85 mg, 0.024 mmol), water (0.5 mL), THF (2 mL), and was evacuated and degassed with N$_2$ for 5 min. The mixture was heated in the microwave at 100° C. for 2 hr, cooled to RT, and concentrated in vacuo. The resulting crude product was purified by FCC (gradient 2%-10% MeOH in DCM) then preparative HPLC to afford 1-(4-(4-(5-(1-hydroxy-2-methylpropan-2-yl)pyridin-2-yl)benzyl)phenyl)-5-methyl-1H-pyrazole-3-carboxamide (18 mg, 16%): LCMS Rt=1.52 min (condition A), MS (M+1)=441.4. $^1$H NMR (400 MHz, Methanol-d$_4$) δ 8.63 (dd, J=2.4, 0.8 Hz, 1H), 7.93 (dd, J=8.4, 2.5 Hz, 1H), 7.90-7.81 (m, 2H), 7.77 (dd, J=8.4, 0.8 Hz, 1H), 7.55-7.30 (m, 6H), 6.67 (d, J=0.9 Hz, 1H), 4.13 (s, 2H), 3.62 (s, 2H), 2.32 (d, J=0.7 Hz, 3H), 1.37 (s, 6H).

Example 58

1-(4-(4-(6-(2-hydroxypropan-2-yl)pyridazin-3-yl)benzyl)phenyl)-5-methyl-1H-pyrazole-3-carboxamide

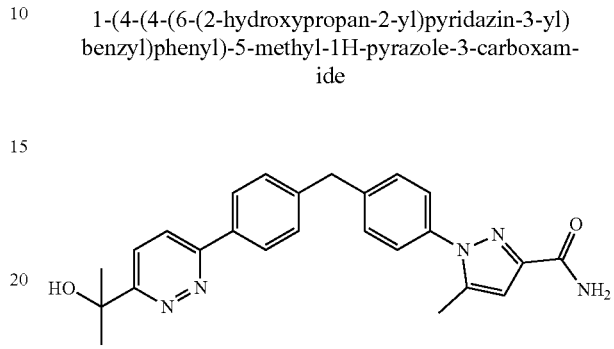

A microwave vial was charged with Intermediate III (100 mg, 0.24 mmol), 2-(6-Bromopyridazin-3-yl)propan-2-ol (52 mg, 0.24 mmol), K$_3$PO$_4$ (153 mg, 0.719 mmol), second generation Xphos Precatalyst (18.85 mg, 0.024 mmol), water (0.5 mL), THF (2 mL), and was evacuated and degassed with N$_2$ for 5 min. The mixture was heated in the microwave at 100° C. for 2 hr, cooled to RT, and concentrated in vacuo. The resulting crude product was purified by FCC (gradient 2%-10% MeOH in DCM) then by preparative HPLC to afford 1-(4-(4-(6-(2-hydroxypropan-2-yl)pyridazin-3-yl)benzyl)phenyl)-5-methyl-1H-pyrazole-3-carboxamide (24 mg, 22%): LCMS Rt=1.79 min (condition A), MS (M+1)=428.3. $^1$H NMR (400 MHz, Methanol-d4) δ 8.11 (d, J=9.0 Hz, 1H), 8.02 (dd, J=8.6, 2.7 Hz, 3H), 7.51-7.35 (m, 6H), 6.67 (d, J=0.9 Hz, 1H), 4.15 (s, 2H), 2.32 (d, J=0.8 Hz, 3H), 1.67 (s, 6H).

Example 59

6-(4-(4-(3-carbamoyl-5-methyl-1H-pyrazol-1-yl)benzyl)phenyl)-N-(2-hydroxy-2-methylpropyl)nicotinamide

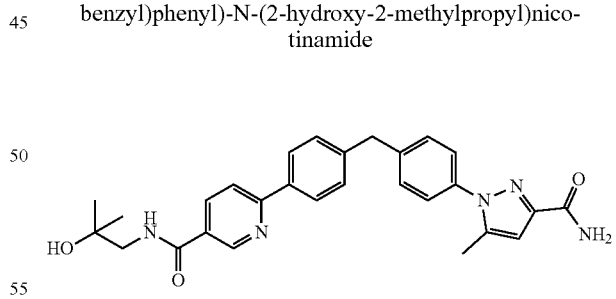

Step 1: Preparation of 6-chloro-N-(2-hydroxy-2-methylpropyl)nicotinamide

To a stirring solution of 6-chloropyridine-3-carboxylic acid (200 mg, 1.269 mmol) in THF (5 mL), was added DIPEA (0.665 mL, 3.81 mmol), followed by 1-amino-2-methylpropan-2-ol (136 mg, 1.523 mmol) and HATU (724 mg, 1.904 mmol). The reaction mixture was stirred at RT overnight, and the mixture was concentrated in vacuo. The resulting crude product was purified by FCC (gradient 2%-10% MeOH in DCM) to afford 6-chloro-N-(2-hydroxy-2-methylpropyl)nicotinamide (240 mg, 83%): LCMS Rt=0.51 min (condition B), MS (M+1)=229.3.

Step 2: Preparation of 6-(4-(4-(3-carbamoyl-5-methyl-1H-pyrazol-1-yl)benzyl)phenyl)-N-(2-hydroxy-2-methylpropyl) nicotinamide A microwave vial was charged with Intermediate III (100 mg, 0.24 mmol), 6-chloro-N-(2-hydroxy-2-methylpropyl)nicotinamide (65.8 mg, 0.288 mmol), K₃PO₄ (153 mg, 0.719 mmol), second generation Xphos Precatalyst (18.85 mg, 0.024 mmol), water (0.5 mL), THF (2 mL), and was evacuated and degassed with N₂ for 5 min. The mixture was heated in the microwave at 100° C. for 2 hr, cooled to RT, and concentrated in vacuo. The resulting crude product was purified by FCC (gradient 2%-10% MeOH in DCM) then by preparative HPLC to afford 6-(4-(4-(3-carbamoyl-5-methyl-1H-pyrazol-1-yl)benzyl)phenyl)-N-(2-hydroxy-2-methylpropyl)nicotinamide (18 mg, 14%): LCMS Rt=1.77 min (condition A), MS (M+1)=484.5. ¹H NMR (400 MHz, Methanol-d₄) δ 9.05 (dd, J=2.3, 0.9 Hz, 1H), 8.29 (dd, J=8.4, 2.3 Hz, 1H), 8.06-7.88 (m, 3H), 7.52-7.34 (m, 6H), 6.68 (d, J=0.9 Hz, 1H), 4.15 (s, 2H), 3.44 (s, 2H), 2.33 (d, J=0.8 Hz, 3H), 1.26 (s, 6H).

Example 60

1-(4-(4-(2-(2-hydroxypropan-2-yl)pyrimidin-5-yl)benzyl)phenyl)-5-methyl-1H-pyrazole-3-carboxamide

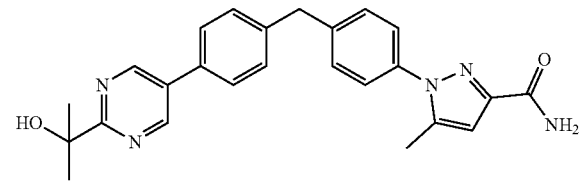 [SMILES: Cc1cc(C(N)=O)nn1-c1ccc(Cc2ccc(-c3cnc(C(C)(C)O)nc3)cc2)cc1]

A microwave vial was charged with Intermediate III (100 mg, 0.24 mmol), 5-bromo-2-(1-hydroxy-1-methylethyl)pyrimidine (62.4 mg, 0.288 mmol), K₃PO₄ (153 mg, 0.719 mmol), second generation Xphos Precatalyst (18.85 mg, 0.024 mmol), water (0.5 mL), THF (2 mL), and was evacuated and degassed with N₂ for 5 min. The mixture was heated in the microwave at 100° C. for 2 hr, cooled to RT, and concentrated in vacuo. The resulting crude product was purified by FCC (gradient 2%-10% MeOH in DCM) then by preparative HPLC to afford 1-(4-(4-(2-(2-hydroxypropan-2-yl)pyrimidin-5-yl)benzyl)phenyl)-5-methyl-1H-pyrazole-3-carboxamide (40 mg, 37%): LCMS Rt=1.99 min (condition A), MS (M+1)=428.4. ¹H NMR (400 MHz, Methanol-d₄) δ 9.00 (s, 2H), 7.72-7.59 (m, 2H), 7.51-7.33 (m, 6H), 6.68 (d, J=0.9 Hz, 1H), 4.59-4.13 (s, 2H), 2.32 (d, J=0.8 Hz, 3H), 1.61 (s, 6H).

Example 61

1-(4-(4-(2-(hydroxymethyl)pyridin-4-yl)benzyl)phenyl)-5-methyl-1H-pyrazole-3-carboxamide

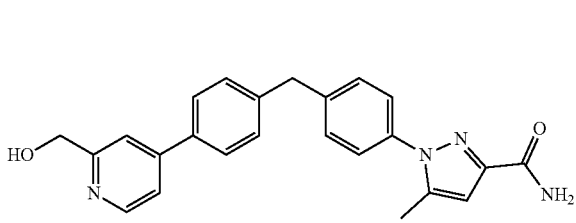 [SMILES: Cc1cc(C(N)=O)nn1-c1ccc(Cc2ccc(-c3ccnc(CO)c3)cc2)cc1]

A microwave vial was charged with Intermediate III (60 mg, 0.144 mmol), (4-chloro-2-pyridinyl)methanol (24.77 mg, 0.173 mmol), K₃PO₄ (92 mg, 0.431 mmol), second generation Xphos Precatalyst (11.31 mg, 0.014 mmol), water (0.5 mL), THF (2 mL), and was evacuated and degassed with N₂ for 5 min. The mixture was heated in the microwave at 100° C. for 2 hr, cooled to RT, and concentrated in vacuo. The resulting crude product was purified by FCC (gradient 2%-10% MeOH in DCM) then by preparative HPLC to afford 1-(4-(4-(2-(hydroxymethyl)pyridin-4-yl)benzyl)phenyl)-5-methyl-1H-pyrazole-3-carboxamide (2 mg, 3%): LCMS Rt=1.23 min (condition A), MS (M+1)=399.4. 1H NMR (400 MHz, Methanol-d₄) δ 8.48 (dd, J=5.3, 0.8 Hz, 1H), 7.82 (dd, J=1.8, 0.9 Hz, 1H), 7.78-7.66 (m, 2H), 7.57 (dd, J=5.3, 1.9 Hz, 1H), 7.51-7.30 (m, 6H), 6.68 (d, J=0.9 Hz, 1H), 4.75 (s, 2H), 4.14 (s, 2H), 2.33 (d, J=0.7 Hz, 3H).

Example 62

(S)-5-methyl-1-(4-((4'-((1-methylpyrrolidin-3-yl)oxy)-[1,1'-biphenyl]-4-yl)methyl)phenyl)-1H-1,2,4-triazole-3-carboxamide

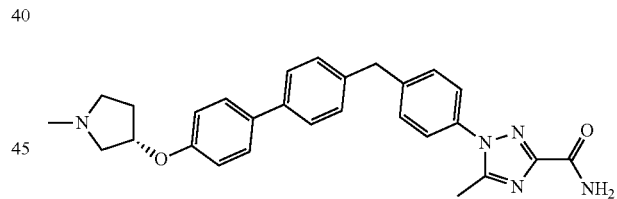

Step 1: Preparation of (S)-3-(4-chlorophenoxy)-1-methylpyrrolidine (S)-(+)-1-Methyl-3-hydroxypyrrolidine (0.189 g, 1.867 mmol) and triphenyl phosphine (0.49, 1.867 mmol) were dissolved in dry THF (10 mL) under nitrogen. The solution was cooled to 0° C. and 4-chlorophenol (0.2 g, 1.556 mmol) was added, followed by DIAD (0.363 mL, 1.867 mmol). After 15 minutes the ice bath was removed and the reaction was stirred overnight. The reaction mixture was concentrated under reduced pressure and the residue was stirred with ether. The solid triphenyl phosphine oxide was filtered off and the solution was washed with sodium hydroxide (1M) and concentrated in vacuo. The resulting crude product was purified by FCC (gradient 2%-10% MeOH in DCM) to afford (S)-3-(4-chlorophenoxy)-1-methylpyrrolidine (0.15 g, 46%): LCMS Rt=0.56 min (condition B), MS (M+1)=212.5.

Step 2: Preparation of (S)-5-methyl-1-(4-((4'-((1-methylpyrrolidin-3-yl)oxy)-[1,1'-biphenyl]-4-yl)methyl)phenyl)-1H-1,2,4-triazole-3-carboxamide A microwave vial was charged with methyl-1-(4-(2-(4-(4,4,5,5-tetramethyl-1,3,2-dioxaborolan-2-yl)phenyl)propan-2-yl)phenyl)-1H-pyrazole-3-carboxamide (Intermediate IX) (0.1 g, 0.239 mmol), (S)-3-(4-chlorophenoxy)-1-methylpyrrolidine (0.056 g, 0.239 mmol), $K_3PO_4$ (0.152 g, 0.717 mmol), second generation Xphos Precatalyst (0.018 g, 0.024 mmol), water (0.5 mL), THF (2 mL), and was evacuated and degassed with $N_2$ for 5 min. The mixture was heated in the microwave at 100° C. for 2 hr, cooled to RT, and concentrated in vacuo. The resulting crude product was purified by FCC (gradient 2%-10% MeOH in DCM) then by preparative HPLC to afford (S)-5-methyl-1-(4-((4'-((1-methylpyrrolidin-3-yl)oxy)-[1,1'-biphenyl]-4-yl)methyl)phenyl)-1H-1,2,4-triazole-3-carboxamide. The product was dissolved in 1 mL MeOH and 0.2 mL ACN was added and solid was precipitated from the solution. The mixture was then concentrated in vacuo and the resulting solid was dried under vacuum overnight to afford (S)-5-methyl-1-(4-((4'-((1-methylpyrrolidin-3-yl)oxy)-[1,1'-biphenyl]-4-yl)methyl)phenyl)-1H-1,2,4-triazole-3-carboxamide (40 mg, 34%): LCMS Rt=1.39 min (condition A), MS (M+1)=468.5. $^1H$ NMR (400 MHz, Methanol-$d_4$) δ 7.55-7.48 (m, 6H), 7.44 (d, J=8.6 Hz, 2H), 7.34-7.23 (m, 2H), 6.98-6.88 (m, 2H), 5.00-4.90 (m, 1H), 4.09 (s, 2H), 2.93-2.76 (m, 3H), 2.53-2.46 (m, 4H), 2.43-2.29 (m, 4H), 2.02-1.96 (m, 1H).

Example 63

(R)-5-methyl-1-(4-((4'-((1-methylpyrrolidin-3-yl)oxy)-[1,1'-biphenyl]-4-yl)methyl)phenyl)-1H-1,2,4-triazole-3-carboxamide

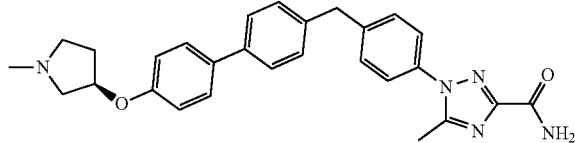 [SMILES: Cc1nc(C(N)=O)nn1-c1ccc(Cc2ccc(-c3ccc(O[C@@H]4CCN(C)C4)cc3)cc2)cc1]

Step 1: Preparation of (R)-3-(4-chlorophenoxy)-1-methylpyrrolidine (R)-(−)-1-Methyl-3-hydroxypyrrolidine (472 mg, 4.67 mmol) and triphenyl phosphine (1224 mg, 4.67 mmol) were dissolved in dry THF (10 mL) under nitrogen. The solution was cooled to 0° C. and 4-chlorophenol (500 mg, 3.89 mmol) was added, followed by DIAD (0.907 mL, 4.67 mmol). After 15 minutes the ice bath was removed and the reaction was stirred overnight. The reaction mixture was concentrated under reduced pressure and the residue was stirred with ether. The solid triphenyl phosphine oxide was filtered off and the solution was washed with sodium hydroxide (1M) and concentrated in vacuo. The resulting crude product was purified by FCC (gradient 2%-10% MeOH in DCM) to afford (R)-3-(4-chlorophenoxy)-1-methylpyrrolidine (600 mg, 72%): LCMS Rt=0.49 min (condition B), MS (M+1)=212.1.

Step 2: Preparation of (R)-5-methyl-1-(4-((4'-((1-methylpyrrolidin-3-yl)oxy)-[1,1'-biphenyl]-4-yl)methyl)phenyl)-1H-1,2,4-triazole-3-carboxamide A microwave vial was charged with methyl-1-(4-(2-(4-(4,4,5,5-tetramethyl-1,3,2-dioxaborolan-2-yl)phenyl)propan-2-yl)phenyl)-1H-pyrazole-3-carboxamide (Intermediate IX) (200 mg, 0.478 mmol), (R)-3-(4-chlorophenoxy)-1-methylpyrrolidine (101 mg, 0.478 mmol), $K_3PO_4$ (304 mg, 1.434 mmol), second generation Xphos Precatalyst (37.6 mg, 0.048 mmol), water (0.5 mL), THF (2 mL), and was evacuated and degassed with $N_2$ for 5 min. The mixture was heated in the microwave at 100° C. for 2 hr, cooled to RT, and concentrated in vacuo. The resulting crude product was purified by FCC (gradient 2%-10% MeOH in DCM) then by preparative HPLC to afford (R)-5-methyl-1-(4-((4'-((1-methyl pyrrolidin-3-yl)oxy)-[1,1'-biphenyl]-4-yl)methyl)phenyl)-1H-1,2,4-triazole-3-carboxamide. The product was dissolved in 1 mL MeOH and 0.2 mL AcCN was added and the solid precipitated from the solution. The solution was concentrated in vacuo and dried under vacuum overnight to afford the product (4 mg, 2%): LCMS Rt=1.41 min (condition A), MS (M+1)=468.4. $^1H$ NMR (400 MHz, Methanol-$d_4$) δ 7.55-7.48 (m, 6H), 7.48-7.42 (m, 2H), 7.33-7.26 (m, 2H), 6.98-6.91 (m, 2H), 5.00-4.91 (m, 1H), 4.10 (s, 2H), 2.96-2.83 (m, 3H), 2.55-2.47 (m, 4H), 2.43-2.33 (m, 4H), 2.07-1.94 (m, 1H).

Example 64

1-(4-((4'-(2-((2-hydroxy-2-methyl propyl)amino)propan-2-yl)-[1,1'-biphenyl]-4-yl)methyl)phenyl)-5-methyl-1H-1,2,4-triazole-3-carboxamide

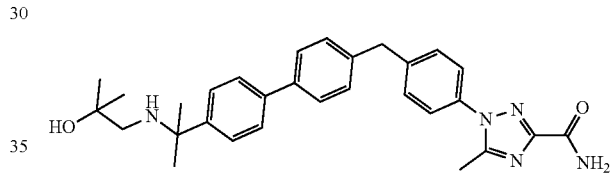

Step 1: Preparation of benzyl (2-(4-chlorophenyl)propan-2-yl)glycinate 1-(4-Chlorophenyl)-1-methylethylamine (0.4 g, 2.358 mmol) was added to THF (10 mL) followed by base $K_2CO_3$ (0.815 g, 5.89 mmol). The mixture was cooled to 0° C. and benzyl 2-bromoacetate (0.448 mL, 2.83 mmol) was added slowly. The reaction was allowed to warm to room temperature and stirred overnight. The resultant slurry was then added to brine and the organic materials extracted into ethyl acetate. The organic layers were dried with magnesium sulfate and reduced under pressure. The resulting crude product was purified by FCC (gradient 2%-10% MeOH in DCM) to afford benzyl (2-(4-chlorophenyl)propan-2-yl) glycinate (0.6 g, 80%): LCMS Rt=0.78 min (condition B), MS (M+1)=318.1.

Step 2: Preparation of 2-(benzyloxy)-N-(2-(4-chlorophenyl)propan-2-yl)-2-methylpropan-1-amine A solution of benzyl (2-(4-chlorophenyl)propan-2-yl) glycinate (0.3 g, 0.944 mmol) in tetrahydrofuran (6 mL) was cooled to −15° C., and treated with zirconium(IV) chloride (0.264 g, 1.133 mmoL). The mixture was stirred at −15° C. for 30 minutes and a 3M solution of methylmagnesium bromide in ether 1.888 mL, 5.66 mmol) was slowly added. The reaction mixture was warmed to RT slowly and stirred overnight. 25% sodium hydroxide aqueous solution was added to quench the reaction. The mixture was extracted with dichloromethane, and the organic layer was washed with water and brine, and concentrated in vacuo. The resulting crude product was purified by FCC (gradient 10-60% hexane in ethyl acetate) to afford 2-(benzyloxy)-N-(2-(4-chlorophenyl)propan-2-yl)-2-methylpropan-1-amine (0.09 g, 28%): LCMS Rt=0.81 min (condition B), MS (M+1)=332.2.

Step 3: Preparation of 1-(4-((4'-(2-((2-hydroxy-2-methylpropyl)amino)propan-2-yl)-[1,1'-biphenyl]-4-yl)methyl)phenyl)-5-methyl-1H-1,2,4-triazole-3-carboxamide A microwave vial was charged with methyl-1-(4-(2-(4-(4,4,5,5-tetramethyl-1,3,2-dioxaborolan-2-yl)phenyl)propan-2-yl)phenyl)-1H-pyrazole-3-carboxamide (Intermediate IX) (100 mg, 0.239 mmol), 2-(benzyloxy)-N-(2-(4-chlorophenyl)propan-2-yl)-2-methylpropan-1-amine (87 mg, 0.263 mmol), $K_3PO_4$ (152 mg, 0.717 mmol), second generation Xphos Precatalyst (18.81 mg, 0.024 mmol), water (0.5 mL), THF (2 mL), and was evacuated and degassed with $N_2$ for 5 min. The mixture was heated in the microwave at 100° C. for 2 hr, cooled to RT, and concentrated in vacuo. The resulting crude product was purified by FCC (gradient 2%-10% MeOH in DCM) then by preparative HPLC to afford 1-(4-((4'-(2-((2-hydroxy-2-methylpropyl)amino)propan-2-yl)-[1,1'-biphenyl]-4-yl)methyl)phenyl)-5-methyl-1H-1,2,4-triazole-3-carboxamide (4 mg, 3%): LCMS Rt=1.44 min (condition A), MS (M+1)=498.4. $^1$H NMR (400 MHz, Methanol-$d_4$) δ 7.60-7.49 (m, 8H), 7.46 (d, J=8.5 Hz, 2H), 7.32 (d, J=8.1 Hz, 2H), 4.11 (s, 2H), 2.52 (s, 3H), 2.28 (s, 2H), 1.49 (s, 6H), 1.16 (s, 6H).

Activity of Compounds

Assay Example 1

FoxO3a Inhibition and Akt Activation Assay

Phosphorylation of Akt on S473 and FoxO3a nuclear to cytoplasmic translocation were used as readouts of PI3K/Akt/mTOR pathway activation downstream of growth factor signaling.

Reporter cell line. U2OS GFP-FoxO3a H212R reporter cell line was established by transducing U2OS cells with the retroviral plasmid pLEGFP-C1 containing FoxO3a H212R transgene and selecting for G418 resistant clones.

Reporter assay. U2OS GFP-FoxO3a H212R cells were plated in 384-well plates at 4000 cells per well in 30 microliters of McCoy's 5A medium containing 10% FBS. On day 1 the cells were washed with serum free medium and serum starved overnight. On day 2 the cells were treated with different doses of the compounds for 30 minutes, fixed with 4% Paraformaldehyde for 1 hour and stained with Phospho-AKT (Ser473) antibody (Cell Signaling Technology, catalog #4060) overnight at 4° C. After nuclei staining with Hoechst 33342 (Life Technologies, catalog # H3570) the plates were imaged with InCell 2000 (GE Healthcare Bio-Sciences). FoxO3a inhibition activity is calculated as the ratio of nuclear to cytosolic GFP intensity in percent. Akt activation is measured as the total cellular intensity of Phospho-Akt antibody staining in percent. DMSO control is set as 0% activity.

Results. The measured FoxO3a inhibition activity and Akt activation activity are reported in the following table:

| Example # | FoxO $AC_{50}$ (μM) | Akt $AC_{50}$ (μM) |
|---|---|---|
| 1 | 0.576 | 1.554 |
| 2 | 0.137 | 0.326 |
| 3-1 | 0.036 | 0.135 |
| 3-2 | 0.236 | 0.341 |
| 3-3 | 0.040 | 0.109 |
| 3-4 | 0.075 | 0.268 |
| 3-5 | 0.061 | 0.156 |
| 3-6 | 0.028 | 0.066 |
| 3-7 | 0.499 | N/A |
| 3-8 | 0.383 | 0.960 |
| 3-9 | 0.029 | 0.063 |
| 3-10 | 0.110 | 0.497 |
| 3-11 | 0.132 | 0.504 |
| 3-12 | 0.036 | 0.122 |
| 3-13 | 0.057 | 0.167 |
| 3-14 | 0.053 | 0.161 |
| 3-15 | 0.031 | 0.083 |
| 4 | 0.325 | 1.215 |
| 5-1 | 0.295 | 1.316 |
| 5-2 | 0.792 | 2.505 |
| 5-3 | 0.136 | 0.425 |
| 5-4 | 0.160 | 0.789 |
| 5-5 | 0.152 | 0.426 |
| 5-6 | 0.312 | 1.037 |
| 5-7 | 0.412 | 1.369 |
| 5-8 | 0.076 | 0.145 |
| 6-1 | 0.115 | 0.292 |
| 6-2 | 0.480 | 1.806 |
| 6-3 | 0.149 | 0.432 |
| 6-4 | 0.517 | 1.044 |
| 6-5 | 0.134 | 0.415 |
| 6-6 | 0.283 | 0.842 |
| 7 | 0.058 | 0.276 |
| 8 | 0.096 | 0.377 |
| 9 | 0.253 | 0.532 |
| 10 | 0.470 | 0.733 |
| 11 | 0.607 | 1.190 |
| 12 | 0.093 | 0.283 |
| 13-1 | 0.128 | 0.375 |
| 13-2 | 0.112 | 0.252 |
| 13-3 | 0.311 | 0.943 |
| 13-4 | 0.429 | 1.241 |
| 13-5 | 0.147 | 0.446 |
| 13-6 | 0.133 | 0.440 |
| 13-7 | 0.159 | 0.504 |
| 13-8 | 0.664 | 1.747 |
| 13-9 | 0.183 | 0.714 |
| 13-10 | 0.489 | 1.181 |
| 13-11 | 0.416 | 1.000 |
| 13-12 | 0.064 | 0.261 |
| 13-13 | 0.179 | 0.506 |
| 13-14 | 0.386 | 1.168 |
| 13-15 | 0.114 | 0.493 |
| 13-16 | 0.377 | 0.926 |
| 14 | 0.113 | 0.180 |
| 15-1 | 0.069 | 0.166 |
| 15-2 | 0.277 | 0.888 |
| 15-3 | 0.060 | 0.188 |
| 15-4 | 0.033 | 0.099 |
| 16-1 | 0.033 | 0.090 |
| 16-2 | 0.138 | 0.426 |
| 16-3 | 0.500 | 0.804 |
| 16-4 | 0.041 | 0.120 |
| 16-5 | 0.011 | 0.036 |
| 16-6 | 0.103 | 0.248 |
| 16-7 | 0.009 | 0.024 |
| 16-8 | 0.117 | 0.300 |
| 17 | 0.029 | 0.101 |
| 18 | 0.095 | 0.394 |
| 19 | 0.071 | 0.209 |
| 20 | 0.091 | 0.208 |
| 21 | 0.155 | 0.723 |
| 22 | 0.042 | 0.187 |
| 23 | 0.121 | 0.639 |
| 24 | 0.033 | 0.155 |
| 25 | 0.135 | 0.726 |
| 26 | 0.075 | 0.480 |
| 27 | 0.213 | N/A |
| 28 | 0.026 | 0.073 |

| Example # | FoxO AC$_{50}$ (µM) | Akt AC$_{50}$ (µM) |
|---|---|---|
| 29 | 0.138 | 0.486 |
| 30 | 0.237 | 0.802 |
| 31-1 | 0.077 | 0.354 |
| 31-2 | 0.373 | 1.620 |
| 31-3 | 0.158 | 0.190 |
| 32 | 0.315 | 0.647 |
| 33 | 0.138 | N/A |
| 34 | 0.300 | 0.576 |
| 35 | 0.743 | 1.491 |
| 36 | 0.183 | N/A |
| 37 | 0.276 | 0.498 |
| 38-1 | 0.002 | N/A |
| 38-2 | 0.048 | 0.230 |
| 38-3 | 0.035 | N/A |
| 38-4 | 0.062 | 0.207 |
| 38-5 | 0.026 | 0.027 |
| 38-6 | 0.074 | N/A |
| 38-7 | 0.015 | 0.031 |
| 38-8 | 0.051 | 0.211 |
| 38-9 | 0.013 | 0.011 |
| 38-10 | 0.175 | 0.397 |
| 39-1 | 0.195 | 0.615 |
| 39-2 | 0.005 | N/A |
| 39-3 | 0.037 | 0.120 |
| 39-4 | 0.026 | 0.092 |
| 39-5 | 0.008 | 0.022 |
| 39-6 | 0.009 | 0.005 |
| 39-7 | 0.029 | N/A |
| 39-8 | 0.864 | N/A |
| 39-9 | 0.123 | N/A |
| 39-10 | 0.013 | N/A |
| 39-11 | 0.241 | N/A |
| 39-12 | 0.181 | N/A |
| 39-13 | 0.079 | N/A |
| 39-14 | 0.054 | N/A |
| 39-15 | 0.005 | N/A |
| 39-16 | 0.056 | N/A |
| 39-17 | 0.085 | N/A |
| 39-18 | 0.081 | N/A |
| 39-19 | 0.065 | N/A |
| 39-20 | 0.140 | N/A |
| 39-21 | 0.060 | N/A |
| 39-22 | 0.098 | N/A |
| 39-23 | 0.018 | N/A |
| 39-24 | 0.406 | N/A |
| 39-25 | 0.105 | N/A |
| 39-26 | 0.031 | N/A |
| 39-27 | 0.046 | N/A |
| 39-28 | 0.039 | N/A |
| 30-29 | 0.180 | N/A |
| 39-30 | 0.032 | N/A |
| 39-31 | 0.049 | N/A |
| 39-32 | 0.048 | 0.085 |
| 39-33 | 0.042 | N/A |
| 39-34 | 0.010 | N/A |
| 39-35 | 0.145 | N/A |
| 39-36 | 0.164 | N/A |
| 39-37 | 0.081 | 0.270 |
| 39-38 | 0.048 | 0.119 |
| 40 | 0.032 | 0.146 |
| 41 | 0.114 | 0.091 |
| 42 | 0.055 | N/A |
| 43 | 0.017 | N/A |
| 44 | 0.134 | N/A |
| 45 | 0.130 | 0.003 |
| 46 | 0.234 | 1.161 |
| 47 | 0.093 | 0.099 |
| 48 | 0.051 | 0.160 |
| 49 | 0.273 | 0.840 |
| 50 | 0.036 | 0.117 |
| 51 | 0.102 | 0.300 |
| 52 | 0.106 | 0.749 |
| 53 | 2.418 | 8.234 |
| 54 | 0.248 | 0.528 |
| 55 | 0.096 | 1.293 |
| 56 | 0.156 | 0.366 |
| 57 | 0.049 | N/A |
| 58 | 0.225 | N/A |
| 59 | 0.058 | N/A |
| 60 | 0.083 | N/A |
| 61 | 0.187 | N/A |
| 62 | 0.020 | N/A |
| 63 | 0.011 | N/A |
| 64 | 0.062 | N/A |

The compounds, compositions, or methods described herein can be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes that come within the meaning and range of equivalency of the claims are intended to be embraced therein.

What is claimed is:
1. A compound of formula (I) or a pharmaceutically acceptable salt thereof:

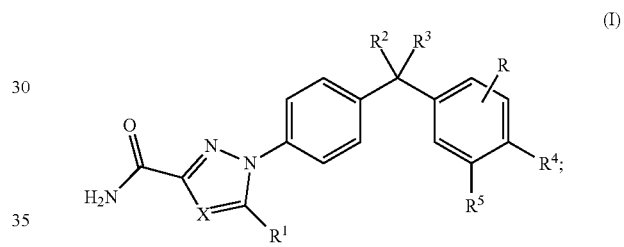

wherein:
X is CH or N;
R is H, halo, —OH, C$_{1-4}$alkyl, C$_{1-4}$alkoxy, C$_{1-4}$haloalkyl or C$_{1-4}$ haloalkoxy;
R$^1$ is H, C$_{1-4}$alkyl, C$_{1-4}$haloalkyl, or 3-6 membered cycloalkyl;
R$^2$ and R$^3$ are each, independently, H or C$_{1-4}$alkyl;
R$^4$ is halo, —C$_6$H$_4$—R$^6$, -(4-10 membered heterocyclyl)-R$^6$, -(5-10 membered heteroaryl)-R$^6$, -(4-10 membered carbocyclyl)-R$^6$, a 6-10 membered fused heterocyclyl-aryl optionally substituted with 1-3 C$_{1-4}$alkyl groups, or a 6-10 membered fused heterocyclyl-heteroaryl optionally substituted with 1-3 C$_{1-4}$alkyl groups;
R$^5$ is H, or R$^4$ and R$^5$ together with the carbon atoms to which they are attached form a benzo[c]chromene ring which is optionally substituted with 1-3 C$_{1-4}$alkyl groups;
R$^6$ is —(CH$_2$)$_m$—(CO)$_n$—(CH$_2$)$_p$—R$^{6a}$, —(CH$_2$)$_m$—(CO)$_n$—(CH$_2$)$_p$—R$^{6b}$, or —(CH$_2$)$_m$—(CO)$_n$—(CH$_2$)$_p$—R$^{6c}$;
R$^{6a}$ is H, —OH, —NR$^7$R$^8$, —CN, oxo, C$_{1-4}$alkyl, C$_{1-4}$haloalkyl, —CH(NR$^7$R$^8$)—C$_{1-3}$haloalkyl, —CH(NR$^7$R$^8$)—C$_{1-3}$alkyl, —SO$_2$C$_{1-4}$alkyl, or —SO$_2$NR$^7$R$^8$; and
R$^{6b}$ is a 4-10 membered heterocyclyl optionally substituted with 1-3 substituents independently selected from a group consisting of —NR$^7$R$^8$, C$_{1-4}$alkyl, —C$_{1-4}$hydroxyalkyl, and —C$_{1-4}$alkyl-NR$^7$R$^8$;
R$^{6c}$ is a 5-10 membered heteroaryl optionally substituted with 1-3 substituents independently selected from a group consisting of —NR$^7$R$^8$, C$_{1-4}$alkyl, —C$_{1-4}$hydroxyalkyl, and —C$_{1-4}$alkyl-NR$^7$R$^8$;

R$^{6d}$ is a 4-10 membered carbocyclyl optionally substituted with 1-3 substituents independently selected from a group consisting of halo, —OH, —NR$^7$R$^8$, C$_{1-4}$alkyl, —C$_{1-4}$haloalkyl, —C$_{1-4}$hydroxyalkyl, —C$_{1-4}$alkyl-NR$^7$R$^8$, —SO$_2$C$_{1-4}$alkyl, and 4-6 membered heterocyclyl;

R$^7$ and R$^8$ are each, independently, selected from a group consisting of H, C$_{1-4}$alkyl, C$_{1-4}$hydroxyalkyl, a 4-6 membered heterocyclyl, and a 4-6 membered cycloalkyl;

m is 0 or 1;

n is 0 or 1; and p is 0 or 1.

2. The compound according to claim 1 or a pharmaceutically acceptable salt thereof, wherein X is N.

3. The compound according to claim 1 or a pharmaceutically acceptable salt thereof, wherein the compound has formula (I-A):

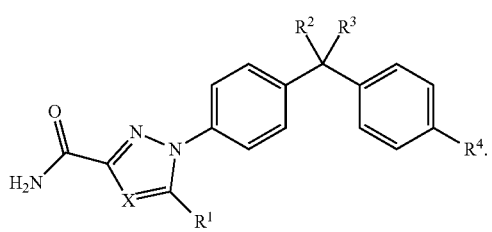

(I-A)

4. The compound according to claim 1 or a pharmaceutically acceptable salt thereof, wherein R$^4$ is selected from a group consisting of:

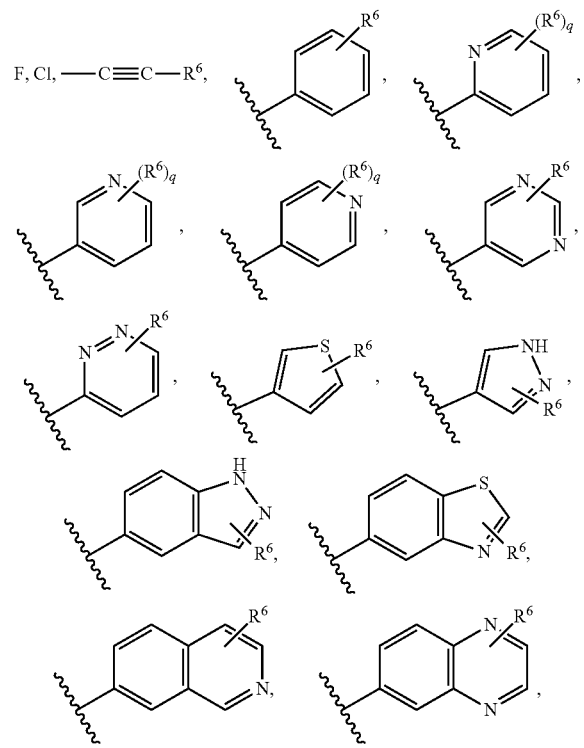

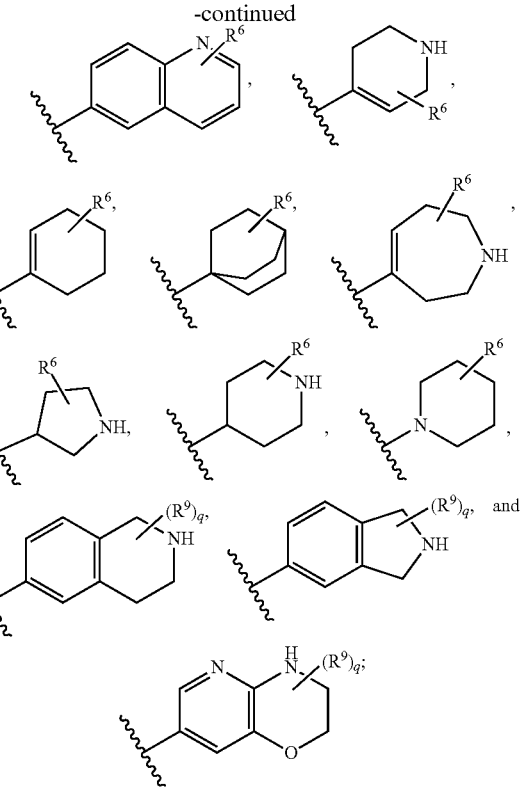

R$^9$ is C$_{1-4}$alkyl; and q is 0, 1, 2, or 3.

5. The compound according to claim 1 or a pharmaceutically acceptable salt thereof, wherein R$^4$ is selected from a group consisting of:

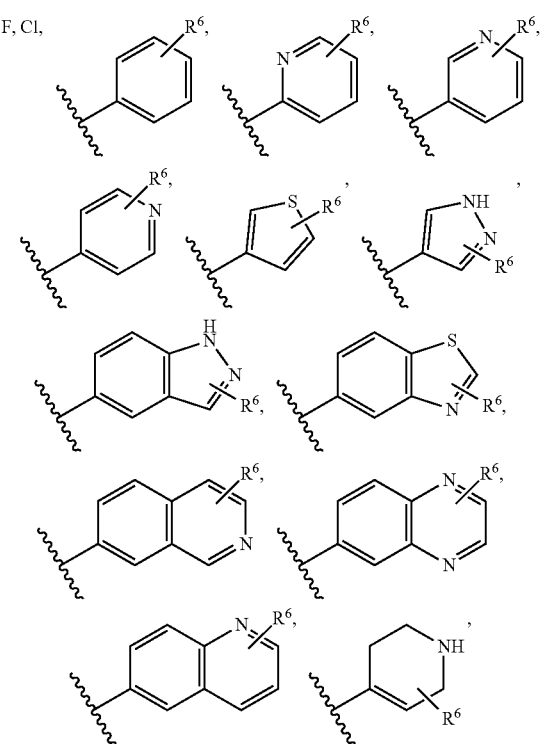

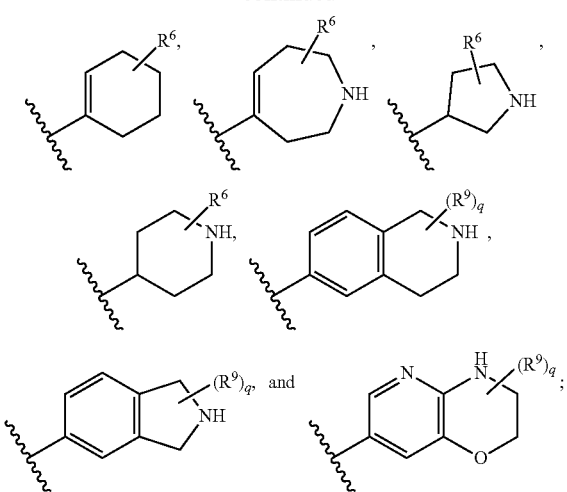
$R^9$ is $C_{1-4}$alkyl; and q is 0, 1, 2, or 3.
6. The compound according to claim 1 or a pharmaceutically acceptable salt thereof, wherein $R^4$ is selected from a group consisting of:
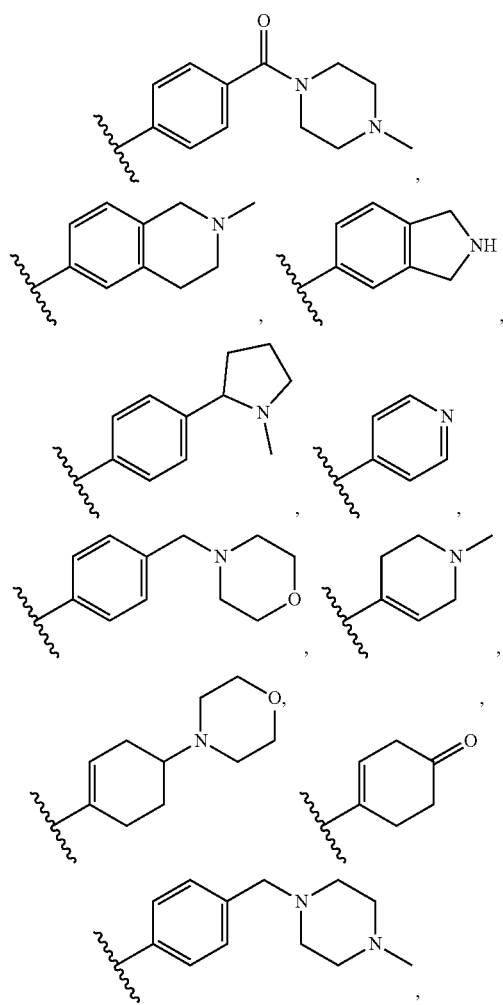
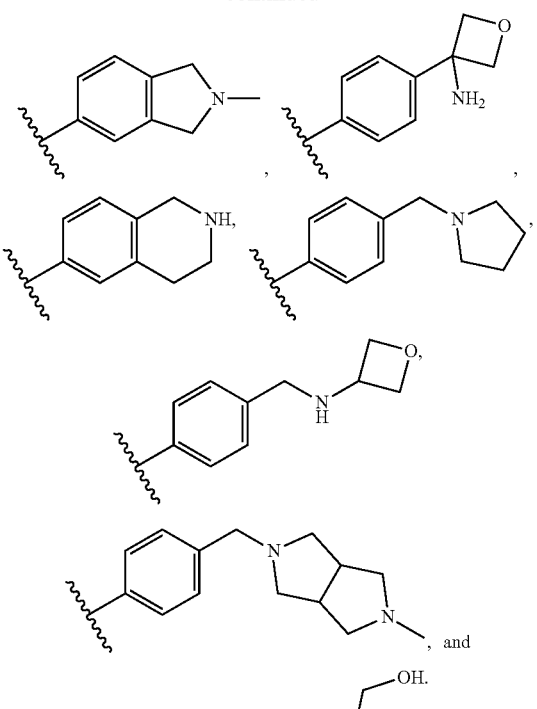
7. The compound according to claim 1 or a pharmaceutically acceptable salt thereof, wherein $R^4$ is selected from a group consisting of:
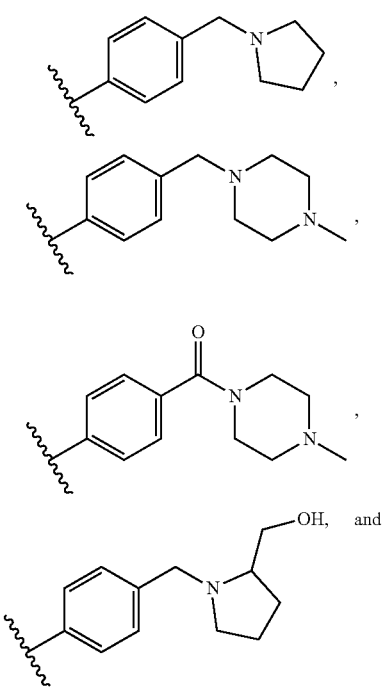

-continued

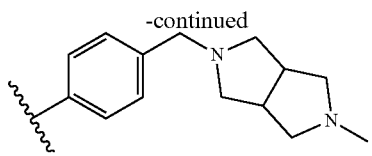

8. The compound according to claim 1 or a pharmaceutically acceptable salt thereof, wherein the compound is selected from a group consisting of:
1-(4-(2-(4-chlorophenyl)propan-2-yl)phenyl)-5-methyl-1H-1,2,4-triazole-3-carboxamide;
1-(4-((6H-benzo[c]chromen-3-yl)methyl)phenyl)-5-methyl-1H-pyrazole-3-carboxamide;
5-methyl-1-(4-((4'-(pyrrolidin-1-ylmethyl)-[1,1'-biphenyl]-4-yl)methyl)phenyl)-1H-pyrazole-3-carboxamide;
1-(4-((4'-((diethylamino)methyl)-[1,1'-biphenyl]-4-yl)methyl)phenyl)-5-methyl-1H-pyrazole-3-carboxamide;
5-methyl-1-(4-(4-(2-methyl-1,2,3,4-tetrahydroisoquinolin-6-yl)benzyl)phenyl)-1H-pyrazole-3-carboxamide;
1-(4-(4-(isoindolin-5-yl)benzyl)phenyl)-5-methyl-1H-pyrazole-3-carboxamide;
5-methyl-1-(4-(4-(pyridin-4-yl)benzyl)phenyl)-1H-pyrazole-3-carboxamide;
5-methyl-1-(4-((4'-(methylsulfonyl)-[1,1'-biphenyl]-4-yl)methyl)phenyl)-1H-pyrazole-3-carboxamide;
5-methyl-1-(4-((3'-(5-methyl-1,3,4-oxadiazol-2-yl)-[1,1'-biphenyl]-4-yl)methyl)phenyl)-1H-pyrazole-3-carboxamide;
1-(4-([1,1'-biphenyl]-4-ylmethyl)phenyl)-5-methyl-1H-pyrazole-3-carboxamide;
5-methyl-1-(4-((4'-(5-methyl-1,3,4-oxadiazol-2-yl)-[1,1'-biphenyl]-4-yl)methyl)phenyl)-1H-pyrazole-3-carboxamide;
5-methyl-1-(4-(4-(pyridin-3-yl)benzyl)phenyl)-1H-pyrazole-3-carboxamide;
1-(4-(4-(1-(dimethylglycyl)-1,2,3,6-tetrahydropyridin-4-yl)benzyl)phenyl)-5-methyl-1H-pyrazole-3-carboxamide;
5-methyl-1-(4-((4'-((4-methylpiperazin-1-yl)methyl)-[1,1'-biphenyl]-4-yl)methyl)phenyl)-1H-pyrazole-3-carboxamide;
5-methyl-1-(4-(4-(2-methylisoindolin-5-yl)benzyl)phenyl)-1H-pyrazole-3-carboxamide;
5-methyl-1-(4-(4-(1,2,3,4-tetrahydroisoquinolin-6-yl)benzyl)phenyl)-1H-pyrazole-3-carboxamide;
5-methyl-1-(4-(4-(1-methyl-1,2,3,6-tetrahydropyridin-4-yl)benzyl)phenyl)-1H-pyrazole-3-carboxamide;
5-methyl-1-(4-(4-(1-methylpiperidin-4-yl)benzyl)phenyl)-1H-pyrazole-3-carboxamide;
5-methyl-1-(4-(4-(1-methylpyrrolidin-3-yl)benzyl)phenyl)-1H-pyrazole-3-carboxamide;
(R)-5-methyl-1-(4-(4-(1-methylpyrrolidin-3-yl)benzyl)phenyl)-1H-pyrazole-3-carboxamide;
(S)-5-methyl-1-(4-(4-(1-methylpyrrolidin-3-yl)benzyl)phenyl)-1H-pyrazole-3-carboxamide;
1-(4-(4-(6-((dimethylamino)methyl)pyridin-3-yl)benzyl)phenyl)-5-methyl-1H-pyrazole-3-carboxamide;
1-(4-(4-(2-((dimethylamino)methyl)pyridin-4-yl)benzyl)phenyl)-5-methyl-1H-pyrazole-3-carboxamide;
5-methyl-1-(4-(4-(6-(pyrrolidin-1-ylmethyl)pyridin-3-yl)benzyl)phenyl)-1H-pyrazole-3-carboxamide;
1-(4-(4-(5-((dimethylamino)methyl)pyridin-3-yl)benzyl)phenyl)-5-methyl-1H-pyrazole-3-carboxamide;
5-methyl-1-(4-(4-(1-methyl-2,3,6,7-tetrahydro-1H-azepin-4-yl)benzyl)phenyl)-1H-pyrazole-3-carboxamide;
5-methyl-1-(4-((4'-(1-methylpyrrolidin-2-yl)-[1,1'-biphenyl]-4-yl)methyl)phenyl)-1H-pyrazole-3-carboxamide;
(S)-5-methyl-1-(4-((4'-(1-methylpyrrolidin-2-yl)-[1,1'-biphenyl]-4-yl)methyl)phenyl)-1H-pyrazole-3-carboxamide;
5-methyl-1-(4-(2-(4'-(pyrrolidin-1-ylmethyl)-[1,1'-biphenyl]-4-yl)propan-2-yl)phenyl)-1H-pyrazole-3-carboxamide;
5-methyl-1-(4-(2-(3'-(methylsulfonyl)-[1,1'-biphenyl]-4-yl)propan-2-yl)phenyl)-1H-pyrazole-3-carboxamide;
5-methyl-1-(4-(2-(4-(pyridin-4-yl)phenyl)propan-2-yl)phenyl)-1H-pyrazole-3-carboxamide;
1-(4-(2-(4-(1H-indazol-5-yl)phenyl)propan-2-yl)phenyl)-5-methyl-1H-pyrazole-3-carboxamide;
1-(4-(2-(4-(2-aminopyridin-4-yl)phenyl)propan-2-yl)phenyl)-5-methyl-1H-pyrazole-3-carboxamide;
5-methyl-1-(4-(2-(4'-(5-methyl-1,3,4-oxadiazol-2-yl)-[1,1'-biphenyl]-4-yl)propan-2-yl)phenyl)-1H-pyrazole-3-carboxamide;
5-methyl-1-(4-(2-(4'-(pyrrolidin-1-ylmethyl)-[1,1'-biphenyl]-4-yl)propan-2-yl)phenyl)-1H-pyrazole-3-carboxamide;
5-methyl-1-(4-(2-(4'-morpholino-2',3',4',5'-tetrahydro-[1,1'-biphenyl]-4-yl)propan-2-yl)phenyl)-1H-pyrazole-3-carboxamide;
1-(4-(2-(4'-hydroxy-2',3',4',5'-tetrahydro-[1,1'-biphenyl]-4-yl)propan-2-yl)phenyl)-5-methyl-1H-pyrazole-3-carboxamide;
5-methyl-1-(4-(2-(4-(pyridin-2-yl)phenyl)propan-2-yl)phenyl)-1H-pyrazole-3-carboxamide;
1-(4-(2-(4'-(3-(aminomethyl)oxetan-3-yl)-[1,1'-biphenyl]-4-yl)propan-2-yl)phenyl)-5-methyl-1H-pyrazole-3-carboxamide;
1-(4-(2-(4'-(3-aminooxetan-3-yl)-[1,1'-biphenyl]-4-yl)propan-2-yl)phenyl)-5-methyl-1H-pyrazole-3-carboxamide;
5-methyl-1-(4-(2-(4'-(pyrrolidin-1-ylmethyl)-[1,1'-biphenyl]-4-yl)propan-2-yl)phenyl)-1H-1,2,4-triazole-3-carboxamide;
1-(4-(2-(4'-(N,N-dimethylsulfamoyl)-[1,1'-biphenyl]-4-yl)propan-2-yl)phenyl)-5-methyl-1H-1,2,4-triazole-3-carboxamide;
5-methyl-1-(4-(2-(4-(quinolin-6-yl)phenyl)propan-2-yl)phenyl)-1H-1,2,4-triazole-3-carboxamide;
5-methyl-1-(4-(2-(4-(quinoxalin-6-yl)phenyl)propan-2-yl)phenyl)-1H-1,2,4-triazole-3-carboxamide;
1-(4-(2-(4-(isoquinolin-7-yl)phenyl)propan-2-yl)phenyl)-5-methyl-1H-1,2,4-triazole-3-carboxamide;
1-(4-(2-(4'-(dimethylcarbamoyl)-[1,1'-biphenyl]-4-yl)propan-2-yl)phenyl)-5-methyl-1H-1,2,4-triazole-3-carboxamide;
1-(4-(2-(4-(benzo[d]thiazol-5-yl)phenyl)propan-2-yl)phenyl)-5-methyl-1H-1,2,4-triazole-3-carboxamide;
5-methyl-1-(4-(2-(4-(1-methyl-1H-pyrazol-4-yl)phenyl)propan-2-yl)phenyl)-1H-1,2,4-triazole-3-carboxamide;
5-methyl-1-(4-(2-(4-(2-methylpyridin-4-yl)phenyl)propan-2-yl)phenyl)-1H-1,2,4-triazole-3-carboxamide;
1-(4-(2-(4-(6-cyanopyridin-3-yl)phenyl)propan-2-yl)phenyl)-5-methyl-1H-1,2,4-triazole-3-carboxamide;
5-methyl-1-(4-(2-(4-(4-methyl-3,4-dihydro-2H-pyrido[3,2-b][1,4]oxazin-7-yl)phenyl)propan-2-yl)phenyl)-1H-1,2,4-triazole-3-carboxamide;
5-methyl-1-(4-(2-(4'-(morpholinomethyl)-[1,1'-biphenyl]-4-yl)propan-2-yl)phenyl)-1H-1,2,4-triazole-3-carboxamide;

5-methyl-1-(4-(2-(3'-(5-methyl-1,3,4-oxadiazol-2-yl)-[1,1'-biphenyl]-4-yl)propan-2-yl)phenyl)-1H-1,2,4-triazole-3-carboxamide;
5-methyl-1-(4-(2-(4-(6-(pyrrolidin-1-yl)pyridin-3-yl)phenyl)propan-2-yl)phenyl)-1H-1,2,4-triazole-3-carboxamide;
5-methyl-1-(4-(2-(4-(6-morpholinopyridin-3-yl)phenyl)propan-2-yl)phenyl)-1H-1,2,4-triazole-3-carboxamide;
5-methyl-1-(4-(2-(4-(thiophen-3-yl)phenyl)propan-2-yl)phenyl)-1H-1,2,4-triazazole-3-carboxamide;
1-(4-(2-(4'-(1-amino-2,2,2-trifluoroethyl)-[1,1'-biphenyl]-4-yl)propan-2-yl)phenyl)-5-methyl-1H-1,2,4-triazole-3-carboxamide;
5-methyl-1-(4-((4'-((4-methylpiperazin-1-yl)methyl)-[1,1'-biphenyl]-4-yl)methyl)phenyl)-1H-1,2,4-triazole-3-carboxamide;
5-methyl-1-(4-(4-(pyridin-3-yl)benzyl)phenyl)-1H-1,2,4-triazole-3-carboxamide;
5-methyl-1-(4-((4'-(4-methylpiperazine-1-carbonyl)-[1,1'-biphenyl]-4-yl)methyl)phenyl)-1H-1,2,4-triazole-3-carboxamide;
5-methyl-1-(4-((4'-(pyrrolidin-1-ylmethyl)-[1,1'-biphenyl]-4-yl)methyl)phenyl)-1H-1,2,4-triazole-3-carboxamide;
1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide;
(S)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide;
1-(4-((4'-(((2-hydroxyethyl)amino)methyl)-[1,1'-biphenyl]-4-yl)methyl)phenyl)-5-methyl-1H-pyrazole-3-carboxamide;
1-(4-((4'-((cyclobutylamino)methyl)-[1,1'-biphenyl]-4-yl)methyl)phenyl)-5-methyl-1H-pyrazole-3-carboxamide;
5-methyl-1-(4-((4'-((oxetan-3-ylamino)methyl)-[1,1'-biphenyl]-4-yl)methyl)phenyl)-1H-pyrazole-3-carboxamide;
5-methyl-1-(4-((4'-((5-methylhexahydropyrrolo[3,4-c]pyrrol-2(1H)-yl)methyl)-[,1'-biphenyl]-4-yl)methyl)phenyl)-1H-pyrazole-3-carboxamide;
5-methyl-1-(4-((4'-((piperidin-1-ylmethyl)-[1,1'-biphenyl]-4-yl)methyl)phenyl)-1H-pyrazole-3-carboxamide;
1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide;
(R)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide; and
1-(4-((4'-(azetidin-1-ylmethyl)-[1,1'-biphenyl]-4-yl)methyl)phenyl)-5-methyl-1H-pyrazole-3-carboxamide.

9. The compound according to claim 1 or a pharmaceutically acceptable salt thereof, wherein the compound is selected from a group consisting of:

1-(4-((4'-((2-hydroxyethyl)sulfonyl)-[1,1'-biphenyl]-4-yl)methyl)phenyl)-5-methyl-1H-pyrazole-3-carboxamide;
1-(4-((4'-((4,4-difluoro-2-(hydroxymethyl)pyrrolidin-1-yl)methyl)-[1,1'-biphenyl]-4-yl)methyl)phenyl)-5-methyl-1H-pyrazole-3-carboxamide
(R)-1-(4-((4'-((4,4-difluoro-2-(hydroxymethyl)pyrrolidin-1-yl)methyl)-[1,1'-biphenyl]-4-yl)methyl)phenyl)-5-methyl-1H-pyrazole-3-carboxamide;
1-(4-(4-(5-(2-hydroxypropan-2-yl)pyridin-2-yl)benzyl)phenyl)-5-methyl-1H-pyrazole-3-carboxamide;
1-(4-(4-(5-(2-hydroxypropan-2-yl)-6-methylpyridin-2-yl)benzyl)phenyl)-5-methyl-1H-pyrazole-3-carboxamide;
1-(4-(4-(5-(2-hydroxypropan-2-yl)pyridin-2-yl)benzyl)phenyl)-5-methyl-1H-1,2,4-triazazole-3-carboxamide;
1-(4-(4-(6-(3-hydroxyoxetan-3-yl)pyridin-3-yl)benzyl)phenyl)-5-methyl-1H-pyrazole-3-carboxamide;
1-(4-(4-(2-(2-hydroxypropan-2-yl)pyridin-4-yl)benzyl)phenyl)-5-methyl-1H-pyrazole-3-carboxamide;
5-methyl-1-(4-((4'-(piperazine-1-carbonyl)-[1,1'-biphenyl]-4-yl)methyl)phenyl)-1H-pyrazole-3-carboxamide;
5-methyl-1-(4-((4'-(piperazine-1-carbonyl)-[1,1'-biphenyl]-4-yl)methyl)phenyl)-1H-1,2,4-triazole-3-carboxamide;
5-methyl-1-(4-(4-(6-(piperazine-1-carbonyl)pyridin-3-yl)benzyl)phenyl)-1H-pyrazole-3-carboxamide;
5-methyl-1-(4-(4-(5-(piperazine-1-carbonyl)pyridin-2-yl)benzyl)phenyl)-1H-pyrazole-3-carboxamide;
1-(4-((4'-(3-(hydroxymethyl)piperazine-1-carbonyl)-[1,1'-biphenyl]-4-yl)methyl)phenyl)-5-methyl-1H-pyrazole-3-carboxamide;
(R)-1-(4-((4'-(3-(hydroxymethyl)piperazine-1-carbonyl)-[1,1'-biphenyl]-4-yl)methyl)phenyl)-5-methyl-1H-pyrazole-3-carboxamide;
5-methyl-1-(4-((4'-(3-methylpiperazine-1-carbonyl)-[1,1'-biphenyl]-4-yl)methyl)phenyl)-1H-1,2,4-triazole-3-carboxamide;
(S)-5-methyl-1-(4-((4'-(3-methylpiperazine-1-carbonyl)-[1,1'-biphenyl]-4-yl)methyl)phenyl)-1H-1,2,4-triazole-3-carboxamide;
1-(4-((4'-(azetidin-3-ylcarbamoyl)-[1,1'-biphenyl]-4-yl)methyl)phenyl)-5-methyl-1H-pyrazole-3-carboxamide;
5-methyl-1-(4-(4-(6-(piperazin-1-ylmethyl)pyridin-3-yl)benzyl)phenyl)-1H-pyrazole-3-carboxamide;
5-methyl-1-(4-(4-(2-(piperazin-1-ylmethyl)pyridin-4-yl)benzyl)phenyl)-1H-pyrazole-3-carboxamide;
5-methyl-1-(4-(4-(5-(piperazin-1-ylmethyl)pyridin-2-yl)benzyl)phenyl)-1H-pyrazole-3-carboxamide;
1-(4-(4-(6-((4-(2-hydroxyethyl)piperazin-1-yl)methyl)pyridin-3-yl)benzyl)phenyl)-5-methyl-1H-pyrazole-3-carboxamide;
5-methyl-1-(4-(4-(5-((4-(oxetan-3-yl)piperazin-1-yl)methyl)pyridin-2-yl)benzyl)phenyl)-1H-pyrazole-3-carboxamide;
5-methyl-1-(4-(4-(6-((4-methylpiperazin-1-yl)methyl)pyridin-3-yl)benzyl)phenyl)-1H-1,2,4-triazole-3-carboxamide;
5-methyl-1-(4-(4-(5-(piperazin-1-ylmethyl)pyridin-2-yl)benzyl)phenyl)-1H-1,2,4-triazazole-3-carboxamide;
5-methyl-1-(4-(4-(6-((3-methylpiperazin-1-yl)methyl)pyridin-3-yl)benzyl)phenyl)-1H-1,2,4-triazole-3-carboxamide;
(S)-5-methyl-1-(4-(4-(6-((3-methylpiperazin-1-yl)methyl)pyridin-3-yl)benzyl)phenyl)-1H-1,2,4-triazole-3-carboxamide;
1-(4-(4-(6-((3,4-dimethylpiperazin-1-yl)methyl)pyridin-3-yl)benzyl)phenyl)-5-methyl-1H-1,2,4-triazole-3-carboxamide;
(S)-1-(4-(4-(6-((3,4-dimethylpiperazin-1-yl)methyl)pyridin-3-yl)benzyl)phenyl)-5-methyl-1H-1,2,4-triazole-3-carboxamide;
1-(4-((4'-((2-oxa-6-azaspiro[3.4]octan-6-yl)methyl)-[1,1'-biphenyl]-4-yl)methyl)phenyl)-5-methyl-1H-1,2,4-triazole-3-carboxamide;
1-(4-((4'-((3,3-difluoropyrrolidin-1-yl)methyl)-[1,1'-biphenyl]-4-yl)methyl)phenyl)-5-methyl-1H-1,2,4-triazole-3-carboxamide;

5-methyl-1-(4-((4'-(((3aR,6aS)-5-methylhexahydropyr-rolo[3,4-c]pyrrol-2(1H)-yl)methyl)-[1,1'-biphenyl]-4-yl)methyl)phenyl)-1H-1,2,4-triazole-3-carboxamide;
1-(4-((4'-((2-oxa-6-azaspiro[3.3]heptan-6-yl)methyl)-[1,1'-biphenyl]-4-yl)methyl)phenyl)-5-methyl-1H-1,2,4-triazole-3-carboxamide;
1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide;
(R)-1-(4-((4'-((2-(hydroxymethyl)pyrrolidin-1-yl)methyl)-[1,1'-biphenyl]-4-yl)methyl)phenyl)-5-methyl-1H-1,2,4-triazole-3-carboxamide;
1-(4-((4'-((2-oxa-6-azaspiro[3.5]nonan-6-yl)methyl)-[1,1'-biphenyl]-4-yl)methyl)phenyl)-5-methyl-1H-1,2,4-triazole-3-carboxamide;
1-(4-((4'-((3,3-dimethylpyrrolidin-1-yl)methyl)-[1,1'-biphenyl]-4-yl)methyl)phenyl)-5-methyl-1H-1,2,4-triazole-3-carboxamide;
1-(4-((4'-((2-oxa-7-azaspiro[3.5]nonan-7-yl)methyl)-[1,1'-biphenyl]-4-yl)methyl)phenyl)-5-methyl-1H-1,2,4-triazole-3-carboxamide;
1-(4-((4'-((3,3-difluoropiperidin-1-yl)methyl)-[1,1'-biphenyl]-4-yl)methyl)phenyl)-5-methyl-1H-1,2,4-triazole-3-carboxamide;
1-(4-((4'-((4,4-dimethylpiperidin-1-yl)methyl)-[1,1'-biphenyl]-4-yl)methyl)phenyl)-5-methyl-1H-1,2,4-triazole-3-carboxamide;
1-(4-((4'-((4-((dimethylamino)methyl)piperidin-1-yl)methyl)-[1,1'-biphenyl]-4-yl)methyl)phenyl)-5-methyl-1H-1,2,4-triazole-3-carboxamide;
1-(4-((4'-((4-(dimethylamino)piperidin-1-yl)methyl)-[1,1'-biphenyl]-4-yl)methyl)phenyl)-5-methyl-1H-1,2,4-triazole-3-carboxamide;
1-(4-((4'-((4-(2-hydroxypropan-2-yl)piperidin-1-yl)methyl)-[1,1'-biphenyl]-4-yl)methyl)phenyl)-5-methyl-1H-1,2,4-triazole-3-carboxamide;
1-(4-((4'-((3-hydroxypyrrolidin-1-yl)methyl)-[1,1'-biphenyl]-4-yl)methyl)phenyl)-5-methyl-1H-1,2,4-triazole-3-carboxamide;
(R)-1-(4-((4'-((3-hydroxypyrrolidin-1-yl)methyl)-[1,1'-biphenyl]-4-yl)methyl)phenyl)-5-methyl-1H-1,2,4-triazole-3-carboxamide;
(S)-1-(4-((4'-((3-hydroxypyrrolidin-1-yl)methyl)-[1,1'-biphenyl]-4-yl)methyl)phenyl)-5-methyl-1H-1,2,4-triazole-3-carboxamide;
1-(4-((4'-((4-hydroxy-4-methylpiperidin-1-yl)methyl)-[1,1'-biphenyl]-4-yl)methyl)phenyl)-5-methyl-1H-1,2,4-triazole-3-carboxamide;
1-(4-((4'-((3-(2-hydroxypropan-2-yl)piperidin-1-yl)methyl)-[1,1'-biphenyl]-4-yl)methyl)phenyl)-5-methyl-1H-1,2,4-triazole-3-carboxamide;
1-(4-((4'-((3-hydroxyazetidin-1-yl)methyl)-[1,1'-biphenyl]-4-yl)methyl)phenyl)-5-methyl-1H-1,2,4-triazole-3-carboxamide;
1-(4-((4'-((3,5-dimethylpiperazin-1-yl)methyl)-[1,1'-biphenyl]-4-yl)methyl)phenyl)-5-methyl-1H-1,2,4-triazole-3-carboxamide;
1-(4-((4'-(((3R,5R)-3,5-dimethylpiperazin-1-yl)methyl)-[1,1'-biphenyl]-4-yl)methyl)phenyl)-5-methyl-1H-1,2,4-triazole-3-carboxamide;
1-(4-((4'-((3-hydroxy-3-methylpyrrolidin-1-yl)methyl)-[1,1'-biphenyl]-4-yl)methyl)phenyl)-5-methyl-1H-1,2,4-triazole-3-carboxamide;
1-(4-((4'-((5-oxa-2-azaspiro[3.4]octan-2-yl)methyl)-[1,1'-biphenyl]-4-yl)methyl)phenyl)-5-methyl-1H-1,2,4-triazole-3-carboxamide;
1-(4-((4'-((3-(hydroxymethyl)piperazin-1-yl)methyl)-[1,1'-biphenyl]-4-yl)methyl)phenyl)-5-methyl-1H-1,2,4-triazole-3-carboxamide;
(R)-1-(4-((4'-((3-(hydroxymethyl)piperazin-1-yl)methyl)-[1,1'-biphenyl]-4-yl)methyl)phenyl)-5-methyl-1H-1,2,4-triazole-3-carboxamide;
1-(4-((4'-((3-fluoropyrrolidin-1-yl)methyl)-[1,1'-biphenyl]-4-yl)methyl)phenyl)-5-methyl-1H-1,2,4-triazole-3-carboxamide;
(R)-1-(4-((4'-((3-fluoropyrrolidin-1-yl)methyl)-[1,1'-biphenyl]-4-yl)methyl)phenyl)-5-methyl-1H-1,2,4-triazole-3-carboxamide;
5-methyl-1-(4-((4'-((3-(methylsulfonyl)pyrrolidin-1-yl)methyl)-[1,1'-biphenyl]-4-yl)methyl)phenyl)-1H-1,2,4-triazole-3-carboxamide;
5-methyl-1-(4-((4'-((5-methylhexahydropyrrolo[3,4-b]pyrrol-1(2H)-yl)methyl)-[1,1'-biphenyl]-4-yl)methyl)phenyl)-1H-1,2,4-triazole-3-carboxamide;
1-(4-((4'-((3-hydroxy-3-methylpiperidin-1-yl)methyl)-[1,1'-biphenyl]-4-yl)methyl)phenyl)-5-methyl-1H-1,2,4-triazole-3-carboxamide;
1-(4-((4'-((4-(tert-butyl)piperazin-1-yl)methyl)-[1,1'-biphenyl]-4-yl)methyl)phenyl)-5-methyl-1H-1,2,4-triazole-3-carboxamide;
1-(4-((4'-((3,3-dimethylpiperazin-1-yl)methyl)-[1,1'-biphenyl]-4-yl)methyl)phenyl)-5-methyl-1H-1,2,4-triazole-3-carboxamide;
1-(4-((4'-(((3S,5R)-3,5-dimethylpiperazin-1-yl)methyl)-[1,1'-biphenyl]-4-yl)methyl)phenyl)-5-methyl-1H-1,2,4-triazole-3-carboxamide;
1-(4-((4'-((4,4-difluoropiperidin-1-yl)methyl)-[1,1'-biphenyl]-4-yl)methyl)phenyl)-5-methyl-1H-1,2,4-triazole-3-carboxamide;
5-methyl-1-(4-((4'-((octahydro-2H-pyrido[1,2-a]pyrazin-2-yl)methyl)-[1,1'-biphenyl]-4-yl)methyl)phenyl)-1H-1,2,4-triazole-3-carboxamide;
1-(4-((4'-((2-(hydroxymethyl)piperidin-1-yl)methyl)-[1,1'-biphenyl]-4-yl)methyl)phenyl)-5-methyl-1H-1,2,4-triazole-3-carboxamide;
(S)-1-(4-((4'-((2-(hydroxymethyl)piperidin-1-yl)methyl)-[1,1'-biphenyl]-4-yl)methyl)phenyl)-5-methyl-1H-1,2,4-triazole-3-carboxamide;
1-(4-((4'-((4-(hydroxymethyl)piperidin-1-yl)methyl)-[1,1'-biphenyl]-4-yl)methyl)phenyl)-5-methyl-1H-1,2,4-triazole-3-carboxamide;
1-(4-((4'-((3-hydroxy-3-methylazetidin-1-yl)methyl)-[1,1'-biphenyl]-4-yl)methyl)phenyl)-5-methyl-1H-1,2,4-triazole-3-carboxamide;
1-(4-((4'-((4-hydroxypiperidin-1-yl)methyl)-[1,1'-biphenyl]-4-yl)methyl)phenyl)-5-methyl-1H-1,2,4-triazole-3-carboxamide;
5-methyl-1-(4-((4'-(((3aR,6aS)-tetrahydro-1H-furo[3,4-c]pyrrol-5(3H)-yl)methyl)-[1,1'-biphenyl]-4-yl)methyl)phenyl)-1H-1,2,4-triazole-3-carboxamide;
1-(4-((4'-((3-fluoropiperidin-1-yl)methyl)-[1,1'-biphenyl]-4-yl)methyl)phenyl)-5-methyl-1H-1,2,4-triazole-3-carboxamide;
5-methyl-1-(4-((4'-((4-methyl-1,4-diazepan-1-yl)methyl)-[1,1'-biphenyl]-4-yl)methyl)phenyl)-1H-1,2,4-triazole-3-carboxamide;
1-(4-((4'-((3,4-dihydroxypyrrolidin-1-yl)methyl)-[1,1'-biphenyl]-4-yl)methyl)phenyl)-5-methyl-1H-1,2,4-triazole-3-carboxamide;
1-(4-((4'-(((3S,4S)-3,4-dihydroxypyrrolidin-1-yl)methyl)-[1,1'-biphenyl]-4-yl)methyl)phenyl)-5-methyl-1H-1,2,4-triazole-3-carboxamide;

5-methyl-1-(4-((4'-((1-methylhexahydropyrrolo[3,4-b]
pyrrol-5-(H)-yl)methyl)-[1,1'-biphenyl]-4-yl)methyl)
phenyl)-1H-1,2,4-triazole-3-carboxamide;

5-methyl-1-(4-((4'-(((3aR,6aR)-1-methylhexahydropyr-
rolo[3,4-b]pyrrol-5(1H)-yl)methyl)-[1,1'-biphenyl]-4-
yl)methyl)phenyl)-1H-1,2,4-triazole-3-carboxamide;

5-methyl-1-(4-((4'-((4-(methylsulfonyl)piperidin-1-yl)
methyl)-[1,1'-biphenyl]-4-yl)methyl)phenyl)-1H-1,2,
4-triazole-3-carboxamide;

1-(4-((4'-((1,1-dioxidothiomorpholino)methyl)-[1,1'-bi-
phenyl]-4-yl)methyl)phenyl)-5-methyl-1H-1,2,4-triaz-
ole-3-carboxamide;

1-(4-((4'-((3,3-difluoroazetidin-1-yl)methyl)-[1,1'-biphe-
nyl]-4-yl)methyl)phenyl)-5-methyl-1H-1,2,4-triazole-
3-carboxamide;

1-(4-((4'-(((1R,5S)-6-(hydroxymethyl)-3-azabicyclo
[3.1.0]hexan-3-yl)methyl)-[1,1'-biphenyl]-4-yl)
methyl)phenyl)-5-methyl-1H-1,2,4-triazole-3-carbox-
amide;

1-(4-((4'-(((1R,5S,6r)-6-(hydroxymethyl)-3-azabicyclo
[3.1.0]hexan-3-yl)methyl)-[1,1'-biphenyl]-4-yl)
methyl)phenyl)-5-methyl-1H-1,2,4-triazole-3-carbox-
amide;

5-methyl-1-(4-((4'-((4-(trifluoromethyl)piperidin-1-yl)
methyl)-[1,1'-biphenyl]-4-yl)methyl)phenyl)-1H-1,2,
4-triazole-3-carboxamide;

1-(4-((4'-((3-(hydroxymethyl)azetidin-1-yl)methyl)-[1,1'-
biphenyl]-4-yl)methyl)phenyl)-5-methyl-1H-1,2,4-tri-
azole-3-carboxamide;

1-(4-((4'-((1-oxa-7-azaspiro[3.5]nonan-7-yl)methyl)-[1,
1'-biphenyl]-4-yl)methyl)phenyl)-5-methyl-1H-1,2,4-
triazole-3-carboxamide;

1-(4-((4'-((2-(hydroxymethyl)pyrrolidin-1-yl)methyl)-[1,
1'-biphenyl]-4-yl)methyl)phenyl)-5-methyl-1H-1,2,4-
triazole-3-carboxamide;

(S)-1-(4-((4'-((2-(hydroxymethyl)pyrrolidin-1-yl)
methyl)-[1,1'-biphenyl]-4-yl)methyl)phenyl)-5-
methyl-1H-1,2,4-triazole-3-carboxamide;

1-(4-((4'-((4-(dimethylamino)piperidin-1-yl)methyl)-[1,
1'-biphenyl]-4-yl)methyl)phenyl)-5-methyl-1H-pyra-
zole-3-carboxamide;

5-methyl-1-(4-((4'-(((3aR, 6aS)-2-methyloctahydrocyclo-
penta[c]pyrrol-5-yl)methyl)-[1,1'-biphenyl]-4-yl)
methyl)phenyl)-1H-1,2,4-triazole-3-carboxamide;

5-methyl-1-(4-(4-(4-(piperazine-1-carbonyl)bicyclo
[2.2.2]octan-1-yl)benzyl)phenyl)-1H-pyrazole-3-car-
boxamide;

5-methyl-1-(4-(4-(4-(4-methylpiperazine-1-carbonyl)bi-
cyclo[2.2.2]octan-1-yl)benzyl)phenyl)-1H-pyrazole-3-
carboxamide;

5-methyl-1-(4-(4-(6-(piperazine-1-carbonyl)spiro[3.3]
heptan-2-yl)benzyl)phenyl)-1H-1,2,4-triazole-3-car-
boxamide;

5-methyl-1-(4-((4'-(piperazin-1-ylmethyl)-[1,1'-biphe-
nyl]-4-yl)methyl)phenyl)-1H-1,2,4-triazole-3-carbox-
amide;

1-(4-(4-(6-(2-hydroxypropan-2-yl)pyridin-3-yl)benzyl)
phenyl)-5-methyl-1H-1,2,4-triazazole-3-carboxamide;

5-methyl-1-(4-((4'-((1-methylpiperidin-4-yl)oxy)-[1,1'-
biphenyl]-4-yl)methyl)phenyl)-1H-1,2,4-triazole-3-
carboxamide;

1-(4-((4'-(1-hydroxy-2-methylpropan-2-yl)-[1,1'-biphe-
nyl]-4-yl)methyl)phenyl)-5-methyl-1H-1,2,4-triazole-
3-carboxamide;

1-(4-(4-(4-(2-hydroxypropan-2-yl)piperidin-1-yl)benzyl)
phenyl)-5-methyl-1H-1,2,4-triazazole-3-carboxamide;

1-(4-((4'-(N-(2-hydroxy-2-methylpropyl)sulfamoyl)-[1,
1'-biphenyl]-4-yl)methyl)phenyl)-5-methyl-1H-1,2,4-
triazole-3-carboxamide;

1-(4-((4'-((2-hydroxy-2-methylpropyl)carbamoyl)-[1,1'-
biphenyl]-4-yl)methyl)phenyl)-5-methyl-1H-1,2,4-tri-
azole-3-carboxamide;

1-(4-(4-(5-(N-(2-hydroxy-2-methylpropyl)sulfamoyl)
pyridin-2-yl)benzyl)phenyl)-5-methyl-1H-1,2,4-triaz-
ole-3-carboxamide;

1-(4-(4-(4-(2-hydroxypropan-2-yl)pyridin-2-yl)benzyl)
phenyl)-5-methyl-1H-1,2,4-triazazole-3-carboxamide;

5-methyl-1-(4-(4-((1-methylpiperidin-4-yl)ethynyl)ben-
zyl)phenyl)-1H-1,2,4-triazazole-3-carboxamide;

1-(4-(4-((1-hydroxycyclohexyl)ethynyl)benzyl)phenyl)-
5-methyl-1H-1,2,4-triazazole-3-carboxamide;

1-(4-(4-(5-(1-hydroxy-2-methylpropan-2-yl)pyridin-2-yl)
benzyl)phenyl)-5-methyl-1H-1,2,4-triazole-3-carbox-
amide;

1-(4-(4-(5-(1-hydroxy-2-methylpropan-2-yl)pyridin-2-yl)
benzyl)phenyl)-5-methyl-1H-pyrazole-3-carboxamide;

1-(4-(4-(6-(2-hydroxypropan-2-yl)pyridazin-3-yl)benzyl)
phenyl)-5-methyl-1H-pyrazole-3-carboxamide;

6-(4-(4-(3-carbamoyl-5-methyl-1H-pyrazol-1-yl)benzyl)
phenyl)-N-(2-hydroxy-2-methylpropyl)nicotinamide;

1-(4-(4-(2-(2-hydroxypropan-2-yl)pyrimidin-5-yl)ben-
zyl)phenyl)-5-methyl-1H-pyrazole-3-carboxamide;

1-(4-(4-(2-(hydroxymethyl)pyridin-4-yl)benzyl)phenyl)-
5-methyl-1H-pyrazole-3-carboxamide;

5-methyl-1-(4-((4'-((1-methylpyrrolidin-3-yl)oxy)-[1,1'-
biphenyl]-4-yl)methyl)phenyl)-1H-1,2,4-triazole-3-
carboxamide;

(S)-5-methyl-1-(4-((4'-((1-methylpyrrolidin-3-yl)oxy)-[1,
1'-biphenyl]-4-yl)methyl)phenyl)-1H-1,2,4-triazole-3-
carboxamide;

5-methyl-1-(4-((4'-((1-methylpyrrolidin-3-yl)oxy)-[1,1'-
biphenyl]-4-yl)methyl)phenyl)-1H-1,2,4-triazole-3-
carboxamide;

(R)-5-methyl-1-(4-((4'-((1-methylpyrrolidin-3-yl)oxy)-
[1,1'-biphenyl]-4-yl)methyl)phenyl)-1H-1,2,4-triazole-
3-carboxamide; and 1-(4-((4'-(2-((2-hydroxy-2-methylpropyl)amino)propan-
2-yl)-[1,1'-biphenyl]-4-yl)methyl)phenyl)-5-methyl-
1H-1,2,4-triazole-3-carboxamide.

10. The compound according to claim 1 or a pharmaceutically acceptable salt thereof, wherein the compound is 1-(4-((4'-((2-(hydroxymethyl)pyrrolidin-1-yl)methyl)-[1,'-biphenyl]-4-yl)methyl)phenyl)-5-methyl-1H-pyrazole-3-carboxamide.

11. The compound according to claim 1 or a pharmaceutically acceptable salt thereof, wherein the compound is (S)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide.

12. The compound according to claim 1 or a pharmaceutically acceptable salt thereof, wherein the compound is (R)-1-(4-((4'-((2-(hydroxymethyl)pyrrolidin-1-yl)methyl)-[1,1'-biphenyl]-4-yl)methyl)phenyl)-5-methyl-1H-pyrazole-3-carboxamide.

13. The compound according to claim 1 or a pharmaceutically acceptable salt thereof, wherein the compound is 5-methyl-1-(4-((4'-((5-methylhexahydropyrrolo[3,4-c]pyrrol-2(1H)-yl)methyl)-[1,1'-biphenyl]-4-yl)methyl)phenyl)-1H-pyrazole-3-carboxamide.

14. The compound according to claim 1 or a pharmaceutically acceptable salt thereof, wherein 5-methyl-1-(4-((4'-((4-methylpiperazin-1-yl)methyl)-[1,'-biphenyl]-4-yl)methyl)phenyl)-1H-1,2,4-triazole-3-carboxamide.

15. A pharmaceutical composition comprising a compound according to claim 1 or a pharmaceutically acceptable salt thereof, and one or more pharmaceutically acceptable carriers.

16. A pharmaceutical combination comprising a compound according to claim 1 or a pharmaceutically acceptable salt thereof, and one or more other therapeutically active agents.

* * * * *